United States Patent
Meyer

(10) Patent No.: US 11,446,313 B2
(45) Date of Patent: *Sep. 20, 2022

(54) METHODS OF TREATING ALPORT SYNDROME USING BARDOXOLONE METHYL OR ANALOGS THEREOF

(71) Applicant: REATA PHARMACEUTICALS HOLDINGS, LLC, Plano, TX (US)

(72) Inventor: Colin J. Meyer, Southlake, TX (US)

(73) Assignee: REATA PHARMACEUTICALS HOLDINGS, LLC, Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/173,340

(22) Filed: Feb. 11, 2021

(65) Prior Publication Data

US 2021/0161914 A1 Jun. 3, 2021

Related U.S. Application Data

(63) Continuation of application No. 16/315,821, filed as application No. PCT/US2017/060701 on Nov. 8, 2017, now Pat. No. 10,953,020.

(60) Provisional application No. 62/580,597, filed on Nov. 2, 2017, provisional application No. 62/535,663, filed on Jul. 21, 2017, provisional application No. 62/419,335, filed on Nov. 8, 2016.

(51) Int. Cl.
| | | |
|---|---|---|
| *A61K 31/56* | (2006.01) | |
| *A61K 47/69* | (2017.01) | |
| *A61P 13/12* | (2006.01) | |
| *A61K 47/32* | (2006.01) | |

(52) U.S. Cl.
CPC .............. *A61K 31/56* (2013.01); *A61K 47/32* (2013.01); *A61K 47/6943* (2017.08); *A61P 13/12* (2018.01)

(58) Field of Classification Search
None
See application file for complete search history.

(56) References Cited

U.S. PATENT DOCUMENTS

| | | | |
|---|---|---|---|
| 4,395,423 A | 7/1983 | Neumann | |
| 5,064,823 A | 11/1991 | Lee et al. | |
| 5,248,807 A | 9/1993 | Fujimoto et al. | |
| 5,603,958 A | 2/1997 | Morein et al. | |
| 6,326,507 B1 | 12/2001 | Gribble et al. | |
| 6,485,756 B1 | 11/2002 | Aust et al. | |
| 6,552,075 B2 | 4/2003 | Gribble et al. | |
| 6,890,946 B2 | 5/2005 | Nakshatri et al. | |
| 6,974,801 B2 | 12/2005 | Honda et al. | |
| 7,288,568 B2 | 10/2007 | Gribble et al. | |
| 7,323,476 B2 | 1/2008 | Dev et al. | |
| 7,435,755 B2 | 10/2008 | Konopleva et al. | |
| 7,714,012 B2 | 5/2010 | Honda et al. | |
| 7,795,305 B2 | 9/2010 | Konopleva et al. | |
| 7,795,306 B2 | 9/2010 | Dev et al. | |
| 7,811,997 B2 | 10/2010 | Zhang et al. | |
| 7,863,327 B2 | 1/2011 | Gribble et al. | |
| 7,915,402 B2 | 3/2011 | Anderson et al. | |
| 7,943,778 B2 | 5/2011 | Jiang et al. | |
| 8,034,389 B2 | 10/2011 | Nawar | |
| 8,034,955 B2 | 10/2011 | Gribble et al. | |
| 8,071,632 B2 | 12/2011 | Jiang et al. | |
| 8,088,824 B2 | 1/2012 | Walling et al. | |
| 8,124,656 B2 | 2/2012 | Anderson et al. | |
| 8,124,799 B2 | 2/2012 | Anderson et al. | |
| 8,129,429 B2 | 3/2012 | Sporn et al. | |
| 8,299,046 B2 | 10/2012 | Sporn et al. | |
| 8,309,601 B2 | 11/2012 | Walling et al. | |
| 8,338,618 B2 | 12/2012 | Jiang et al. | |
| 8,394,967 B2 | 3/2013 | Jiang et al. | |
| 8,410,173 B2 | 4/2013 | Zisman | |
| 8,440,820 B2 | 5/2013 | Anderson et al. | |
| 8,440,854 B2 | 5/2013 | Anderson et al. | |
| 8,455,544 B2 | 6/2013 | Sporn et al. | |
| 8,586,775 B2 | 11/2013 | Gribble et al. | |
| 8,633,243 B2 | 1/2014 | Walling et al. | |
| 8,747,901 B2 | 6/2014 | Zhang et al. | |
| RE45,288 E | 12/2014 | Anderson et al. | |
| 8,921,419 B2 | 12/2014 | Gribble et al. | |
| RE45,325 E | 1/2015 | Anderson et al. | |
| 8,993,640 B2 | 3/2015 | Anderson et al. | |
| 9,090,574 B2 | 7/2015 | Anderson et al. | |
| 9,102,681 B2 | 8/2015 | Anderson et al. | |
| 9,249,089 B2 | 2/2016 | Jiang et al. | |
| 9,278,912 B2 | 3/2016 | Jiang et al. | |
| 9,278,913 B2 | 3/2016 | Gribble et al. | |
| 9,290,536 B2 | 3/2016 | Anderson et al. | |
| 9,512,094 B2 | 12/2016 | Jiang et al. | |

(Continued)

FOREIGN PATENT DOCUMENTS

| | | |
|---|---|---|
| CA | 2917336 | 7/2016 |
| CN | 102070697 | 5/2011 |

(Continued)

OTHER PUBLICATIONS

Guan et al., "Peroxisome proliferator-activated receptor-γ activity is associated with renal microvasculature", *Am. J. Physiol. Renal Physiol.*, 281:F1036-F1046, 2001.

Imano et al., "Effect of troglitazene on microalbuminuria in patients with incipient diabetic nephropathy", *Diabetes Care*, 21:2135-2139, 1998.

Office Communication issued in corresponding U.S. Appl. No. 15/675,862, dated Jun. 28, 2021.

Okada et al., "Thiazolidinediones ameliorate diabetic nephropathy via cell cycle-dependent mechanisms", *Diabetes*, 55:1666-1677, 2006.

(Continued)

*Primary Examiner* — Layla D Berry
(74) *Attorney, Agent, or Firm* — Parker Highlander PLLC

(57) ABSTRACT

The present invention provides methods of treating or preventing Alport syndrome in a patients in need thereof using bardoxolone methyl or analogs thereof, and/or improving the kidney function of patients who have been diagnosed with Alport syndrome.

30 Claims, 16 Drawing Sheets

(56) References Cited

U.S. PATENT DOCUMENTS

| | | |
|---|---|---|
| 9,556,222 B2 | 1/2017 | Anderson et al. |
| 9,593,074 B2 | 3/2017 | Bender et al. |
| 9,670,147 B2 | 6/2017 | Anderson et al. |
| 9,701,709 B2 | 7/2017 | Anderson et al. |
| 9,757,359 B2 | 9/2017 | Sporn et al. |
| 9,856,286 B2 | 1/2018 | Sheikh et al. |
| 9,889,143 B2 | 2/2018 | Jiang et al. |
| 10,093,614 B2 | 10/2018 | Anderson et al. |
| 10,105,372 B2 | 10/2018 | Meyer et al. |
| 10,398,711 B2 | 9/2019 | Jiang et al. |
| 2002/0042535 A1 | 4/2002 | Gribble et al. |
| 2003/0119732 A1 | 6/2003 | Konopleva et al. |
| 2003/0236303 A1 | 12/2003 | Gribble et al. |
| 2004/0002463 A1 | 1/2004 | Honda et al. |
| 2004/0102361 A1 | 5/2004 | Bodin |
| 2005/0288363 A1 | 12/2005 | Gribble et al. |
| 2006/0148732 A1 | 7/2006 | Gutterman et al. |
| 2007/0155742 A1 | 7/2007 | Honda et al. |
| 2007/0249561 A1 | 10/2007 | Taylor |
| 2008/0220057 A1 | 9/2008 | Gribble et al. |
| 2008/0233195 A1 | 9/2008 | Sporn et al. |
| 2008/0254055 A1 | 10/2008 | Oblong et al. |
| 2009/0036465 A1 | 2/2009 | Roscigno et al. |
| 2009/0036524 A1 | 2/2009 | Dev et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0326063 A1 | 12/2009 | Sporn et al. |
| 2010/0041904 A1 | 2/2010 | Jiang et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0190313 A1 | 8/2011 | Pascoe et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0022156 A1 | 1/2012 | Zhang et al. |
| 2012/0071684 A1 | 3/2012 | Walling et al. |
| 2012/0101149 A1 | 4/2012 | Honda et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2013/0005711 A1 | 1/2013 | Fong |
| 2013/0237721 A1 | 9/2013 | Gribble et al. |
| 2013/0274480 A1 | 10/2013 | Honda et al. |
| 2013/0303607 A1 | 11/2013 | Gribble et al. |
| 2013/0303797 A1 | 11/2013 | Gribble et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0073700 A1 | 3/2014 | Wagner et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0323579 A1 | 10/2014 | Sheikh et al. |
| 2015/0011627 A1 | 1/2015 | Gribble et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0259377 A1 | 9/2015 | Anderson et al. |
| 2015/0376121 A1 | 12/2015 | Anderson et al. |
| 2017/0165278 A1 | 6/2017 | Jiang et al. |
| 2018/0161311 A1 | 6/2018 | Sporn et al. |
| 2019/0153022 A1 | 5/2019 | Visnick et al. |

FOREIGN PATENT DOCUMENTS

| | | |
|---|---|---|
| CN | 102875634 | 1/2013 |
| CN | 102887936 | 1/2013 |
| CN | 103665087 | 3/2014 |
| DE | 10 2005 041613 | 3/2007 |
| JP | 2001-240573 | 9/2001 |
| JP | 2005-314381 | 11/2005 |
| JP | 2008-110962 | 5/2008 |
| WO | WO 1999/065478 | 12/1999 |
| WO | WO 2000/073253 | 12/2000 |
| WO | WO 2002/003996 | 1/2002 |
| WO | WO 2002/047611 | 6/2002 |
| WO | WO 2003/100033 | 12/2003 |
| WO | WO 2004/064723 | 8/2004 |
| WO | WO 2005/042002 | 5/2005 |
| WO | WO 2005/046732 | 5/2005 |
| WO | WO 2005/063295 | 7/2005 |
| WO | WO 2005/102317 | 11/2005 |
| WO | WO 2006/029221 | 3/2006 |
| WO | WO 2007/005879 | 1/2007 |
| WO | WO 2008/016095 | 2/2008 |
| WO | WO 2008/064132 | 5/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/089545 | 7/2009 |
| WO | WO 2009/129546 | 10/2009 |
| WO | WO 2009/129548 | 10/2009 |
| WO | WO 2009/129545 | 11/2009 |
| WO | WO 2009/146216 | 12/2009 |
| WO | WO 2010/053817 | 5/2010 |
| WO | WO 2010/059245 | 5/2010 |
| WO | WO 2010/093944 | 8/2010 |
| WO | WO 2011/130302 | 10/2011 |
| WO | WO 2012/096718 | 7/2012 |
| WO | WO 2012/125488 | 9/2012 |
| WO | WO 2013/163344 | 10/2013 |
| WO | WO 2013/169740 | 11/2013 |
| WO | WO 2013/188818 | 12/2013 |
| WO | WO 2014/040052 | 3/2014 |
| WO | WO 2014/040056 | 3/2014 |
| WO | WO 2014/040060 | 3/2014 |
| WO | WO 2014/040073 | 3/2014 |
| WO | WO 2014/058881 | 4/2014 |
| WO | WO 2014/100728 | 6/2014 |
| WO | WO 2014/176415 | 10/2014 |
| WO | WO 2015/027206 | 2/2015 |
| WO | WO 2016/029027 | 2/2016 |
| WO | WO 2017/053868 | 3/2017 |

OTHER PUBLICATIONS

"Effect of an Nrf2-activating agent on hypoxemia-induced pulmonary hypertension," *J. Jap. Respir. Soc.*, 49(Suppl.):150, pp. 62, 2011. (English translation appended).

"RTA 402, Therapeutic Properties I," slides/handouts presented by Reata Pharmaceuticals, Inc. at private partnering meetings at BioSquare 2006 conference, Mar. 8-10, 2006, Geneva, Switzerland.

"RTA 402, Therapeutic Properties II," slides/handouts presented by Reata Pharmaceuticals, Inc. at private partnering meetings at BIO 2006 conference, Apr. 9-12, 2006, Chicago, Illinois.

"RTA 402, Therapeutic Properties III," slides presented by Reata Pharmaceuticals, Inc. as a podium presentation at BIO 2006 conference, Apr. 9-12, 2006, Chicago, Illinois.

"RTA 402, Therapeutic Properties IV," slides/handouts presented by Reata Pharmaceuticals, Inc. at private partnering meetings at BioPartnering Europe 2006 conference, Oct. 8-10, 2006, London, England.

"RTA 402, Therapeutic Properties IX," slides/handouts presented by Reata Pharmaceuticals, Inc. at a private partnering meeting at BIO Europe 2007 conference, Nov. 12-14, 2007, Hamburg, Germany.

"RTA 402, Therapeutic Properties V," slides/handouts presented by Reata Pharmaceuticals, Inc. at private partnering meetings at BIO 2007 conference, May 6-9, 2007, Boston Massachusetts.

(56) References Cited

OTHER PUBLICATIONS

"RTA 402, Therapeutic Properties VI," slides/handouts presented by Reata Pharmaceuticals, Inc. at private partnering meetings at BIO 2007 conference, May 6-9, 2007, Boston, Massachusetts.
"RTA 402, Therapeutic Properties VII," slides presented by Reata Pharmaceuticals, Inc. as a podium presentation at BIO 2007 conference, May 6-9, 2007, Boston, Massachusetts.
"RTA 402, Therapeutic Properties VIII," slides/handouts presented by Reata Pharmaceuticals, Inc. at private partnering meetings at BIO Europe 2007 conference, Nov. 12-14, 2007, Hamburg, Germany.
Abboud, "Synthetic oleanane triterpenoids: magic bullets or not?" *Kidney International*, 83(5):785-787, 2013.
Abraham and Kappas, "Heme oxygenase and the cardiovascular-renal system," Free Radic. Biol. Med., 39:1-25, 2005.
Agarwal et al., "A pilot randomized controlled trial of renal protection with pioglitazone in diabetic nephropathy," *Kidney Int.*, 68(1):285-292, 2005.
Aggarwal, "Targeting inflammation-induced obesity and metabolic diseases by curcumin and other nutraceuticals," Annu. Rev. Nutr, 30:173-199, 2010.
Ahmad et al., "Combining the FLT3 Inhibitor PKC412 and the Triterpenoid CDDO-Me Synergistically Induces Apoptosis in Acute Myeloid Leukemia with the Internal Tandem Duplication Mutation," *Mol. Cancer Res.*, 8(7):986-993, 2010.
Ahmad et al., "Triterpenoid CDDO-Me blocks the NF-κB pathway by direct inhibition of IKKbeta on Cys-179," J. Biol. Chem., 281:35764-35769, 2006.
Ahmad et al., "Triterpenoid CDDO-methyl ester inhibits the Janus-activated kinase-1 (JAKI)—-> signal transducer and activator of transcription-3 (STAT3) pathway by direct inhibition of JAK1 and STAT3," Cancer Res., 68:2920-2926, 2008.
Alabran et al., "Human neuroblastoma cells rapidly enter cell cycle arrest and apoptosis following exposure to C-28 derivatives of the synthetic triterpenoid CDDO," Cancer Biology & Therapy, 7:709-717, 2008.
Ames et al., "The Triterpenoid CDDO-Me Promotes Hematopoietic Progenitor Expansion and Myelopoiesis in Mice," *Biology of Blood and Marrow Transplantation*, 18(3):396-405, 2012.
Araujo et al., "Systemic rather than local heme oxygenase-1 overexpression improves cardiac allograft outcomes in a new transgenic mouse," J. Immunol., 171:1572-1580, 2003.
Ardestani et al., "Effects of dexamethasone and betamethasone as COX-2 gene expression inhibitors on rigidity in a rat model of Parkinson's disease," Indian J. Pharmacol., 39:235-9, 2007.
Auletta et al., "The Synthetic Triterpenoid, CDDO-Me, Modulates the Proinflammatory Response to In Vivo Lipopolysaccharide Challenge," *J. Interferon Cytokine Res.*, 30(7):497-508, 2010.
Baeuerle, "NF-κB: ten years after," Cell, 87:13-20, 1996.
Baigent and Lennon, "Should We Increase GFR with Bardoxolone in Alport Syndrome?" J. Am. Soc. Nephrol., 29:357-359, 2018.
Baldwin, "The NF-κB and IκB proteins: new discoveries and insights," Annu. Rev. Immunol., 14:649-681, 1996.
Balkwill et al., "Smoldering and polarized inflammation in the initiation and promotion of malignant disease," Cancer Cell, 7 (3): 211-217, 2005.
Barkett and Gilmore, "Control of apoptosis by Rel/NF-κB transcription factors," Oncogene, 18:6910-6924, 1999.
Barnes and Karin, "Nuclear factor-κB—a pivotal transcription factor in chronic inflammation diseases," N. Engl. J. Med., 336:1066-1071, 1997.
Bauer et al., "Rodent models of PAH: are we there yet?" Am. J. Physiol. Lung Cell Mol. Physiol., 293:L580-L582, 2007.
Beal, "Mitochondria, free radicals, and neurodegeneration," Curr. Opin. Neurobiol., 6:661-666, 1996.
Bensasson et al., "Potency ranking of triterpenoids as inducers of a cytoprotective enzyme and as inhibitors of a cellular inflammatory response via their electron affinity and their electrophilicity index," *Chem. Biol. Interact.*, 186(2):118-126, 2010.
Birukov, "Cyclic stretch, reactive oxygen species, and vascular remodeling," Antioxid. Redox Signal., 11:1651-1667, 2009.
Blann et al., "Circulating endothelial cells: Biomarker of vascular disease," Thromb. Haemost., 93:228-235, 2005.
Bogaard et al., "Chronic pulmonary artery pressure elevation is insufficient to explain right heart failure," Circulation, 120:1951-1960, 2009.
Bolignano et al., "Pulmonary hypertension in CDK," Am. J. Kidney Dis., 61:612-622, 2013.
Bonnett et al., "Dehydroepiandrosterone (DHEA) prevents and reverses chronic hypoxic pulmonary hypertension," Proc. Natl. Acad. Sci. USA, 100:9488-9493, 2003.
Boos et al., "Circulating Endothelial Cells in Cardiovascular Disease," *J. Am. Coll. Cardiol.*, 48(8):1538-1547, 2006.
Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," Cancer Res., 67:1793-1802, 2007.
Brown and DuBois, "COX-2: a molecular target for colorectal cancer prevention," J. Clin. Oncol., 23 (12): 2840-2855, 2005.
Burger and Dayer, "Inhibitory cytokines and cytokine inhibitors," Neurology, 45 (6S-6):S39-S43, 1995.
Burger and Touyz, "Cellular biomarkers of endothelial health: microparticles, endothelial progenitor cells, and circulating endothelial cells," J. Am. Soc. Hyperten., 6:85-99, 2012.
Buzoni-Gatel et al., "Murine ileitis after intracellular parasite infection is controlled by TGF-beta-producing intraepithelial lymphocytes," Gastroenterolog, 120:914-924, 2001.
Cai et al., "Local and systemic insulin resistance resulting from hepatic activation of IKK-beta and NF-kappaB," Nat. Med., 11 (2): 183-190, 2005.
Camer et al., "Bardoxolone methyl prevents insulin resistance and the development of hepatic steatosis in mice fed a high-fat diet," *Molecular and Cellular Endocrinology*, 412:36-43, 2015.
Chadalapaka et al., "Structure-dependent inhibition of bladder and pancreatic cancer cell growth by 2-substituted glycyrrhetinic and ursolic acid derivatives," Bioorganic & Medicinal Chemistry Letters, 18:2633-2639, 2008.
Channick and Williamson, "Diagnosis and treatment of pulmonary arterial hypertension," Cardiol. Clin., 22:441-452, 2004.
Chartoumpekis and Sykiotis, "Bardoxolone Methyl in Type 2 Diabetes and Advanced Chronic Kidney Disease, Letter to the Editor," New Eng. J. Med., 370(18):1767-1769, 2014.
Chin et al., "Bardoxolone methyl analogs RTA 405 and dh404 are well tolerated and exhibit efficacy in rodent models of Type 2 diabetes and obesity," *Am. J. Physiology*, 304(6, Part 2):F1438-F1446, 2013.
Chin et al., "Mechanisms contributing to adverse cardiovascular events in patients with type 2 diabetes mellitus and stage 4 chronic kidney disease treated with bardoxolone methyl," *Am. J. Nephrology*, 39(6):499-508, 2014.
Chin et al., "Risk factors for heart failure in patients with type 2 diabetes mellitus and stage 4 chronic kidney disease treated with bardoxolone methyl," *J. Cardiac Fail.*, 20(12):953-958, 2014.
Chintharlapalli et al., "2-Cyano-3,12-dioxoolean-1,9-dien-28-oic acid and related compounds inhibit growth of colon cancer cells through peroxisome proliferator-activated receptor γ-dependent and -independent pathways," Mol. Pharmacol., 68:119-128, 2005.
Chintharlapalli et al., "2-Cyano-lup-1-en-3-oxo-20-oic acid, a cyano derivative of betulinic acid, activates peroxisome proliferator-activated receptor [gamma] in colon and pancreatic cancer cells.," Carcinogenesis, 28 (11): 2337-2346, 2007.
Cho et al., "The transcription factor NRF2 protects against pulmonary fibrosis," FASEB Journal, 18:1-29, 2004.
Choi et al., "Effects of redox modulating Nrf2 activators on chronic kidney disease," *Molecules*, 19(8):12727-12759, 2014.
Christmann et al., "Interferon and Alternative Activation of Monocyte/Macrophages in Systemic Sclerosis-Associated Pulmonary Arterial Hypertension," *Arthritis Rheum.*, 63(6):1718-1728, 2011.
Clinicaltrial.gov Study NCT00322140, "CDDO to Treat Solid Tumors and Lymphomas," and associated updates, first published May 4, 2006.

(56) References Cited

OTHER PUBLICATIONS

Clinicaltrial.gov Study NCT00508807, "RTA 402 in Advanced Solid Tumors or Lymphoid Malignancies," and associated updates, first published Jul. 30, 2007.
Clinicaltrial.gov Study NCT00529113, "Study With Gemcitabine and RTA 402 for Patients With Unresectable Pancreatic Cancer," and associated updates, first published Sep. 14, 2007.
Clinicaltrial.gov Study NCT00529438, "RTA 402 in Patients With Advanced Solid Tumors or Lymphoid Malignancies," and associated updates, first published Sep. 14, 2007.
Clinicaltrial.gov Study NCT00535314, "Study of Two Dose Levels of RTA 402 in Patients With Advanced Malignant Melanoma," and associated updates, first published Sep. 26, 2007.
Clinicaltrial.gov Study NCT00550849, "Study to Assess the Safety, Tolerability, and Pharmacodynamics of RTA 402 in Patients With Hepatic Dysfunction," and associated updates, first published Oct. 30, 2007.
Clinicaltrial.gov Study NCT00664027, "Phase IIa Trial to Determine the Effects of Bardoxolone Methyl on Renal Function in Patients With Diabetic Nephropathy," and associated updates, first published Apr. 22, 2008.
Clinicaltrial.gov Study NCT00811889, "Trial to Determine the Effects of Bardoxolone Methyl on eGFR in Patients With Type 2 Diabetes and Chronic Kidney Disease," and associated updates, first published Dec. 19, 2008.
Clinicaltrial.gov Study NCT01053936, "Phase II Pharmacodynamic Trial to Determine the Effects of Bardoxolone Methyl on eGFR in Patients With Type 2 Diabetes and Chronic Kidney Disease," and associated updates, first published Jan. 22, 2010.
Clinicaltrial.gov Study NCT01351675, "Bardoxolone Methyl Evaluation in Patients With Chronic Kidney Disease and Type 2 Diabetes," and associated updates, first published May 11, 2011.
Clinicaltrial.gov Study NCT01461161, "A Single-Dose, Open-Label, Randomized, Food Effect and Blinded, Randomized, Dose Proportionality Study in Healthy Volunteers With Bardoxolone Methyl," and associated updates, first published Oct. 27, 2011.
Clinicaltrial.gov Study NCT01500798, "A Pharmacodynamic Study of Measured Glomerular Filtration Rate in Patients With Chronic Kidney Disease and Type 2 Diabetes," and associated updates, first published Dec. 28, 2011.
Clinicaltrial.gov Study NCT01503866, "A Phase I Study to Investigate the Absorption, Metabolism and Excretion in Healthy Male Subjects," and associated updates, first published Jan. 4, 2012.
Clinicaltrial.gov Study NCT01549769, "Pharmacokinetic and Pharmacodynamic Study of Bardoxolone Methyl in Patients With Chronic Kidney Disease and Type 2 Diabetes," and associated updates, first published Mar. 9, 2012.
Clinicaltrial.gov Study NCT01551446, "Pilot Assessment of the Effects of Bardoxolone Methyl on Renal Perfusion, Systemic Haemodynamics and Cardiac Function in Patients With Chronic Kidney Disease and Type 2 Diabetes," and associated updates, first published Mar. 12, 2012.
Clinicaltrial.gov Study NCT01563562, "Single-Dose, Open-Label Pharmacokinetic Study of Bardoxolone Methyl in Subjects With Mild, Moderate, and Severe Hepatic Impairment and Normal Hepatic Function," and associated updates, first published Mar. 27, 2012.
Clinicaltrial.gov Study NCT01576887, "A Double-Blind, Randomized, Placebo-Controlled Safety Study Evaluating the Effects of Residual Renal Function (RFF) in Patients With End-Stage Renal Disease and Type 2 Diabetes Mellitus on Peritoneal Dialysis," and associated updates, first published Apr. 13, 2012.
Clinicaltrial.gov Study NCT01598363, "An Open-Label Study of the Effect of Bardoxolone Methyl on the Single Dose Pharmacokinetics of Digoxin and Rosuvastatin in Healthy Volunteers," and associated updates, first published May 15, 2012.
Clinicaltrial.gov Study NCT01655186, "A Double-Blind, Randomized, Placebo-Controlled Study Evaluating the Effects of Bardoxolone Methyl on Body Composition in Patients With Stage 4 Chronic Kidney Disease and Type 2 Diabetes Mellitus," and associated updates, first published Aug. 1, 2012.

Clinicaltrial.gov Study NCT01689116, "Multiple-Dose Study of Effect of Bardoxolone Methyl on QT/QTC Interval Volunteers," and associated updates, first published Sep. 21, 2012.
Clinicaltrial.gov Study NCT02029716, "RTA 408 Lotion in Healthy Volunteers," and associated updates, first published Jan. 8, 2014.
Clinicaltrial.gov Study NCT02029729, "RTA 408 in the Treatment of Advanced Solid Tumors (NSCLC & Melanoma)—DISCOVER," and associated updates, first published Jan. 8, 2014.
Clinicaltrial.gov Study NCT02036970, "Bardoxolone Methyl Evaluation in Patients With Pulmonary Hypertension (PH)—LARIAT," and associated updates, first published Jan. 15, 2014.
Clinicaltrial.gov Study NCT02065375, "RTA 408 Ophthalmic Suspension for the Treatment of Ocular Inflammation and Pain Following Ocular Surgery," and associated updates, first published Feb. 19, 2014.
Clinicaltrial.gov Study NCT02128113, "RTA 408 Ophthalmic Suspension for the Prevention of Corneal Endothelial Cell Loss Following Cataract Surgery—GUARD," and associated updates, first published May 1, 2014.
Clinicaltrial.gov Study NCT02142959, "RTA 408 Lotion in Patients at Risk for Radiation Dermatitis—PRIMROSE," and associated updates, first published May 20, 2014.
Clinicaltrial.gov Study NCT02255422, "RTA 408 Capsules in Patients With Mitochondrial Myopathy—MOTOR," and associated updates, first published Oct. 2, 2014.
Clinicaltrial.gov Study NCT02255435, "RTA 408 Capsules in Patients With Friedreich's Ataxia—MOXIe," and associated updates, first published Oct. 2, 2014.
Clinicaltrial.gov Study NCT02259231, "RTA 408 Capsules in Patients With Melanoma—REVEAL," and associated updates, first published Oct. 8, 2014.
Clinicaltrial.gov Study NCT02657356, "Bardoxolone Methyl in Patients With Connective Tissue Disease-associated Pulmonary Arterial Hypertension—CATALYST," and associated updates, first published Jan. 15, 2016.
Clinicaltrial.gov Study NCT03019185, "A Phase 2/3 Trial of the Efficacy and Safety of Bardoxolone Methyl in Patients With Alport Syndrome—CARDINAL," and associated updates, first published Jan. 12, 2017.
Clinicaltrial.gov Study NCT03068130, "Extended Access Program to Assess Long-term Safety of Bardoxolone Methyl in Patients With Pulmonary Hypertension RANGER," and associated updates, first published Mar. 1, 2017.
Clinicaltrial.gov Study NCT03264079, "Effect of Itraconazole on the Pharmacokinetics of Bardoxolone Methyl in Healthy Adults," and associated updates, first published Aug. 28, 2017.
Clinicaltrial.gov Study NCT03366337, "A Phase 2 Trial of the Safety and Efficacy of Bardoxolone Methyl in Patients With Rare Chronic Kidney Diseases—PHOENIX," and associated updates, first published Dec. 8, 2017.
Clinicaltrial.gov Study NCT03593499, "Expanded Access to Omaveloxolone for Melanoma for Patients Previously Enrolled in 408-C-1401," and associated updates, first published Jul. 20, 2018.
Clinicaltrial.gov Study NCT03664453, "A Pharmacokinetic Study of Omaveloxolone in Healthy Volunteers," and associated updates, first published Sep. 10, 2018.
Clinicaltrial.gov Study NCT03749447, "An Extended Access Program for Bardoxolone Methyl in Patients With CKD (EAGLE)," and associated updates, first published Nov. 21, 2018.
Clinicaltrial.gov Study NCT03902002, "A Pharmacokinetic Study of Omaveloxolone in Subjects With Hepatic Impairment and Normal Hepatic Function," and associated updates, first published Apr. 3, 2019.
Clinicaltrial.gov Study NCT03918447, "A Trial of Bardoxolone Methyl in Patients With ADPKD—FALCON," and associated updates, first published Apr. 17, 2019.
Clinicaltrial.gov Study NCT03931590, "A Human AME Study for Omaveloxolone," and associated updates, first published Apr. 30, 2019.
Clinicaltrial.gov Study NCT04008186, "A Clinical Drug-Drug Interaction (DDI) Study With Omaveloxolone," and associated updates, first published Jul. 4, 2019.

(56) References Cited

OTHER PUBLICATIONS

Cohen et al., "A general method for removal of a 4-methyl group from triterpenoids. Synthesis of 4beta-demethylglycyrrhetinic acid," J Chem. Soc, Perkin Trans 1, (19): 2076-2082, 1973.
Couch et al., "Studies on the reactivity of CDDO, a promising new chemopreventive and chemotherapeutic agent: implications for a molecular mechanism of action," Bioorganic and Medicinal Chemistry Letters, 15:2215-2219, 2005.
Crowell et al., "Is inducible nitric oxide synthase a target for chemoprevention," Mol. Cancer Ther., 2:815-823, 2003.
Cui, "A material science perspective of pharmaceutical solids," Int. J. Pharmaceutics, 339 (1-2): 3-18, 2007.
Davignon and Ganz, "Role of endothelial dysfunction in atherosclerosis," Circulation, 109:III-27-III-32, 2004.
De Zeeuw et al., "Bardoxolone Methyl in Type 2 Diabetes and Stage 4 Chronic Kidney Disease", *New Engl. J. Med.*, 369(26):2492-2503, 2013.
De Zeeuw et al., "Rationale and Trial Design of Bardoxolone Methyl Evaluation in Patients with Chronic Kidney Disease and Type 2 Diabetes: The Occurrence of Renal Events (BEACON)," *Am. J. Nephrology*, 37(3):212-222, 2013.
Dean et al., "Halogenolysis of methyl glycyrrhetate with lithium iodidedimethylformamide," J. Chem. Soc., 6655-6659, 1965.
Deeb et al., "CDDO-Me inhibits proliferation, induces apoptosis, down-regulates Akt, mTOR, NF-κB and NF-κB-regulated antiapoptotic and proangiogenic proteins in TRAMP prostate cancer cells," J. Experimental Therapeutics and Oncology, 7:31-39, 2007.
Deeb et al., "CDDO-Me: a novel synthetic triterpenoid for the treatment of pancreatic cancer," *Cancers*, 2:1779-1793, 2010.
Deeb et al., "Oleanane triterpenoid CDDO-Me inhibits growth and induces apoptosis in prostate cancer cells through a ROS-dependent mechanism," *Biochem. Pharmacol.*, 79(3):350-360, 2010.
Deeb et al., "Oleanane triterpenoid CDDO-Me inhibits growth and induces apoptosis in prostate cancer cells by independently targeting pro-survival Akt and mTOR," *Prostate*, 69(8):851-860, 2009.
Dezube et al., "Interim results of a phase I trial with a novel orally administered synthetic triterpenoid RTA 402 (CDDO-Me) in patients with solid tumors and lymphoid malignancies," ASCO Annual Meeting Proceedings, J. Clin. Oncol., 25(18S):14101, 2007.
Dinarello, "Interleukin-1, interleukin-1 receptors and interleukin-1 receptor antagonist," Int. Rev. Immunol., 16:457-499, 1998.
Ding et al., "Macrophage deactivating factor and transforming growth factors-b 1 b2 and b3, inhibit induction of macrophage nitrogen oxide synthesis by IFNγ1," J. Immunol., 145:940-944, 1990.
Ding et al., "The synthetic triterpenoid, RTA 405, increases the glomerular filtration rate and reduces angiotensin II-induced contraction of glomerular mesangial cells," *Kidney International*, 83(5):845-854, 2013.
Dinkova-Kostova et al., "Direct evidence that sulfhydryl groups of Keap1 are the sensors regulating induction of phase 2 enzymes that protect against carcinogens and oxidants," Proc. Natl. Acad. Sci. USA, 99:11908-11913, 2002.
Dinkova-Kostova et al., "Extremely potent triterpenoid inducers of the phase 2 response: correlations of protection against oxidant and inflammatory stress," Proc. Natl. Acad. Sci. USA, 102:4584-4589, 2005.
Dragnev et al., "Specific chemopreventive agents trigger proteasomal degradation of G1 cyclins: implications for combination therapy," Clin. Cancer Research, 10 (7): 2570-2577, 2004.
Du et al., "Chapter VI Treatment of Pulmonary Hypertension", English translation appended, *Peking Univ. Med. Press*, p. 156, 2010.
Duan et al., "CDDO-Me, a synthetic triterpenoid, inhibits expression of IL-6 and Stat3 phosphorylation in multi-drug resistant ovarian cancer cells," Cancer Chemother. Pharmacol., 63(4):681-689, 2009.
Duan et al., "Di- and triterpenoids from Triptergium hypoglaucum," Phytochemistry, 46(3):535-543, 1997.

Dweik et al., "Pulmonary Hypertension," <URL=http://www.clevelandclinicmeded.com/medicalpubs/diseasemanagement/pulmonary/pulmonary-hypertension/>, 2011.
Eba et al., "The Nuclear Factor Erythroid 2-Related Factor 2 Activator Oltipraz Attenuates Chronic Hypoxia-Induced Cardiopulmonary Alterations in Mice," *Am. J. Respir. Cell Mol. Biol.*, 49(2):324-333, 2013.
Eikelenboom et al., "Neuroinflammation in Alzheimer's disease and prion disease," Glia, 40(2): 232-239, 2002.
Elliot et al., "The triterpenoid CDDO inhibits expression of matrix metalloproteinase-1, matrix metalloproteinase-13 and Bcl-3 in primary human chondrocytes," Arthritis Res. Ther., 5:R285-R291, 2003.
Elsawa et al., "CDDO-imidazolide mediated inhibition of malignant cell growth in Waldenstroem macroglobulinemia," *Leukemia Res.*, 32(12):1895-1902, 2008.
Elsawa et al., "Preferential Inhibition of Malignant Cell Growth by CDDO in Waldenstrom Macroglobulinemia," Blood, 108:2528, 2006.
Erdbruegger et al., "Circulating endothelial cells: a novel marker of endothelial damage," *Clinica Chimica Acta*, 373(1-2):17-26, 2006.
Eskiocak et al., "CDDO-Me protects against space radiation-induced transformation of human colon epithelial cells," *Radiat. Res.*, 174(1):27-36, 2010.
Ferguson, "PPARγ Ligands Have Potent Anti-Fibrotic Activity: Mechanism of Action and Implications for Therapy of Pulmonary Fibrosis," Dissertation, University of Rochester, 2008.
Finlay et al., "Novel A-ring cleaved analogs of oleanolic and ursolic acids which affect growth regulation in NRP.152 prostate cells," Biorg. Med. Chem. Lett., 7(13): 1769-1772, 1997.
Forstermann, "Janus-faced role of endothelial NO synthase in vascular disease: uncoupling of oxygen reduction from NO synthesis and its pharmacological reversal," Biol. Chem., 387:1521-1533, 2006.
Galie et al., "Pulmonary arterial hypertension associated to connective tissue disease," Lupus, 14:713-717, 2005.
Galley and Webster, "The immuno-inflammatory cascade," Br. J. Anaesth., 77:11-16, 1996.
Gao et al., "Immunomodulatory Activity of Synthetic Triterpenoids: Inhibition of Lymphocyte Proliferation, Cell-Mediated Cytotoxicity, and Cytokine Gene Expression Through Suppression of NF-κB," *Immunopharmacol. Immunotoxicol.*, 30(3):581-600, 2008.
Gao et al., "Synthetic triterpenoids inhibit growth, induce apoptosis and suppress pro-survival Akt, mTOR and NF-KB signaling protein in colorectal cancer cells," *Anticancer Res.*, 30(3):785-792, 2010.
Gheeya et al., "Screening a panel of drugs with diverse mechanisms of action yields potential therapeutic agents against neuroblastoma," Cancer Biol. Ther., 8(24):2386-2395, 2009.
Ghosh et al., "NF-κB and Rel proteins: evolutionarily conserved mediators of immune response," Annu Rev Immunol., 16:225-260, 1998.
Giaid et al., "Expression of Endothelin-1 in the Lungs of Patients with Pulmonary Hypertension," *N. Engl. J. Med.*, 328(24):1732-1739, 1993.
Gomez et al., "Anti-microRNA-21 oligonucleotides prevent Alport nephropathy progression by stimulating metabolic pathways", *J. Clin. Invest.*, 125(1):141-156, 2015.
Graber et al., "Synthetic Triterpenoid CDDO Derivatives Modulate Cytoprotective or Immunological Properties in Astrocytes, Neurons, and Microglia," *J. Neuroimmune Pharmacol.*, 6(1):107-120, 2010.
Grieco and Speake, "Synthetic Studies on Quassinoids: Total Synthesis and Biological Evaluation of (+)-Des-D-chaparrinone," J. Org. Chem., 63:5929-5936, 1998.
Gross and Kashtan, "Treatment of Alport syndrome: Beyond animal models," Kidney Int., 76(6):599-603, 2009.
Gross et al., "Advances and unmet needs in genetic, basic and clinical science in Alport syndrome," Nephrol Dial Transplant., 32(6):916-924, 2017.
Guttridge et al., "NF-κB controls cell growth and differentiation through transcriptional regulation of cyclin D1," Mol. Cell. Biol., 19:5785-5799, 1999.

(56) References Cited

OTHER PUBLICATIONS

Hail et al., "Evidence supporting a role for calcium in apoptosis induction by the synthetic triterpenoid 2-cyano-3,12-dioxooleana-1,9-dien-28-oic acid (CDDO)," J. Biol. Chem., 279:11179-11187, 2004.
Han et al., "CDDO-Imidazolide inhibits growth and survival of c-Myc-induced mouse B cell and plasma cell neoplasms," Molecular Cancer, 5:22, 2006.
Hansson et al., "Inflammation and atherosclerosis," Annu. Rev. Pathol: Mech. Dis., 1:297-329, 2006.
Harris, "The Best-Laid Plans," Am. J. Physiology, 304(4):F1086-F1087, 2013.
Hashimoto et al., "Oxidative stress markers in patients with connective tissue diseases complicated by pulmonary arterial hypertension," English full-text translation, Clin. Rheumatol., 22:288-293, 2010.
Hatamizadeh et al., "Cardiorenal syndrome: pathophysiology and potential targets for clinical management," Nat. Rev. Nephrol., 9:99-111, 2013.
Hayes and Dinkova-Kostova, "The Nrf2 regulatory network provides an interface between redox and intermediary metabolism," Trends Biochem. Sci., 39(4):199-218, 2014.
Hayes and McMahon, "NRF2 and KEAP1 mutations: permanent activation of an adaptive response in cancer," Trends Biochem. Sci., 34(4):176-188, 2009.
He and Karin, "NF-κB and STAT3—key players in liver inflammation and cancer", Cell Research, 2011, 21:159-168.
Heiss et al., "Active NF-E2-related Factor (Nrf2) Contributes to Keep Endothelial NO Synthase (eNOS) in the Coupled State", (with supplemental information), J. Biol. Chem., 284(46):31579-31586, 2009.
Heiss et al., "Impact of the Synthetic Triterpenoid CDDO-Im and Nrf2 Activation on the Endothelial Redox System," Poster Presentation at 2008 Nordic Pharmacological Society, Abstract in Basic and Clinical Pharmacology & Toxicology, 102(Supp 1):21-57, 2008.
Hevener et al., "The 2009 stock conference report: Inflammation, obesity and metabolic disease," Obes Rev., 11(9):635-644, 2010.
Higgins and Hayes, "Mechanisms of induction of cytosolic and microsomal glutathione transferase (GST) genes by xenobiotics and pro-inflammatory agents," Drug Metabolism Reviews, 43(2):92-137, 2011.
Hill et al., "Synthetical approaches to the pristimerin chromophore," J. of the Chemical Society, 361-375, 1965.
Hinz et al., "NF-κB function in growth control: regulation of cyclin D1 expression and G0/G1-to-S-phase transition," Mol. Cell. Biol., 19:2690-2698, 1999.
Hirota et al., "Suppression of tumor promoter-induced inflammation of mouse ear by ursolic acid and 4,4-dimethycholestane derivatives," Agric. Biol. Chem., 54:1073-1075, 1990.
Honda et al., "2-Cyano-3,10-dioxooleana-1,9(11)-dien-28-oic acid anhydride. A novel and highly potent anti-inflammatory and cytoprotective agent," Bioorg. Med. Chem. Lett., 20(7):2275-2278, 2010.
Honda et al., "A novel dicyanotriterpenoid, 2-cyano-3,12-dioxooleana-1,9(11)-dien-28-onitrile, active at picomolar concentrations for inhibition of nitric oxide production," Bioorg. Med. Chem. Lett., 12:1027-1030, 2002.
Honda et al., "Design and synthesis of 23,24-dinoroleanolic acid derivatives, novel triterpenoid-steroid hybrid molecules," J. Org. Chem., 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," Bioorg. Med. Chem. Lett., 8:2711-2714, 1998.
Honda et al., "Design, synthesis, and biological evaluation of biotin conjugates of 2-cyano-3,12-dioxooleana-1,9(11)-dien-28-oic acid for the isolation of the protein targets," J. Med. Chem., 47 (20): 4923-4932, 2004.
Honda et al., "Efficient synthesis of (-)- and (+)-tricyclic compounds with enome functionalities in rings A and C. A novel class of orally active anti-inflammatory and cancer chemopreventive agents," Org. Biomol. Chem., 1:4384-4391, 2003.
Honda et al., "New enone derivatives of oleanolic acid and ursolic acid as inhibitors of nitric oxide production in mouse macrophages," Bioorg. Med. Chem. Lett., 7:1623-1628, 1997.
Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," J. Med. Chem., 43:1866-1877, 2000.
Honda et al., "Novel synthetic oleanane triterpenoids: a series of highly active inhibitors of nitric oxide production in mouse macrophages," Bioorg. Med. Chem. Lett., 9:3429-3434, 1999.
Honda et al., "Synthesis of (±)-3,3-ethylenedioxy-14a-hydroxy-5-picrasene-11,16-dione, a 14aH-picrasane derivative," Chem. Lett., 299-302, 1981.
Honda et al., "Synthetic oleanane and ursane triterpenoids with modified rings A and C: A series of highly active inhibitors of nitric oxide production in mouse macrophages," J. Med. Chem., 43:4233-4246, 2000.
Hong et al., "A Phase I First-in-Human Trial of Bardoxolone Methyl in Patients with Advanced Solid Tumors and Lymphomas," Clinical Cancer Research, 18:3396-3406, 2012.
Hotamisligil, "Inflammation and metabolic disorders," Nature, 444:860-867, 2006.
Hughes et al., "The Synthetic Triterpenoid CDDO-Im Inhibits Fatty Acid Synthase Expression and Has Antiproliferative and Proapoptotic Effects in Human Liposarcoma Cells," Cancer Investigation, 26:118-127, 2008.
Humbert et al., "Early detection and management of pulmonary arterial hypertension," Eur. Respir. Rev., 21:306-312, 2012.
Hybertson et al., "Oxidative stress in health and disease: The therapeutic potential of Nrf2 activation," Molecular Aspects of Medicine, 32:234-246, 2011.
Ikeda et al., "The novel triterpenoid CDDO and its derivatives induce apoptosis by disruption of intracellular redox balance," Cancer Res., 63:5551-5558, 2003.
Impellizzeri et al., "Targeting inflammation: new therapeutic approaches in chronic kidney disease (CKD)," Pharmacological Research, 81:91-102, 2014.
Inoue et al., "CDDO induces apoptosis via the intrinsic pathway in lymphoid cells," Leukemia, 18:948-952, 2004.
International Preliminary Report on Patentability issued in corresponding PCT Application No. PCT/US2017/060701, dated May 23, 2019.
International Search Report and Written Opinion issued in corresponding PCT Application No. PCT/US2017/060701, dated Apr. 4, 2018.
Ishikawa et al., "Heme oxygenase-1 inhibits atherogenesis in Watanabe heritable hyperlipidemic rabbits," Circulation, 104:1831-1836, 2001.
Ito et al., "The novel triterpenoid 2-cyano-3, 12-dioxoolean-1,9-dien-28-oic acid induces apoptosis of human myeloid leukemia cells by a caspase-8-dependent mechanism," Cell Growth & Differentiation, 11:261-267, 2000.
Ito et al., "The novel triterpenoid CDDO induces apoptosis and differentiation of human osteosarcoma cells by a caspase-8 dependent mechanism," Mol. Pharmacol., 59:1094-1099, 2001.
Jais et al., "X-linked Alport syndrome: Natural history and genotype-phenotype correlations in girls and women belonging to 195 families: A "European Community Alport Syndrome Concerted Action" study", J Am Soc Nephrol., 14(10):2603-2610, 2003.
Jais et al., "X-linked Alport syndrome: natural history in 195 families and genotype-phenotype correlations in males," J. Am. Soc. Nephrol., 11:649-657, 2000.
Jedlicka et al., "Interstitial inflammation in Alport syndrome", Hum. Pathol., 41(4):582-593, 2010.
Johansen et al., "Pharmacology and preclinical pharmacokinetics of the triterpenoid CDDO methyl ester," Proc. Amer. Assoc. Cancer Res., 44:1728, 2003.

(56) References Cited

OTHER PUBLICATIONS

Joyce et al., "Integration of Rac-dependent regulation of cyclin D1 transcription through a nuclear factor-κB-dependent pathway," J. Biol. Chem., 274:25245-25249, 1999.
Jutooru et al., "Methyl 2-cyano-3,12-dioxooleana-1,9-dien-28-oate decreases specificity protein transcription factors and inhibits pancreatic tumor growth: role of microRNA-27a," Mol. Pharmacol., 78(2):226-236, 2010.
Kansanen et al., "Regulation of Nrf2-dependent gene expression by 15-deoxy-Delta12,14-prostaglandin J2," Free Radic. Biol. Med., 47(9):1310-7, 2009.
Karin et al, "NF-κB in cancer: From innocent bystander to major culprit," Nat. Rev., 2:301-303, 2002.
Karin et al., "Nuclear factor-κB in cancer development and progression," Nature, 441:431-436, 2006.
Kashtan et al., "Alport syndrome and thin glomerular basement membrane disease", J. Am. Soc. Nephrol., 9(9):1736-1750, 1998.
Kashtan et al., "Alport syndrome: a unified classification of genetic disorders of collagen IV a345: a position paper of the Alport Syndrome Classification Working Group," Kidney Int., 93:1045-1051, 2018.
Kashtan et al., "Clinical practice recommendations for the treatment of Alport syndrome: A statement of the Alport Syndrome Research Collaborative," Pediatr Nephrol. 28(1):5-11, 2013.
Kasinski et al., "Inhibition of IkappaB kinase-nuclear factor-kappaB signaling pathway by 3,5-bis(2-flurobenzylidene)piperidin-4-one (EF24), a novel monoketone analog of curcumin," Mol. Pharmacology, 74 (3): 654-661, 2008.
Khan et al., "A dichotomous role for nitric oxide during acute Toxoplasma gondii infection in mice," Proc. Natl. Acad. Sci. USA, 94:13955-13960, 1997.
Kim and Vaziri, "Contribution of impaired Nrf2-Keap1 pathway to oxidative stress and inflammation in chronic renal failure," Am. J. Physiol. Renal Physiol., 298:F662-F671, 2010.
Kim et al., "Caspase-3 activation is involved in apoptosis induced by a synthetic triterpenoid in Non-small cell lung cancer (NSCLC) cells," Proc. Amer. Assoc. Cancer Res., 41:770, Abstract #4894, 2000.
Kim et al., "Identification of a novel synthetic triterpenoid, methyl-2-cyano-3,12-dioxooleana-1,9-dien-28-oate, that potently induces caspase-mediated apoptosis in human lung cancer cells," Molecular Cancer Therapeutics, 1:177-184, 2002.
Kim et al., "Targeting of Nrf2 induces DNA damage signaling and protects colonic epithelial cells from ionizing radiation," Proc. Natl. Acad. Sci. USA, 109(43):E2949-E2955, 2012.
Kim et al., "Vascular inflammation, insulin resistance, and reduced nitric oxide production precede the onset of peripheral insulin resistance," Arterioscler. Thromb. Vasc. Biol., 28(11):1982-8, 2008.
Klyne et al., "The molecular rotations of polycyclic compounds. III. Polycyclic alcohols and their derivatives," J Chem Soc., 1979-1988, 1954.
Kobayashi and Yamamoto, "Molecular mechanisms activating the Nrf2-Keap1 pathway of antioxidant gene regulation," Antioxid. Redox. Signal., 7:385-394, 2005.
Kobayashi et al., "The antioxidant defense system Keap1-Nrf2 comprises a multiple sensing mechanism for responding to a wide range of chemical compounds," Mol. Cell Biol., 29:493-502, 2009.
Kolak et al., "Antioxidant and anticholinesterase constituents of Salvia poculata," Turkish Journal of Chemistry, 33(6): 813-823, 2009.
Kolyada and Madias, "Transcriptional Regulation of Human iNOS Gene by IL-1β in Endothelial Cells," Molecular Medicine, 7(4):329-343, 2001.
Kong et al., "Synthetic triterpenoids have cytotoxicity in pediatric acute lymphoblastic leukemia cell lines but cytotoxicity is independent of induced ceramide increase in MOL T-4 cells," Leukemia, 22(6):1258-1262, 2008.
Konopleva et al., "Activation of nuclear transcription factor PPARgamma by the novel triterpenoid CDDO as targeted therapy in breast cancer," 2002 Keystone Symposium, Abstract No. 539, 2002.

Konopleva et al., "Mechanisms and Activity of PPARγ-Active Triterpenoids CDDO and CDDO-Me in Leukemias," Blood, 106:2460, 2005.
Konopleva et al., "Novel synthetic triterpenoid CDDO-Me: potent antiproliferative, proapoptotic and differentiating agent in AML," Blood, 96(11), Part 1: 121A, abstract # 522, 2000.
Konopleva et al., "Novel triterpenoid CDDO-Me is a potent inducer of apoptosis and differentiation in acute myelogenous leukemia," Blood, 99:326-335, 2002.
Konopleva et al., "PPARg nuclear receptor as a novel therapeutic target in AML," Blood, 96(11):460a, Abstract #1982, 2000.
Konopleva et al., "PPARg nuclear receptor as a novel therapeutic target in AML," Proc. of the AACR, , 42, Abstract #4458, 2001.
Konopleva et al., "PPARgamma Ligand CDDO Induces Apoptosis in Leukemias via Multiple Apoptosis Pathways," Abstracts of the 44th Annual Meeting of the American Society of Hematology, Abstract No. 2209, 2002.
Konopleva et al., "PPARγ Nuclear Receptor as a Novel Molecular Target in Leukemia Therapy," Proc. Amer. Assoc. Cancer Res., 43:4730, 2002.
Konopleva et al., "Suppression of ERK Activation is Required for Triterpenoid Methyl-CDDO-Induced Apoptosis in AML," Blood, 102:1404, 2003.
Konopleva et al., "Synthetic triterpenoid 2-cyano-3,12-dioxooleana-1,9-dien-28-oic acid induces growth arrest in HER2-overexpressing breast cancer cells," Mol. Cancer Ther., 5:317-328, 2006.
Konopleva et al., "Synthetic triterpenoid CDDO as a novel therapy for resistant breast cancer," Proc. Amer. Assoc. Cancer Res., 44:2726, 2003.
Konopleva et al., "The novel triterpenoid CDDO-Me suppresses MAPK pathways and promotes p38 activation in acute myeloid leukemia cells," Leukemia, 19:1350-1354, 2005.
Konopleva et al., "The synthetic triterpenoid 2-cyano-3,12-dioxooleana-1,9-dien-28-oic acid induces caspase-dependent and -independent apoptosis in acute myelogenous leukemia," Cancer Res., 64:7927-7935, 2004.
Konopleva et al., "Triterpenoid methyl-CDDO is a potent inducer of apoptosis in CD34+ AML progenitor cells via activation of SAPK pathways and inhibition of MAPK cascades," Blood, 104:2533, 2004.
Kovács et al., "Efficient targeted next generation sequencing-based workflow for differential diagnosis of Alport-related disorders," PLoS One. 11(3):e0149241, 2016.
Kress et al., "Triterpenoids display single agent anti-tumor activity in a transgenic mouse model of chronic lymphocytic leukemia and small B cell lymphoma," PLoS ONE, 6(e559):1-11, 2007.
Kruegel et al., "Alport syndrome—insights from basic and clinical research," Nat. Rev. Nephrol., 9:170-178, 2013.
Kulkarni et al., "The triterpenoid CDDO-Me inhibits bleomycin-induced lung inflammation and fibrosis," PLoS One, 8(5):e63798, 2013.
Kurinna et al., "The novel triterpenoid CDDO-Me promotes apoptosis in Gleevec-resistant chronic myeloid leukemia cells by caspase-independent mechanisms," Proc. Amer. Assoc. Cancer Res., 46:2240, 2005.
Kweider et al., "A possible protective role of Nrf2 in preeclampsia," Annals of Anatomy, 196:268-277, 2014.
Lala et al., "Role of nitric oxide in tumor progression: lessons from experimental tumors," Cancer and Metastasis Reviews, 17: 91-106, 1998.
Lambers et al., "Baseline characteristics in the bardoxolone methyl evaluation in patients with chronic kidney disease and type 2 diabetes mellitus: the occurrence of renal events (BEACON) trials," Nephrology, Dialysis, Transplantation, 28(11):2841-2850, 2013.
Langleben et al., "Sustained Symptomatic, Functional, and Hemodynamic Benefit With the Selective Endothelin-A Receptor Antagonist, Sitaxsentan, in Patients With Pulmonary Arterial Hypertension: A 1-Year Follow-up Study," Chest, 126(4):1377-1381, 2004.
Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," Cancer Res., 63:5926-5939, 2003.

(56) References Cited

OTHER PUBLICATIONS

Lavie et al., "Studies on epoxides. IV. Rearrangements in triterpenoids," Tetrahedron Letters, 17: 2097-2100, 1968.

Le Brocq et al., "Endothelial Dysfunction: From Molecular Mechanisms to Measurement, Clinical Implications, and Therapeutic Opportunities", *Antioxid. Redox Signal.*, 10(9):1631-1673, 2008.

Le Pavec et al., "Systemic Sclerosis-associated Pulmonary Arterial Hypertension", *Am. J. Respir. Crit. Care Med.*, 181(12):1285-1293, 2010.

Lee, "Collaborative Power of Nrf2 and PPARγ Activators against Metabolic and Drug-Induced Oxidative Injury," *Oxidative Medicine and Cellular Longevity*, 2017:1378175, 14 pages, 2017.

Li and Nel, "Role of the Nrf2-mediated signaling pathway as a negative regulator of inflammation: implications for the impact of particulate pollutants on asthma," Antioxidants & Redox Signaling, 8:88-98, 2006.

Li et al., "The triterpenoid CDDO-Me delays murine acute graft-versus-host disease with the preservation of graft-versus-tumor effects after allogeneic bone marrow transplantation," *Biol. Blood Marrow Transplant.*, 16(6):739-750, 2010.

Liby and Sporn, "Synthetic oleanane triterpenoids: multifunctional drugs with a broad range of applications for prevention and treatment of chronic diseases," *Pharmacological Reviews*, 64(4):972-1003, 2012.

Liby et al., "Novel semisynthetic analogues of betulinic acid with diverse cytoprotective, antiproliferative, and proapoptotic activities," Mol. Cancer. Ther., 6:2113-2119, 2007.

Liby et al., "Prevention and Treatment of Experimental Estrogen Receptor-Negative Mammary Carcinogenesis by the Synthetic Triterpenoid CDDO-Methyl Ester and the Rexinoid LG100268," *Clin. Cancer Res.*, 14(14):4556-4563, 2008.

Liby et al., "Synthetic triterpenoids prolong survival in a transgenic mouse model of pancreatic cancer," *Cancer Prevent. Res.*, 3(11):1427-1434, 2010.

Liby et al., "The rexinoid LG100268 and the synthetic triterpenoid CDDO-methyl amide are more potent than erlotinib for prevention of mouse lung carcinogenesis," Mol. Cancer Ther., 7:1251-1257, 2008.

Liby et al., "The synthetic triterpenoid CDDO-Imidazolide suppresses STAT phosphorylation and induces apoptosis in myeloma and lung cancer cells," Clinical Cancer Research, 12:4288-4293, 2006.

Liby et al., "The synthetic triterpenoids CDDO-Methyl ester and CDDO-ethyl amid prevent lung cancer induced by vinyl carbamate in A/J mice," Cancer Research, 67:1-7, 2007.

Liby et al., "The synthetic triterpenoids, CDDO and CDDO-imidazolide, are potent inducers of heme oxygenase-1 and Nrf2/ARE signaling," Cancer Res., 65:4789-4798, 2005.

Liby et al., "Triterpenoids and rexinoids as multifunctional agents for the prevention and treatment of cancer," Nat. Rev. Cancer, 7:357-369, 2007.

Liby et al., "Triterpenoids CDDO-methyl ester or CDDO-ethyl amide and rexinoids LG100268 or NRX194204 for prevention and treatment of lung cancer in mice," *Cancer Prev. Res.*, 2(12):1050-1058, 2009.

Ling et al., "The novel triterpenoid C-28 methyl ester of 2-cyano-3,12-dioxoolen-1,9-dien-28-oic acid inhibits metastatic murine breast tumor growth through inactivation of STAT3 signaling," Cancer Res., 67:4210-4218, 2007.

Ling et al., "The novel triterpenoid C-28 methyl ester of 2-cyano-3,12-dioxoolen-1,9-dien-28-oic acid inhibits metastatic murine breast tumor growth through inactivation of STAT3 signaling," [Correction], *Cancer Res.*, 68(12):4958, 2008.

Liu et al., "Coordinate regulation of the enzyme markers for inflammation and for protection against oxidants and electrophiles," Proc. Natl. Acad. Sci., 105(41):15926-15931, 2008.

Liu et al., "Heme oxygenase-1 (HO-1) inhibits postmyocardial infarct remodeling and restores ventricular function," FASEB J., 20:207-216, 2006.

Liu et al., "New lupane-type triterpenoid saponins from leaves of Oplopanax horridus (Devil's Club)," Nat Prod Comm., 5(7): 1019-1022, 2010.

Liu et al., "The novel triterpenoid RTA 408 protects human retinal pigment epithelial cells against H2O2-induced cell injury via NF-E2-related factor 2 (Nrf2) activation," Redox Biol., 8:98-109, 2016.

Liu et al., "The nrf2 triterpenoid activator, CDDO-imidazolide, protects kidneys from ischemia-reperfusion injury in mice," *Kidney International*, 85(1):134-141, 2014.

Liu, "Pathogenesis of diabetic nephropathy and new viewpoint of targeted therapy," *Zhonghua Linchuang Yishi Zazhi*, 7(14):6569-6571, 2013 (Chinese, English Abstract).

Lozano et al., "Losartan reduces microalbuminuria in hypertensive microalbuminuric type 2 diabetics," Nephrol. Dial. Transplant, 16(Suppl 1):85-89, 2001.

Luo et al., "IKK/NF-κB signaling: balancing life and death—a new approach to cancer therapy," J. Clin. Invest., 115:2625-2631, 2005.

Ma et al., "Multiorgan autoimmune inflammation, enhanced lymphoproliferation, and impaired homeostasis of reactive oxygen species in mice lacking the antioxidant-activated transcription factor Nrf2," Am. J. Pathol., 168:1960-1974, 2006.

Maines and Gibbs, "30 some years of heme oxygenase: from a 'molecular wrecking ball' to a 'mesmerizing' trigger of cellular events," Biochem. Biophys. Res. Commun., 338:568-577, 2005.

Mantovani et al., "Inflammation by remote control," Nature, 435:752-753, 2005.

Marty et al., "RTA 402 (CDDO-Me) increases survival of mice administered high doses of cytotoxic chemotherapy," presented by Reata Pharmaceuticals, Nov. 2005.

Mazur et al., "Acetylsalicylic acid (ASA) blocks influenza virus propagation via its NF-kappaB-inhibiting activity," Cell Microbiol., 9 (7): 1683-1694, 2007.

Mazzoni et al., "Myeloid suppressor lines inhibit T cell responses by an NO-dependent mechanism," J. Immunol., 168 (2): 689-695, 2002.

McCullough and Ali, "Cardiac and renal function in patients with type 2 diabetes who have chronic kidney diseases: potential effects of bardoxolone methyl," *Drug Design, Development and Therapy*, 6:141-149, 2012.

McLaughlin, "Looking to the future: a new decade of pulmonary arterial hypertension therapy," 20:262-269, 2011.

McMahon and Forman, "Bardoxolone Methyl, Chronic Kidney Disease, and Type 2 Diabetes: Letter to the Editor," New Eng. J. Med., 365(18):1746, 2011.

McQuaid and Keenan, "Physiological Society Symposium: Impaired Endothelial and Smooth Muscle Cell Function in Oxidative Stress: Endothelial Barrier Dysfunction and Oxidative Stress: Roles for Nitric Oxide?" Experimental Physiology, 82:369-376, 1997.

Meyer et al., "MP142A Phase 2/3 Study of the Efficacy and Safety of Bardoxolone Methyl in Patients With Alport Syndrome", *Nephrol. Dial. Transplant.*, 32(Suppl. 3):iii480-iii480, 2017.

Minns et al., "A novel triterpenoid induces transforming growth factor beta production by intraepithelial lymphocytes to prevent ileitis," Gastroenterology, 127:119-126, 2004.

Mix et al., "A synthetic triterpenoid selectively inhibits the induction of matrix metalloproteinases 1 and 13 by inflammatory cytokines," Arthritis Rheum., 44:1096-1104, 2001.

Miyata et al., "Diabetic nephropathy: are there new and potentially promising therapies targeting oxygen biology?" *Kidney International*, 84(4):693-702, 2013.

Moncada et al., "Nitric oxide: physiology, pathophysiology, and pharmacology," Pharmacol. Rev., 43:109-142, 1991.

Morse and Choi, "Heme oxygenase-1: from bench to bedside," Am. J. Respir. Crit. Care Med., 172:660-670, 2005.

Morse and Choi, "Heme oxygenase-1: the 'emerging molecule' has arrived," Am. J. Respir. Crit. Care Med., 27:8-16, 2002.

Mudau et al., "Endothelial dysfunction: the early predictor of atherosclerosis," *Cardiovasc. J. Afr.*, 23(4):222-231, 2012.

Na and Surh, "Transcriptional regulation via cysteine thiol modification: a novel molecular strategy for chemoprevention and cytoprotection," Mol. Carcinog., 45:368-380, 2006.

(56) References Cited

OTHER PUBLICATIONS

Nagaraj et al., "Anti-inflammatory Triterpenoid Blocks Immune Suppressive Function of MDSCs and Improves Immune Response in Cancer," *Clin. Cancer Res.*, 16(6):1812-1823, 2010.
Nanduri et al., "Biological investigation and structure-activity relationship studies on azadirone from azadirachta indica A. juss," Bioorganic and Medicinal Chemistry, 13 (22): 4111-4115, 2003.
Nath et al., "Progression of progressive multifocal leukoencephalopathy despite treatment with beta-interferon," Neurology, 66(1): 149-150, 2006.
Nath, "Heme oxygenase-1: a provenance for cytoprotective pathways in the kidney and other tissues," Kidney Int., 70:432-443, 2006.
Nathan and Xie, "Nitric oxide synthases: roles, tolls, and controls," Cell, 78:915-918, 1994.
Nathan, "Points of control in inflammation," Nature, 420:846-852, 2002.
Navaneethan et al., "Presence and outcomes of kidney disease in patients with pulmonary hypertension," *Clin. Am. J. Soc. Nephrol.*, 9(5):855-863, 2014.
Neymotin et al., "Neuroprotective effect of Nrf2/ARE activators, CDDO ethylamide and CDDO trifluoroethylamide, in a mouse model of amyotrophic lateral sclerosis," *Free Radical Biology & Medicine*, 51(1):88-96, 2011.
Nguyen et al., "The Nrf2-antioxidant response element signaling pathway and its activation by oxidative stress," J. Biol Chem., 284:13291-13295, 2009.
Nichols, "NF-κB and reperfusion injury," Drug News Perpect., 17:99-104, 2004.
Niikura et al., "The effects of synthetic triterpenoids on superficial zone protein synthesis in articular chondrocytes," Abstract, Orthopedic Research Society, San Diego, 2007.
Nishimura et al., "Activity-guided isolation of triterpenoid acyl CoA cholesteryl acyl transferase (ACAT) inhibitors from Ilex kudincha," J Nat Prod., 62(7): 1061-1064, 1999.
Noone and Licht, "An update on the pathomechanisms and future therapies of Alport syndrome," Pediatr Nephrol., 28(7):1025-1036, 2013.
Olsen et al., "Fatty acid synthesis is a therapeutic target in human liposarcoma," *Int. J. Oncol.*, 36(5):1309-1314, 2010.
Olsen et al., "Inhibition of transglutaminase 2, a novel target for pulmonary fibrosis, by two small electrophilic molecules," *Am. J. Respiratory Cell and Molecular Biology*, 50(4):737-747, 2014.
Osburn et al., "Genetic of pharmacologic amplification of Nrf2 signaling inhibits acute inflammatory liver injury in mice," Toxicological Sciences, 104:218-227, 2008.
Pabst et al., "Pulmonary hypertension in patients with chronic kidney disease on dialysis and without dialysis: results of the PEPPER-study," PLoS ONE, 7:e35310, 2012.
Pahl, "Activators and target genes of Rel/NF-κB transcription factors," Oncogene, 18:6853-6866, 1999.
Pall, "Nitric oxide synthase partial uncoupling as a key switching mechanism for the NO/ONOO-cycle," Med. Hypoth., 69:821-825, 2007.
Palsamy and Subramanian, "Resveratrol protects diabetic kidney by attenuating hyperglycemia-mediated oxidative stress and renal inflammatory cytokines via Nrf2-Keap1 signaling," Biochimica et Biophysica Acta, 1812(7):719-731, 2011.
Paulin et al., "From oncoproteins/tumor suppressors to microRNAs, the newest therapeutic targets for pulmonary arterial hypertension," J. Mol. Med., 89:1089-1101, 2011.
Paulin et al., "Signal Transducers and Activators of Transcription-3/Pim1Axis Plays a Critical Role in the Pathogenesis of Human Pulmonary Arterial Hypertension," *Circulation*, 123(11):1205-1215, 2011.
Paulin et al., "STAT3 signaling in pulmonary arterial hypertension," JAK-STAT, 1:4:223-233, Oct./Nov./Dec. 2012.
Pedersen et al., "The triterpenoid CDDO induces apoptosis in refractory CLL B cells," Blood, 100:2965-2972, 2002.

Pepine, "Clinical implications of endothelial dysfunction," Clin. Cardiol., 21:795-799, 1998.
Pergola et al., "Bardoxolone Methyl and Kidney Function in CKD with Type 2 Diabetes," Supplementary Appendix appended, N. Engl. J. Med., 365:327-336, 2011.
Pergola et al., "Bardoxolone Methyl, Chronic Kidney Disease, and Type 2 Diabetes: Reply to Letters to the Editor," New Eng. J. Med., 365(18):1746-1747, 2011.
Pernow et al., "New perspectives on endothelin-1 in atherosclerosis and diabetes mellitus," Life Sci., 91:507-516, 2012.
Place et al., "The novel synthetic triterpenoid, CDDO-imidazolide, inhibits inflammatory response and tumor growth in vivo," Clin. Cancer Res., 9:2798-2806, 2003.
Place, "Pre-Clinical Evaluation of the Novel Synthetic Triterpenoid CDDO-imidazolide," Dissertation, Dartmouth College, May 4, 2005.
Price et al., "Inflammation in pulmonary arterial hypertension," *Chest*, 141(1):210-221, 2012.
Qin et al., "Identification of unique sensitizing targets for anti-inflammatory CDDO-Me in metastatic melanoma by a large-scale synthetic lethal RNAi screening," *Pigment Cell & Melanoma Research*, 26(11):97-112, 2013.
Rabinovitch, "Molecular pathogenesis of pulmonary arterial hypertension," J. Clin. Invest., 122:4306-4313, 2012.
Rajakariar et al., "Hematopoietic prostaglandin $D_2$ synthase controls the onset and resolution of acute inflammation through $PGD_2$ and 15-deoxy$\Delta^{12-14}$ $PGJ_2$," Proc. Natl. Acad. Sci. USA, 104:20979-20984, 2007.
Ramachandra Row and Subba Rao, "Chemistry of Terminalia Species-VI the constitution of tomentosic acid, a new triterpene carboxylic acid from Terminalia Tomentosa, wight et arn*," Tetrahedron, 18:827-838, 1962.
Rangasamy et al., "Disruption of Nrf2 enhances susceptibility to severe airway inflammation and asthma in mice," Journal of Experimental Medicine, 202:47-59, 2005.
Raval and Lee, "Heme oxygenase-1 in lung disease," Curr. Drug Targets, 11:1532-1540, 2010.
Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor γ-independent pathway," Exp. Hematology, 34:1202-1211, 2006.
Reisman et al., "Bardoxolone methyl decreases megalin and activates Nrf2 in the kidney," *J. Am. Soc. Nephrology*, 23(10):1663-1673, 2012.
Reisman et al., "Topical application of synthetic triterpenoid RTA 408 protects mice from radiation-induced dermatitis," *Radiation Research*, 181(5):512-520, 2014.
Reisman et al., "Topical application of the synthetic triterpenoid RTA 408 activates Nrf2 and induces cytoprotective genes in rat skin," *Archives of Dermatological Research*, 306(5):447-454, 2014.
Rheault et al., "Change in glomerular filtration rate and renal biomarkers in patients with chronic kidney disease due to Alport syndrome: interim results from the ATHENA study, a prospectively designed natural history study," Nephrol. Dial. Transplant, 31:126, 2016.
Ribo et al., "Synthesis of methyl 1, 11-dioxooleanan-2, 12-dien-30-oate and its 24-nor derivative," Afinidad, 38(373): 197-200, 1981.
Rogacev et al., "Bardoxolone Methyl, Chronic Kidney Disease, and Type 2 Diabetes: Letter to the Editor," *New Eng. J. Med.*, 365(18):1745-1746, 2011.
Rojas-Rivera et al., "Antioxidants in kidney diseases: the impact of bardoxolone methyl," *International J. of Nephrology*, 321714, 2012.
Ross et al., "Breast cancer biomarkers and molecular medicine," Expert Rev. Mol. Diagn., 3(5): 573-585, 2003.
Ross et al., "HER-2/neu testing in breast cancer," Am. J. Clin. Pathol., 120(Suppl):S53-71, 2003.
Rossi et al., "Anti-inflammatory cyclopentenone prostaglandins are direct inhibitors of IκB kinase," Nature, 403:103-108, 2000.
Rossing, "Diabetic neuropathy: could problems with bardoxolone methyl have been predicted?" *Nature Reviews: Nephrology*, 9:128-130, 2013.

(56) References Cited

OTHER PUBLICATIONS

Rouquette et al., "A ring-D functionalized nor-triterpenoid of the lupane series as a key intermediate in the formation of widespread hydrocarbon derivatives of higher plant origin in petroleum," Organic Geochemistry, 36(9): 1227-1233, 2005.
Rubin et al., "Bosentan therapy for Pulmonary Arterial Hypertension," *N. Engl. J. Med.*, 346(12):896-903, 2002.
Ruiz et al., "Targeting the transcription factor Nrf2 to ameliorate oxidative stress and inflammation in chronic kidney disease," *Kidney International*, 83(6):1029-1041, 2013.
Ruvolo et al., "The novel triterpenoid methyl-CDDO inhibits Bcl2 phosphorylation and potently kills U937 cells," Blood, 94(Suppl. 1, Part 1):280A, abstract #1251, 1999.
Ryu et al., "Activation of signal transducer and activator of transcription 3 (Stat3) pathway in osteosarcoma cells and overexpression of phosphorylated-Stat3 correlates with poor prognosis," *J. Orthop. Res.*, 28(7):971-978, 2010.
Ryu et al., "Oleanane triterpenoid CDDO-Me induces apoptosis in multidrug resistant osteosarcoma cells through inhibition of Stat3 pathway," BMC Cancer, 10:187, 2010.
Salvemini et al., "Nitric oxide activates cyclooxygenase enzymes," Proc. Natl. Acad. Sci. USA, 90:7240-7244, 1993.
Samudio et al., "2-Cyano-3,12-dioxooleana-1,9-dien-28-imidazolide (CDDO-Im) directly targets mitochondrial glutathione to induce apoptosis in pancreatic cancer," J. Biol. Chem., 280:36273-36282, 2005.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," Mol. Pharmacol., 69:1182-1193, 2006.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," Blood, 106(11):4462, 2005.
Samudio et al., "Inhibition of mitochondrial metabolism by methyl-2-cyano-3,12-dioxoolean-1,9-diene-28-oate induces apoptotic or autophagic cell death in chronic myelogenous leukemia cells," Mol. Cancer Ther., 7:1130-1139, 2008.
Samudio et al., "The novel triterpenoid CDDOme potently synergizes with inhibition of bcl-2 function to induce apoptosis in AML via disruption of intracellular redox homeostasis," Proc. Amer. Assoc. Cancer Res., 46:Abstract No. 4955, 2005.
Sarchielli et al., "NF-κB activity and iNOS expression in monocytes from internal jugular blood of migraine without aura patients during attacks," Cephalalgia, 26:1071-1079, 2006.
Satoh et al., "Activation of the Keap1/Nrf2 pathway for neuroprotection by electrophillic phase II inducers," PNAS, 103 (3): 768-773, 2006.
Sauvageau et al., "Change in pharmacological effect of endothelin receptor antagonists in rats with pulmonary hypertension: Role of ETB-receptor expression levels," *Pulm. Pharmacol. Ther.*, 22(4):311-317, 2009.
Savige et al., "Alport syndrome in women and girls," Clin J Am Soc Nephrol., 11(9):1713-1720, 2016.
Savige et al., "Expert guidelines for the management of Alport syndrome and thin basement membrane nephropathy," J Am Soc Nephrol. 24(3):364-375, 2013.
Savige, "Alport syndrome: Its effects on the glomerular filtration barrier and implications for future treatment," J Physiol., 592(18):4013-4023, 2014.
Scholz et al., "Sensitive and specific methods for the determination of CDDO methyl ester in mouse, rat, dog, monkey, and human plasma by LC-tandem mass spectrometry," Proc. Amer. Assoc. Cancer Res., 4:Abstract No. 6321, 2003.
Schulz et al., "Nitric oxide, tetrahydrobiopterin, oxidative stress, and endothelial dysfunction in hypertension," Antioxid. Redox. Sig., 10:1115-1126, 2008.
Seibert and Masferrer, "Role of inducible cyclooxygenase (COX-2) in inflammation," Receptor, 4:17-23, 1994.

Sengul et al., "Beneficial effect of lisinopril plus telmisartan in patients with type 2 diabetes, microalbuminuria and hypertension," Diabetes Research and Clinical Practice, 71:210-219, 2006.
Serhan et al., "Resolving inflammation: dual anti-inflammatory and pro-resolution lipid mediators," Nat. Rev., 8:349-361, 2008.
Shelton et al., "Role of Nrf2 in protection against acute kidney injury," *Kidney Int.*, 84(6):1090-1095, 2013.
Shimzu et al., "Hemin Treatment Abrogates Monocrotaline-Induced Pulmonary Hypertension", *Med. Chem.*, 4(6):572-576, 2008.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," Molecular and Cellular Biology, 27(20):7188-7197, 2007.
Shin et al., "Role of Nrf2 in prevention of high-fat diet-induced obesity by synthetic triterpenoid CDDO-imidazolidem," Eur. J. Pharmacol., 620:138-144, 2009.
Shishodia et al., "A synthetic triterpenoid, CDDO-Me, inhibits IκBα kinase and enhances apoptosis induced by TNF and chemotherapeutic agents through down-regulation of expression of nuclear factor κB-regulated gene products in human leukemic cells," Clin. Cancer Res., 12:1828-1838, 2006.
Siddiqui et al., "Kanerin and 12, 13-dihydroursolic acid, two new pentacyclic triterpenes from the leaves of Nerium oleander," J Nat Prod., 52(1): 57-62, 1989.
Simonian and Coyle, "Oxidative stress in neurodegenerative diseases," Annu. Rev. Pharmacol. Toxicol., 36:83-106, 1996.
Simonneau et al., "Updated clinical classification of pulmonary hypertension," J. Am. Coll. Card., 54:S43-S54, 2009.
Singh and Evans, "Nitric oxide, the biological mediator of the decade: fact or fiction?" Eur. Respir. J., 10:699-707, 1997.
Singh et al., "Anti-inflammatory activity of oleanolic acid in rats and mice," J. Pharm. Pharmacol., 44:456-458, 1992.
Sitbon and Morrell, "Pathways in pulmonary arterial hypertension: the future is here," Eur. Respir. Rev., 21:321-327, 2012.
Sjöholm and Nyström, "Inflammation and the etiology of type 2 diabetes," Diabetes Metab. Res. Rev., 22: 4-10, 2006.
Sogno et al., "Anti-angiogenic activity of a novel class of chemopreventive compounds: oleanic acid terpenoids," Recent Results Cancer Res., 181:209-212, 2009.
Sporn and Roberts, "Peptide growth factors and inflammation, tissue repair, and cancer," J. Clin. Invest., 78:329-332, 1986.
Sporn et al., "Prospects for prevention and treatment of cancer with selective PPARγ modulators (SPARMs)," Trends in Molecular Medicine, 7:395-400, 2001.
Sporn et al., "Transforming growth factor-β: biological function and chemical structure," Science, 233:532-534, 1986.
Stack et al., "Triterpenoids CDDO-ethyl amide and CDDO-trifluoroethyl amide improve the behavioral phenotype and brain pathology in a transgenic mouse model of Huntington's disease", Free Radic. Biol. Med., 49:147-158, 2010.
Stadheim et al., "The novel triterpenoid 2-cyano-3,12-dioxooleana-1,9-dien-28-oic acid (CDDO) potently enhances apoptosis induced by tumor necrosis factor in human leukemia cells," J. Biol. Chem., 277:16448-16455, 2002.
Strutz, "Antifibrotic therapy: is an antioxidative regimen the answer?" *J. Am. Soc. Nephrology*, 25(1):3-5, 2014.
Subba Rao et al., "Chemical modifications of natural triterpenes—glycyrrhetinic and boswellic acids: evaluation of their biological activity," Tetrahedron, 64:11541-11548, 2008.
Sud and Black, "Endothelin-1 impairs nitric oxide signaling in endothelial cells through a protein kinase Cδ-dependent activation of STAT3 and decreased endothelial nitric oxide synthase expression," DNA Cell Biol., 28:543-553, 2009.
Suh et al., "A novel synthetic oleanane triterpenoid, 2-cyano-3,12-dioxoolean-1,9-dien-28-oic acid, with potent differentiating, antiproliferative, and anti-inflammatory activity," Cancer Res., 59:336-341, 1999.
Suh et al., "New triterpenoids as cancer preventive and anti-inflammatory agents," Proc. Amer. Assoc. Cancer Res., Abstract No. 1457, 38:216, 1997.

(56) References Cited

OTHER PUBLICATIONS

Suh et al., "Novel triterpenoids suppress inducible nitric oxide synthase (iNOS) and inducible cyclooxygenase (COX-2) in mouse macrophages," Cancer Res., 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to TRAIL," Leukemia, 17:2122-2129, 2003.
Suh et al., "Synthetic triterpenoids enhance transforming growth factor β/Smad signaling," Cancer Res., 63:1371-1376, 2003.
Sultana et al., "Phytochemical studies on Alstonia scholaris," Zeitschrift für Naturforschung. B, a Journal of Chemical Sciences, 65(2):203-210, 2010.
Sung et al., "Oxidative stress and nucleic acid oxidation in patients with chronic kidney disease," *Oxidative Medicine and Cellular Longevity*, 301982, 2013.
Sussan et al., "Disruption of Nrf2, a key inducer of antioxidant defenses, attenuates ApoE-mediated atherosclerosis in mice," PLoS One, 3:1-9, 2008.
Sussan et al., "Targeting Nrf2 with the triterpenoid CDDO-imidazolide attenuates cigarette smoke-induced emphysema and cardiac dysfunction in mice," Proc. Natl. Acad. Sci. USA, 106:250-255, 2009.
Sutendra and Michelakis, "The Metabolic Basis of Pulmonary Arterial Hypertension," Cell Metab., 19(4):558-573, 2014.
Tabe et al., "Chromatin-Mediated Transcriptional Activation with Novel Peroxisome Proliferator-Activated Receptor gamma(PPARγ) Ligand 2-cyano-1,9-dien-28-oic Acid (CDDO) in Acute Promyelocytic Leukemia Cells," Abstracts of the 44th Annual Meeting of the American Society of Hematology, Abstract No. 2191, 2002.
Tagore et al., "Natriuretic Peptides in Chronic Kidney Disease," Clin. J. Am. Soc. Nephrol., 3:1644-1651, 2008.
Takahashi et al., "Increased expression of inducible and endothelial constitutive nitric oxide synthases in rat colon tumors induced by azoxymethane," Cancer Res., 57:1233-1237, 1997.
Takahashi et al., "Organ protective role of heme oxygenase-1 against oxidative stress," Folia Pharmacolgica Japonica, 130:252-256, 2007. (English translation).
Takaishi et al., "Triterpenoid inhibitors of interleukin-1 secretion and tumor-promotion from *Tripterygium wilfordii* var. *regelii*," Phytochemistry, 45(5): 969-974, 1997.
Tamir and Tannebaum, "The role of nitric oxide (NO) in the carcinogenic process," Biochim. Biophys. Acta, 1288:F31-F36, 1996.
Tan et al., "A derivative of Bardoxolone methyl, dh404, in an inverse dose-dependent manner, lessens diabetes-associated atherosclerosis and improves diabetic kidney disease," Diabetes, 63:3091-3103, 2014.
Tanaka et al., "Coordinated induction of Nrf2 target genes protects against iron nitrilotriacetate (FeNTA)-induced nephrotoxicity," Toxicol. Appl. Pharmacol., 231(3):364-373, 2008.
Thaler et al., "Hypothalamic inflammation and energy homeostasis: Resolving the paradox," Front. Neuroendocrinol., 31:79-84, 2010.
Thimmulappa et al., "Nrf2 is a critical regulator of the innate immune response and survival during experimental sepsis," J. Clinical Investigation, 116:984-995, 2006.
Thimmulappa et al., "Nrf2-dependent protection from LPS induced inflammatory response and mortality by CDDO-imidazolide," Biochem. Biophys. Res. Commun., 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," Antioxid. Redox Signal., 9:1963-1970, 2007.
Thornalley and Rabbani, "Dietary and Synthetic Activators of the Antistress Gene Response in Treatment of Renal Disease," *J. Renal Nutrition*, 22(1):195-202, 2012.

To et al., "Synthetic Triterpenoids Target the Arp2/3 Complex and Inhibit Branched Actin Polymerization," *J. Biol. Chem.*, 285(36):27944-27957, 2010.
To et al., "The synthetic triterpenoid 2-cyano-3,12-dioxooleana-1,9-dien-28-oic acid-imidazolide alters transforming growth factor B-dependent signaling and cell migration by affecting the cytoskeleton and the polarity complex," J. Biol. Chem., 283:11700-11713, 2008.
Tsao et al., "DRIP205 co-activator overexpression enhances PPARγ-mediated differentiation of leukemia cells by CDDO," Proc. Amer. Assoc. Cancer Res., 46:Abstract No. 1855, 2005.
Tsao et al., "Targeted Induction of Apoptosis in Leukemias by PPARγ Ligation," American Society of Hematology 43rd Annual Meeting and Exposition, Abstract No. 2381, 2001.
Tsujii and DuBois, "Alterations in cellular adhesion and apoptosis in epithelial cells overexpressing prostaglandin endoperoxide synthase 2," Cell, 83(3):493-501, 1995.
Tsujii et al., "Cyclooxygenases regulates angiogenesis induced by colon cancer cells," Cell, 93:705-716, 1998.
Upadhyay et al., "Bardoxolone Methyl, Chronic Kidney Disease, and Type 2 Diabetes: Letter to the Editor," *New Eng. J. Med.*, 365(18):1746, 2011.
Vachierty and Gaine, "Challenges in the diagnosis and treatment of pulmonary arterial hypertension," Eur. Respir. Rev., 21:313-320, 2012.
Van Kiem et al., "A new 24-nor-lupane-glycoside of Acanthopanax trifoliatus" Arch Pharm Res., 26(9): 706-708, 2003.
Van Laecke and Vanholder, "Bardoxolone Methyl, Chronic Kidney Disease, and Type 2 Diabetes: Letter to the Editor," *New Eng. J. Med.*, 365(18):1745, 2011.
Van Laecke et al., "The paradox of bardoxolone methyl: a call for every witness on the stand," *Diabetes, Obesity, and Metabolism*, 17(1):9-14, 2015.
Vannini et al., "The synthetic oleanane triterpenoid, CDDO-methyl ester, is a potent antiangiogenic agent," Molecular Cancer Therapeutics, 6(12):3139-3146, 2007.
Vazquez et al., "Human immunodeficiency virus type 1-induced macrophage gene expression includes the p21 gene, a target for viral regulation," J. Virol., 79:4479-4491, 2005.
Vene et al., "Glycogen Synthase Kinase 3B Regulates Cell Death Induced by Synthetic Triterpenoids," Cancer Res., 68:6987-6996, 2008.
Vilayur and Harris, "Emerging therapies for chronic kidney disease: what is their role?" Nature Reviews, 5:375-383, 2009.
Voelkel et al., "Antioxidants for the treatment of patients with severe angioproliferative pulmonary hypertension," Antioxid. Redox Signal., 18:1810-1817, 2013.
Wang et al., "A synthetic triterpenoid, 2-cyano-3,12-dioxooleana-1,9-dien-28-oic acid (CDDO), is a ligand for the peroxisome proliferator-activated receptor γ," Mol. Endocrin., 14:1550-1556, 2000.
Wang et al., "Bardoxolone methyl (CDDO-Me) as a therapeutic agent: an update on its pharmacokinetic and pharmacodynamic properties," *Drug Des. Devel. Ther.*, 8:2075-2088, 2014.
Wang et al., "Cytoprotection of human endothelial cells against oxidative stress by 1-[2-cyano-3,12-dioxooleana-1,9(11)-dien-28-oyl]imidazole (CDDO-Im): Application of systems biology to understand the mechanism of action," *European J. of Pharmacology*, 734:122-131, 2014.
Wang et al., "Synthetic triterpenoid CDDO and its derivatives increase ceramides and are cytotoxic to pediatric acute lymphoblastic leukemia cell lines," Proc. Am. Assoc. Cancer Res., 47:4643, 2006.
Wang, "Differentiating and anti-inflammatory activities of the triterpenoid, CDDO," Thesis, Dartmouth College, May 4, 2001.
Waratchareeyakul et al., "2,19-Dihydroxy-3-oxo-(2,4,19)-24-nor-olean-12-en-28-oic acid monohydrate," Acta. Cryst., E63, o4062-o4063, 2007.
Wardle, "Nuclear factor kappaB for the nephrologist," Nephrol. Dial. Transplant., 16(9):1764-8, 2001.
Wei et al., "A synthetic PPAR-γ agonist triterpenoid ameliorates experimental fibrosis: PPAR-γ independent suppression of fibrotic responses," *Annals of Rheumatic Diseases*, 73(2):446-454, 2014.
Whaley-Connell and Sowers, "Oxidative Stress in the Cardiorenal Metabolic Syndrome," *Curr. Hypertens. Rep.*, 14(4):360-365, 2012.

(56) References Cited

OTHER PUBLICATIONS

White et al., "A novel demethylated oxygenated triterpenoid in crude oils from the Canadian Beaufort sea and northeast Alaska," Tetrahedron Letters, 39(19): 3031-3034, 1998.
Wilkins, "Pulmonary hypertension: the science behind the disease spectrum," Eur. Respir. Rev., 21:19-26, 2012.
Wu et al., "Bardoxolone methyl (BARD) ameliorates ischemic AKI and increases expression of protective genes Nrf2, PPARγ, and HO-1", Am. J. Physiol. Renal Physiol., 300(5):F1180-F1192, 2011.
Wu et al., "Beneficial role of Nrf2 in regulating NADPH generation and consumption," Tox. Sci., 123:590-600, 2011.
Wu et al., "Dietary approach to attenuate oxidative stress, hypertension, and inflammation in the cardiovascular system," Proc. Natl. Acad. Sci., USA, 101(18):7094-7099, 2004.
Xie et al., "ARE- and TRE-mediated regulation of gene expression: response to xenobiotics and antioxidants," J. Biol. Chem., 270:6894-6900, 1995.
Xing et al., "Triterpenoid dihydro-CDDO-trifluoroethyl amide protects against maladaptive cardiac remodeling and dysfunction in mice: a critical role of Nrf2," PLoS One, 7:e44899, 2012.
Xu et al., "Inhibition of the Signal Transducer and Activator of Transcription-3 (STAT3) Signaling Pathway by 4-Oxo-1-phenyl-1,4-dihydroquinoline-3-carboxylic acid esters," J. Med. Chem., 51:4115-4121, 2008.
Xu et al., "The role of nitric oxide in cancer", Cell Res., 12:311-320, 2002.
Xue et al., "Activation of NF-E2-related factor-2 reverses biochemical dysfunction of endothelial cells induced by hyperglycemia linked to vascular disease," Diabetes, 57:2809-2817, 2008.
Yamamoto and Yanagita, "Reversibility of CKD learned from the effect of bardoxolone methyl on CKD," Igaku no Ayumi, 249(7):627-629, 2014. (Japanese, English Abstract).
Yang et al., "Neuroprotective effects of the triterpenoid, CDDO methyl amide, a potent inducer of Nrf2-mediated transcription", PLoS One, 4:e5757, 2009.
Yates et al., "Pharmacodynamic characterization of chemopreventive triterpenoids as exceptionally potent inducers of Nrf2-regulated genes," Mol. Cancer Ther., 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," Cancer Res., 66:2488-2494, 2006.
Yore et al., "Proteomic analysis shows synthetic oleanane triterpenoid binds to mTOR," PLoS One, 6(7):e22862, 2011.
Yore et al., "The synthetic triterpenoid 1-[2-cyano-3,12-dioxooleana-1,9(11)-dien-28-oyl] imidazole blocks nuclear factor-κB activation through direct inhibition of IκB kinase beta," Mol. Cancer Ther., 5:3232-3239, 2006.
You et al., "Synthesis and cytotoxic activity of a-ring modified betulinic acid derivatives," Bioorganic and Medicinal Chemistry Letters, 13 (19): 3137-3140, 2003.

Yu and Kensler, "Nrf2 as a target for cancer chemoprevention," Mutat. Res., 591:93-102, 2005.
Yue et al., "Depletion of intracellular glutathione contributes to JNK-mediated death receptor 5 upregulation and apoptosis induction by the novel synthetic triterpenoid methyl-2-cyano-3,12-dioxooleana-1,9-dien-28-oate (CDDO-Me)," Cancer Biol. Ther., 5:492-497, 2006.
Zapata et al., "CDDO and CDDO-Im Reduce Tumor Burden in a Transgenic Mouse Model of CLL," Blood, 104:3477, 2004.
Zapata et al., "Triterpenoids show activity against leukemic cells in a transgenic mouse model of CLL," Proc. Amer. Assoc. Cancer Res., 46:Abstract No. 5179, 2005.
Zeller et al., "Pulmonary hypertension," JAMA, 302(13):1490, 2009.
Zhang et al., "Simvastatin protects against the development of monocrotiline-induced pulmonary hypertension in rats via a heme oxygenase-1-dependent pathway", Exp. Lung Res., 37(8):492-499, 2011.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," J. Invest. Dermatol., 123:380-387, 2004.
Zhou et al., "A new triterpenoid from the roots of Tripterygium wildfordii," Chinese Chemical Letters, 21(5): 600-602, 2010.
Zhou et al., "Heme oxygenase-1 mediates the protective effects of rapamycin in monocrotiline-induced pulmonary hypertension", Lab. Invest., 86(1):62-71, 2006.
Zingarelli et al., "Nuclear factor-κB as a therapeutic target in critical care medicine," Crit. Care Med., 31:S105-S111, 2003.
Zoja et al., "Analogs of Bardoxolone Methyl Worsen Diabetic Nephropathy in Rats with Additional Adverse Events," Am. J. Physiology, 304(3, Part 2):F808-F819, 2013.
Zou et al., "c-FLIP downregulation contributes to apoptosis induction by the novel synthetic triterpenoid methyl-2-cyano-3,12-dioxooleana-1,9-dien-28-oate (CDDO-Me) in Human Lung Cancer Cells," Cancer Biol. Ther., 6:1614-1620, 2007.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," Cancer Res., 64:7570-7578, 2004.
Zou et al., "Coupling of Endoplasmic Reticulum Stress to CDDO-Me-Induced Up-Regulation of Death Receptor 5 via a CHOP-Dependent Mechanism Involving JNK Activation," Cancer Research, 68:7484-7492, 2008.
Zou et al., "PPARγ ligands enhance TRAIL-induced apoptosis through DR5 upregulation and c-FLIP downregulation in human lung cancer cells," Cancer Biol. Ther., 6:99-106, 2007.
Kashtan, "Alport syndrome. An inherited disorder of renal, ocular, and cochlear basement membranes," Rev. Mol. Med., 78(5):338-360, 1999.

FIGS. 1A-C

METHODS OF TREATING ALPORT SYNDROME USING BARDOXOLONE METHYL OR ANALOGS THEREOF

This application is a continuation of U.S. patent application Ser. No. 16/315,821, filed Jan. 7, 2019, which is a national phase application under 35 U.S.C. § 371 of International application number PCT/US2017/060701, filed Nov. 8, 2017, which claims the priority benefit of U.S. provisional application No. 62/580,597, filed Nov. 2, 2017, U.S. provisional application No. 62/535,663, filed Jul. 21, 2017, and U.S. provisional application No. 62/419,335, filed Nov. 8, 2016, the entire contents of each of which is incorporated herein by reference.

BACKGROUND OF THE INVENTION

1. Field of the Invention

The present invention relates generally to the fields of biology and medicine. More particularly, it concerns, in some aspects, methods for treating or preventing Alport syndrome or symptoms thereof using bardoxolone methyl and analogs thereof.

2. Description of Related Art

Alport syndrome is a rare and serious hereditary disease caused by mutations in the genes encoding Type IV collagen, a major structural component of the glomerular basement membrane (GBM) in the kidney. Patients with Alport syndrome exhibit ultrastructural changes in the GBM due to the abnormal expression of Type IV collagen chains in the kidney. Loss of GBM integrity results in abnormal leakage of proteins, such as albumin, which are then excessively reabsorbed in the tubules and activate pro-inflammatory signaling pathways in glomerular endothelial cells, mesangial cells, and podocytes. Chronic activation of pro-inflammatory pathways in these kidney cells promotes glomerular filtration rate (GFR) loss by several mechanisms: (a) in glomerular endothelial cells, inflammation-associated reactive oxygen species (ROS) induce the production of peroxynitrite, which depletes vasodilatory nitric oxide and results in endothelial dysfunction, vasoconstriction and reduced glomerular surface area for filtration; (b) inflammation-associated ROS induce a contractile response in mesangial cells, further reducing filtration; and (c) ROS-mediated activation of inflammatory pathways leads to fibrosis, promoting structural alterations in the mesangium and GBM thickening that contributes to GFR decline. GFR decline from these processes inevitably leads to end stage renal disease (ESRD).

Bardoxolone methyl has been shown to improve both estimated glomerular filtration rate (eGFR) and measured glomerular filtration rate (mGFR) in patients with CKD due to Type 2 diabetes. Bardoxolone methyl and several of its analogues also have been shown to inhibit pro-fibrotic signaling pathways and reduce oxidative stress and inflammation in multiple models of CKD. These compounds have also shown inhibition of inflammatory signaling and fibrosis in animal models of liver, skin, and lung disorders.

Despite the severe consequences of Alport syndrome including ESRD, there remain only limited treatment options for this condition. Therefore, there remains a therapeutic need to develop new and effective methods of treating and/or preventing Alport syndrome, the associated symptoms thereof, as well as preventing the onset of such symptoms.

SUMMARY OF THE INVENTION

In one aspect, the present invention provides methods of treating or preventing Alport syndrome in a patients in need thereof, and/or improving the kidney function of patients who has been diagnosed with Alport syndrome. Such methods are described in the sections below, including for example the claims section, which is incorporated herein by reference.

In some embodiments, the compound is bardoxolone methyl (CDDO-Me or RTA 402). And in some of these embodiments, at least a portion of the CDDO-Me is present as a polymorphic form, wherein the polymorphic form is a crystalline form having an X-ray diffraction pattern (CuKα) comprising significant diffraction peaks at about 8.8, 12.9, 13.4, 14.2 and 17.4° 2θ. In non-limiting examples, the X-ray diffraction pattern (CuKα) is substantially as shown in FIG. 1A or FIG. 1B. In other variations, at least a portion of the CDDO-Me is present as a polymorphic form, wherein the polymorphic form is an amorphous form having an X-ray diffraction pattern (CuKα) with a halo peak at approximately 13.5° 2θ, substantially as shown in FIG. 1C, and a $T_g$. In some variations, the compound is an amorphous form. In some variations, the compound is a glassy solid form of CDDO-Me, having an X-ray powder diffraction pattern with a halo peak at about 13.5° 2θ, as shown in FIG. 1C, and a $T_g$. In some variations, the $T_g$ value falls within a range of about 120° C. to about 135° C. In some variations, the $T_g$ value is from about 125° C. to about 130° C.

In some embodiments, the compound is administered locally. In some embodiments, the compound is administered systemically. In some embodiments, the compound is administered orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, orally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or any combination thereof. For example, in some variations, the compound is administered intravenously, intra-arterially or orally. For example, in some variations, the compound is administered orally.

In some embodiments, the compound is formulated as a hard or soft capsule, a tablet, a syrup, a suspension, a solid dispersion, a wafer, or an elixir. In some variations, the soft capsule is a gelatin capsule. In variations, the compound is formulated as a solid dispersion. In some variations the hard capsule, soft capsule, tablet or wafer further comprises a protective coating. In some variations, the formulated compound comprises an agent that delays absorption. In some variations, the formulated compound further comprises an agent that enhances solubility or dispersibility. In some variations, the compound is dispersed in a liposome, an oil-in-water emulsion or a water-in-oil emulsion.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound. In some variations, the daily dose is from about 2.5 mg to about 30 mg of the compound. In some variations, the daily dose is about 2.5 mg of the compound. In other variations, the daily dose is about 5 mg of the compound. In other variations, the daily dose is about 10 mg of the compound. In other variations, the daily dose is about 15 mg of the compound. In other variations, the daily dose is about 20 mg of the compound. In still other variations, the daily dose is about 30 mg of the compound.

In some embodiments, the pharmaceutically effective amount is a daily dose of 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is administered in a single dose per day. In some embodiments, the pharmaceutically effective amount is administered in two or more doses per day.

In some embodiments, the patient is a mammal such as primate. In some variations, the primate is a human. In other variations, the patient is a cow, horse, dog, cat, pig, mouse, rat or guinea pig.

In some variations of the above methods, the compound is substantially free from optical isomers thereof. In some variations of the above methods, the compound is in the form of a pharmaceutically acceptable salt. In other variations of the above methods, the compound is not a salt.

In some embodiments, the compound is formulated as a pharmaceutical composition comprising (i) a therapeutically effective amount of the compound and (ii) an excipient selected from the group consisting of (A) a carbohydrate, carbohydrate derivative, or carbohydrate polymer, (B) a synthetic organic polymer, (C) an organic acid salt, (D) a protein, polypeptide, or peptide, and (E) a high molecular weight polysaccharide. In some variations, the excipient is a synthetic organic polymer. In some variations, the excipient is selected from the group consisting of a hydroxypropyl methyl cellulose, a poly[1-(2-oxo-1-pyrrolidinyl)ethylene] or copolymer thereof, and a methacrylic acid methylmethacrylate copolymer. In some variations, the excipient is hydroxypropyl methyl cellulose phthalate ester. In some variations, the excipient is PVP/VA. In some variations, the excipient is a methacrylic acid ethyl acrylate copolymer. In some variations, the methacrylic acid and ethyl acrylate may be present at a ratio of about 1:1. In some variations, the excipient is copovidone.

Any embodiment discussed herein with respect to one aspect of the invention applies to other aspects of the invention as well, unless specifically noted.

Further aspects and embodiments of this invention are elaborated in greater detail, for example, in the claims section, which is incorporated herein by reference.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows unmicronized Form A; FIG. 1B shows micronized Form A; FIG. 1C shows Form B.

FIG. 8A shows dosing with 20 mg BARD on Study Day 1. FIG. 8B shows dosing with 20 mg BARD on Study Day 6. FIG. 8C shows dosing with 80 mg BARD on Study Day 1. FIG. 8D shows dosing with 80 mg BARD on Study Day 6.

FIG. 10B). Time-to-first event analysis for avosentan-induced fluid overload events in ASCEND and heart failure in BEACON. Avosentan-induced fluid overload events in ASCEND were taken from the adverse event reports of the local investigators. Individual signs and symptoms on the adverse event forms indicating fluid overload included: heart failure, edema, fluid overload, fluid retention, hypervolemia, dyspnea, pleural and pericardial effusions, ascites, weight increase, pulmonary rales, and pulmonary edema. Analysis includes only heart failure events occurring on or prior to study drug termination date (Oct. 18, 2012) that were positively adjudicated by an independent Event Adjudication Committee, as outlined in the BEACON EAC Charter.

DESCRIPTION OF ILLUSTRATIVE EMBODIMENTS

Figure 1:
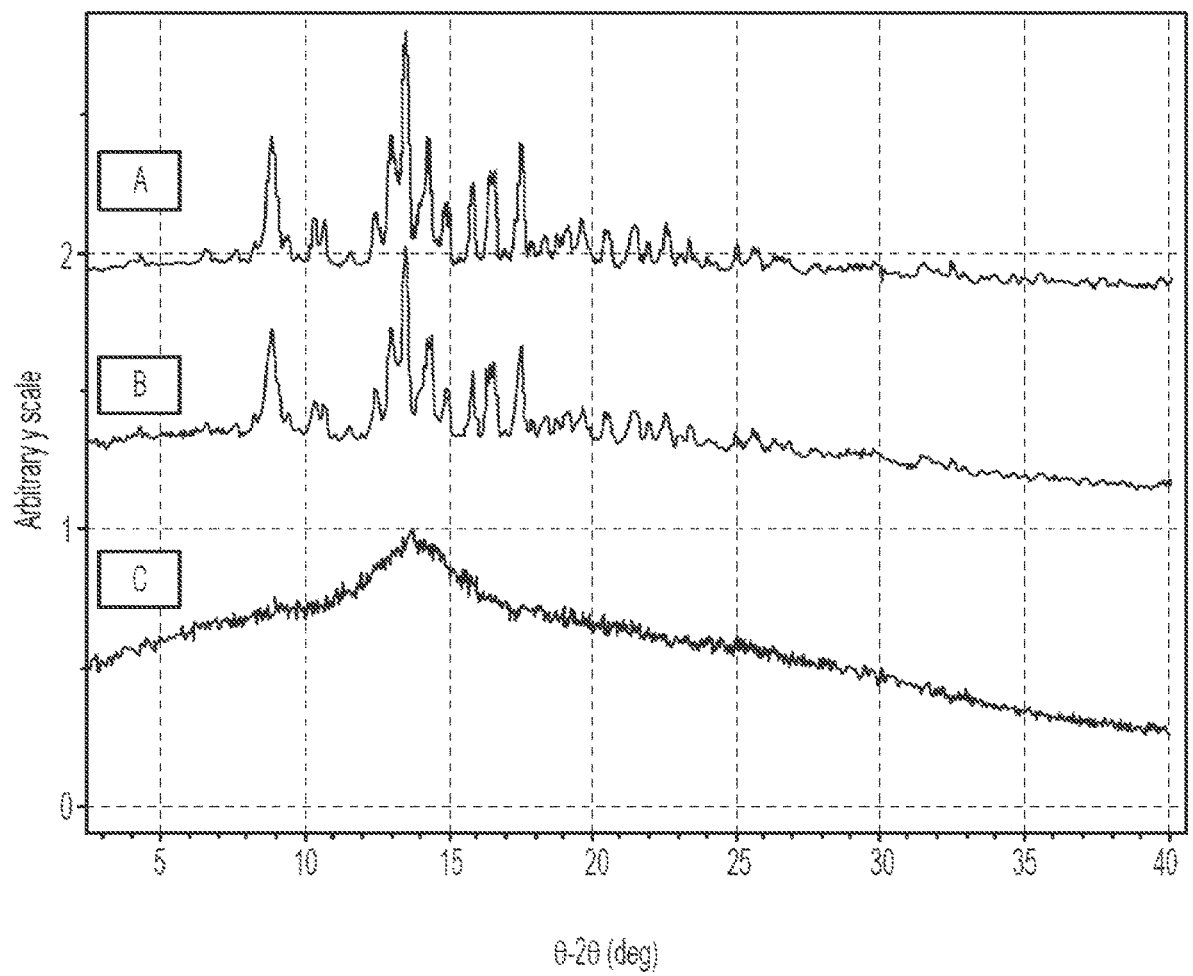
FIGS. 1A-C—X-ray Powder Diffraction (XRPD) Spectra of Forms A and B of RTA 402.

In one aspect, the present invention provides new methods for treating or preventing Alport syndrome or a symptom thereof or preventing the onset of symptoms of Alport syndrome in patients using bardoxolone methyl and analogs thereof. These and other aspects of the invention are described in greater detail below.

I. CHARACTERISTICS OF PATIENTS WHO SHOULD BE EXCLUDED FROM TREATMENT WITH BARDOXOLONE METHYL

Several clinical studies have shown that treatment with bardoxolone methyl improved markers of renal function (including estimated glomerular filtration rate, or eGFR), insulin resistance, and endothelial dysfunction (Pergola et al., 2011). These observations led to the initiation of a large Phase 3 trial (BEACON) of bardoxolone methyl in patients with stage 4 CKD and type 2 diabetes. The primary endpoint in the BEACON trial was a composite of progression to end-stage renal disease (ESRD) and all-cause mortality. This trial was terminated due to excess severe adverse events and mortality in the group of patients treated with bardoxolone methyl.

As discussed below, subsequent analysis of the data from the BEACON trial showed that most of the severe adverse events and mortality involved heart failure and were highly correlated with the presence of one or more risk factors including: (a) elevated baseline levels of B-type natriuretic peptide (BNP; e.g., >200 pg/mL); (b) baseline eGFR <20; (c) history of left-sided heart disease; (d) high baseline albumin-to-creatinine ratio (ACR; e.g., >300 mg/g as defined by dipstick proteinuria of 3+); and (e) advanced age (e.g., >75 years). The analysis indicated that heart failure events were likely related to the development of acute fluid overload in the first three to four weeks of bardoxolone methyl treatment and that this was potentially due to inhibition of endothelin-1 signaling in the kidney. A previous trial of an endothelin receptor antagonist in stage 4 CKD patients was terminated due to a pattern of adverse events and mortality very similar to that found in the BEACON trial. Subsequent non-clinical studies confirmed that bardoxolone methyl, at physiologically relevant concentrations, inhibits endothelin-1 expression in renal proximal tubule epithelial cells and inhibits endothelin receptor expression in human mesangial and endothelial cells. Accordingly, patients at risk of adverse events from inhibition of endothelin signaling should be excluded from future clinical use of bardoxolone methyl.

The present invention concerns new methods of treating Alport syndrome that include modification of the glomerular basement membrane as a significant contributing factor. It also concerns the preparation of pharmaceutical compositions for the treatment of such disorders. In some embodiments of the present invention, patients for treatment are selected on the basis of several criteria: (1) diagnosis of a disorder that involves endothelial dysfunction as a significant contributing factor; (2) lack of elevated levels of B-type natriuretic peptide (BNP; e.g., BNP titers must be <200 pg/mL); (3) lack of chronic kidney disease (e.g., eGFR >60) or lack of advanced chronic kidney disease (e.g., eGFR>45); (4) lack of a history of left-sided myocardial disease; and (5) lack of a high ACR (e.g., ACR below 300 mg/g). In some embodiments of the invention, patients with a diagnosis of type 2 diabetes are excluded. In some embodiments of the invention, patients with a diagnosis of cancer are excluded. In some embodiments, patients of advanced age (e.g., >75 years) are excluded. In some embodiments, patients are closely monitored for rapid weight gain suggestive of fluid overload. For example, patients may be instructed to weigh themselves daily for the first four weeks of treatment and contact the prescribing physician if increases of greater than five pounds are observed.

A. BEACON Study

1. Design of Study

Study 402-C-0903, titled "Bardoxolone Methyl Evaluation in Patients with Chronic Kidney Disease and Type 2 Diabetes: The Occurrence of Renal Events" (BEACON) was a phase 3, randomized, double-blind, placebo-controlled, parallel-group, multinational, multicenter study designed to compare the efficacy and safety of bardoxolone methyl (BARD) to placebo (PBO) in patients with stage 4 chronic kidney disease and type 2 diabetes. A total of 2,185 patients were randomized 1:1 to once-daily administration of bardoxolone methyl (20 mg) or placebo. The primary efficacy endpoint of the study was the time-to-first event in the composite endpoint defined as end-stage renal disease (ESRD; need for chronic dialysis, renal transplantation, or renal death) or cardiovascular (CV) death. The study had three secondary efficacy endpoints: (1) change in estimated glomerular filtration rate (eGFR); (2) time-to-first hospitalization for heart failure or death due to heart failure; and (3) time-to-first event of the composite endpoint consisting of non-fatal myocardial infarction, non-fatal stroke, hospitalization for heart failure, or cardiovascular death.

A subset of the BEACON patients consented to additional 24-hour assessments including ambulatory blood pressure monitoring (ABPM) and 24-hour urine collections. An independent Events Adjudication Committee (EAC), blinded to study treatment assignment, evaluated whether renal events, cardiovascular events, and neurological events met the pre-specified definitions of the primary and secondary endpoints. An IDMC, consisting of external clinical experts supported by an independent statistical group, reviewed unblinded safety data throughout the study and made recommendations as appropriate.

2. Demographics and Baseline Characteristics of the Population

Table 1 presents summary statistics on select demographic and baseline characteristics of patients enrolled in BEACON. Demographic characteristics were comparable across the two treatment groups. In all treatment groups combined, the average age was 68.5 years and 57% of the patients were male. The bardoxolone methyl arm had slightly more patients in the age subgroup ≥75 years than the placebo arm (27% in bardoxolone methyl arm versus 24% in the placebo arm). Mean weight and BMI across both treatment groups was 95.2 kg and 33.8 kg/m$^2$, respectively. Baseline kidney function was generally similar in the two treatment groups; mean baseline eGFR, as measured by the 4-variable Modified Diet in Renal Disease (MDRD) equation, was 22.5 mL/min/1.73 m$^2$ and the geometric mean albumin/creatinine ratio (ACR) was 215.5 mg/g for the combined treatment groups.

TABLE 1

Select Demographics and Baseline Characteristics of Bardoxolone Methyl (BARD) versus Placebo (PBO) Patients in BEACON (ITT Population)

| | BARD N = 1088 | PBO N = 1097 | Total N = 2185 |
|---|---|---|---|
| Sex, n (%) | | | |
| Male | 626 (58) | 625 (57) | 1251 (57) |
| Female | 462 (42) | 472 (43) | 934 (43) |
| Age at informed consent (years) | | | |
| n | 1088 | 1097 | 2185 |
| Mean (SD) | 68.9 (9.7) | 68.2 (9.4) | 68.5 (9.6) |
| Range (min, max) | 32, 92 | 29, 93 | 29, 93 |
| Age subgroup, n (%) | | | |
| <75 | 786 (72) | 829 (76) | 1615 (74) |
| ≥75 | 302 (27) | 268 (24) | 570 (26) |
| Weight (kg) | | | |
| n | 1087 | 1097 | 2184 |
| Mean (SD) | 95.1 (22.0) | 95.3 (21.1) | 95.2 (21.5) |
| Range (min, max) | 46, 194 | 45, 186 | 45, 194 |
| BMI (kg/m$^2$) | | | |
| n | 1087 | 1097 | 2184 |
| Mean (SD) | 33.7 (7.1) | 33.9 (7.2) | 33.8 (7.1) |
| Range (min, max) | 19, 93 | 19, 64 | 19, 93 |
| eGFR (mL/min/1.73 m$^2$) mean (SD) | | | |
| n | 1088 | 1097 | 2185 |
| Mean (SD) | 22.4 (4.3) | 22.5 (4.6) | 22.5 (4.5) |
| Range (min, max) | 13, 34 | 13, 58 | 13, 58 |
| eGFR MDRD subgroup, n (%) | | | |
| 15-<20 | 325 (30) | 347 (32) | 672 (31) |
| 20-<25 | 399 (37) | 366 (33) | 765 (35) |
| 25-<30 | 311 (29) | 318 (29) | 629 (29) |
| ACR (mg/g) geometric mean | | | |
| n | 1088 | 1097 | 2185 |
| Geometric mean | 210.4 | 220.7 | 215.5 |
| (95% CI) | (188, 236) | (196, 249) | (198, 234) |
| Range (min, max) | <1, 4581 | <1, 79466 | <1, 79466 |
| ACR subgroup, n (%) | | | |
| <30 | 200 (18) | 211 (19) | 411 (19) |
| 30-300 | 348 (32) | 308 (28) | 656 (30) |
| >300 | 540 (50) | 578 (53) | 1118 (51) |

Patients were administered placebo or 20 mg of bardoxolone methyl once daily.

B. BEACON Results

1. Effect of Bardoxolone Methyl on eGFR

Figure 2:
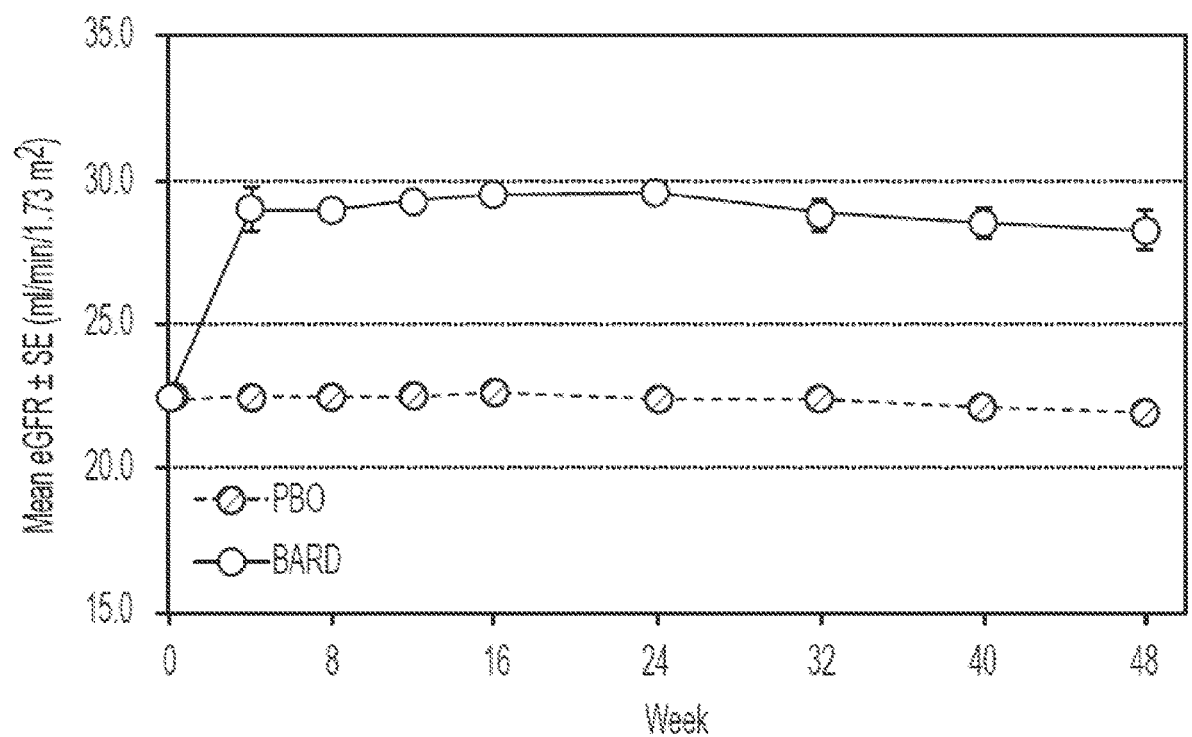
FIG. 2—Mean eGFR Over Time in BEACON (Safety Population). Mean observed eGFR over time by treatment week in placebo (PBO) versus bardoxolone methyl (BARD) patients. Only includes assessments of eGFR collected on or before a patient's last dose of study drug. Visits are derived relative to a patient's first dose of study drug. Data are mean SE.
Figure 3A:
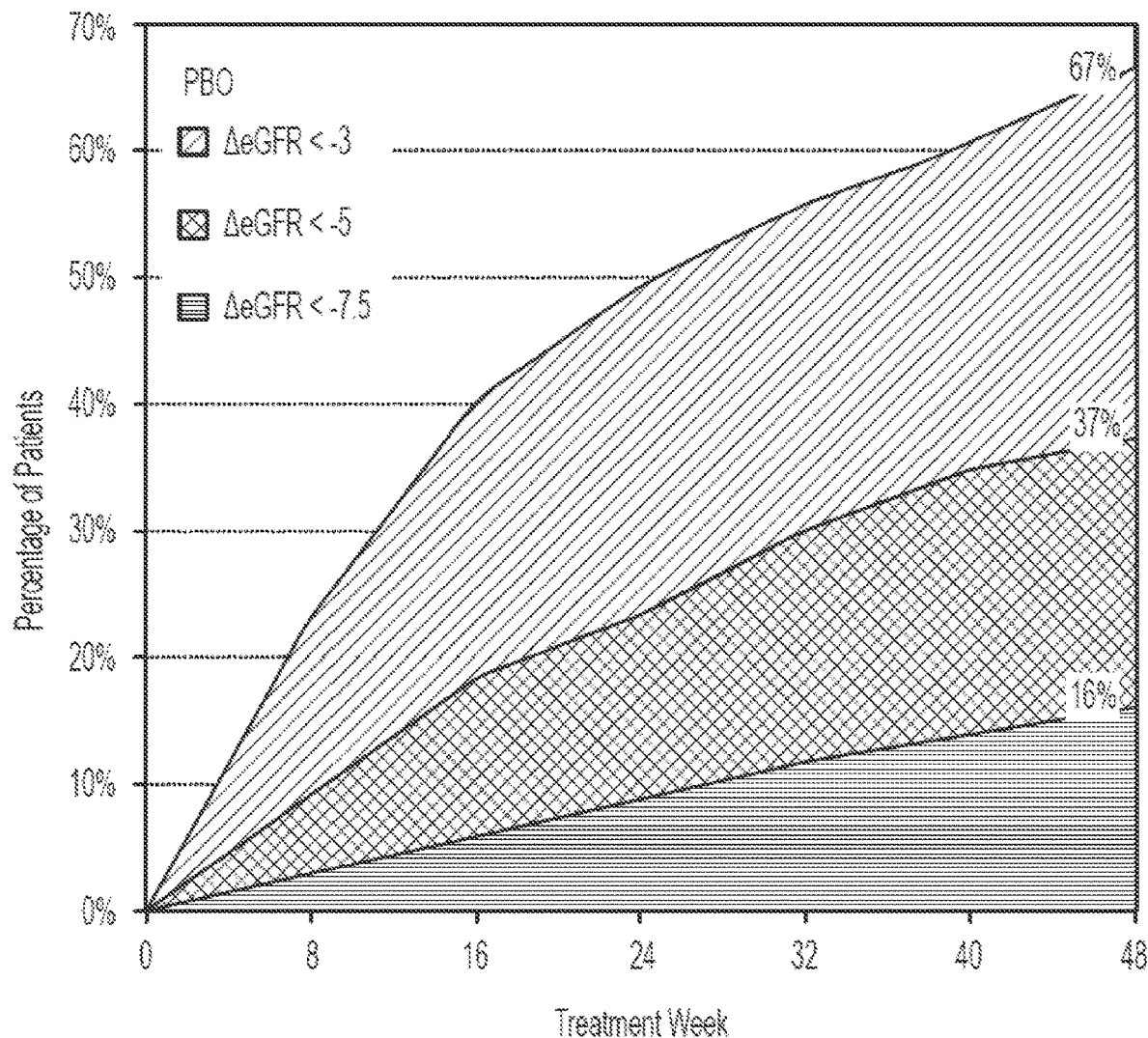
FIGS. 3A-B—Percentage of eGFR Decliners in Bardoxolone Methyl vs. Placebo Patients in BEACON (Safety Population). Percentage of patients with changes in eGFR from baseline of <−3, <−5, or <−7.5 mL/min/1.73 m$^2$ by treatment week in placebo (PBO) (FIG. 3A) versus bardoxolone methyl (BARD) (FIG. 3B) patients. Only includes assessments of eGFR collected on or before a patient's last dose of study drug. Visits are derived relative to a patient's first dose of study drug. Percentages calculated relative to number of patients with available eGFR data at each visit. The number of placebo patients with data for FIG. 3A were 1093 at Week 0, 1023 at Week 8, 885 at Week 16, 726 at Week 24, 547 at Week 32, 402 at Week 40, and 281 at Week 48. The number of placebo patients with data for FIG. 3B were 1092 at Week 0, 958 at Week 8, 795 at Week 16, 628 at Week 24, 461 at Week 32, 345 at Week 40, and 241 at Week 48.
Figure 3B:
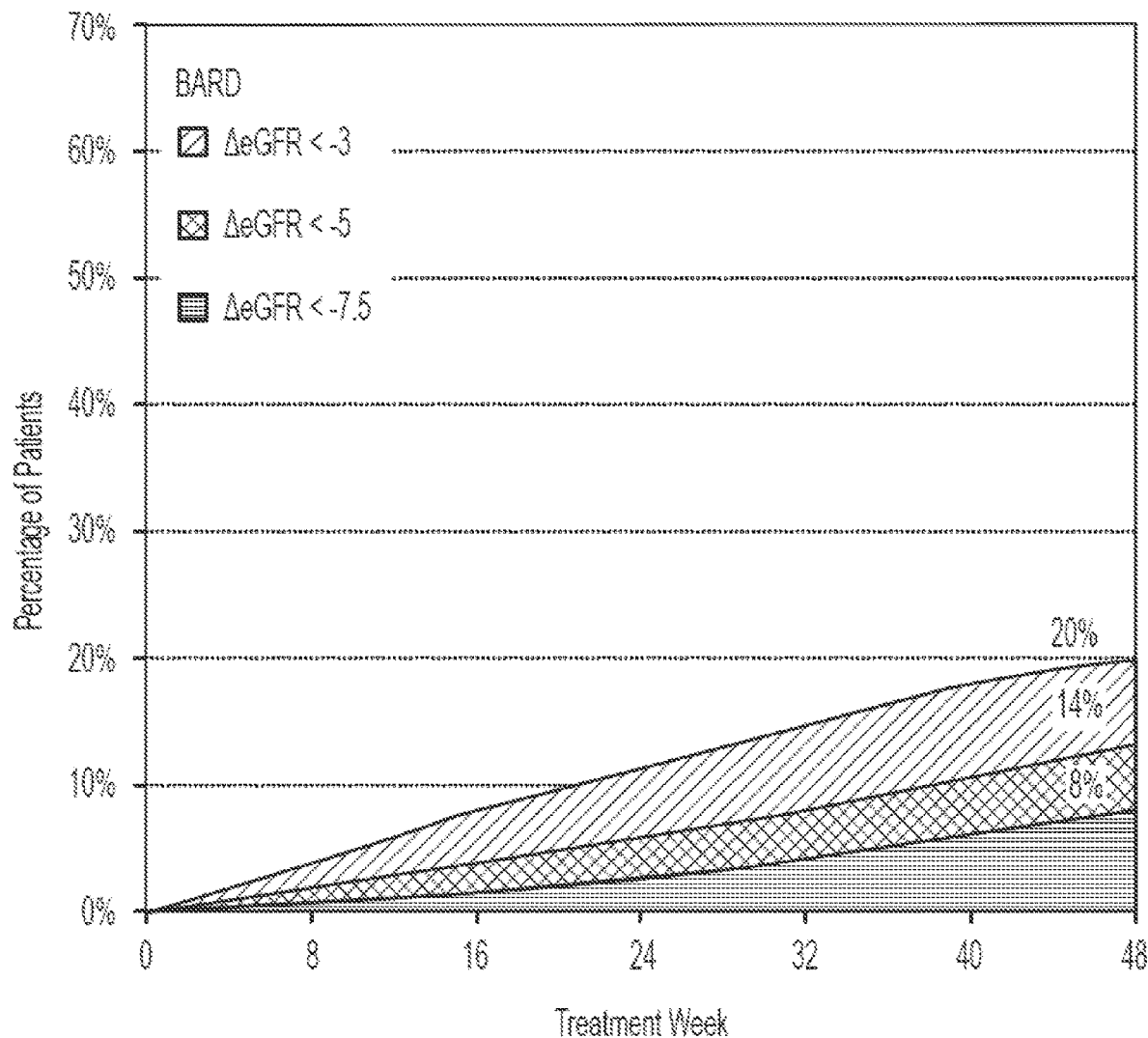

The mean eGFR values for bardoxolone methyl-treated and placebo-treated patients are shown in FIG. 2. On average, bardoxolone methyl patients had expected increases in eGFR that occurred by Week 4 of treatment and remained above baseline through Week 48. In contrast, placebo-treated patients on average had unchanged or slight decreases from baseline. The proportion of patients with eGFR declines was markedly reduced in bardoxolone methyl-versus placebo-treated patients (FIGS. 3A-B). The eGFR trajectories and the proportions of decliners observed in BEACON after one year of treatment were consistent with modeled expectations and results from the BEAM study (RTA42-C-0804). As shown in Table 2, the number of patients who experienced a renal and urinary disorder serious adverse event (SAE) was lower in the bardoxolone methyl group than in the placebo group (52 vs. 71, respectively). Additionally, and as discussed in the following section, slightly fewer ESRD events were observed in the bardoxolone methyl group than in the placebo group. Collectively, these data suggest that bardoxolone methyl treatment did not worsen renal status acutely or over time.

TABLE 2

Incidence of Treatment-Emergent Serious Adverse Events in BEACON within Each Primary System Organ Class (Safety Population)

| MedDRA System Organ Class | Placebo N = 1093 n (%) | Bardoxolone methyl N = 1092 n (%) |
|---|---|---|
| Patients with any serious adverse event | 295 (27) | 363 (33) |
| Number of serious adverse events | 557 | 717 |
| Cardiac disorders | 84 (8) | 124 (11) |
| Infections and infestations | 63 (6) | 79 (7) |
| Renal and urinary disorders | 71 (6) | 52 (5) |
| Metabolism and nutrition disorders | 42 (4) | 51 (5) |
| Gastrointestinal disorders | 39 (4) | 46 (4) |
| Respiratory, thoracic and mediastinal disorders | 32 (3) | 43 (4) |
| Nervous system disorders | 35 (3) | 37 (3) |
| General disorders and administration site conditions | 20 (2) | 29 (3) |
| Vascular disorders | 18 (2) | 20 (2) |
| Injury, poisoning and procedural complications | 17 (2) | 19 (2) |
| Musculoskeletal and connective tissue disorders | 13 (1) | 21 (2) |
| Blood and lymphatic system disorders | 11 (1) | 20 (2) |
| Neoplasms benign, malignant and unspecified (incl. cysts and polyps) | 10 (1) | 11 (1) |
| Hepatobiliary disorders | 8 (1) | 4 (<1) |
| Psychiatric disorders | 3 (<1) | 3 (<1) |
| Eye disorders | 2 (<1) | 3 (<1) |
| Investigations | 2 (<1) | 3 (<1) |
| Reproductive system and breast disorders | 3 (<1) | 2 (<1) |
| Skin and subcutaneous tissue disorders | 1 (<1) | 4 (<1) |
| Ear and labyrinth disorders | 1 (<1) | 3 (<1) |
| Endocrine disorders | 1 (<1) | 1 (<1) |
| Immune system disorders | 0 | 2 (<1) |
| Surgical and medical procedures | 0 | 2 (<1) |

Table includes only serious adverse events with onset more than 30 days after a patient's last dose of study drug. Column header counts and denominators are the number of patients in the safety population. Each patient is counted at most once in each System Organ Class and Preferred Term.

2. Primary Composite Outcome in BEACON

Figure 4:
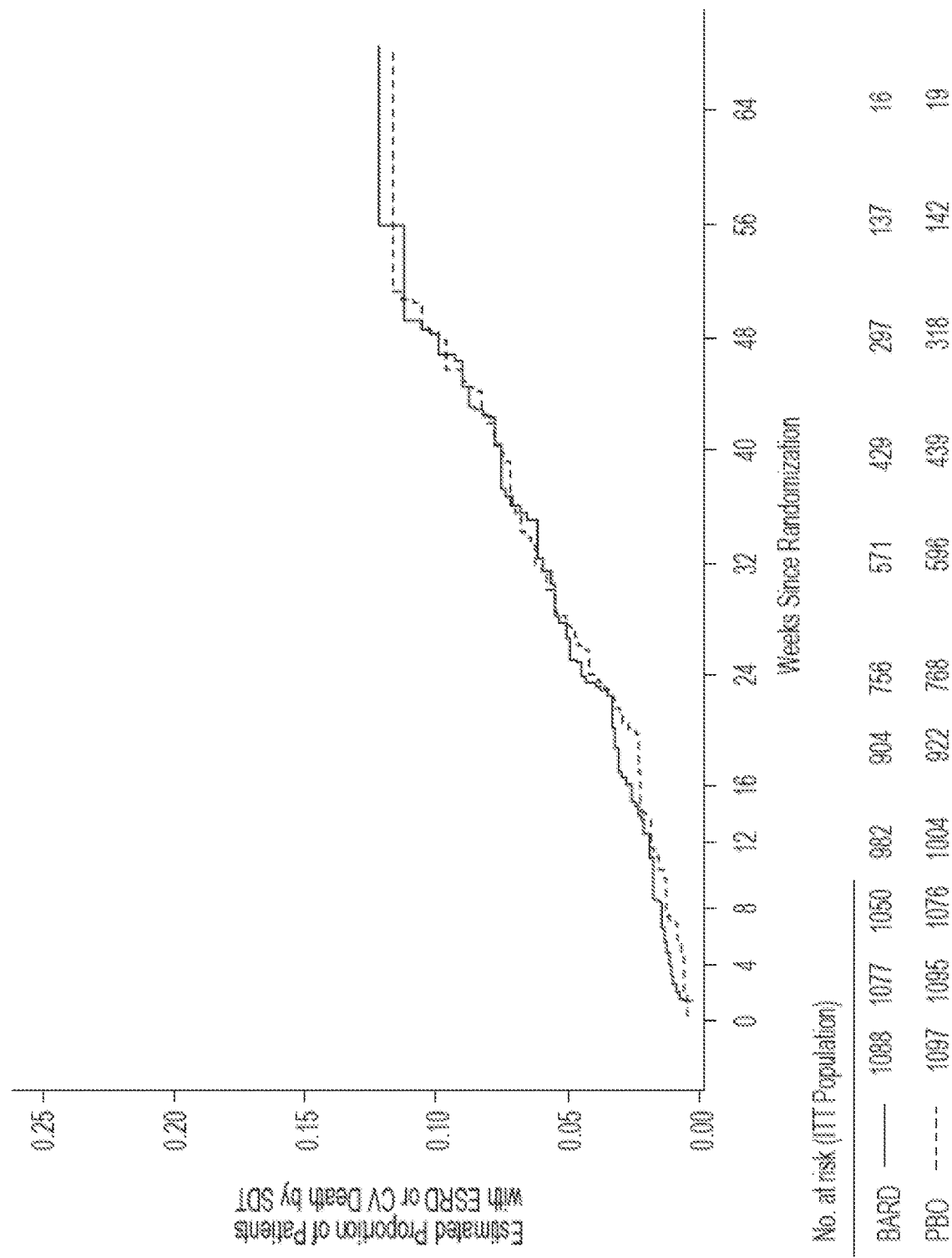
FIG. 4—Time to Composite Primary Outcome Event in BEACON (ITT Population). Results from a randomized, double-blind, placebo-controlled phase 3 study in T2D patients with Stage 4 CKD (BEACON, RTA402-C-0903). Patients were administered placebo (PBO) or 20 mg of bardoxolone methyl (BARD) once daily. Analysis includes only end-stage renal disease (ESRD) or cardiovascular (CV) death events occurring on or prior to study drug termination date (SDT) (Oct. 18, 2012) that were positively adjudicated by an independent Event Adjudication Committee, as outlined in the BEACON EAC Charter.

Table 3 provides a summary of adjudicated primary endpoints that occurred on or before the date of study termination (Oct. 18, 2012). Despite the slight reduction in the number of ESRD events in the bardoxolone methyl vs. placebo treatment groups, the number of composite primary endpoints was equal in the two treatment groups (HR=0.98) due to a slight increase in cardiovascular death events, as depicted in plots of time-to-first composite primary event analysis (FIG. 4).

TABLE 3

Adjudicated Primary Endpoints in Bardoxolone Methyl (BARD) vs. Placebo (PBO) Patients in BEACON (ITT Population)

|  | PBO N = 1097 n(%) | BARD N = 1088 n(%) | Hazard ratio (95% CI)[a] | p-value[b] |
|---|---|---|---|---|
| Composite primary efficacy outcome Patient's first event | 69 (6) | 69 (6) | 0.98 (0.70, 1.37) | 0.92 |
| End stage renal disease (ESRD) | 51 (5) | 43 (4) | | |
| Chronic dialysis | 47 (4) | 40 (4) | | |
| Renal transplant | 3 (<1) | 1 (<1) | | |
| Renal death | 1 (<1) | 2 (<1) | | |
| CV death | 18 (2) | 26 (2) | | |

[a]Hazard ratio (bardoxolone methyl/placebo) and 95% confidence interval (CI) were estimated using a Cox proportional hazards model with treatment group, continuous baseline eGFR, and continuous baseline log ACR as covariates. Breslow's method of handling ties in event time was used.
[b]Treatment group comparisons used SAS's Type 3 chi-square test and two-sided p-value associated with the treatment group variable in the Cox proportional hazards model.

C. Effects of Bardoxolone Methyl on Heart Failure and Blood Pressure

1. Adjudicated Heart Failure in BEACON

The data in Table 4 present a post-hoc analysis of demographic and select laboratory parameters of BEACON patients stratified by treatment group and occurrence of an adjudicated heart failure event. The number of patients with heart failure includes all events through last date of contact (ITT Population).

Comparison of baseline characteristics of patients with adjudicated heart failure events revealed that both bardoxolone methyl-treated and placebo-treated patients with heart failure were more likely to have had a prior history of cardiovascular disease and heart failure and had higher baseline values for B-type natriuretic peptide (BNP) and QTc interval with Fredericia correction (QTcF). Even though the risk for heart failure was higher in the bardoxolone methyl-treated patients, these data suggest that development of heart failure in both groups appeared to be associated with traditional risk factors for heart failure. Baseline ACR was significantly higher in bardoxolone methyl-treated patients with heart failure events than those without. Also of note, the mean baseline level of BNP in patients who experienced heart failure in both treatment groups was meaningfully elevated and suggested that these patients were likely retaining fluid and in sub-clinical heart failure prior to randomization.

TABLE 4

Select Demographic and Baseline Characteristics for Bardoxolone Methyl vs.
Placebo Patients Stratified by Heart Failure Status

| | Patients | | | | | |
|---|---|---|---|---|---|---|
| | With Heart Failure | | Without Heart Failure | | Total | |
| | BARD (N = 103) | PBO (N = 57) | BARD (N = 985) | PBO (N = 1040) | BARD (N = 1088) | PBO (N = 1097) |
| Age (years), Mean ± SD | 70.3 ± 9 | 69.2 ± 8.2 | 68.7 ± 9.8 | 68.1 ± 9.5 | 68.9 ± 9.7 | 68.2 ± 9.4 |
| History of CVD, N (%) | 80 (78)[a] | 47 (82)[b] | 529 (54) | 572 (55) | 609 (56) | 619 (56) |
| History of HF, N (%) | 36 (35)[a] | 21 (37)[b] | 130 (13) | 133 (13) | 166 (15) | 154 (14) |
| History of MI, N (%) | 33 (32)[a] | 22 (39)[b] | 185 (19) | 188 (18) | 218 (20) | 210 (19) |
| History of A-FIB, N (%) | 4 (4) | 3 (5) | 46 (5) | 40 (4) | 50 (5) | 43 (4) |
| Concomitant Med Use, N (%) | | | | | | |
| ACEi/ARB | 35 (34)[a] | 16 (28)[b] | 659 (67) | 701 (67) | 694 (64) | 717 (65) |
| Diuretic | 39 (38)[a] | 15 (26)[b] | 528 (54) | 586 (56) | 567 (52) | 601 (55) |
| Beta-Blocker | 38 (37)[a] | 23 (40) | 482 (49) | 506 (49) | 520 (48) | 529 (48) |
| Statin | 57 (55) | 26 (46)[b] | 640 (65) | 721 (69) | 697 (64) | 747 (68) |
| Calcium Channel Blocker | 25 (24)[a] | 17 (30)[b] | 406 (41) | 467 (45) | 431 (40) | 484 (44) |
| eGFR (mL/min/1.73 m$^2$), Mean ± SD | 21.7 ± 4.6 | 22.2 ± 4.7 | 22.5 ± 4.2 | 22.5 ± 4.6 | 22.4 ± 4.3 | 22.5 ± 4.6 |
| ACR (mg/g), Geo Mean | 353.9[a] | 302.0 | 199.3 | 216.9 | 210.4 | 220.7 |
| SBP (mmHg), Mean ± SD | 139.5 ± 13.3 | 142.3 ± 11.2 | 139.5 ± 11.6 | 139.6 ± 11.8 | 139.5 ± 11.7 | 139.8 ± 11.8 |
| DBP (mmHg), Mean ± SD | 66.4 ± 9.1[a] | 69.1 ± 8.8 | 70.4 ± 8.7 | 70.8 ± 8.6 | 70.1 ± 8.8 | 70.7 ± 8.7 |
| BNP (pg/mL) | | | | | | |
| Mean ± SD | 526.0 ± 549.4[a] | 429.8 ± 434.3[b] | 223.1 ± 257.5 | 232.3 ± 347.1 | 251.2 ± 309.1 | 242.7 ± 354.7 |
| >100, N (%) | 78 (76)a | 43 (75)[b] | 547 (56) | 544 (52) | 625 (57) | 587 (54) |
| QTcF (ms) | | | | | | |
| Mean ± SD | 447.9 ± 31.2[a,c] | 432.5 ± 27.6[b] | 425.3 ± 27.8 | 424.7 ± 27.9 | 427.4 ± 28.9 | 425.1 ± 28 |
| >450, N (%) | 40 (39)[a] | 14 (25) | 170 (17) | 167 (16) | 210 (19) | 181 (16) |

[a] $p < 0.05$ for BARD patients with HF vs. BARD patients without HF
[b] $p < 0.05$ for PBO patients with HF vs. PBO patients without HF
[c] $p < 0.05$ for BARD vs. PBO patients with HF 2. Assessment of Clinical Parameters Associated with BNP Increases As a surrogate of fluid retention, a post-hoc analysis was performed on a subset of patients for whom BNP data were available at baseline and Week 24. Patients in the bardoxolone methyl arm experienced a significantly greater increase in BNP than patients in the placebo arm (Mean±SD: 225±598 vs. 34±209 pg/mL, $p<0.01$). Also noted was a higher proportion of bardoxolone methyl-vs. placebo-treated patients with increases in BNP at Week 24 (Table 5).

BNP increases at Week 24 did not appear to be related to baseline BNP, baseline eGFR, changes in eGFR, or changes in ACR. However, in bardoxolone methyl-treated patients only, baseline ACR was significantly correlated with Week 24 changes from baseline in BNP, suggesting that the propensity for fluid retention may be associated with baseline severity of renal dysfunction, as defined by albuminuria status, and not with the general changes in renal function, as assessed by eGFR (Table 6).

Further, these data suggest that increases in eGFR, which are glomerular in origin, are distinct anatomically, as sodium and water regulation occurs in the renal tubules.

TABLE 5

Analysis of BNP and eGFR Values of Bardoxolone Methyl vs. Placebo Patients Stratified by Changes from Baseline in BNP at Week 24

| WK24 BNP Change | Treatment | N | Median BL BNP | Mean BL eGFR | Mean WK24 ΔeGFR |
|---|---|---|---|---|---|
| <25% Increase | PBO | 131 | 119.0 | 23.5 | −0.6 |
| | BARD | 84 | 187.0 | 22.3 | 6.1 |
| 25% to 100% Increase | PBO | 48 | 102.5 | 22.0 | 0.4 |
| | BARD | 45 | 119.0 | 22.7 | 5.5 |
| ≥100% Increase | PBO | 37 | 143.5 | 23.1 | 0.1 |
| | BARD | 82 | 155.0 | 21.9 | 7.6 |

Post-hoc analysis of changes in BNP in BEACON at Week 24.

TABLE 6

Correlations between Changes from Baseline in BNP at Week 24 and Baseline ACR in Bardoxolone Methyl vs. Placebo Patients in BEACON

| Treatment | N | Correlation Coefficient | P-value |
|---|---|---|---|
| PBO | 216 | 0.05 | 0.5 |
| BARD | 211 | 0.20 | <0.01 |

Post-hoc analysis of changes in BNP in BEACON at Week 24. Only patients with baseline and Week 24 BNP values included in analysis.

3. Serum Electrolytes

Figure 5:
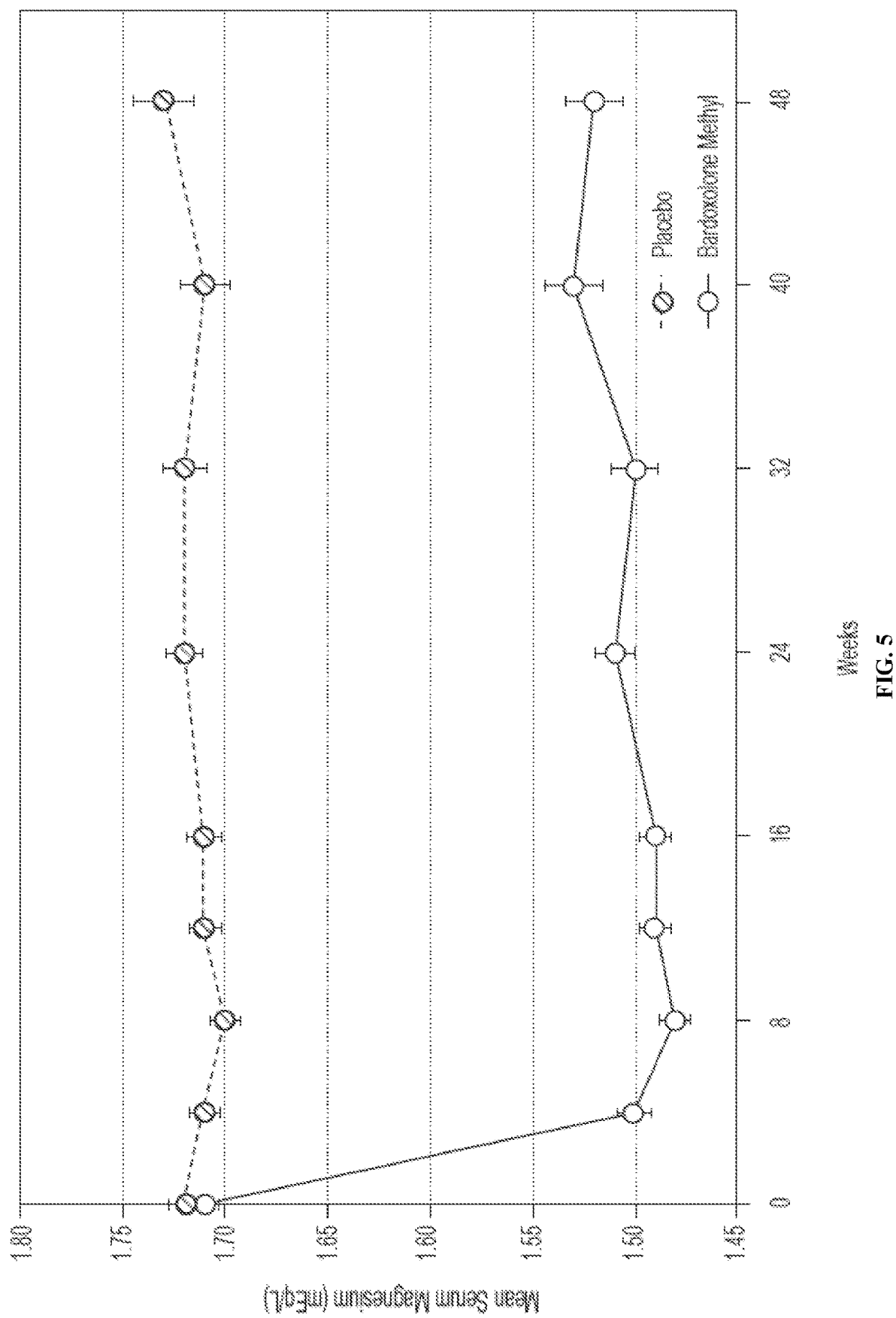
FIG. 5—Mean Serum Magnesium Levels in Bardoxolone Methyl vs. Placebo Patients in BEACON. Mean observed serum magnesium levels over time by treatment week in placebo vs. bardoxolone methyl patients. Only includes assessments of serum magnesium collected on or before a patient's last dose of study drug. Visits are derived relative to a patient's first dose of study drug. Data are mean SE. Top line is placebo; bottom line is bardoxolone methyl.

No clinically meaningful changes were noted in serum potassium or serum sodium for the subset of patients with 24-hr urine collections (Table 7). The change in serum magnesium levels in bardoxolone methyl-treated patients was consistent with changes observed in prior studies (FIG. 5).

TABLE 7

Week 4 Changes from Baseline in Serum Electrolytes in Bardoxolone Methyl vs. Placebo 24-hour ABPM Sub-Study Patients

| | | Serum Potassium (mmol/L) | | | Serum Sodium (mmol/L) | | | Serum Magnesium (mEq/L) | | |
|---|---|---|---|---|---|---|---|---|---|---|
| | | BL | WK4 | WK4 Δ | BL | WK4 | WK4 Δ | BL | WK4 | WK4 Δ |
| PBO | n | 88 | 87 | 87 | 88 | 87 | 87 | 88 | 87 | 87 |
| | Mean ± SE | 4.8 ± 0.1 | 4.7 ± 0.1 | −0.10 ± 0.04* | 140.2 ± 0.2 | 139.7 ± 0.3 | −0.3 ± 0.2 | 1.72 ± 0.03 | 1.69 ± 0.03 | −0.03 ± 0.02 |
| BARD | n | 83 | 77 | 77 | 83 | 77 | 77 | 83 | 77 | 77 |
| | Mean ± SE | 4.7 ± 0.1 | 4.8 ± 0.1 | 0.10 ± 0.05*† | 140.1 ± 0.3 | 140.3 ± 0.3 | 0.2 ± 0.3 | 1.74 ± 0.02 | 1.53 ± 0.03 | −0.21 ± 0.02*† |

Data include only BEACON patients enrolled in the 24-hour ABPM sub-study.
Changes in serum electrolyte values only calculated for patients with baseline and Week 4 data.
*$p < 0.05$ for Week 4 versus baseline values within each treatment group;
†$p < 0.05$ for Week 4 changes in BARD vs. PBO patients.

4. 24-Hour Urine Collections

A subset of patients consented to additional 24-hr assessments (sub-study) of ambulatory blood pressure monitoring (ABPM) and 24-hr urine collection at selected visits. Urinary sodium excretion data from BEACON sub-study patients revealed a clinically meaningful reduction in urine volume and excretion of sodium at Week 4 relative to baseline in the bardoxolone methyl-treated patients (Table 8). These decreases were significantly different from Week 4 changes in urine volume and urinary sodium observed in placebo-treated patients. Also of note, reductions in serum magnesium were not associated with renal loss of magnesium.

Additionally, in a pharmacokinetic study in patients with type 2 diabetes and stage 3b/4 CKD administered bardoxolone methyl for eight weeks (402-C-1102), patients with stage 4 CKD had significantly greater reductions of urinary sodium and water excretion than stage 3b CKD patients (Table 9).

TABLE 8

Week 4 Changes from Baseline in 24-hour Urine Volume, Urinary Sodium, and Urinary Potassium in Bardoxolone Methyl vs. Placebo 24-hour ABPM Sub-Study Patients

| | | Urine Volume (mL) | | | Urinary Sodium (mmol/24 h) | | | Urinary Potassium (mmol/24 h) | | | Urinary Magnesium (mmol/24 h) | | |
|---|---|---|---|---|---|---|---|---|---|---|---|---|---|
| | | BL | WK4 | WK4 Δ | BL | WK4 | WK4 Δ | BL | WK4 | WK4 Δ | BL | WK4 | WK4 Δ |
| PBO | n | 87 | 72 | 71 | 81 | 68 | 62 | 81 | 68 | 62 | 59 | 53 | 46 |
| | Mean ± SE | 2053 ± 82 | 1928 ± 89 | −110 ± 71 | 160 ± 8 | 145 ± 8 | −11 ± 9 | 55 ± 3 | 52 ± 3 | −3 ± 3 | 7.5 ± 0.5 | 6.0 ± 0.5 | −0.6 ± 0.4 |
| BARD | n | 82 | 64 | 63 | 77 | 61 | 57 | 77 | 61 | 57 | 56 | 43 | 40 |
| | Mean ± SE | 2024 ± 83 | 1792 ± 84 | −247 ± 71* | 164 ± 9 | 140 ± 9 | −27 ± 9* | 60 ± 3 | 52 ± 2 | −7 ± 3* | 7.0 ± 0.4 | 6.0 ± 0.4 | −0.9 ± 0.5 |

Data include only BEACON patients enrolled in the 24-hour ABPM sub-study.
Changes at Week 4 only calculated for patients with baseline and Week 4 data.
*$p < 0.05$ for Week 4 versus baseline values within each treatment group;
† $p < 0.05$ for Week 4 changes in BARD versus PBO patients.

TABLE 9

Week 8 Changes from Baseline in 24-h Urine Volume and 24-h
Urinary Sodium Bardoxolone Methyl-treated Patients Grouped
by CKD Severity (from a Patient Pharmacokinetic Study)

| CKD Stage | N | Urine Volume (mL) WK8 Δ | p-value | Urinary Sodium (mmol/24 h) WK8 Δ | p-value |
|---|---|---|---|---|---|
| Stage 3b | 9 | 355 | 0.04 | −12 | 0.02 |
| Stage 4 | 6 | −610 | | −89 | |

Patients were treated with 20 mg bardoxolone methyl once daily for 56 consecutive days; post-treatment follow-up visit occurred on Study Day 84. Data are means. Data include patients with baseline and Week 8 data.

5. Hospital Records from EAC Adjudication Packets

The first scheduled post-baseline assessment in BEACON was at Week 4. Since many of the heart failure events occurred prior to Week 4, the clinical database provides limited information to characterize these patients. Post-hoc review of the EAC case packets for heart failure cases that occurred prior to Week 4 was performed to assess clinical, vitals, laboratory, and imaging data collected at the time of the first heart failure event (Tables 10 and 11).

Examination of these records revealed common reports of rapid weight gain immediately after randomization, dyspnea and orthopnea, peripheral edema, central/pulmonary edema on imaging, elevated blood pressure and heart rate, and preserved ejection fraction. The data suggest that heart failure was caused by rapid fluid retention concurrent with preserved ejection fraction and elevated blood pressure. The preserved ejection fraction is consistent with clinical characteristics of heart failure caused by diastolic dysfunction stemming from ventricular stiffening and impaired diastolic relaxation. This collection of signs and symptoms differs in clinical characteristics from heart failure with reduced ejection fraction, which occurs because of weakened cardiac pump function or contractile impairment (Vasan et al., 1999). Therefore, rapid fluid accumulation in patients with stiff ventricles and minimal renal reserve likely resulted in increased fluid back-up into the lungs and the noted clinical presentation.

Baseline central laboratory values from the clinical database were compared to local laboratory values obtained on admission for heart failure that were included in the EAC packets. Unchanged serum creatinine, sodium, and potassium concentrations in bardoxolone methyl-treated patients with heart failure events that occurred within the first four weeks after randomization (Table 11) suggest that heart failure was not associated with acute renal function decline or acute kidney injury. Overall, the clinical data suggest that the etiology of heart failure is not caused by a direct renal or cardiotoxic effect, but is more likely to be due to sodium and fluid retention.

TABLE 10

Post-Hoc Analysis of Cardiovascular Parameters of Bardoxolone Methyl vs. Placebo
Patients with Heart Failure Events Occurring Within First Four Weeks of Treatment

| | | LVEF HF | SBP (mmHg) BL | SBP HF | SBP Δ | DBP (mmHg) BL | DBP HF | DBP Δ | Heart Rate (bpm) BL | HR HF | HR Δ |
|---|---|---|---|---|---|---|---|---|---|---|---|
| PBO | n | 4 | 8 | 6 | 6 | 8 | 6 | 6 | 8 | 5 | 5 |
| | Mean ± SE | 49% ± 6% | 141 ± 5 | 148 ± 11 | 4.7 ± 7.2 | 65 ± 3 | 65 ± 5 | 1.2 ± 3.6 | 70 ± 3 | 65 ± 3 | −3.6 ± 2.9 |
| BARD | n | 23 | 42 | 33 | 33 | 42 | 34 | 34 | 42 | 32 | 32 |
| | Mean ± SE | 52% ± 2% | 142 ± 2 | 154 ± 4 | 10.5 ± 3.1 | 67 ± 2 | 75 ± 2 | 7.9 ± 2.1 | 67 ± 1 | 81 ± 3 | 14.5 ± 2.7 |

Post-hoc analyses of heart failure cases in BEACON.
Vital signs at baseline calculated from the average of three standard cuff measurements.
Vital signs from HF hospitalization gathered from admission notes included in EAC Adjudication packets and represent singular assessments using different BP monitoring equipment.
LVEF only assessed during HF hospitalization.
Timing of HF admission calculated from event start date and treatment start date and varied from Weeks 0-4 for each patient.

TABLE 11

Post-Hoc Analysis of Serum Electrolytes of Bardoxolone Methyl vs. Placebo Patients
with Heart Failure Events Occurring Within First Four Weeks of Treatment

| | | Serum Creatinine (mg/dL) BL | HF | Δ | Serum Sodium (mmol/L) BL | HF | Δ | Serum Potassium (mmol/L) BL | HF | Δ |
|---|---|---|---|---|---|---|---|---|---|---|
| PBO | n | 8 | 8 | 8 | 8 | 8 | 8 | 8 | 8 | 8 |
| | Mean ± SE | 3.4 ± 0.2 | 3.3 ± 0.2 | −0.1 ± 0.2 | 140.0 ± 1.0 | 137.0 ± 1.0 | −2.5 ± 0.6 | 4.5 ± 0.2 | 4.4 ± 0.1 | −0.1 ± 0.2 |
| BARD | n | 42 | 38 | 38 | 42 | 30 | 30 | 42 | 34 | 34 |
| | Mean ± SE | 2.8 ± 0.1 | 2.7 ± 0.1 | −0.1 ± 0.1 | 140.0 ± 0.0 | 139.0 ± 1.0 | −1.0 ± 0.5 | 4.7 ± 0.1 | 4.8 ± 0.1 | 0.1 ± 0.1 |

Post-hoc analyses of heart failure cases in BEACON.
Baseline clinical chemistries assessed at central laboratory.
Clinical chemistries from HF hospitalization gathered from hospital notes included in EAC Adjudication packets and represent assessments made at different local laboratories.

6. Blood Pressure in BEACON

Figure 6A:
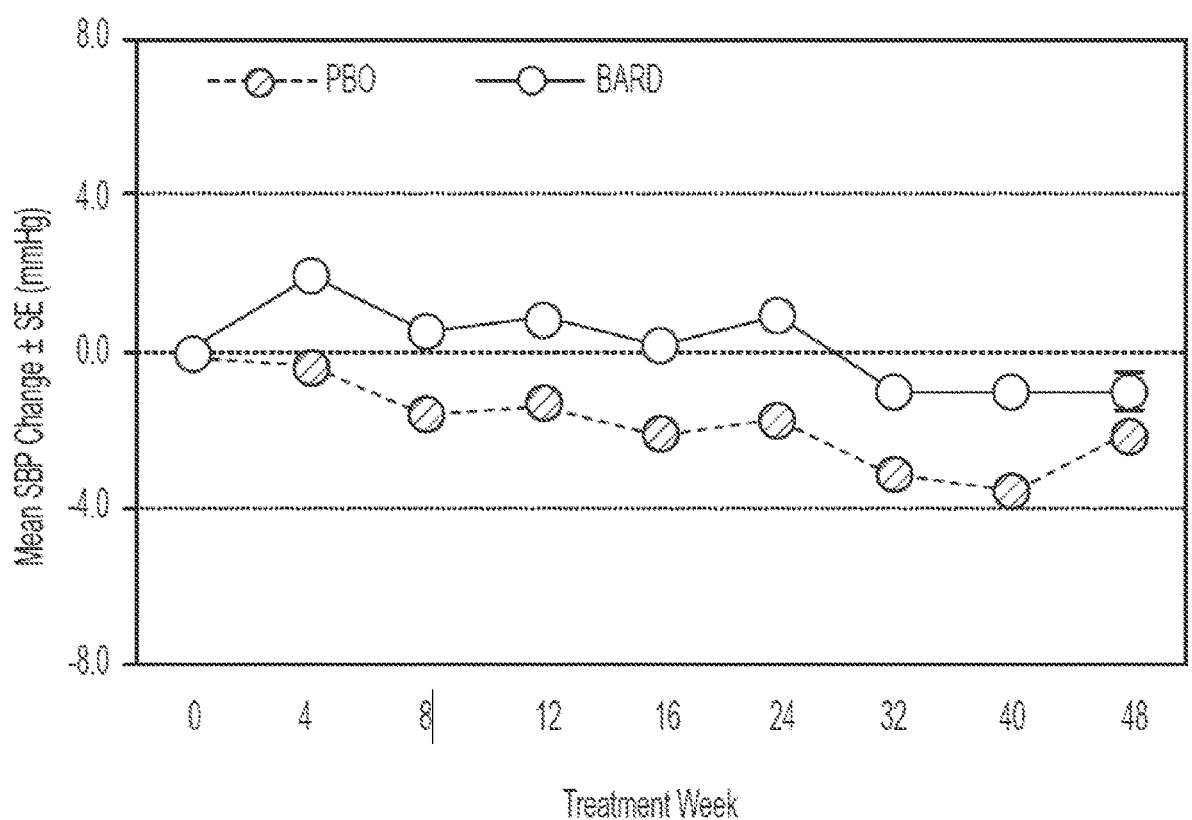
FIGS. 6A-B—Changes from Baseline over Time in Systolic Blood Pressure (SBP) (FIG. 6A) and Diastolic Blood Pressure (DBP) (FIG. 6B) in Bardoxolone Methyl (BARD) vs. Placebo (PBO) Patients in BEACON (Safety Population). Data includes only vital assessments collected on or before a patient's last dose of study drug. Visits are derived relative to a patient's first dose of study drug. Data are mean SE.
Figure 6B:
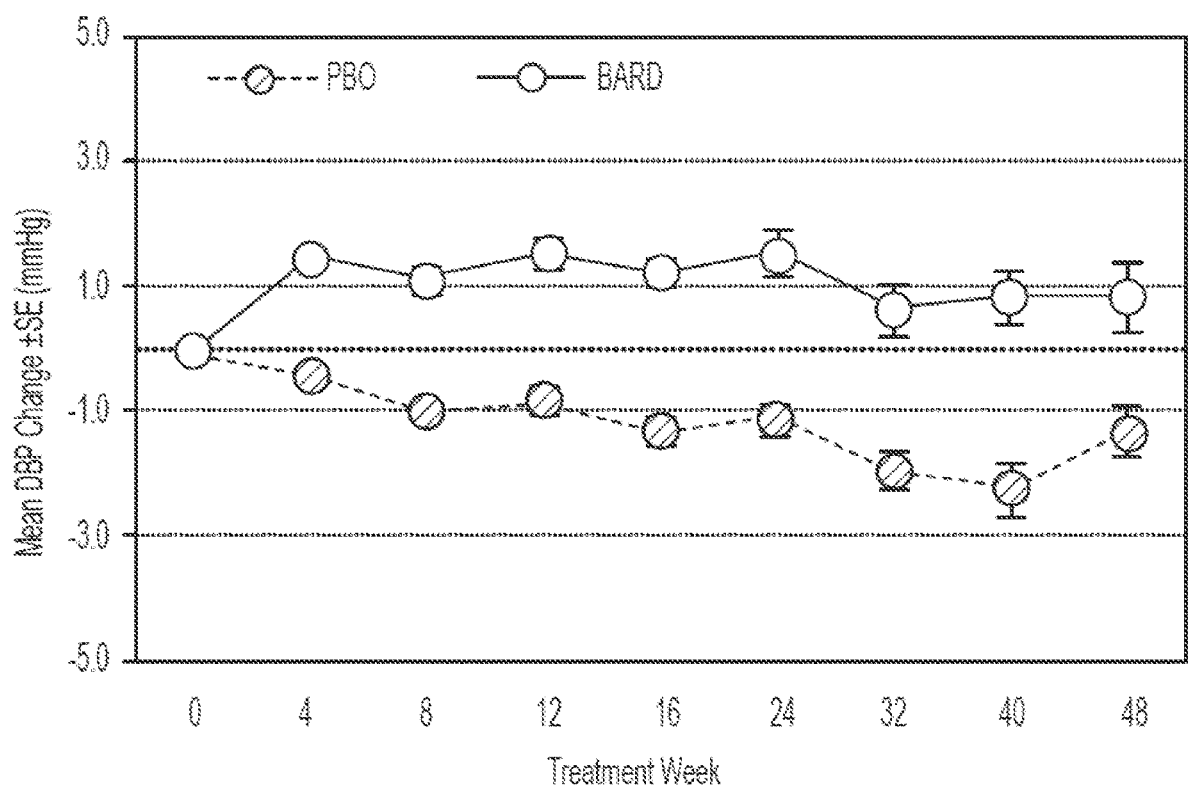

Mean changes from baseline in systolic and diastolic blood pressures for bardoxolone methyl-treated and placebo-treated patients, based on the average of triplicate standardized blood pressure cuff measurements collected at each visit, are shown in FIGS. 6A-B. Blood pressure was increased in the bardoxolone methyl group relative to the placebo group, with mean increases of 1.9 mmHg in systolic and 1.4 mmHg in diastolic blood pressures noted in the bardoxolone methyl group by Week 4 (the first post-randomization assessment). The increases in systolic blood pressure (SBP) appeared to diminish by Week 32, while diastolic blood pressure (DBP) increases were sustained.

Figure 7A:
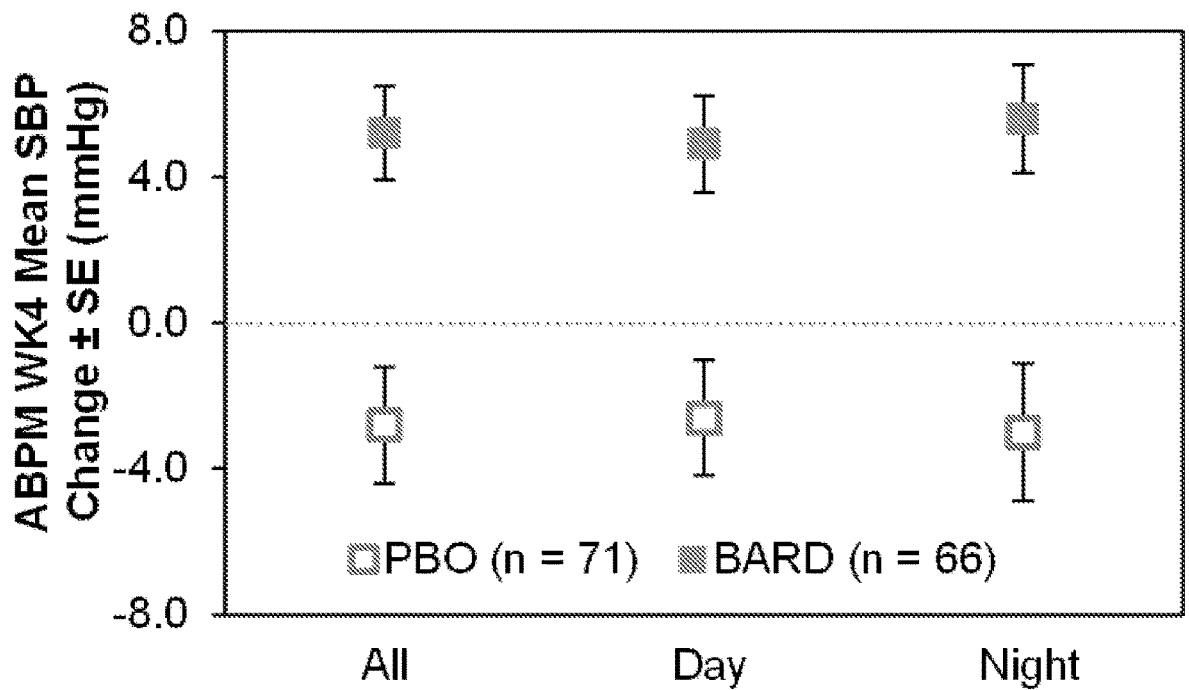
FIGS. 7A-B—Twenty-four-hour Ambulatory Blood Pressure Monitoring (ABPM) Sub-Study: Week 4 Changes from Baseline to Week 4 in Systolic Blood Pressure (SBP) (FIG. 7A) and Diastolic Blood Pressure (DBP) (FIG. 7B) in Bardoxolone Methyl (BARD) vs. Placebo (PBO) Patients. Data include only patients with baseline and Week 4 24-h ABPM values. Changes in systolic blood pressure are calculated using the averages of all valid measurements taken from a patient's ambulatory blood pressure monitoring device during the entire 24-h period, daytime (6 A.M. to 10 P.M.), or nighttime (10 P.M. to 6 A.M. the next day). Data are mean±SE.
Figure 7B:
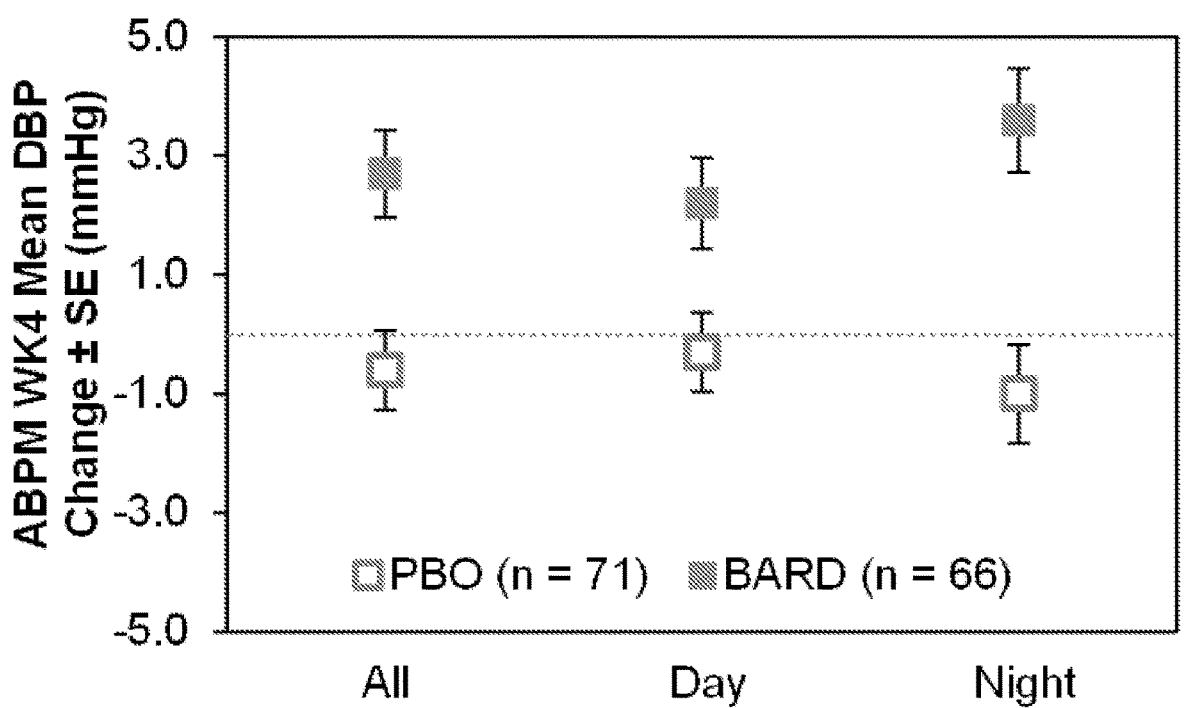
Figure 8A:
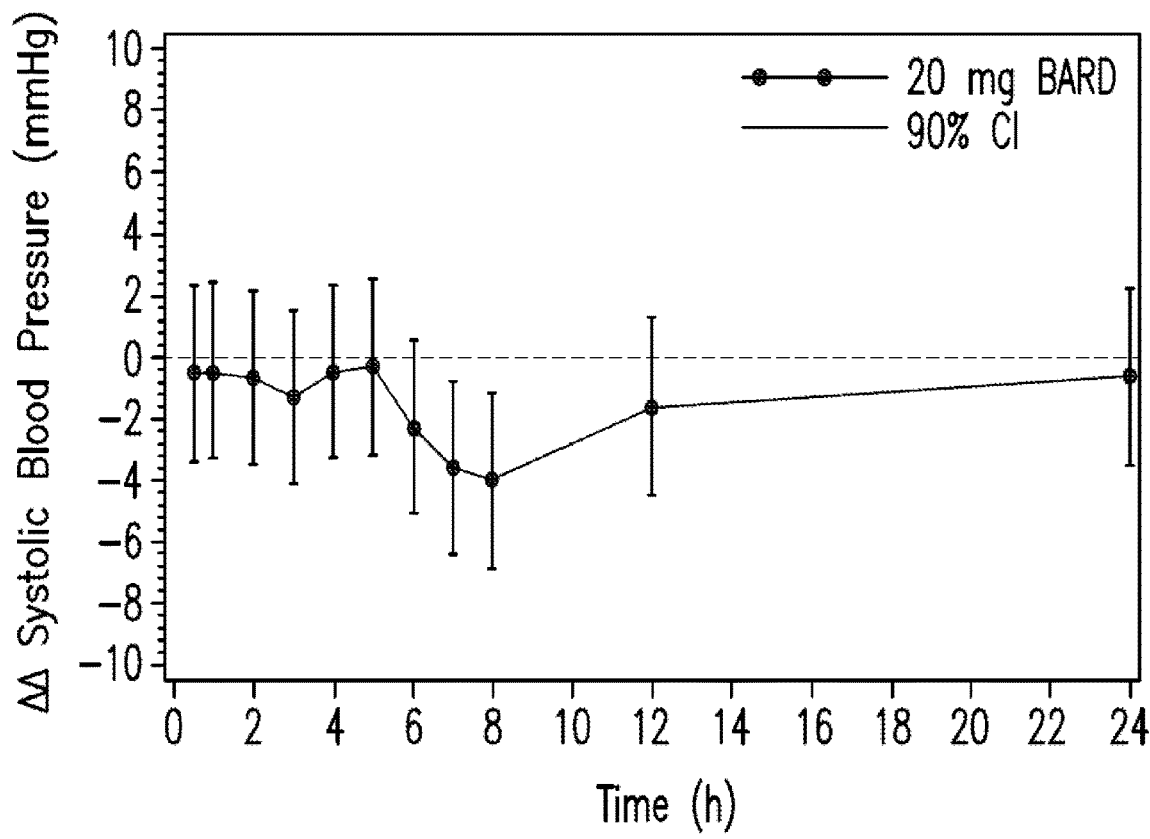
FIGS. 8A-D—Placebo-Corrected Changes from Baseline in Systolic Blood Pressure on Study Days 1 and 6 in Healthy Volunteers Administered Bardoxolone Methyl (BARD). Results from a multiple-dose, randomized, double-blind, placebo-controlled thorough QT study in healthy volunteers (RTA402-C-1006). Patients were treated with placebo, 20 mg or 80 mg of bardoxolone methyl, or 400 mg of moxifloxacin (active comparator) once daily for six consecutive days. Data are mean changes (SD) from baseline 0-24 hours post-dose on Study Day 1 and Study Day 6.
Figure 8B:
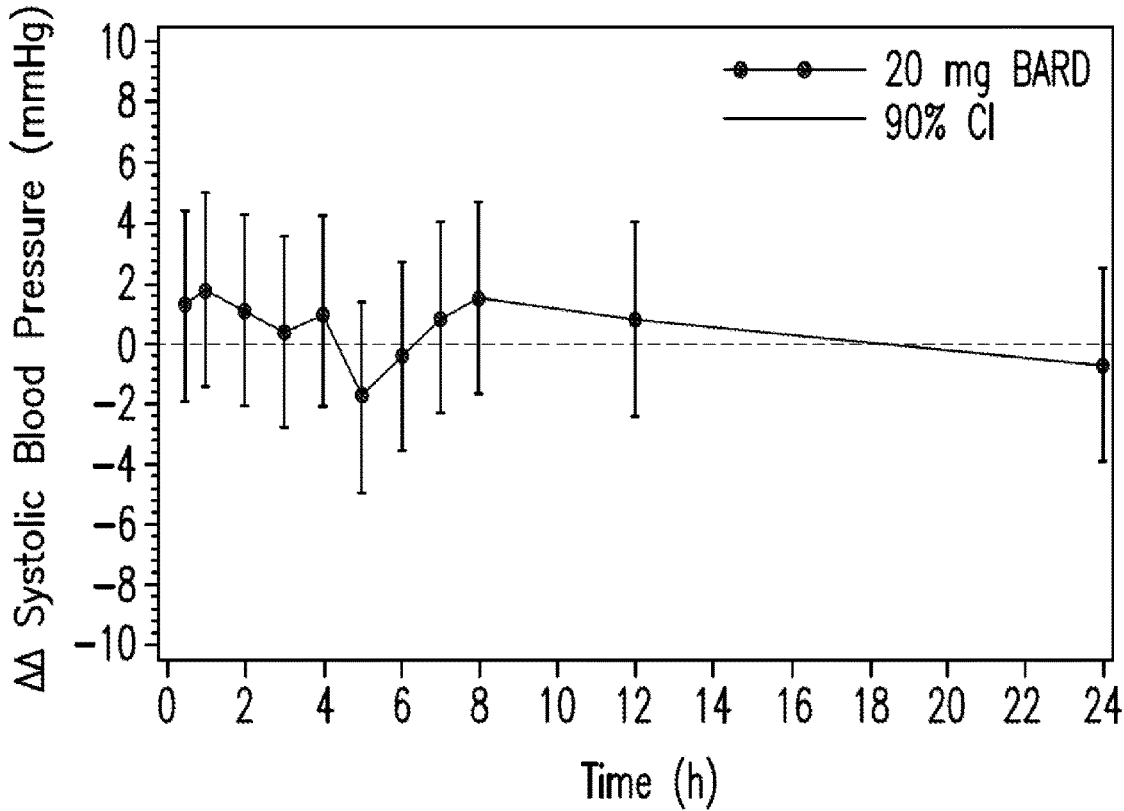
Figure 8C:
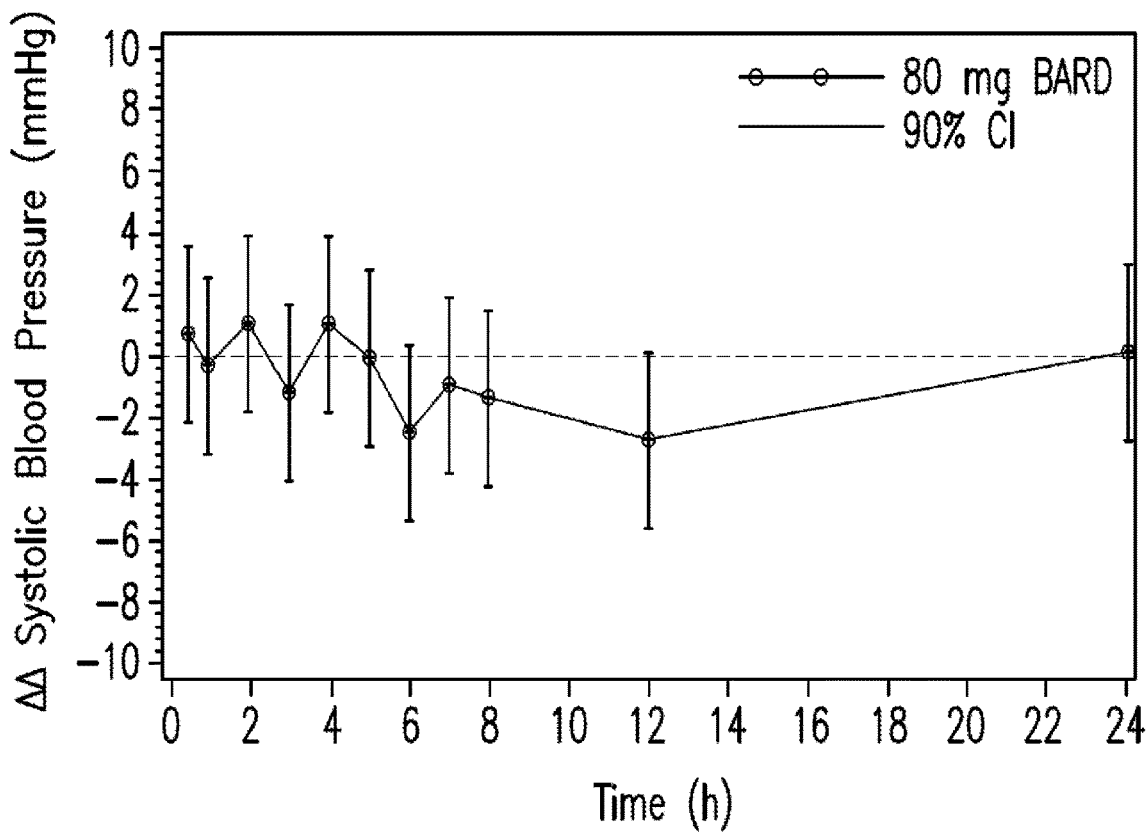
Figure 8D:
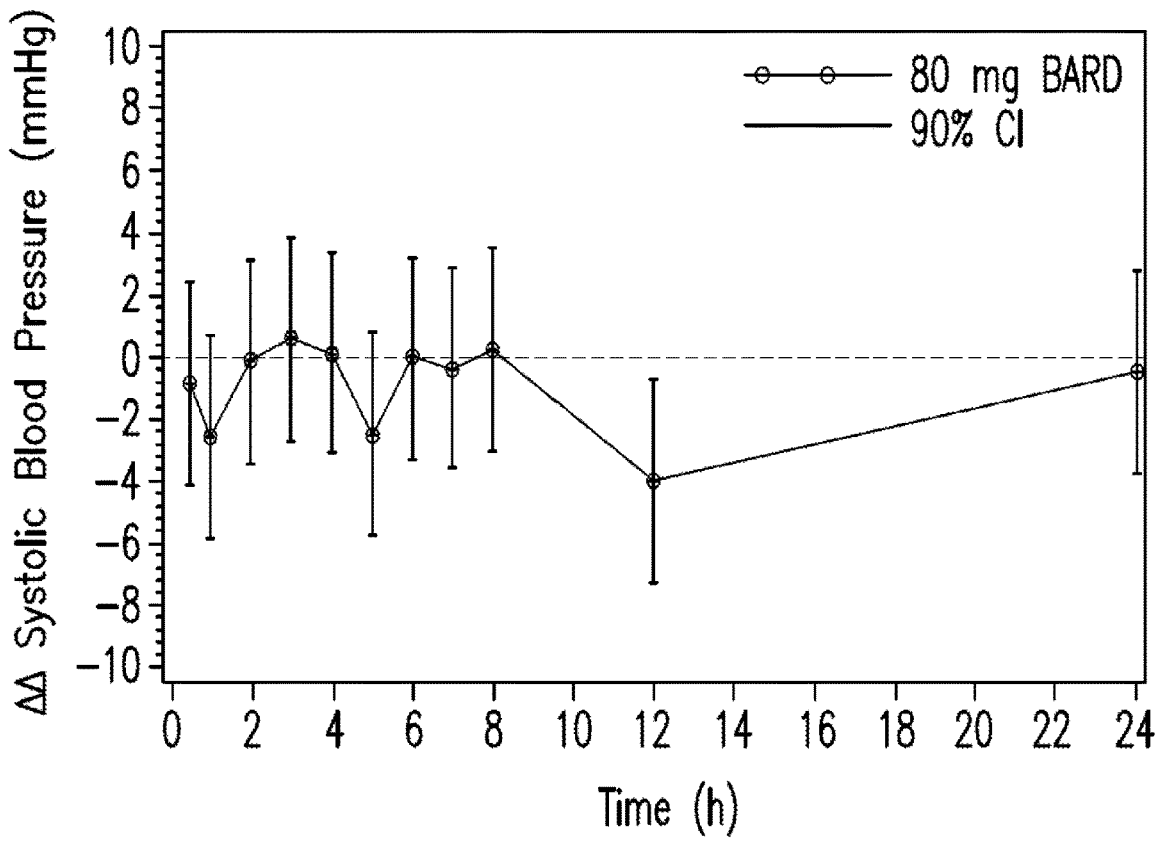

The Week 4 SBP and DBP increases in bardoxolone methyl-treated patients relative to placebo-treated patients were more apparent in the ABPM measurements (FIGS. 7A-B). This difference in magnitude could be due to the different techniques that were used or to differences in baseline characteristics in the ABPM sub-study patients. Patients in the ABPM sub-study had a higher baseline ACR than the entire population. Regardless, the data demonstrate that bardoxolone methyl increased blood pressure in the BEACON patient population.

7. Blood Pressure Changes in Prior CKD Studies

In an open label, dose-ranging study in type 2 diabetic patients with stage 3b-4 CKD (402-C-0902), no dose-related trend in blood pressure changes or change at any individual dose level was noted following 85 consecutive days of treatment at doses ranging from 2.5 to 30 mg of bardoxolone methyl (amorphous dispersion formulation, as used in BEACON). Post-hoc analysis of blood pressure data stratified by CKD stage suggests that bardoxolone methyl-treated patients with stage 4 CKD tended to have increases in blood pressure relative to baseline levels, with the effect most appreciable in the three highest dose groups, whereas bardoxolone methyl-treated patients with stage 3b CKD had no apparent change (Table 12). Although sample sizes in the dose groups stratified by CKD stage are small, these data suggest that the effect of bardoxolone methyl treatment on blood pressure may be related to CKD stage.

Blood pressure values from a phase 2b study with bardoxolone methyl (BEAM, 402-C-0804), which used an earlier crystalline formulation of the drug and employed a titration design, were highly variable and despite noted increases in some bardoxolone methyl treatment groups, no clear dose-related trend was observed in blood pressure.

TABLE 12

Changes from Baseline in Systolic and Diastolic Blood Pressure in Patients with Type 2 Diabetes and Stage 3b-4 CKD Stratified by Baseline CKD Stage Dosed with Bardoxolone Methyl

| Dose (mg) | CKD Stage | N | ASBP | ADBP |
|---|---|---|---|---|
| 2.5 | 3b/4 | 14 | 0.1 ± 4.2 | 0.2 ± 1.8 |
| | 3b | 10 | 0 ± 4.4 | 1 ± 2 |
| | 4 | 4 | 0.3 ± 11 | −1.5 ± 3.9 |
| 5 | 3b/4 | 24 | −1.5 ± 2.3 | −1.4 ± 1.5 |
| | 3b | 19 | −2.1 ± 2 | −1.3 ± 1.4 |
| | 4 | 5 | 0.5 ± 9.1 | −1.4 ± 5.6 |
| 10 | 3b/4 | 24 | −2.4 ± 3.1 | 0.3 ± 1.3 |
| | 3b | 20 | −4.2 ± 3.4 | −0.3 ± 1.3 |
| | 4 | 4 | 6.1 ± 6.7 | 3.6 ± 4.5 |
| 15 | 3b/4 | 48 | 1.1 ± 2.3 | −1 ± 1.2 |
| | 3b | 26 | −2.2 ± 3.3 | −1.3 ± 1.5 |
| | 4 | 22 | 5 ± 2.8 | −0.6 ± 1.9 |
| 30 | 3b/4 | 12 | 7.2 ± 6.2 | 3.2 ± 2.2 |
| | 3b | 3 | −0.4 ± 13.8 | −1.8 ± 3.9 |
| | 4 | 9 | 9.7 ± 7.3 | 4.7 ± 2.5 |

Patients were administered 2.5, 5, 10, 15, or 30 mg doses of bardoxolone methyl once daily for 85 days.

8. Blood Pressure and QTcF in Healthy Volunteers

Figure 9A:
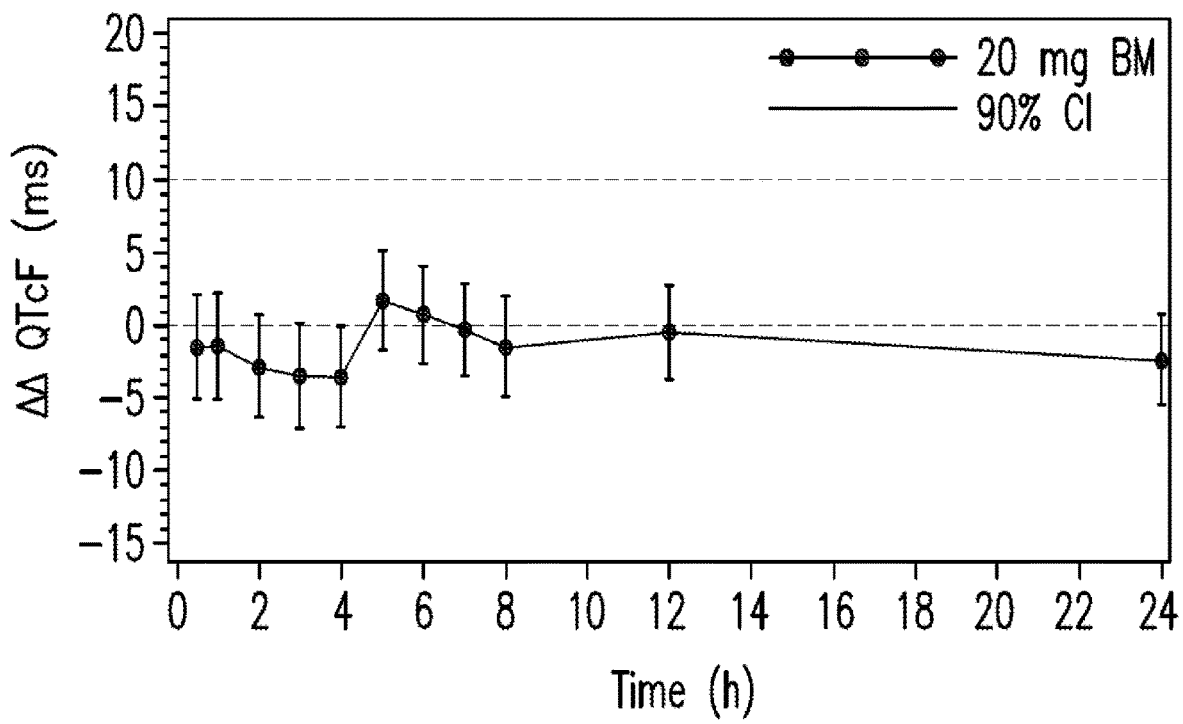
FIGS. 9A-B—Placebo-Corrected Changes from Baseline in QTcF in Healthy Volunteers Administered Bardoxolone Methyl (BM). Results from a multiple-dose, randomized, double-blind, placebo-controlled thorough QT study in healthy volunteers (RTA402-C-1006). QTcF interval changes in subjects administered bardoxolone methyl (20 mg or 80 mg—FIG. 9A and FIG. 9B, respectively) are shown relative to changes in patients receiving placebo treatment for six consecutive days. Data are mean values±90% CI, assessed 0-24 hours post-dose on Study Day 6, where the upper limit of the 90% CI is equivalent to the 1-sided, upper 95% confidence limit. The 10 ms threshold reference line is relevant to the upper confidence limits.
Figure 9B:
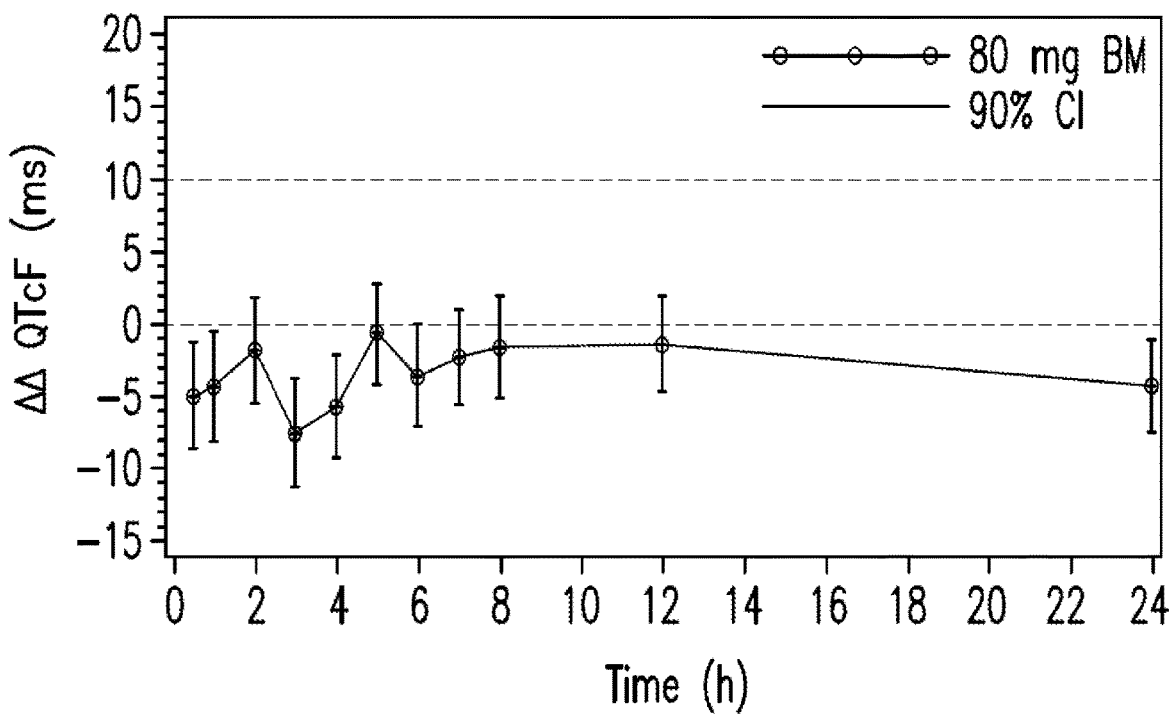

Intensive blood pressure monitoring was employed in a separate Thorough QT Study, which was conducted in healthy volunteers. In both bardoxolone methyl-treated groups, one given the therapeutic dose, 20 mg, which was also studied in BEACON, and one given the supratherapeutic dose of 80 mg, the change in blood pressure did not differ from changes observed in placebo-treated patients (FIGS. 8A-D) after 6 days of once daily administration. Bardoxolone methyl did not increase QTcF as assessed by placebo-corrected QTcF changes (ΔΔQTcF) after 6 days of treatment at 20 or 80 mg (FIGS. 9A-B).

Bardoxolone methyl has also been tested in non-CKD disease settings. In early clinical studies of bardoxolone methyl in oncology patients (RTA 402-C-0501, RTA 402-C-0702), after 21 consecutive days of treatment at doses that ranged from 5 to 1300 mg/day (crystalline formulation), no mean change in blood pressure was observed across all treatment groups. Similarly, in a randomized, placebo-controlled study in patients with hepatic dysfunction (RTA 402-C-0701), 14 consecutive days of bardoxolone methyl treatment at doses of 5 and 25 mg/day (crystalline formulation) resulted in mean decreases in systolic and diastolic blood pressure (Table 13).

Collectively, these data suggest that bardoxolone methyl does not prolong the QT interval and does not cause blood pressure increases in patients who do not have baseline cardiovascular morbidity or stage 4 CKD.

TABLE 13

Changes from Baseline in Blood Pressure in Patients with Hepatic Dysfunction Treated with Bardoxolone Methyl

| | | Mean ΔSBP ± SE (mmHg) | | Mean ΔDBP ± SE (mmHg) | |
|---|---|---|---|---|---|
| Dose | N | D7 | D14 | D7 | D14 |
| PBO | 4 | −10 ± 8.5 | −1.3 ± 5.5 | −4.0 ± 2.0 | 0.0 ± 3.1 |
| 5 mg | 6 | −12.8 ± 5.2 | −8.8 ± 5.1 | −2.0 ± 2.3 | −1.7 ± 3.2 |
| 25 mg | 6 | −11.5 ± 5.2 | −1.2 ± 3.6 | −4.0 ± 2.8 | −1.5 ± 4.1 |

9. Summary and Analysis of Heart Failure

Comparison of baseline characteristics of patients with heart failure events revealed that while the risk for heart failure was higher in the bardoxolone methyl-treated patients, both bardoxolone methyl-treated and placebo-treated patients with heart failure were more likely to have had a prior history of cardiovascular disease and heart failure and on average, had higher baseline ACR, BNP, and QTcF. Thus, development of heart failure in these patients was likely associated with traditional risk factors for heart failure. Additionally, many of the patients with heart failure were in subclinical heart failure prior to randomization, as indicated by their high baseline BNP levels.

As a surrogate of fluid retention after randomization, post-hoc analysis was performed on a subset of patients for whom BNP data were available, and increases were significantly greater in bardoxolone methyl-treated patients vs. placebo-treated patients at Week 24, with the BNP increases in bardoxolone methyl-treated patients directly correlated with baseline ACR. Urinary sodium excretion data from BEACON ABPM sub-study patients revealed a clinically meaningful reduction in urine volume and excretion of sodium at Week 4 relative to baseline in the bardoxolone methyl-treated patients only. In another study, urinary sodium levels and water excretion were reduced in stage 4 CKD patients but not in stage 3b CKD patients. Together, these data suggest that bardoxolone methyl differentially affects sodium and water handling, with retention of these more pronounced in patients with stage 4 CKD.

Consistent with this phenotype for fluid retention, post-hoc review of the narrative descriptions for heart failure events provided in hospital admission notes, together with anecdotal reports from investigators, indicates that heart failure events in bardoxolone methyl-treated patients were often preceded by rapid fluid weight gain and were not associated with acute decompensation of the kidneys or heart.

Blood pressure changes, indicative of overall volume status, were also increased in the bardoxolone methyl group relative to the placebo group as measured by standardized blood pressure cuff monitoring in BEACON. Pre-specified blood pressure analysis in healthy volunteer studies demonstrated no changes in either systolic or diastolic blood pressure. While the intent-to-treat (ITT) analyses of phase 2 CKD studies conducted with bardoxolone methyl showed no clear changes in blood pressure, post-hoc analyses of these studies suggest that increases in both systolic and diastolic blood pressure are dependent on CKD stage. Taken together, these data suggest that the effects of bardoxolone methyl treatment on blood pressure may be associated with CKD disease severity.

Thus, the urinary electrolyte, BNP, and blood pressure data collectively support that bardoxolone methyl treatment can differentially affect volume status, having no clinically detectable effect in healthy volunteers or early-stage CKD patients, while likely promoting fluid retention in patients with more advanced renal dysfunction and with traditional risk factors associated with heart failure at baseline. The increases in eGFR are likely due to glomerular effects whereas effects on sodium and water regulation are tubular in origin. As eGFR change was not correlated with heart failure, the data suggest that effects on eGFR and sodium and water regulation are anatomically and pharmacologically distinct.

The increased risk for heart failure and related adverse events with bardoxolone methyl treatment was not observed in prior studies (Table 14). However, since prior studies of bardoxolone methyl enrolled 10-fold fewer patients, the increased risk, if present, may have been undetectable. Moreover, BEACON limited enrollment to patients with stage 4 CKD, a population known to be at higher risk for cardiovascular events relative to patients with stage 3b CKD. Thus, the advanced nature of renal disease and significant cardiovascular risk burden of the BEACON population (manifested, among other markers, by low baseline eGFR, high baseline ACR, and high baseline BNP levels) were likely important factors in the observed pattern of cardiovascular events.

To examine further the relationship between key endpoints in BEACON and clinically meaningful thresholds of traditional risk factors of fluid overload, an additional post-hoc analysis was performed. Various eligibility criteria related to these risk factors were applied to exclude patients at most risk and explore the resulting outcomes from BEACON. Combinations of select criteria, including exclusion of patients with eGFR of 20 mL/min/1.73 $m^2$ or less, markedly elevated levels of proteinuria, and either age over 75 or BNP greater than 200 pg/mL abrogate the observed imbalances (Table 15). Applying these same criteria to SAEs also markedly improves or abrogates the noted imbalances (Table 16). Taken together, these findings suggest utility of these and other renal and cardiovascular risk markers in future selection criteria for clinical studies with bardoxolone methyl.

TABLE 14

Frequency of Treatment-Emergent Adverse Events Related to Heart Failure[1] by Primary System Organ Class (SOC) Observed in Prior Chronic Kidney Disease Studies with Bardoxolone Methyl

| | | | Study | | | | | | | |
|---|---|---|---|---|---|---|---|---|---|---|
| | | | 0804 (BEAM) BARD (Crystalline) | | | | 0902 BARD (SDD) | | | |
| SOC | | Preferred Term | PBO (N = 57) | 25 mg (N = 57) | 75 mg (N = 57) | 150 mg (N = 56) | 2.5 mg (N = 14) | 5 mg (N = 25) | 10 mg (N = 28) | 15 mg (N = 50) | 30 mg (N = 14) |
| AEs | Metab | Oedema peripheral | 3 (5) | 3 (5) | 1 (2) | 3 (5) | 0 | 0 | 0 | 0 | 1 (7) |
| | | Fluid overload | 0 | 3 (5) | 2 (4) | 0 | — | — | — | — | — |
| | Genrl | Oedema peripheral | 11 (19) | 11 (19) | 10 (18) | 11 (20) | 0 | 3 (12) | 5 (18) | 3 (6) | 3 (21) |
| | | Generalised oedema | 0 | 2 (4) | 0 | 0 | — | — | — | — | — |
| | Resp | Dyspnoea | 5 (9) | 2 (4) | 6 (11) | 4 (7) | 0 | 0 | 0 | 0 | 1 (7) |
| | | Dyspnoea exertional | 0 | 1 (2) | 0 | 3 (5) | 1 (7) | 0 | 0 | 0 | 0 |
| | | Orthopnoea | 1 (2) | 0 | 0 | 0 | — | — | — | — | — |
| | | Pulmonary oedema | 0 | 0 | 1 (2) | 0 | — | — | — | — | — |
| | Inv | Ejection fraction decreased | 0 | 1 (2) | 0 | 0 | — | — | — | — | — |
| | Card | Oedema peripheral | 1 (2) | 4 (7) | 3 (5) | 4 (7) | 0 | 0 | 1 (4) | 1 (2) | 0 |
| | | Cardiac failure congestive | 3 (5) | 2 (4) | 3 (5) | 3 (5) | 0 | 0 | 1 (4) | 0 | 1 (7) |
| | | Dyspnoea paroxysmal nocturnal | 0 | 0 | 1 (2) | 0 | — | — | — | — | — |

TABLE 14-continued

Frequency of Treatment-Emergent Adverse Events Related to Heart Failure[1] by Primary System Organ Class (SOC) Observed in Prior Chronic Kidney Disease Studies with Bardoxolone Methyl

| | | | Study | | | | | | | |
|---|---|---|---|---|---|---|---|---|---|---|
| | | | 0804 (BEAM) BARD (Crystalline) | | | | 0902 BARD (SDD) | | | |
| SOC | Preferred Term | PBO (N = 57) | 25 mg (N = 57) | 75 mg (N = 57) | 150 mg (N = 56) | 2.5 mg (N = 14) | 5 mg (N = 25) | 10 mg (N = 28) | 15 mg (N = 50) | 30 mg (N = 14) |
| SAEs Card | Cardiac failure congestive | 3 (5) | 2 (4) | 2 (4) | 2 (4) | 0 | 0 | 1 (4) | 0 | 1 (7) |
| Genrl | Oedema peripheral | 0 | 0 | 0 | 1 (2) | — | — | — | — | — |
| Metab | Fluid overload | 0 | 1 (2) | 1 (2) | 0 | — | — | — | — | — |
| Resp | Dyspnoea | 1 (2) | 0 | 0 | 0 | — | — | — | — | — |
| | Pulmonary oedema | 0 | 0 | 1 (2) | 0 | — | — | — | — | — |

In 402-C-0804, patients were administered 25, 75, 150 mg of bardoxolone methyl (crystalline formulation) or placebo once daily for 52 weeks.
In RTA402-C-0903, patients were administered 2.5, 5, 10, 15, or 30 mg doses of bardoxolone methyl (SDD formulation) once daily for 85 days.
[1]Adverse events with preferred terms matching Standardized MedDRA Queries for cardiac failure outlined in the BEACON EAC Charter (Submission Serial 133, dated Feb. 2, 2012).

TABLE 15

Effect of Excluding Patients with Select Baseline Characteristics on Primary Endpoints, Heart Failure, and All-Cause Mortality in BEACON

| | | Observed | Eligibility Criteria (N) | | | | | | |
|---|---|---|---|---|---|---|---|---|---|
| Event | | N | BL BNP ≤ 200 | No h/o HF | BL ACR ≤ 1000 | BL eGFR > 20 | Age ≤ 75 | BL ACR ≤ 1000, eGFR > 20, Age ≤ 75 | BL ACR ≤ 300, eGFR > 20, BNP ≤ 200 |
| Heart Failure | BARD | 103 | 22 | 67 | 63 | 56 | 75 | 19 | 5 |
| | PBO | 57 | 16 | 36 | 40 | 37 | 45 | 20 | 3 |
| All-Cause Death | BARD | 44 | 14 | 35 | 32 | 27 | 20 | 11 | 5 |
| | PBO | 31 | 8 | 24 | 21 | 18 | 23 | 11 | 4 |
| ESRD | BARD | 47 | 12 | 35 | 21 | 18 | 38 | 9 | 1 |
| | PBO | 55 | 22 | 44 | 27 | 14 | 46 | 6 | 1 |
| Randomized Patients | BARD | 1088 | 559 | 922 | 798 | 735 | 786 | 368 | 209 |
| | PBO | 1097 | 593 | 943 | 792 | 718 | 829 | 400 | 217 |

Post-hoc analysis of outcomes in BEACON.
Observed totals for number of patients with heart failure, all-cause and cardiovascular deaths, and ESRD includes all events through last date of contact (ITT Population).

TABLE 16

Effect of Excluding Patients with Select Baseline Characteristics on Treatment-Emergent Serious Adverse Events by Primary SOC in BEACON (ITT Population)

| | Primary SOC | | | | | |
|---|---|---|---|---|---|---|
| | All Patients | | BL ACR ≤ 1000, eGFR > 20, Age ≤ 75 | | BL ACR ≤ 300, eGFR > 20, BNP ≤ 200 | |
| | Treatment | | | | | |
| | PBO (N = 1097) | BARD (N = 1088) | PBO (N = 400) | BARD (N = 368) | PBO (N = 217) | BARD (N = 209) |
| Blood and lymphatic system disorders | 11 (1) | 20 (2) | 3 (<1) | 4 (<1) | 2 (<1) | 0 |
| Cardiac disorders | 84 (8) | 124 (11) | 32 (3) | 35 (3) | 10 (1) | 16 (1) |
| Ear and labyrinth disorders | 1 (<1) | 3 (<1) | 1 (<1) | 1 (<1) | 0 | 1 (<1) |
| Endocrine disorders | 1 (<1) | 1 (<1) | 1 (<1) | 1 (<1) | 1 (<1) | 1 (<1) |
| Eye disorders | 2 (<1) | 3 (<1) | 1 (<1) | 1 (<1) | 1 (<1) | 0 |
| Gastrointestinal disorders | 39 (4) | 46 (4) | 13 (1) | 10 (1) | 8 (1) | 7 (1) |
| General disorders and administration site conditions | 20 (2) | 29 (3) | 3 (<1) | 2 (<1) | 2 (<1) | 3 (<1) |
| Hepatobiliary disorders | 8 (1) | 4 (<1) | 2 (<1) | 1 (<1) | 0 | 1 (<1) |
| Immune system disorders | 0 | 2 (<1) | 0 | 0 | 0 | 0 |
| Infections and infestations | 63 (6) | 79 (7) | 20 (2) | 20 (2) | 12 (1) | 9 (1) |

TABLE 16-continued

Effect of Excluding Patients with Select Baseline Characteristics on Treatment-Emergent Serious Adverse Events by Primary SOC in BEACON (ITT Population)

| | Primary SOC | | | | | |
|---|---|---|---|---|---|---|
| | All Patients | | BL ACR ≤ 1000, eGFR > 20, Age ≤ 75 | | BL ACR ≤ 300, eGFR > 20, BNP ≤ 200 | |
| | Treatment | | | | | |
| | PBO (N = 1097) | BARD (N = 1088) | PBO (N = 400) | BARD (N = 368) | PBO (N = 217) | BARD (N = 209) |
| Injury, poisoning and procedural complications | 17 (2) | 19 (2) | 3 (<1) | 4 (<1) | 0 | 2 (<1) |
| Investigations | 2 (<1) | 3 (<1) | 1 (<1) | 2 (<1) | 0 | 0 |
| Metabolism and nutrition disorders | 42 (4) | 51 (5) | 11 (1) | 14 (1) | 9 (1) | 5 (<1) |
| Musculoskeletal and connective tissue disorders | 13 (1) | 21 (2) | 6 (1) | 9 (1) | 3 (<1) | 6 (1) |
| Neoplasms benign, malignant and unspecified | 10 (1) | 11 (1) | 6 (1) | 3 (<1) | 2 (<1) | 1 (<1) |
| Nervous system disorders | 35 (3) | 37 (3) | 13 (1) | 6 (1) | 9 (1) | 4 (<1) |
| Psychiatric disorders | 3 (<1) | 3 (<1) | 1 (<1) | 2 (<1) | 1 (<1) | 1 (<1) |
| Renal and urinary disorders | 71 (6) | 52 (5) | 14 (1) | 9 (1) | 2 (<1) | 4 (<1) |
| Reproductive system and breast disorders | 3 (<1) | 2 (<1) | 0 | 0 | 0 | 0 |
| Respiratory, thoracic and mediastinal disorders | 32 (3) | 43 (4) | 11 (1) | 15 (1) | 7 (1) | 6 (1) |
| Skin and subcutaneous tissue disorders | 1 (<1) | 4 (<1) | 1 (<1) | 1 (<1) | 1 (<1) | 1 (<1) |
| Surgical and medical procedures | 0 | 2 (<1) | 0 | 1 (<1) | 0 | 1 (<1) |
| Vascular disorders | 18 (2) | 20 (2) | 5 (<1) | 4 (<1) | 2 (<1) | 2 (<1) |

Post-hoc analyses of treatment-emergent serious adverse events in BEACON.
Event totals include only SAEs with onset no more than 30 days after a patient's last dose of study drug.

D. Potential Mechanisms of Fluid Overload in BEACON

Data presented in prior sections suggest that bardoxolone methyl promotes fluid retention in a subset of patients who are at most risk of developing heart failure independent of drug administration. The data suggest that the effects are not associated with acute or chronic renal or cardiac toxicity. Therefore, a comprehensive list of well-established renal mechanisms that affect volume status (Table 17) was explored to determine if any of the etiologies matched the clinical phenotype observed with bardoxolone methyl.

Initial investigation focused on possible activation of the renin-angiotensin-aldosterone system. Activation of this pathway reduces serum potassium due to increased renal excretion. However, bardoxolone methyl did not affect serum potassium and slightly reduced urinary potassium in the BEACON sub-study (Table 7).

Another potential mechanism that was investigated was whether transtubular ion gradient changes may have resulted in sodium and consequent water resorption, since bardoxolone methyl affects serum magnesium and other electrolytes. However, this mechanism also involves potassium regulation, and baseline serum magnesium did not appear to be associated with fluid retention or heart failure hospitalizations.

After other etiologies were excluded for reasons listed in Table 16, suppression of endothelin signaling was the primary remaining potential mechanism of volume regulation that was consistent with the bardoxolone methyl treatment effect in BEACON. Therefore, an extensive investigation of modulation of the endothelin pathway as a potential explanation for fluid retention observed in the BEACON study was conducted.

TABLE 17

Established Renal Mechanisms Affecting Volume Status

| Mechanism | $Na^+$ Retention | $K^+$ Retention | Effect on GFR | Comments |
|---|---|---|---|---|
| Bardoxolone Methyl | ↑ | None | ↑ | ↑ $Na^+$ retention independent of $K^+$ in Stage 4 CKD patients, ↑ GFR |
| Endothelin | ↓ | None | ↓ | Suppression of endothelin fits BARD pattern |
| Endothelial Nitric Oxide (NO) | ↓ | None | ↑ | NO ↓ $Na^+$ reabsorption and ↑ GFR BARD ↑ both $Na^+$ and GFR BARD has been shown in vitro and in vivo to increase bioavailable endothelial NO, but $Na^+$ effect is likely independent of NO and GFR changes |
| Antidiuretic Hormone (ADH) | ↑ | ↑ | ↓ at ↑ levels of ADH | ADH ↑$Na^+$ and $K^+$ while ↓GFR BARD does not affect $K^+$ and ↑ GFR |
| Transtubular ion gradients | ↑ with ↑ GFR | ↑ | No direct effect | Ion gradients have dual effect on $Na^+$ and $K^+$; Cl•$HCO_3^-$ gradient often generated as $HCO_3^-$ absorption dependent on $Na^+$ absorption BARD does not affect $K^+$ or $HCO_3^-$ |

TABLE 17-continued

Established Renal Mechanisms Affecting Volume Status

| Mechanism | Na+ Retention | K+ Retention | Effect on GFR | Comments |
|---|---|---|---|---|
| Renin-Angiotensin-Aldosterone (RAAS) | ↑ | ↓ | ↑ | RAAS signaling ↑ K urinary excretion and ↓ serum levels BARD does not affect K+ levels and has been shown to ↓ AII levels in CKD patients and suppress AII signaling in vitro and in vivo |
| Pressure Natriuresis | ↓ | ↓ | Slight ↑ | Volume expansion leads to ↑ medullary plasma flow and ↓ hypertonicity; ↓ water absorption in the loop of Henle with ↓ of Na+ and K+ BARD-mediated magnitude of volume expansion unlikely sufficient to promote this effect; BARD ↑ Na+ and does not affect K+ |
| Prostaglandins (PGE$_2$, PGI$_2$) | ↓ | Slight ↓ | ↑ | PGs ↑GFR and ↑Na+ urine excretion BARD ↑ Na+ retention, not excretion |
| Natriuretic peptides | ↓ | Slight ↓ | ↑ | Natriuretic peptides have divergent effects on Na+ and GFR with slight effect on K+ BNP and other natriuretic peptides ↑ Na+ urine excretion BARD ↑ Na+ retention, not excretion BARD does no interfere with natriuretic peptides, as GFR would likely ↓ |
| Peritubular factors | ↑ with ↑ GFR | ↑ with ↑ GFR | None | Na+ and K+ move with GFR BARD does not affect K+ |

Mechanisms and characteristics of fluid retention.

1. Modulation of the Endothelin System

The most directly analogous clinical data for comparison of the effects of known endothelin pathway modulators to the BEACON study are those with the endothelin receptor antagonist (ERA) avosentan. Avosentan was studied in stage 3-4 CKD patients with diabetic nephropathy in the ASCEND study, a large outcomes study to assess the time to first doubling of serum creatinine, ESRD, or death (Mann et al., 2010). While the baseline eGFR in this study was slightly above the mean baseline eGFR in BEACON, patients in the ASCEND study had a mean ACR that was approximately seven-fold higher than BEACON (Table 18). Therefore, the overall cardiovascular risk profile was likely similar between the two studies.

Figure 10A:
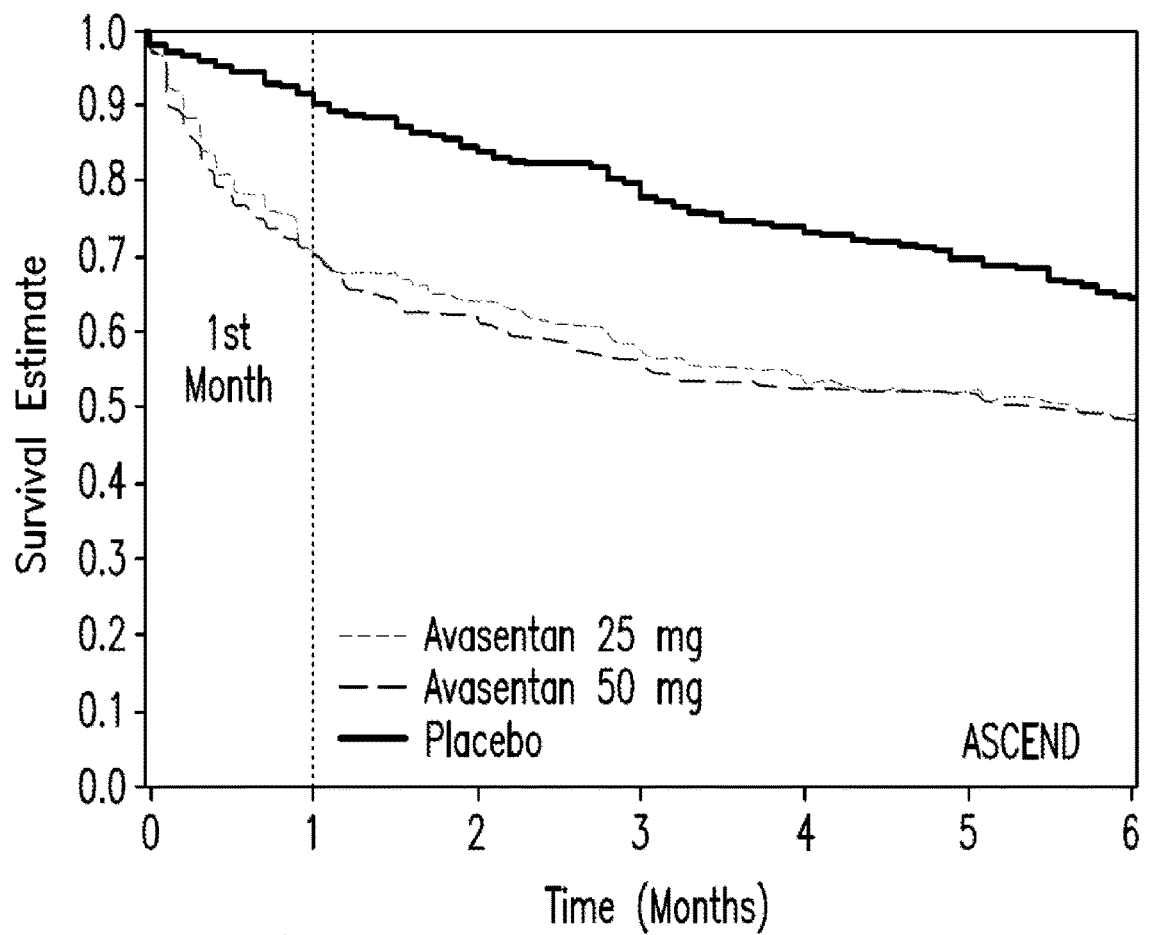
FIGS. 10A-B—Kaplan-Meier Plots for Fluid Overload Events in ASCEND (FIG. 10A) and Heart Failure Events in BEACON (ITT Population.
Figure 10B:
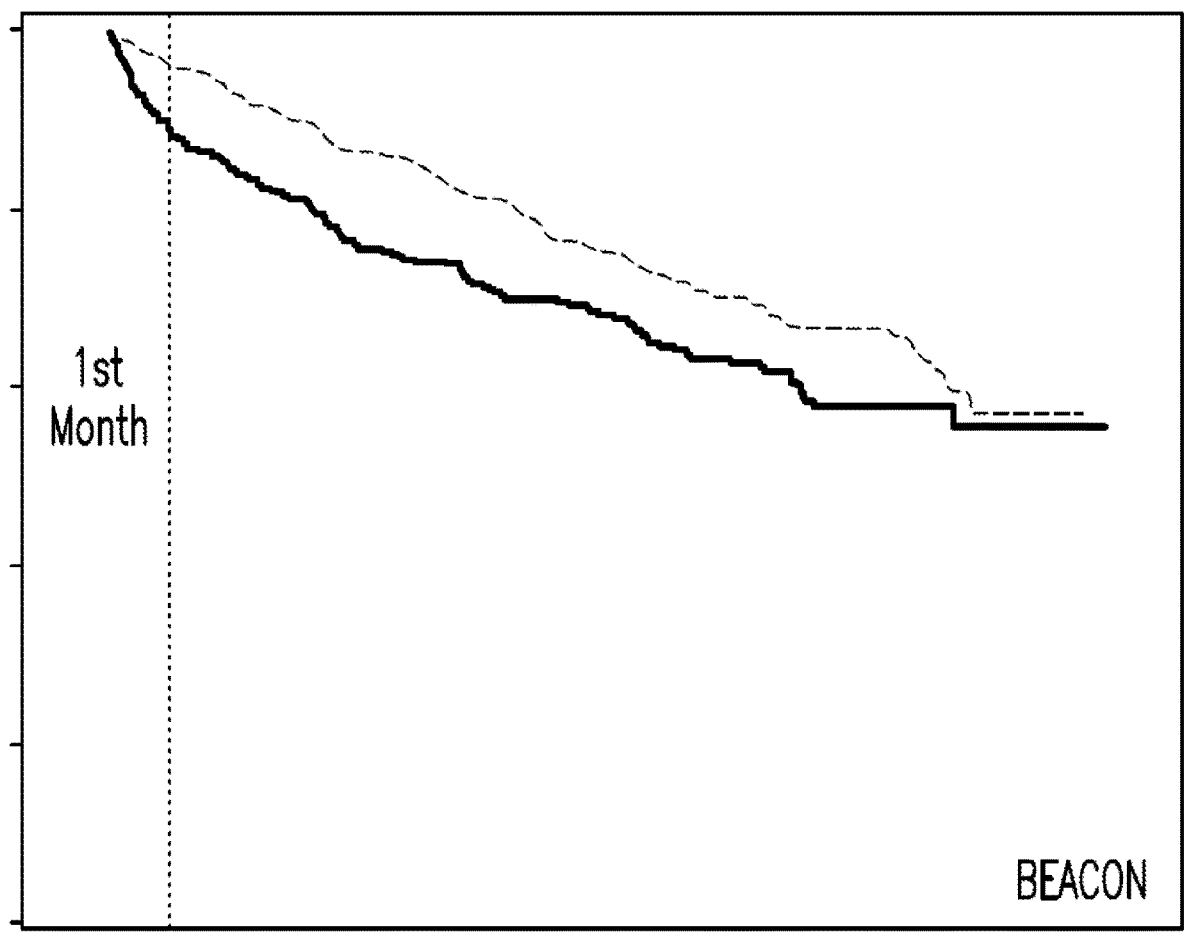

As in BEACON, the ASCEND study was terminated prematurely due to an early imbalance in heart failure hospitalization and fluid overload events. Importantly, avosentan-induced fluid overload-related adverse events, including serious and non-serious, were increased only within the first month of treatment (FIGS. 10A-B).

Examination of key endpoints in the ASCEND study reveals an approximate three-fold increase in risk of congestive heart failure (CHF) with a modest, non-significant increase in death. Additionally, a small, numerical reduction in ESRD events was also observed. The BEACON study demonstrated similar findings, albeit with a lower incidence of heart failure events. Nonetheless, the two studies showed striking similarities in clinical presentation and timing of heart failure, as well as influences on other key endpoints (Table 19).

TABLE 18

Select Demographic and Baseline Characteristics for Patients in ASCEND* and BEACON (ITT Population)

| | ASCEND | | | BEACON | |
|---|---|---|---|---|---|
| BL Characteristic | PBO (N = 459) | Avosentan 25 mg (N = 455) | Avosentan 50 mg (N = 478) | PBO (N = 1097) | BARD 20 mg (N = 1088) |
| Age | 61 ± 9 | 61 ± 9 | 61 ± 9 | 68 ± 9 | 69 ± 10 |
| History of CHF (% of patients) | 13.5% | 14.5% | 14.4% | 15% | 14% |
| Systolic Blood Pressure (mmHg) | 135 ± 15 | 137 ± 14 | 137 ± 14 | 140 ± 12 | 140 ± 12 |
| BMI (kg/m$^2$) | 30 ± 6 | 30 ± 6 | 30 ± 7 | 34 ± 7 | 34 ± 7 |
| eGFR (mL/min/1.73 m$^2$) | 33 ± 11 | 34 ± 11 | 33 ± 11 | 22 ± 5 | 22 ± 4 |
| Median ACR (mg/g) | 1540 | 1416 | 1474 | 221 | 210 |
| ACEi/ARB (% of patients) | 100% | 100% | 100% | 84% | 85% |
| Diuretics (% of patients) | 65% | 64% | 65% | 64% | 64% |

*Results from a randomized, double-blind, placebo-controlled trial of 1392 patients with type 2 diabetes and overt nephropathy receiving avosentan (25 or 50 mg) or placebo in addition to continued angiotensin-converting enzyme inhibition and/or angiotensin receptor blockade (ASCEND).

TABLE 19

Occurrence of Death, End Stage Renal Disease, or Heart Failure in ASCEND and BEACON (ITT Population)

| | ASCEND | | | BEACON | |
|---|---|---|---|---|---|
| | | Avosentan | Avosentan | | |
| Event | PBO (N = 459) | 25 mg (N = 455) | 50 mg (N = 478) | PBO (N = 1097) | BARD 20 mg (N = 1088) |
| CHF | 2.2% | 5.9%* | 6.1%* | 5.0% | 8.8%* |
| Death | 2.6% | 3.6% | 4.6% | 2.8% | 4.0% |
| ESRD | 6.5% | 4.4% | 5.0% | 4.6% | 4.0% |

Occurrence of adjudicated CHF, death, and ESRD events in ASCEND and BEACON. In ASCEND, for an event to be qualified as CHF, the patient had to have typical signs and/or symptoms of heart failure and receive new therapy for CHF and be admitted to the hospital for at least 24 hours; ESRD was defined as need for dialysis or renal transplantation or an eGFR < 15 mL/min/1.73 m$^2$. Percentages for BEACON include all CHF and ESRD events through last date of contact and total number of deaths at the time of database lock (Mar. 21, 2013). ESRD in BEACON was defined as need for chronic dialysis, renal transplantation, or renal death; additional details and definitions for heart failure are outlined in the BEACON EAC Charter.
*p < 0.05 vs. placebo.

2. Mechanism of Endothelin Receptor Antagonist-Induced Fluid Overload

The role of endothelin in fluid overload has been extensively investigated. Through the use of knock-out models in mice, investigators have demonstrated that acute disruption of the endothelin pathway followed by a salt challenge promotes fluid overload. Specific knock-out of endothelin-1 (ET-1), endothelin receptor type A (ETA), endothelin receptor type B (ETB), or the combination of ETA and ETB have all been shown to promote fluid overload in animals with a clinical phenotype consistent with ERA-mediated fluid overload in patients. These effects are caused by acute activation of the epithelial sodium channel (ENaC), which is expressed in the collecting ducts of the kidney, where it reabsorbs sodium and promotes fluid retention (Vachiery and Davenport, 2009).

3. Relationship between Plasma and Urinary Endothelin-1 in Humans

An assessment of plasma and urinary levels of endothelin-1 (ET-1) in humans with eGFR values ranging from stage 5 CKD to supra-normal (8 to 131 mL/min/1.73 m$^2$) has been previously reported (Dhaun et al., 2009). Plasma levels significantly and inversely correlated with eGFR, but due to the modest slope of the curve, meaningful differences of ET-1 were not readily apparent across the large eGFR range assessed. As a surrogate for kidney production of ET-1, the organ where the most ET-1 is produced, fractional excretion of ET-1 was calculated by assessing the plasma and urinary levels of ET-1. From eGFRs >100 to approximately 30 mL/min/1.73 m$^2$, urinary levels were relatively unchanged. However, ET-1 levels appear to increase exponentially with decreasing eGFR in patients with stage 4 and 5 CKD. These data suggest that renal ET-1 is primarily dysregulated in patients with advanced (stage 4 and 5) CKD. Based on these published data, the inventors hypothesized that the differential effects on fluid handling by bardoxolone methyl, if due to endothelin modulation, could be due to the disparate endogenous production of ET-1 in the kidney, which is meaningfully increased in stage 4 and 5 CKD patients.

4. Bardoxolone Methyl Modulates Endothelin Signaling

As described above, bardoxolone methyl reduces ET-1 expression in human cell lines, including mesangial cells found in the kidney as well as endothelial cell. Furthermore, in vitro and in vivo data suggest that bardoxolone methyl and analogs modulate the endothelin pathway to promote a vasodilatory phenotype by suppressing the vasoconstrictive ETA receptor and restoring normal levels of the vasodilatory ETB receptor. Thus, the potent activation of Nrf2-related genes with bardoxolone methyl is associated with suppression of pathological endothelin signaling and facilitates vasodilation by modulating expression of ET receptors.

E. Rationale for BEACON Termination

1. Adjudicated Heart Failure

Figure 11:
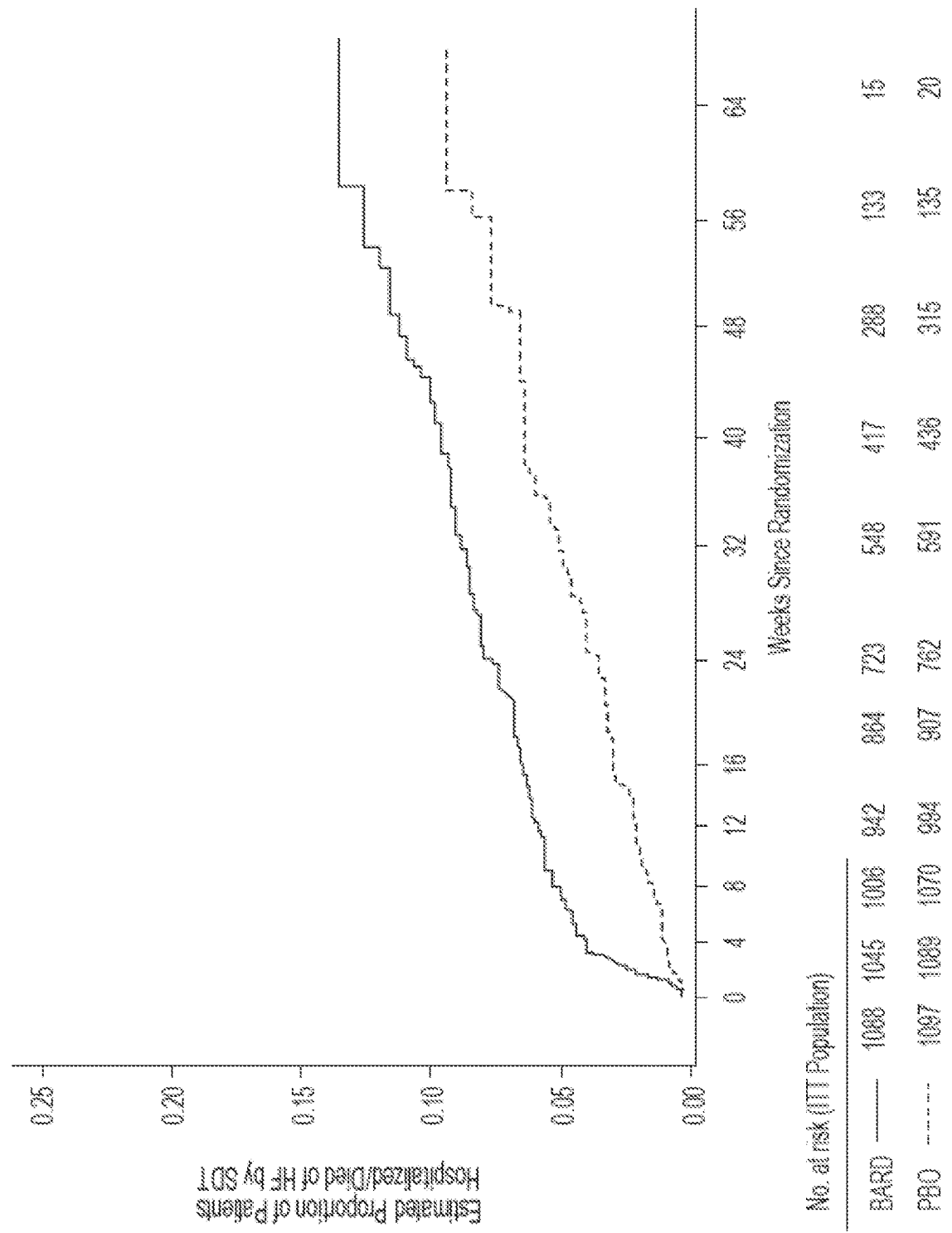
FIG. 11—Time to First Hospitalization for Heart Failure or Death Due to Heart Failure Event in BEACON (ITT Population). Analysis includes only heart failure (HF) events occurring on or prior to study drug termination date (SDT) (Oct. 18, 2012) that were positively adjudicated by an independent Event Adjudication Committee, as outlined in the BEACON EAC Charter. Top line is bardoxolone methyl (BARD); bottom line is placebo (PBO).

Hospitalizations for heart failure or death due to heart failure were among the cardiovascular events adjudicated by the EAC. An imbalance in adjudicated heart failure and related events was the major finding that contributed to the early termination of BEACON. Additionally, heart failure-related AEs, such as edema, contributed to a higher discontinuation rate than expected. The overall imbalance in time-to-first adjudicated heart failure appeared to result from the large contribution of events occurring within the first three to four weeks after initiation of treatment. The Kaplan-Meyer analysis shows that after this initial period the event rates between the treatment arms appear to maintain parallel trajectories. The pattern reflected in FIG. 11 suggests an acute, physiologic effect that precipitated hospitalization for heart failure versus a cumulative toxic effect.

2. Mortality

Figure 12:
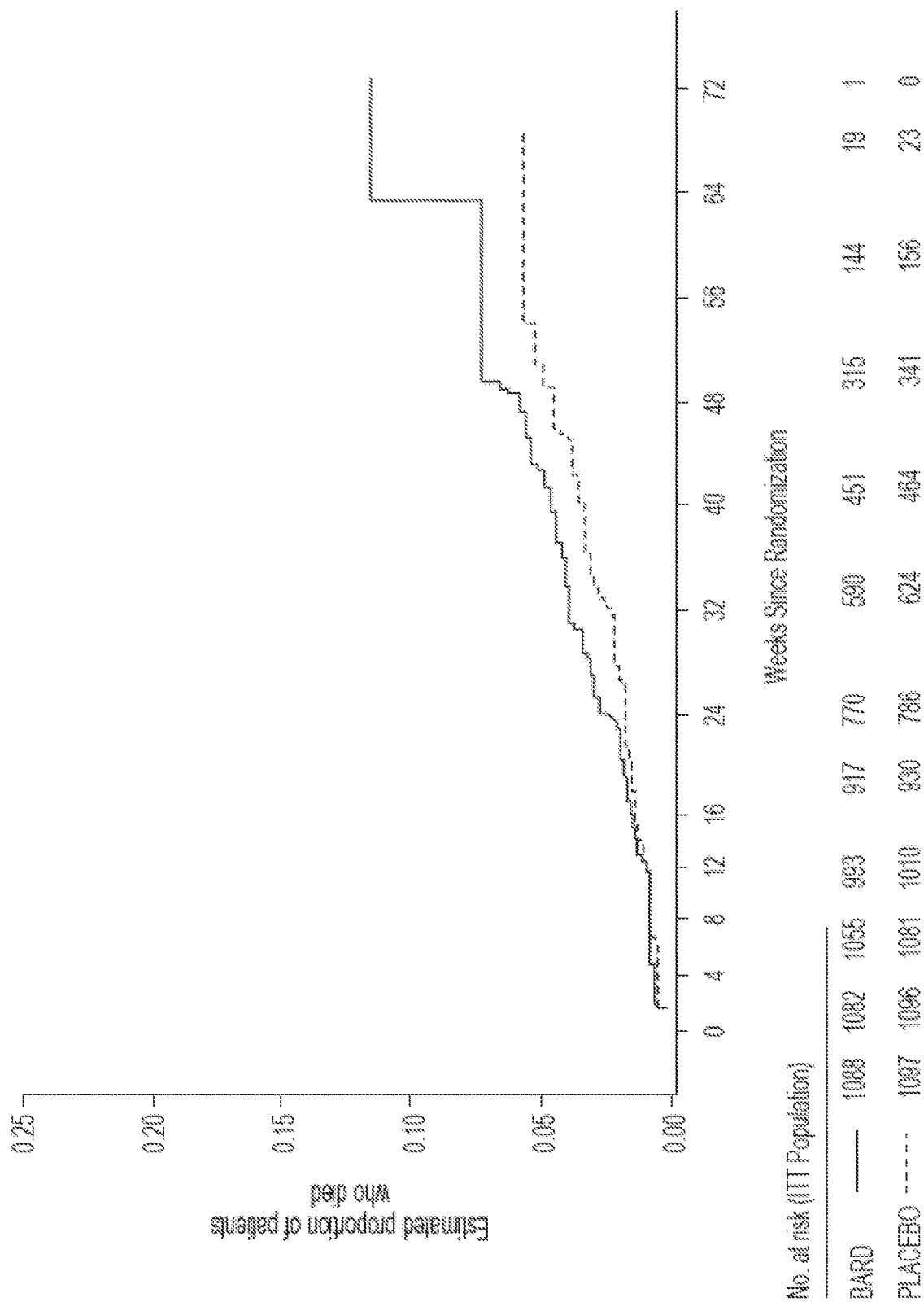
FIG. 12—Overall Survival of Bardoxolone Methyl vs. Placebo Patients in BEACON. Results from a randomized, double-blind, placebo-controlled phase 3 study in T2D patients with Stage 4 CKD (BEACON, RTA402-C-0903). Patients were administered placebo or 20 mg of bardoxolone methyl once daily. Analysis includes all deaths occurring prior to database lock (Mar. 4, 2013). Top line is bardoxolone methyl (BARD); bottom line is placebo.

At the time of the termination of the study, more deaths had occurred in the bardoxolone methyl group than in the placebo group, and the relationship between mortality and heart failure was unclear. A majority of the fatal outcomes (49 of the 75 deaths) occurring prior to clinical database lock (Mar. 4, 2013) were confirmed as being cardiovascular in nature (29 bardoxolone methyl patients vs. 20 placebo patients). Most of the cardiovascular deaths were classified as "cardiac death—not otherwise specified," based on pre-specified definitions outlined in the BEACON EAC charter. On final analysis, the Kaplan-Meier analysis for overall survival showed no apparent separation until approximately Week 24 (FIG. 12). There were three fatal heart failure events, all in bardoxolone methyl-treated patients. In addition, as reflected in Table 16, the percentage of deaths occurring in patients that were over 75 years old was higher in bardoxolone methyl-treated patients compared to placebo-treated patients. Notably, if patients over 75 years old are excluded, the numbers of fatal events in the bardoxolone methyl arm compared to the placebo arm are 20 and 23, respectively.

3. Summary of Other Safety Data from BEACON

In addition to the effects of bardoxolone methyl treatment on eGFR and renal SAEs, the number of hepatobiliary SAEs was reduced in the bardoxolone methyl group relative to the placebo group (4 versus 8, respectively; Table 2), and no Hy's Law cases were observed. The number of neoplasm-related SAEs was also balanced across both groups. Lastly, bardoxolone methyl treatment was not associated with QTc prolongation, as assessed by ECG assessments at Week 24 (Table 20).

TABLE 20

Change from Baseline in QTcF at Week 24 in Bardoxolone Methyl versus Placebo Patients in BEACON (Safety Population)

| Timepoint/QTcF interval (msec) | Observed | | Change from baseline | |
|---|---|---|---|---|
| | Placebo N = 1093 | Bardoxolone methyl N = 1092 | Placebo N = 1093 | Bardoxolone methyl N = 1092 |
| n | 719 | 639 | 719 | 637 |
| Mean (SD) | 428.8 (29.2) | 425.8 (26.5) | 3.6 (16.4) | −0.9 (19.2) |
| Range (min, max) | 362, 559 | 355, 518 | −59, 82 | −88, 69 |
| Quartiles (25th, median, 75th) | 408, 426, 445 | 407, 425, 443 | −7, 3, 13 | −13, −1, 10 |

Data includes only ECG assessments collected on or before a patient's last dose of study drug. Visits are derived relative to a patient's first dose of study drug.

F. BEACON Conclusions

In summary, interrogation of data from studies conducted with bardoxolone methyl revealed that the drug can differentially regulate fluid retention, with no clinically detectable effect in healthy volunteers or early-stage CKD patients, while likely pharmacologically promoting fluid retention in patients with advanced renal dysfunction. Since the development of heart failure in both bardoxolone methyl- and placebo-treated patients was associated with traditional risk factors for heart failure, this pharmacological effect in patients with baseline cardiac dysfunction may explain the increased risk for heart failure with bardoxolone methyl treatment in BEACON. These data suggest that decreasing the overall risk for heart failure in future clinical studies by selecting a patient population with lower baseline risk for heart failure should avoid increases in heart failure associated with bardoxolone methyl treatment. Importantly, the available data show that fluid overload in BEACON was not caused by a direct renal or cardiac toxicity. The clinical phenotype of fluid overload is similar to that observed with ERAs in advanced CKD patients, and preclinical data demonstrate that bardoxolone methyl modulates the endothelin pathway. As acute disruption of the endothelin pathway in advanced CKD patients is known to activate a specific sodium channel (ENaC) that can promote acute sodium and volume retention (Schneider, 2007), these mechanistic data, along with the clinical profile of bardoxolone methyl patients with heart failure, provide a reasonable hypothesis to the mechanism of fluid retention in BEACON. Because compromised renal function may be an important factor that contributes to a patient's inability to compensate for short-term fluid overload, and because relatively limited numbers of patients with earlier stages of CKD have been treated to date, exclusion of patients with CKD (e.g., patients with an eGFR <60) from treatment with BARD and other AIMs may be prudent and may be included as an element of the present invention.

II. COMPOUNDS FOR THE TREATMENT OF ALPORT SYNDROME OR SYMPTOMS THEREOF OR THE PREVENTION OF SYMPTOMS OF ALPORT SYNDROME

In one aspect of the present disclosure, there are provided methods of treating or reducing the symptoms of Alport syndrome in a patient comprising administering to the patient a therapeutically effective amount of bardoxolone methyl, an analog thereof, or a composition comprising either bardoxolone methyl or an analog thereof. Analogs of bardoxolone methyl include compounds of the formula:

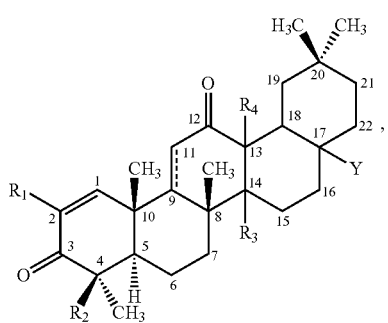

(I)

wherein:
$R_1$ is —CN, halo, —CF$_3$, or —C(O)R$_a$, wherein R$_a$ is —OH, alkoxy$_{(C1-4)}$, —NH$_2$, alkylamino$_{(C1-4)}$, or —NH—S(O)$_2$-alkyl$_{(C1-4)}$;
$R_2$ is hydrogen or methyl;
$R_3$ and $R_4$ are each independently hydrogen, hydroxy, methyl or as defined below when either of these groups is taken together with group $R_c$; and
Y is:
—H, —OH, —SH, —CN, —F, —CF$_3$, —NH$_2$ or —NCO;
alkyl$_{(C≤8)}$, cycloalkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤8)}$, heterocycloalkyl$_{(C≤12)}$, alkoxy$_{(C≤8)}$, cycloalkoxy$_{(C≤8)}$, aryloxy$_{(C≤12)}$, acyloxy$_{(C≤8)}$, alkylamino$_{(C≤8)}$, cycloalkylamino$_{(C≤8)}$, dialkylamino$_{(C≤8)}$, arylamino$_{(C≤8)}$, aralkylamino$_{(C≤8)}$, alkylthio$_{(C≤8)}$, acylthio$_{(C≤8)}$, alkylsulfonylamino$_{(C≤8)}$, cycloalkylsulfonylamino$_{(C≤8)}$, or substituted versions of any of these groups;
alkanediyl$_{(C≤8)}$—R$_b$, -alkenediyl$_{(C≤8)}$-R$_b$, or a substituted version of any of these groups, wherein R$_b$ is: hydrogen, hydroxy, halo, amino or mercapto; or
heteroaryl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, cycloalkylamino$_{(C≤8)}$, dialkylamino$_{(C≤8)}$, arylamino$_{(C≤8)}$, aralkylamino$_{(C≤8)}$, heteroarylamino$_{(C≤8)}$, alkylsulfonylamino$_{(C≤8)}$, cycloalkylsulfonylamino$_{(C≤8)}$, amido$_{(C≤8)}$, —OC(O)NH-alkyl$_{(C≤8)}$, or a substituted version of any of these groups;
—(CH$_2$)$_m$C(O)R$_c$, wherein m is 0-6 and R$_c$ is: hydrogen, hydroxy, halo, amino, —NHOH, or mercapto; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, cycloalkylamino$_{(C≤8)}$, dialkylamino$_{(C≤8)}$, arylamino$_{(C≤8)}$, alkylsulfonylamino$_{(C≤8)}$, cycloalkylsulfonylamino$_{(C≤8)}$, amido$_{(C≤8)}$, —NH-alkoxy$_{(C≤8)}$, —NH-heterocycloalkyl$_{(C≤8)}$, —NH-amido$_{(C≤8)}$, or a substituted version of any of these groups;
$R_c$ and $R_3$, taken together, are —O— or —NR$_d$—, wherein R$_d$ is hydrogen or alkyl$_{(C≤4)}$; or
$R_c$ and $R_4$, taken together, are —O— or —NR$_d$—, wherein R$_d$ is hydrogen or alkyl$_{(C≤4)}$; or
—NHC(O)R$_e$, wherein R$_e$ is:
hydrogen, hydroxy, amino; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, cycloalkylamino$_{(C≤8)}$, dialkylamino$_{(C≤8)}$, arylamino$_{(C≤8)}$, or a substituted version of any of these groups;
or a pharmaceutically acceptable salt thereof.

These compounds are known as antioxidant inflammation modulators. These compounds have shown the ability to activate Nrf2, as measured by elevated expression of one or more Nrf2 target genes (e.g., NQO1 or HO-1; Dinkova-Kostova et al., 2005). Further, these compounds are capable of indirect and direct inhibition of pro-inflammatory transcription factors including NF-κB and STAT3 (Ahmad et al., 2006; Ahmad et al., 2008). In some aspects, there are provided methods of preventing progression of Alport syndrome or a symptom thereof in a subject or patient in need thereof comprising administering to the subject or patient bardoxolone methyl or an analog thereof in an amount sufficient to prevent progression of Alport syndrome or a symptom thereof in the subject or patient. Additionally, one or more of the compounds described herein may be used in methods to prevent the onset of one or more symptoms of Alport syndrome or prevent the progression of Alport syndrome.

Triterpenoids, biosynthesized in plants by the cyclization of squalene, are used for medicinal purposes in many Asian countries; and some, such as ursolic and oleanolic acid, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). An ongoing effort for the improvement of anti-inflammatory and antiproliferative activity of oleanolic and ursolic acid analogs led to the discovery of 2-cyano-3,12-dioxooleane-1,9(11)-dien-28-oic acid (CDDO) and related compounds (Honda et al., 1997, 1998, 1999, 2000a, 2000b, 2002; Suh et al., 1998; 1999; 2003; Place et al., 2003; Liby et al., 2005). Several potent derivatives of oleanolic acid were identified, including methyl-2-cyano-3,12-dioxooleana-1,9-dien-28-oic acid (CDDO-Me; RTA 402; bardoxolone methyl). RTA 402, an antioxidant inflammation modulator (AIM), suppresses the induction of several important inflammatory mediators, such as iNOS, COX-2, TNFα, and IFNγ, in activated macrophages, thereby restoring redox homeostasis in inflamed tissues. RTA 402 has also been reported to activate the Keap1/Nrf2/ARE signaling pathway resulting in the production of several anti-inflammatory and antioxidant proteins, such as heme oxygenase-1 (HO-1). It induces the cytoprotective transcription factor Nrf2 and suppresses the activities of the pro-oxidant and pro-inflammatory transcription factors NF-κB and STAT3. In vivo, RTA 402 has demonstrated significant single agent anti-inflammatory activity in several animal models of inflammation such as renal damage in the cisplatin model and acute renal injury in the ischemia-reperfusion model. In addition, significant reductions in serum creatinine have been observed in patients treated with RTA 402.

Accordingly, in pathologies involving oxidative stress alone or oxidative stress exacerbated by inflammation, treatment may comprise administering to a subject or patient a therapeutically effective amount of a compound of this invention, such as those described above or throughout this specification. Treatment may be administered preventively in advance of a predictable state of oxidative stress (e.g., organ transplantation or the administration of therapy to a cancer patient), or it may be administered therapeutically in settings involving established oxidative stress and inflammation.

Non-limiting examples of triterpenoids that may be used in accordance with the methods of this invention are shown here.

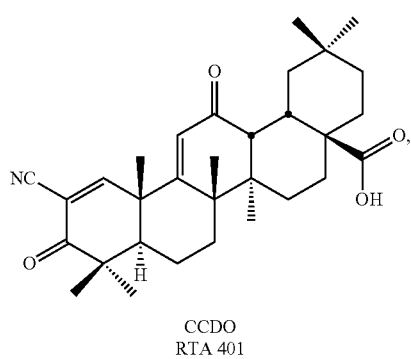

CCDO
RTA 401

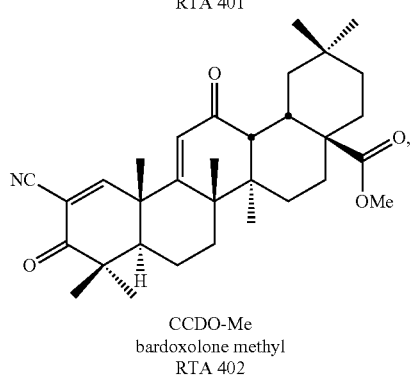

CCDO-Me
bardoxolone methyl
RTA 402

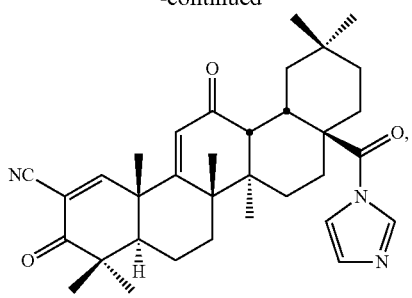

CCDO-Im
CDDO-IM
RTA 403

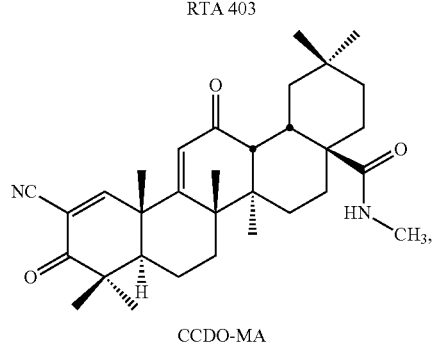

CCDO-MA

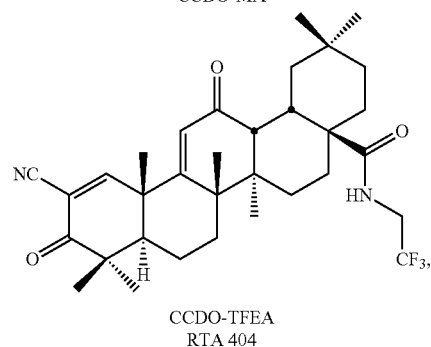

CCDO-TFEA
RTA 404

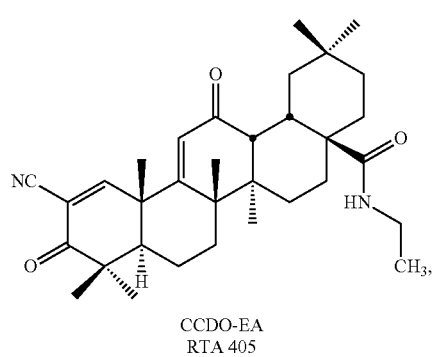

CCDO-EA
RTA 405

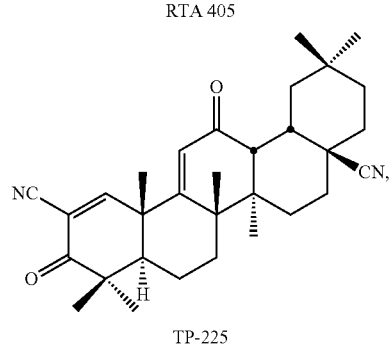

TP-225

33
-continued
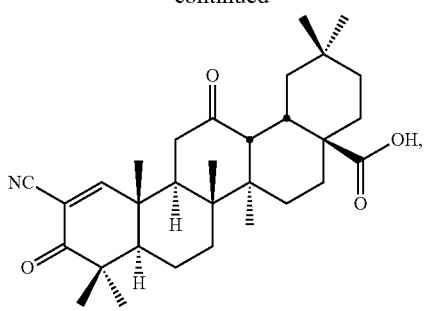
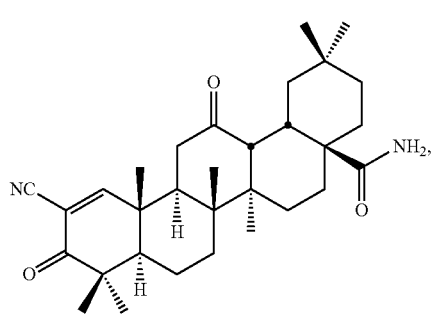
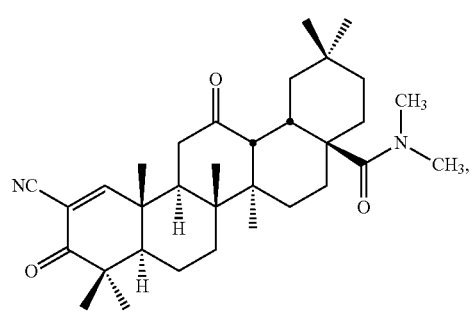
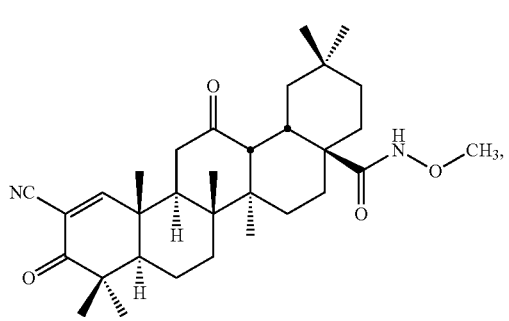
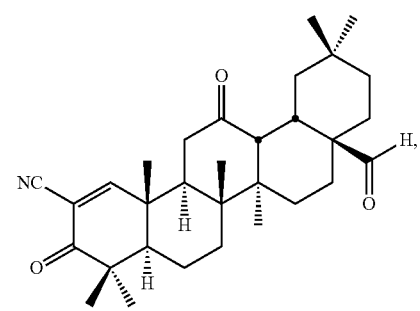
34
-continued
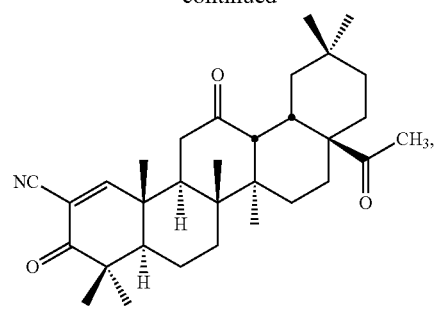
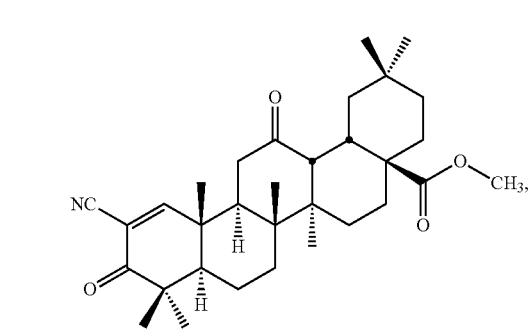
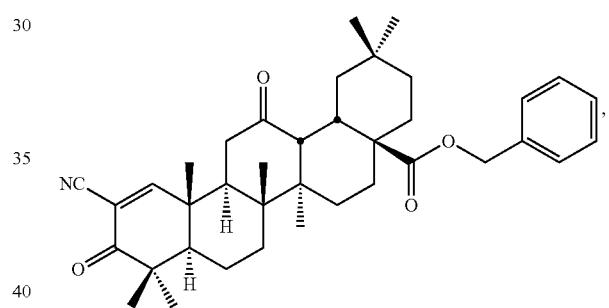
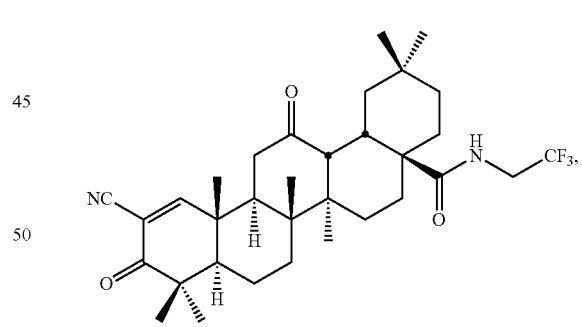
RTA dh404
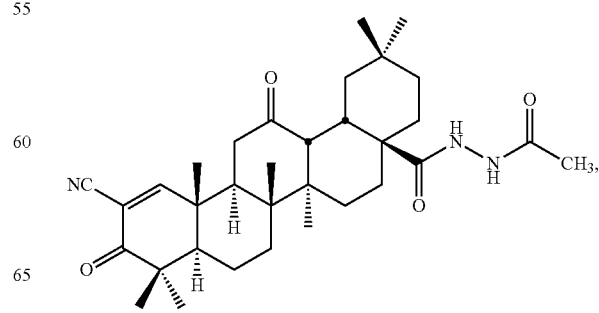

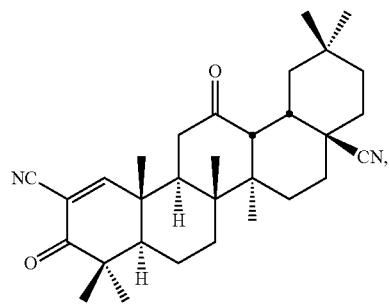
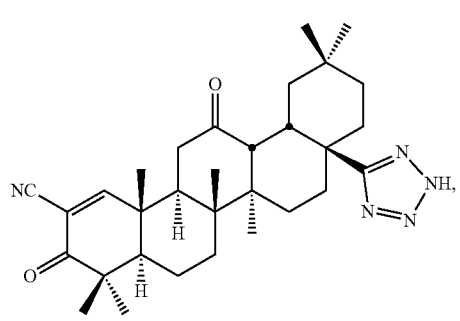
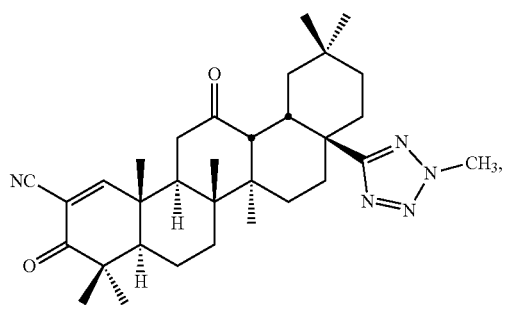
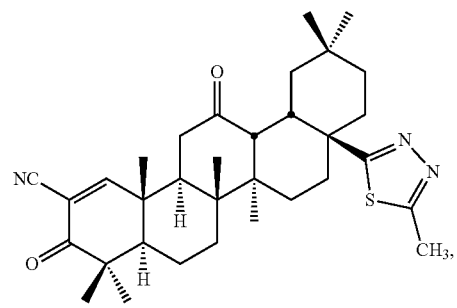
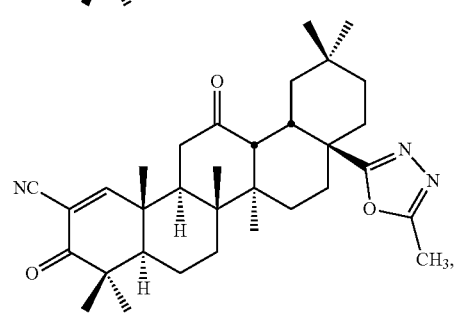
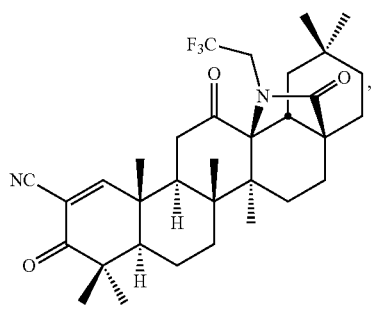
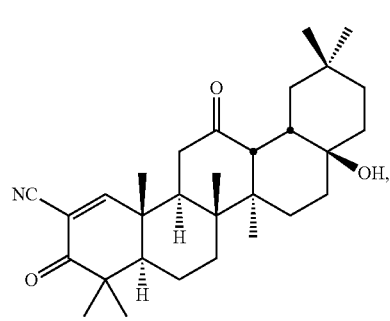
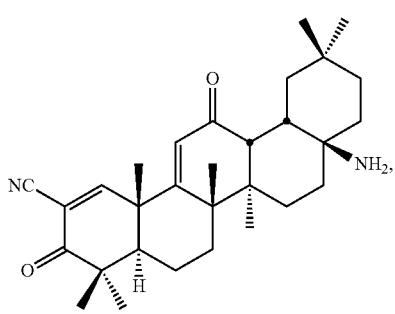
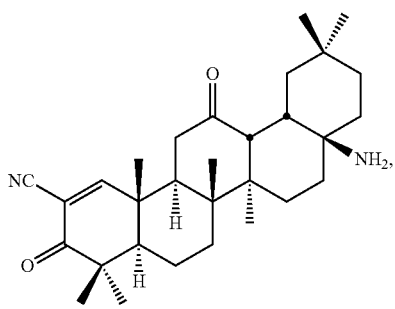
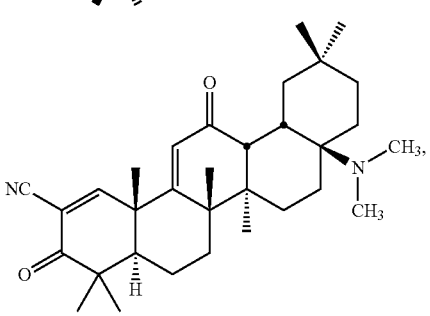

-continued
37
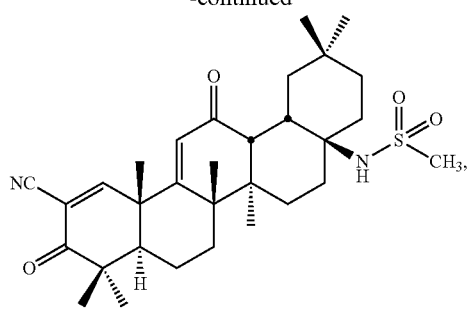
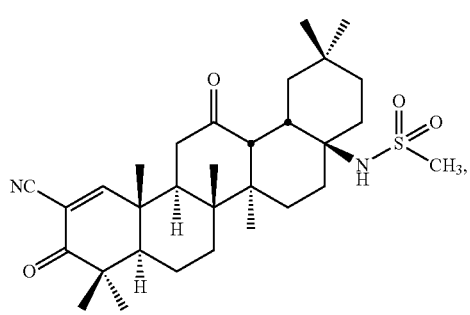
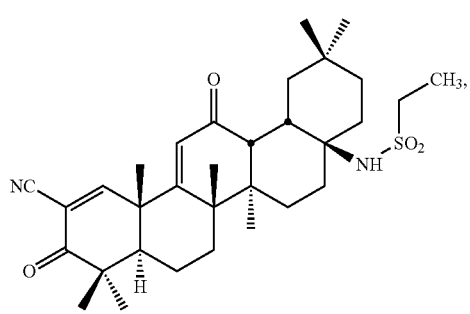
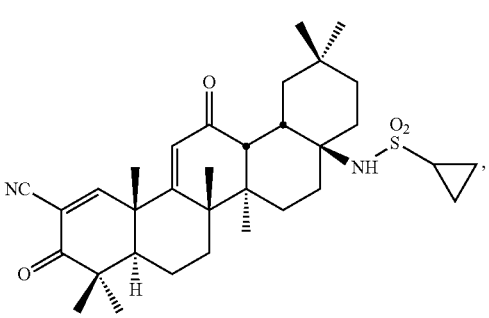
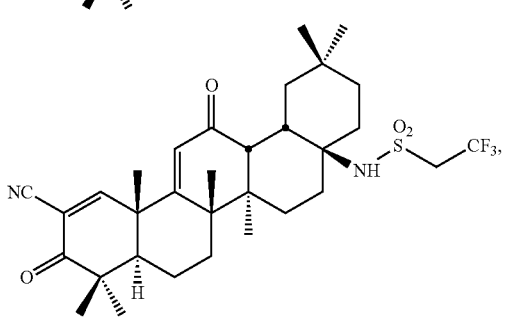
38
-continued
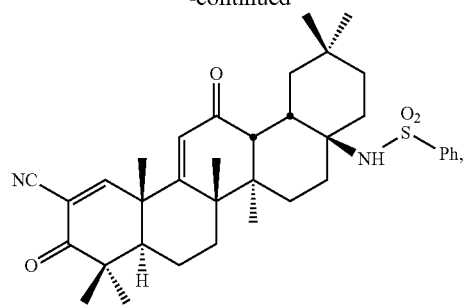
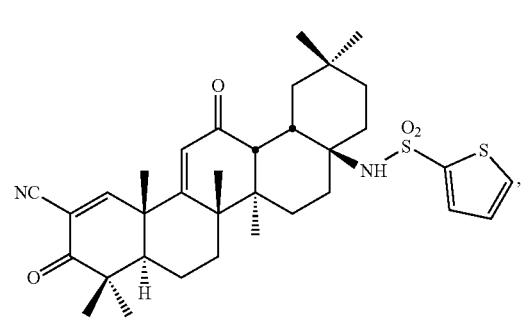
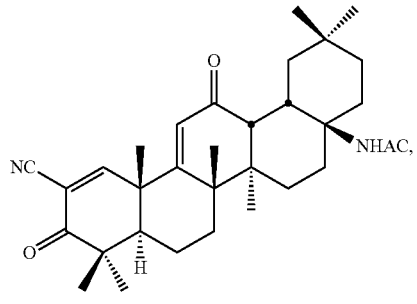
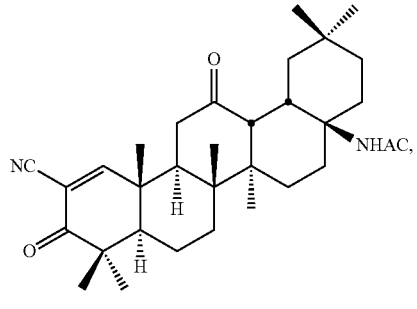
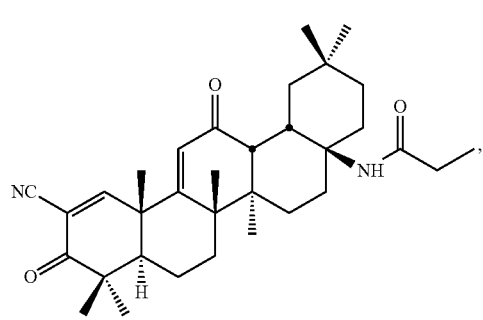

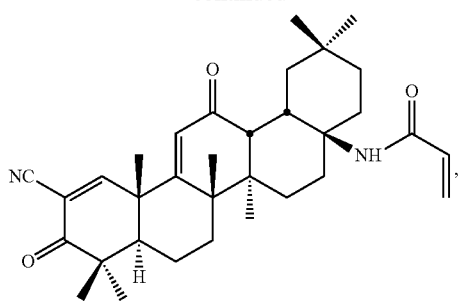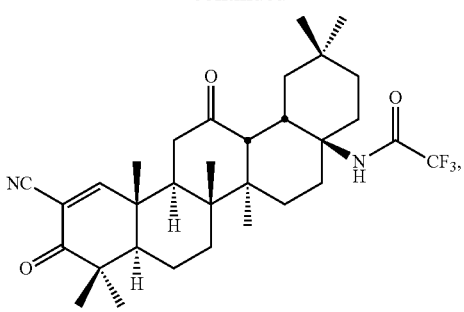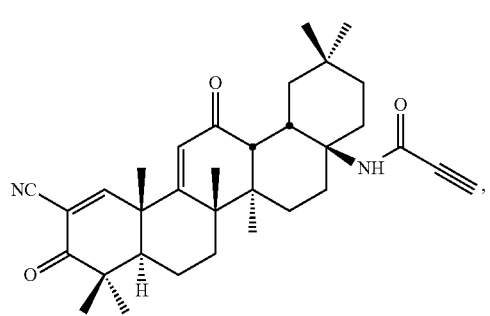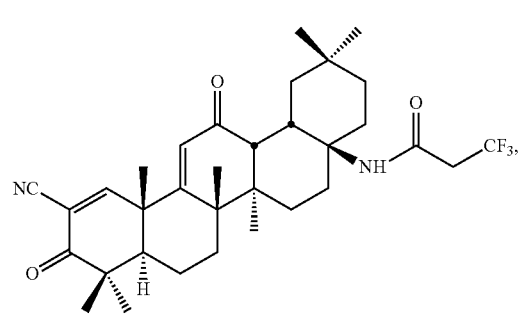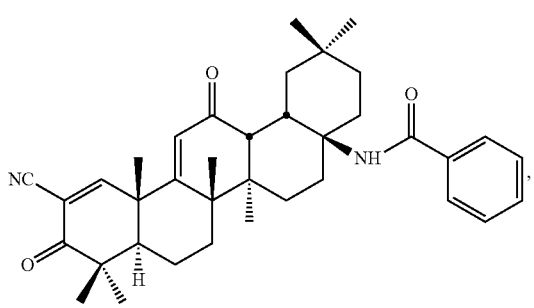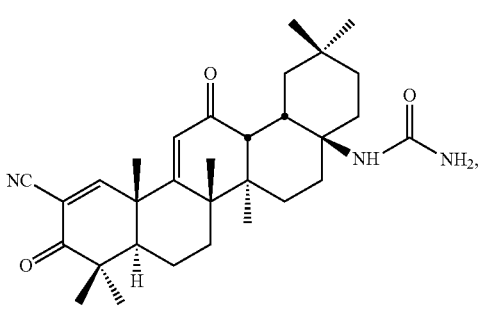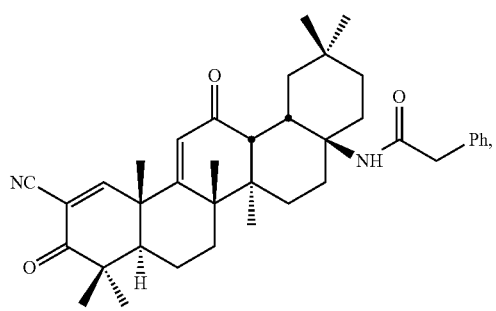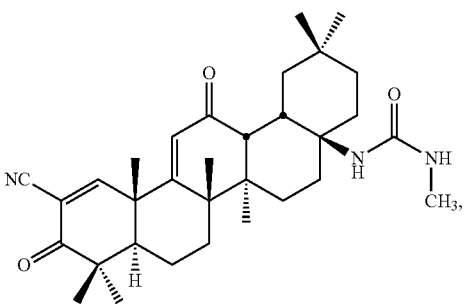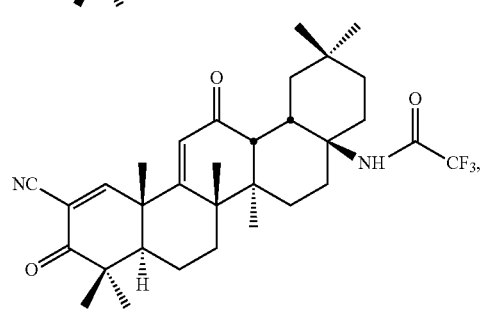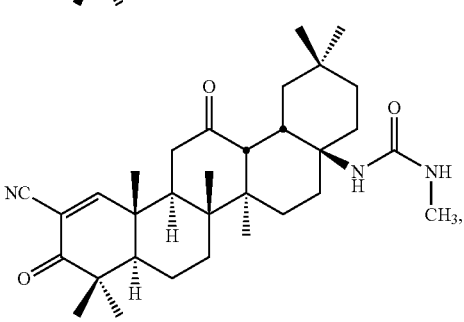

41
-continued
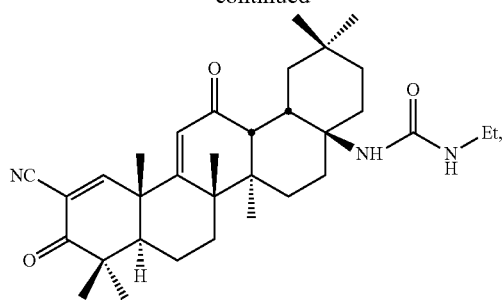
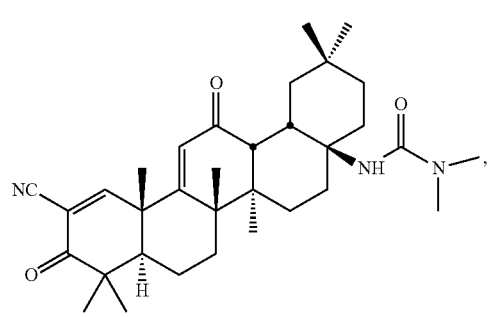
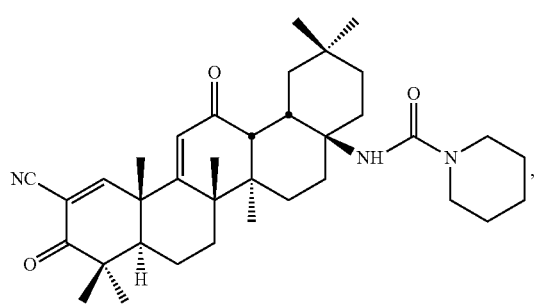
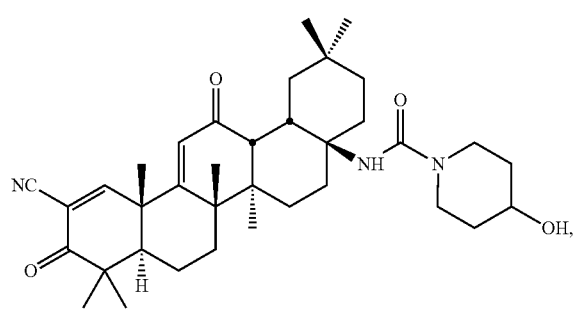
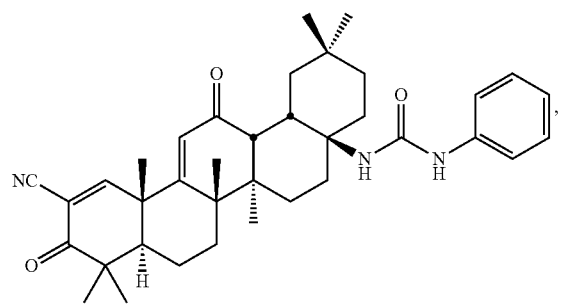
42
-continued
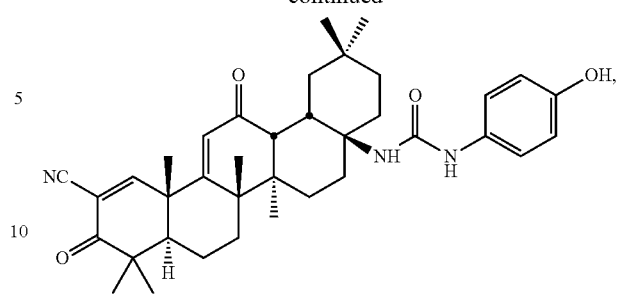
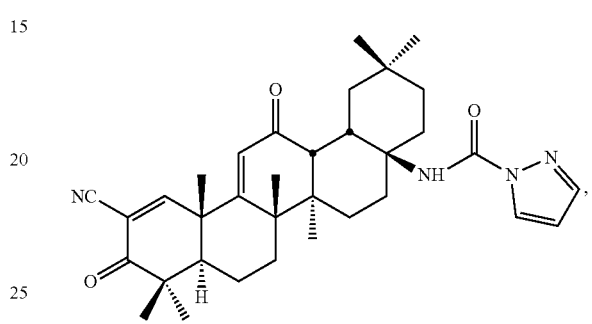
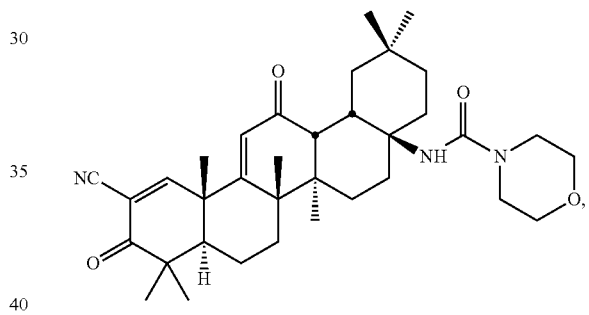
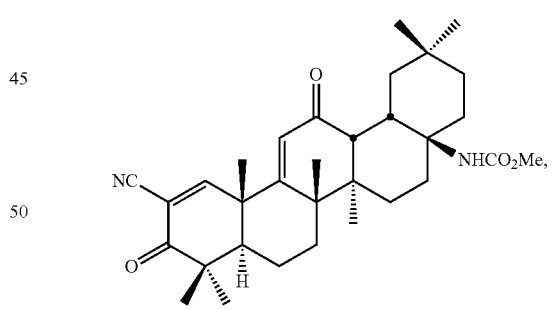
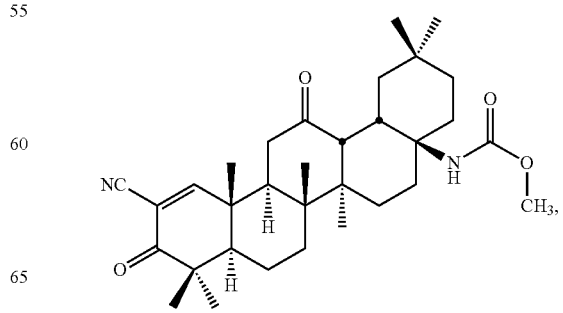

-continued
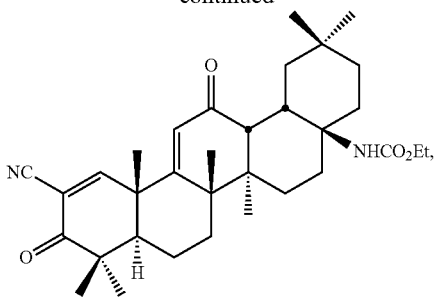
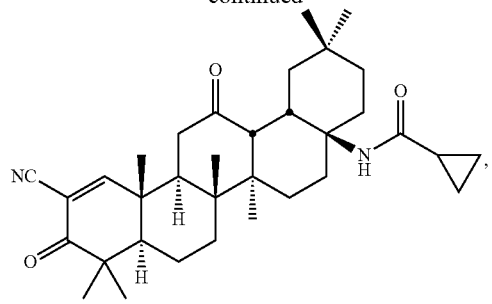
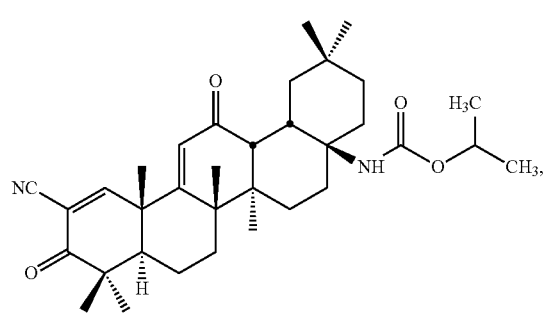
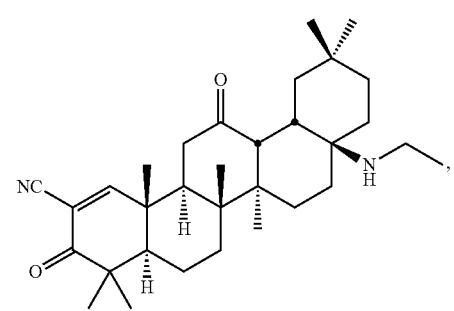
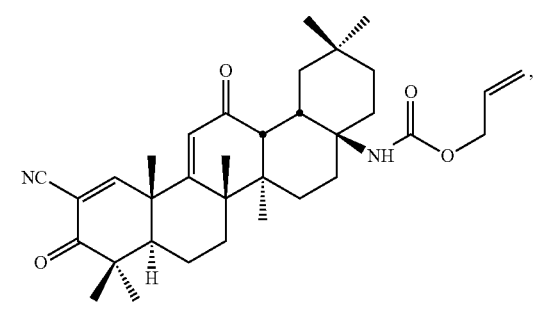
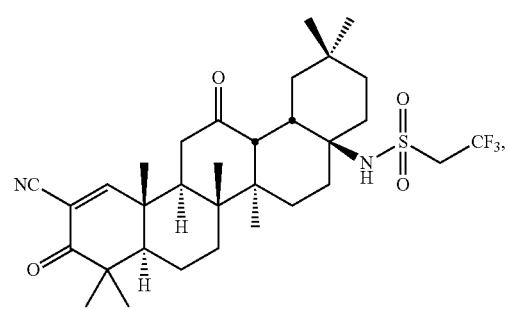
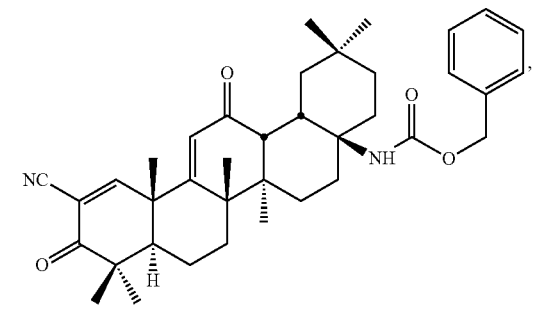
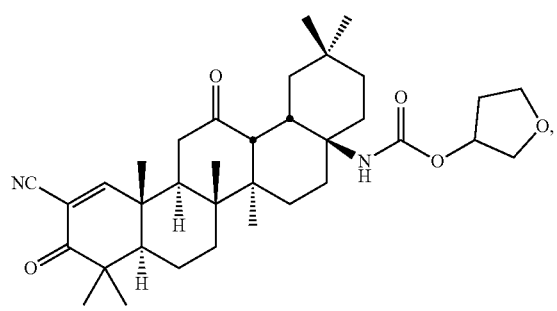
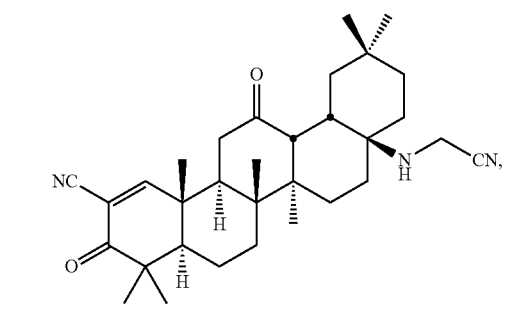
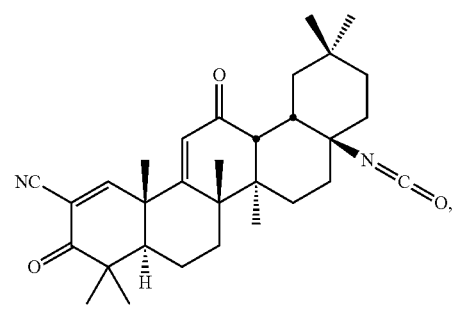

-continued
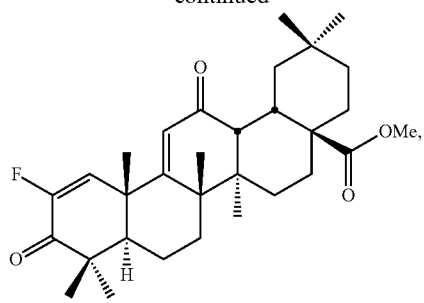
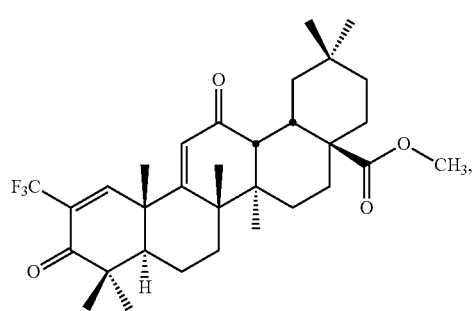
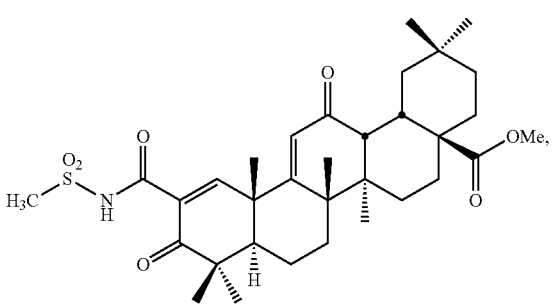
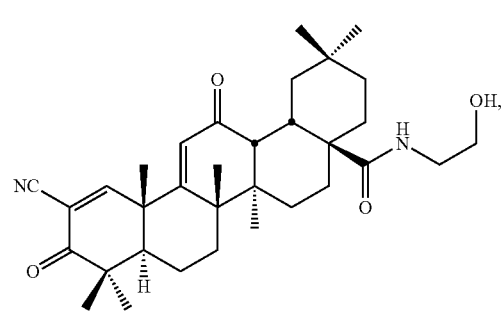
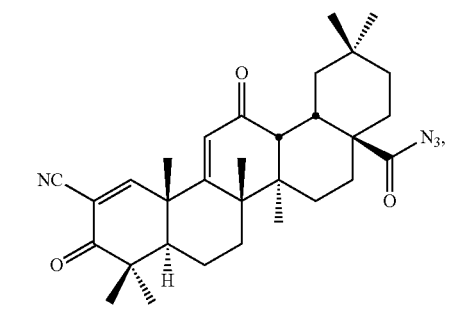
-continued
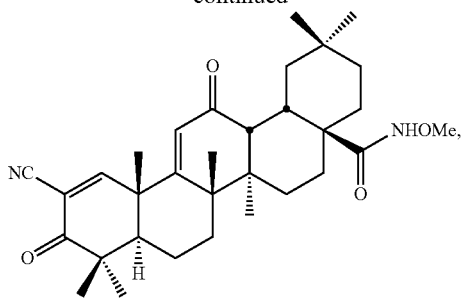
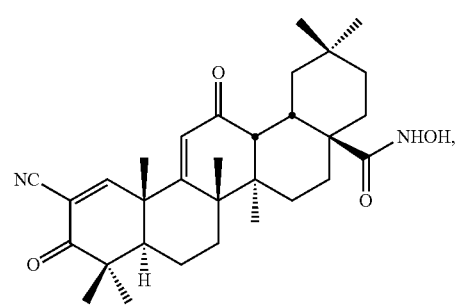
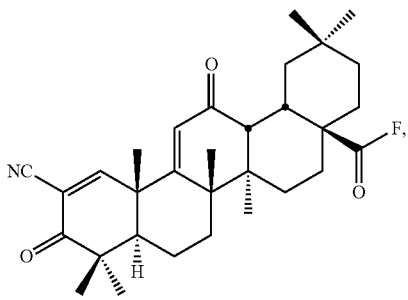
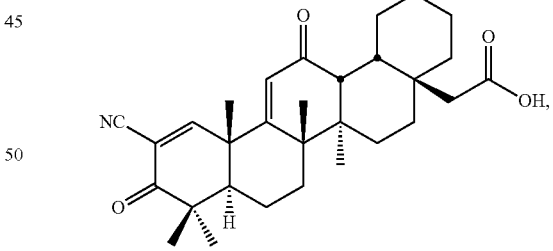
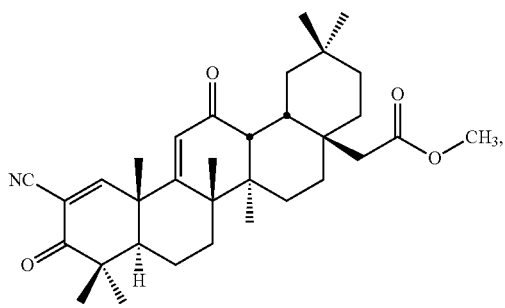

-continued
47
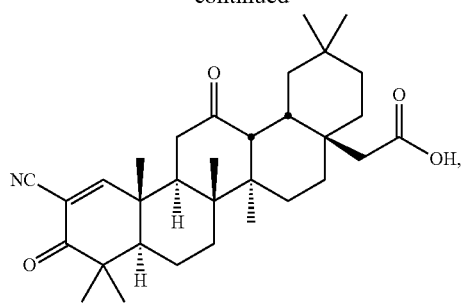
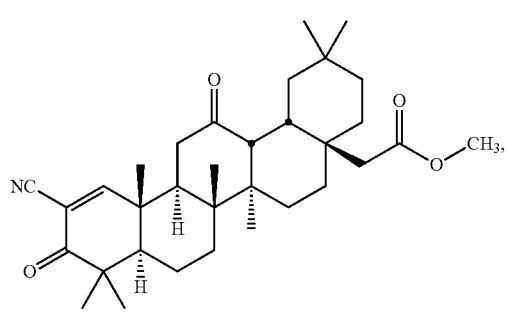
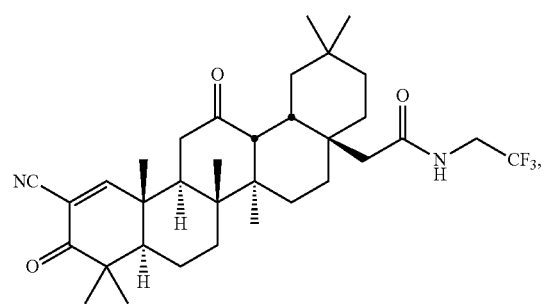
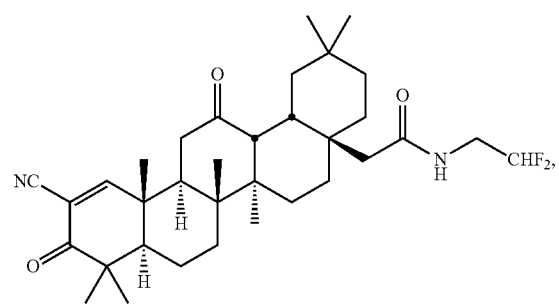
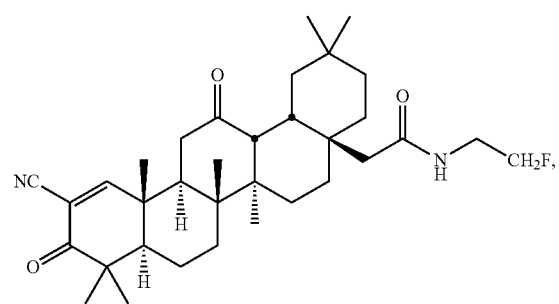
48
-continued
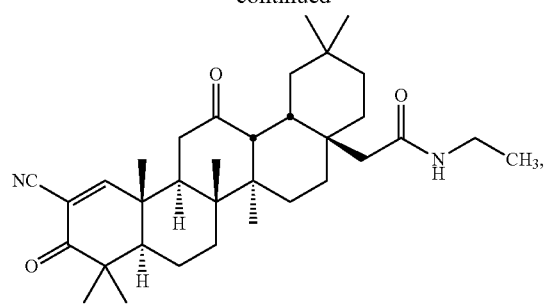
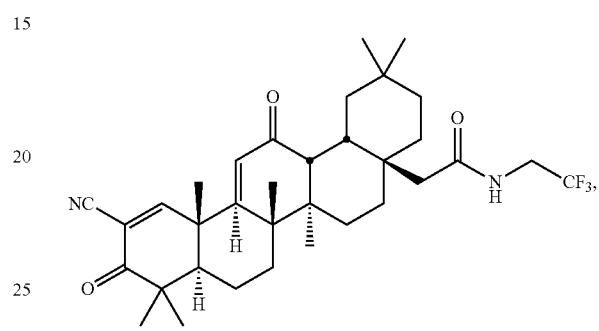
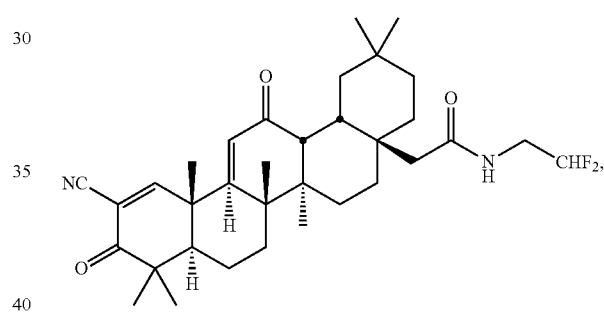
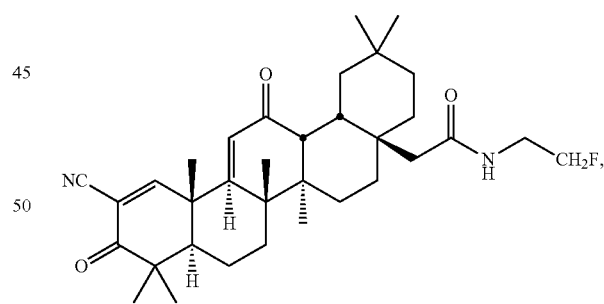
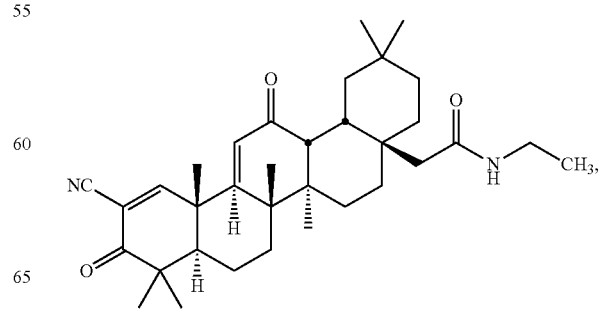

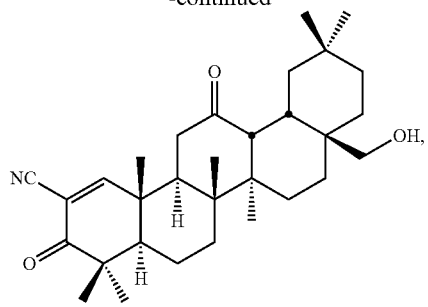
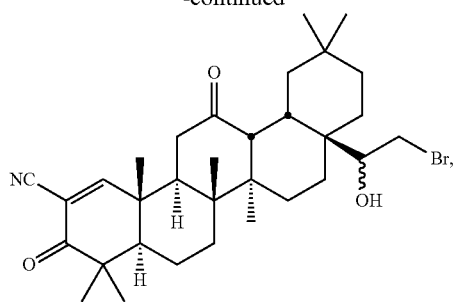
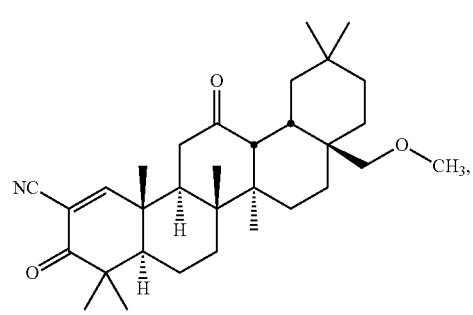
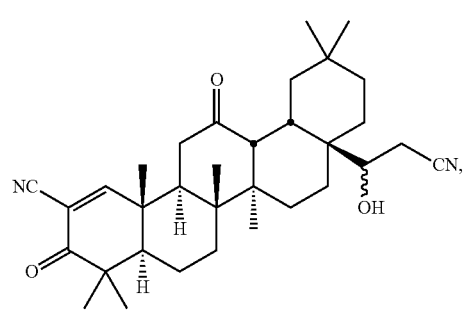
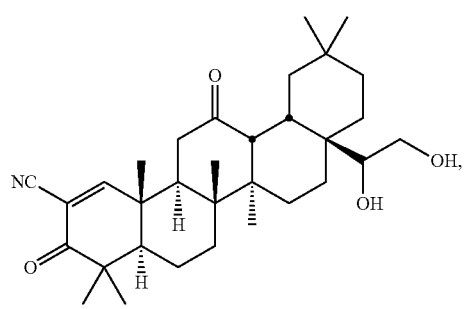
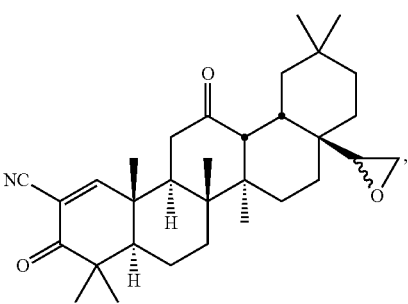
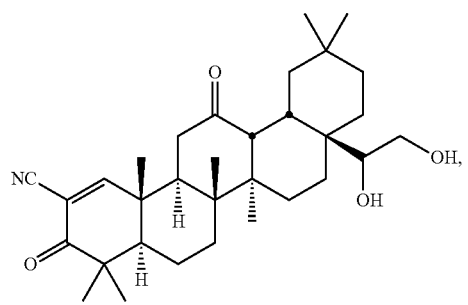
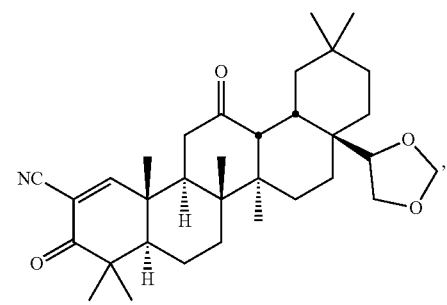
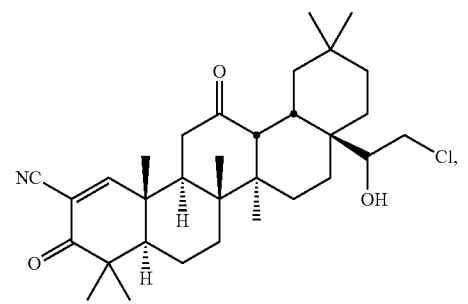
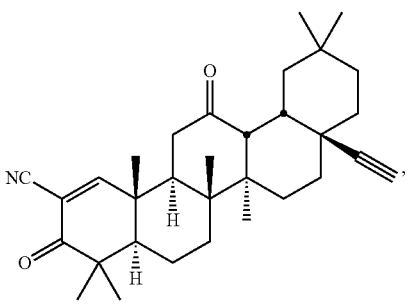

51
-continued
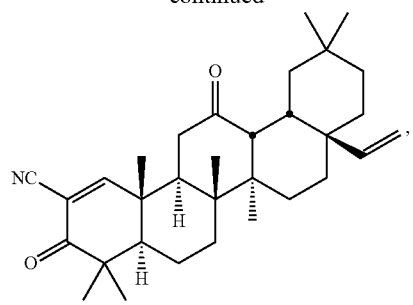
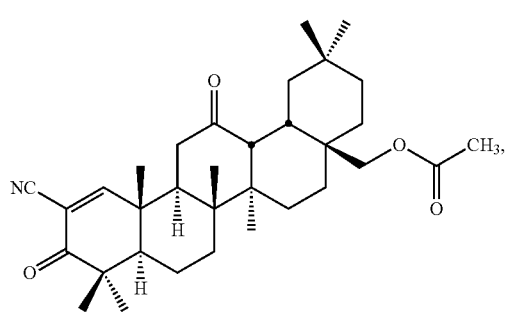
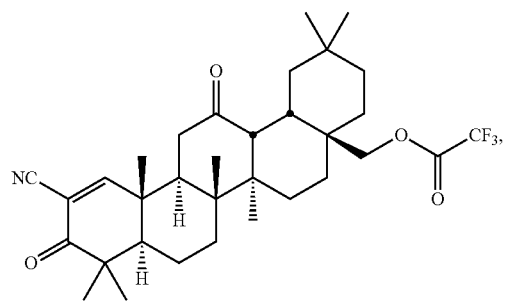
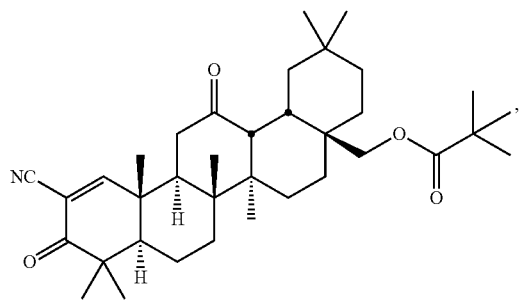
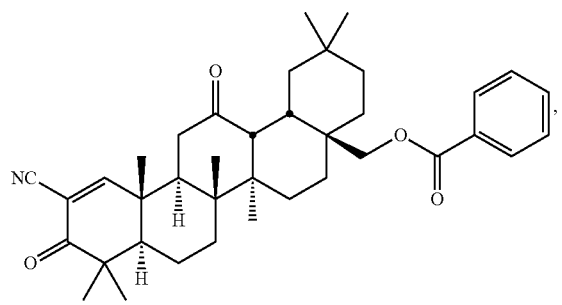
52
-continued
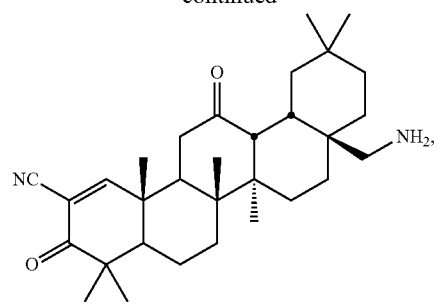
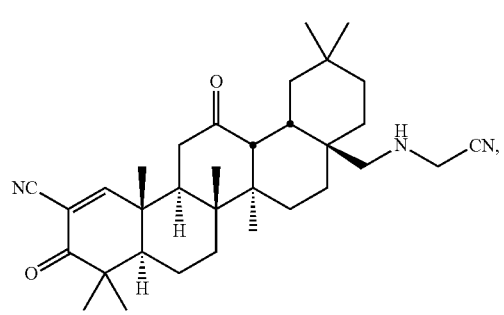
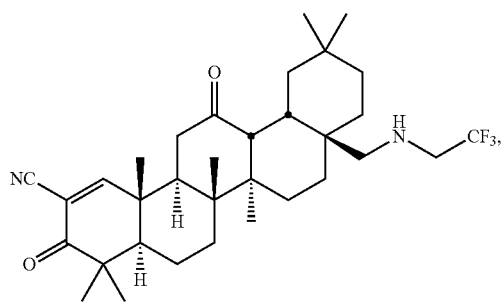
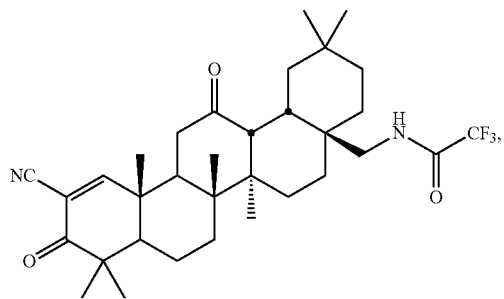
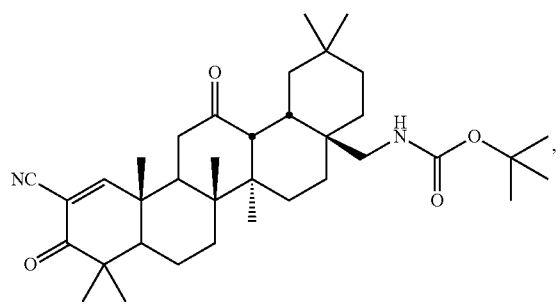

-continued
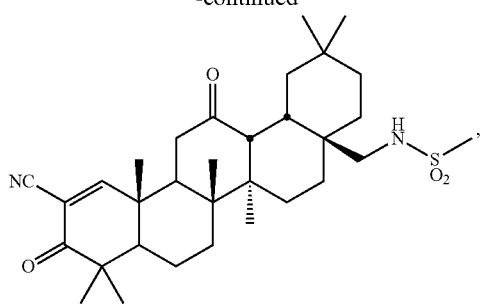
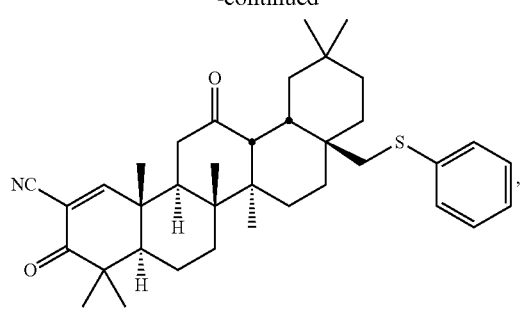
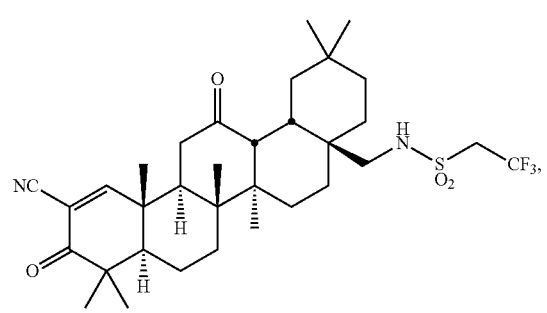
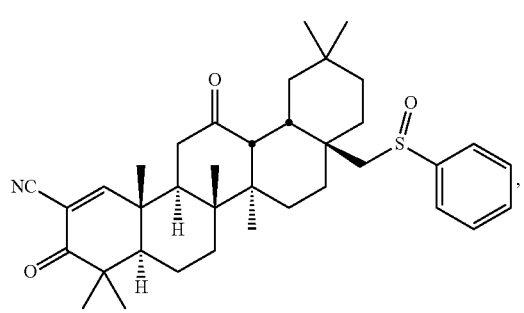
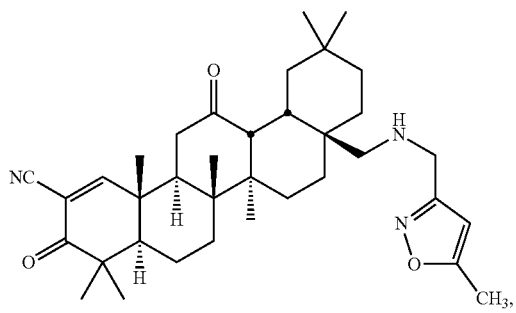
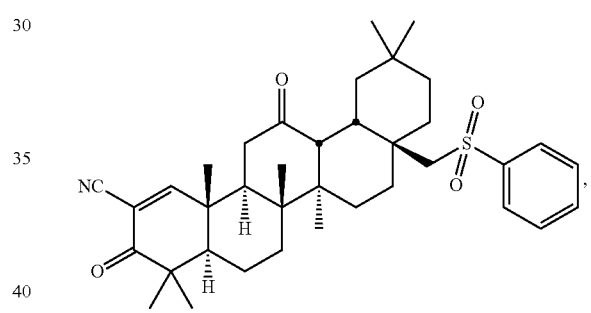
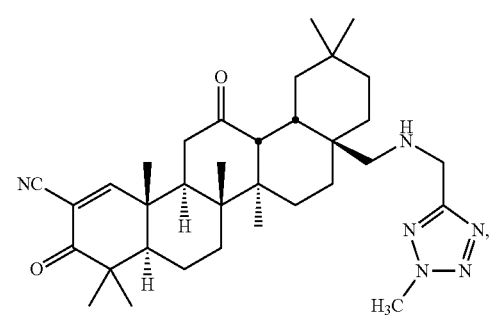
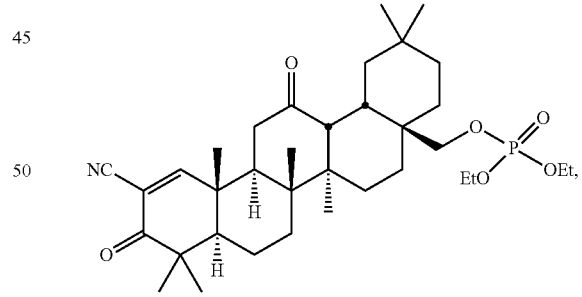
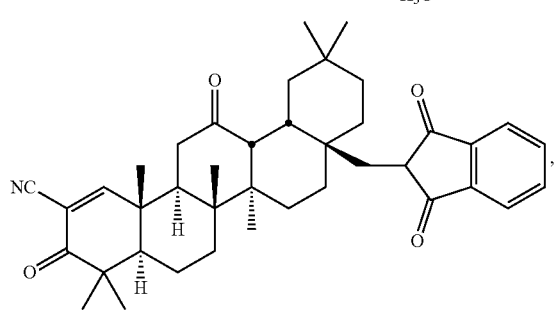
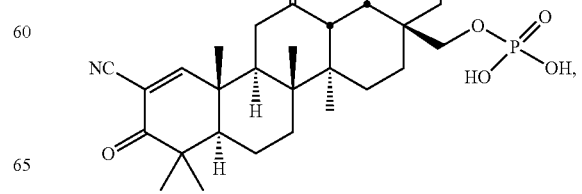

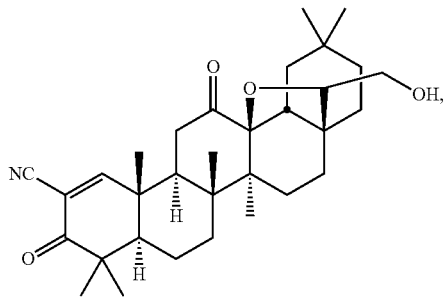
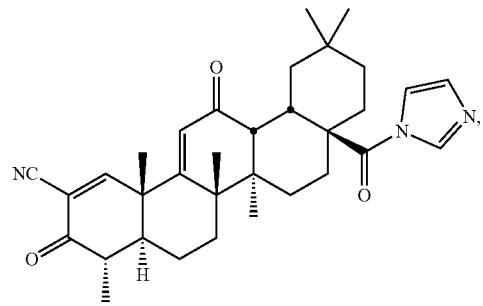
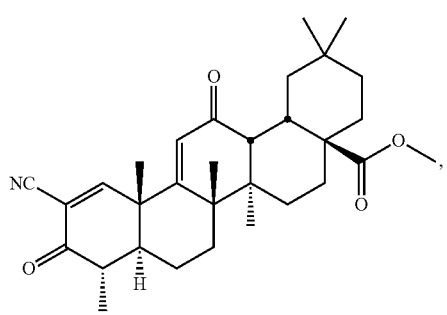
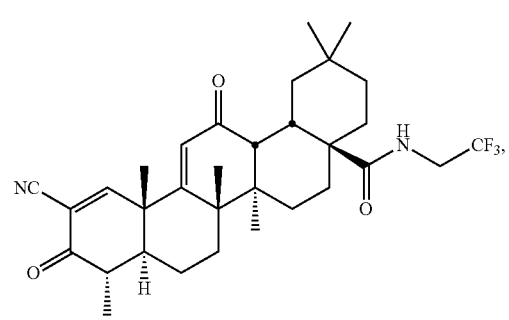
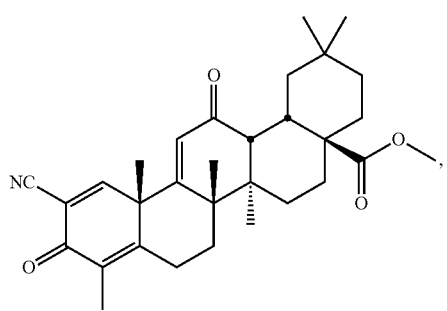
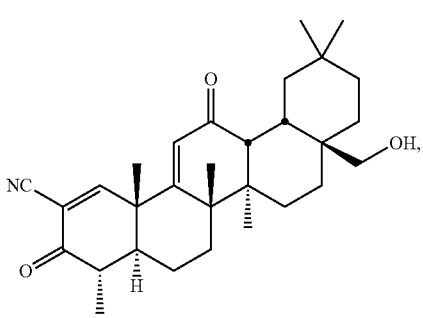
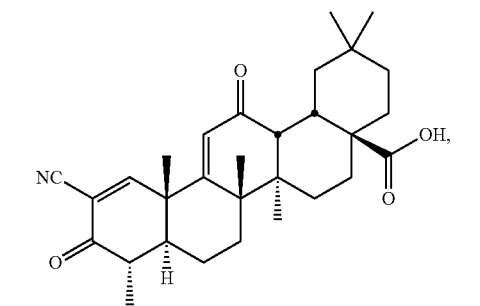
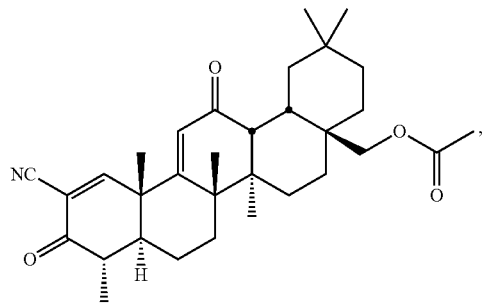
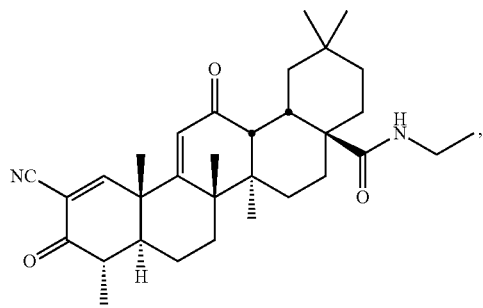
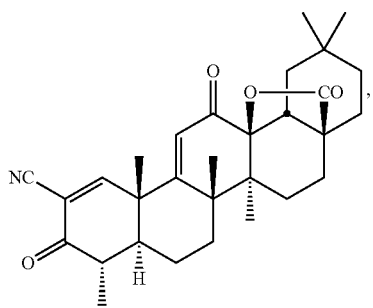

57
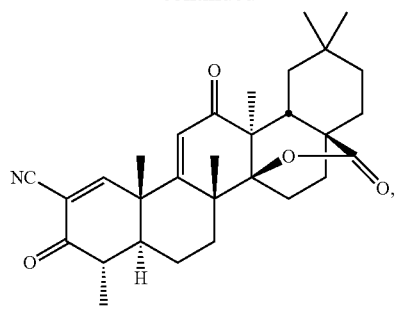
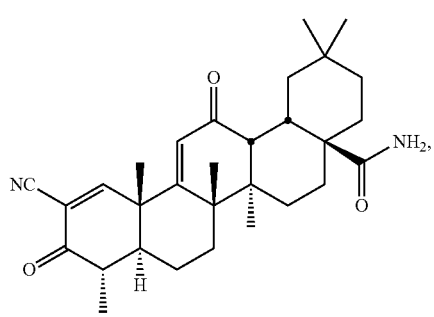
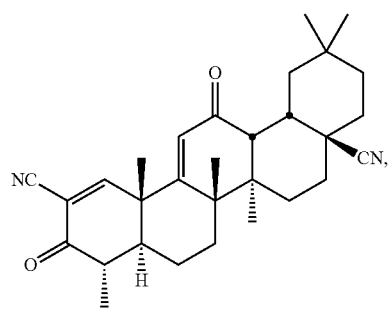
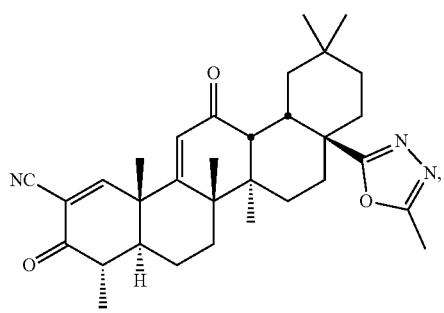
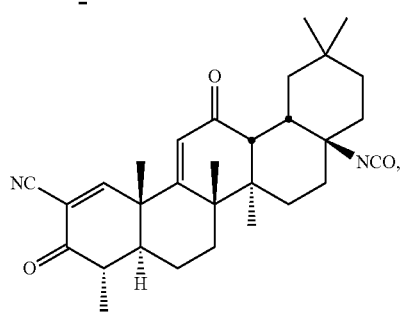
58
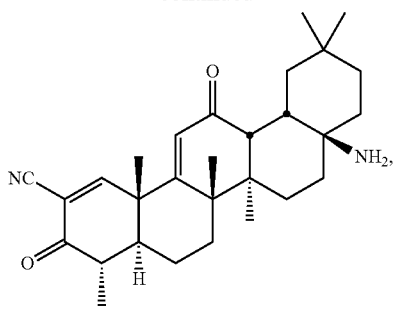
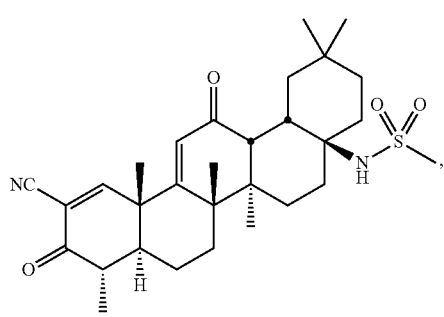
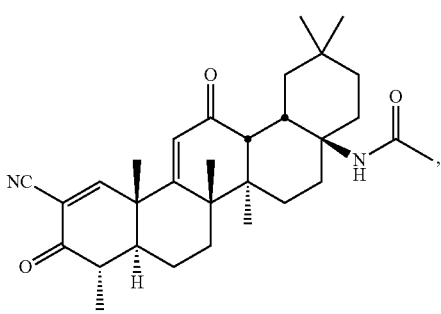
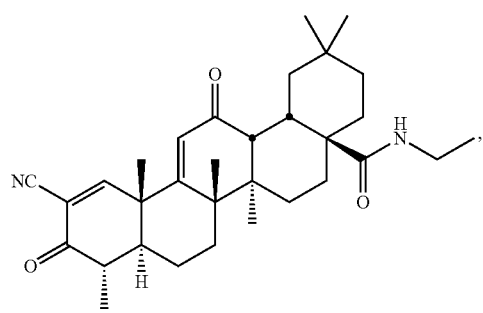
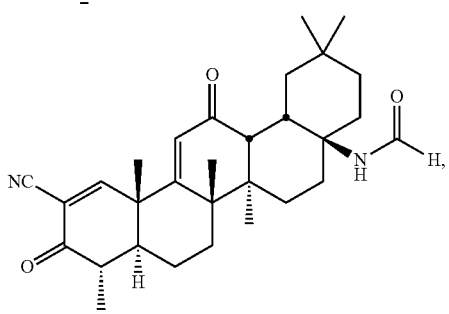

-continued
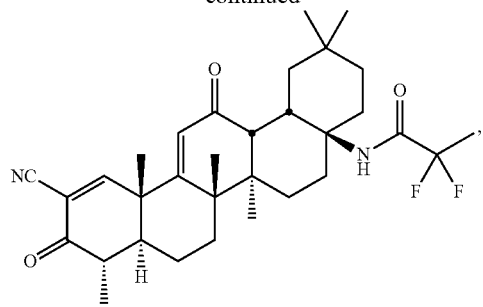
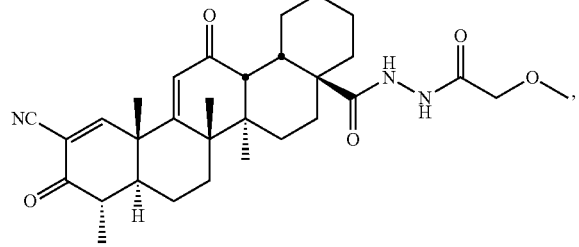
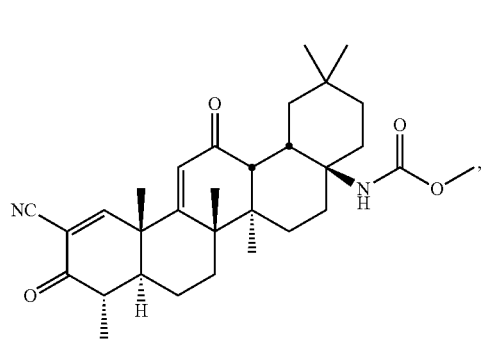
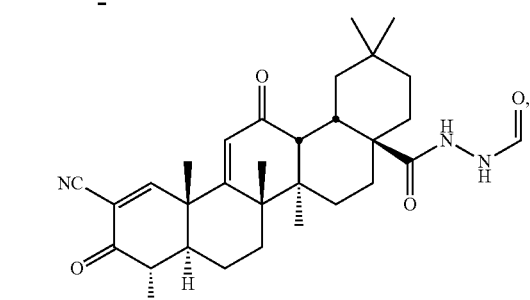
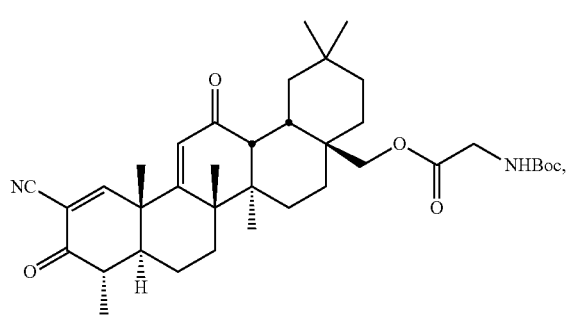
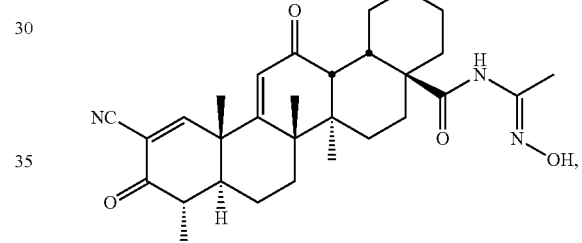
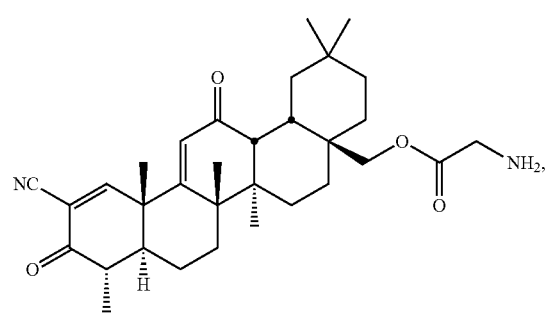
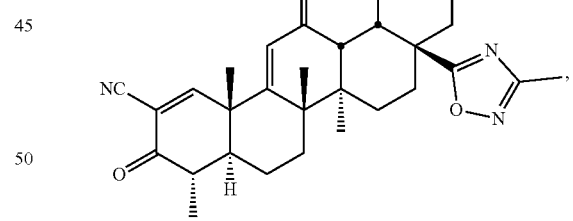
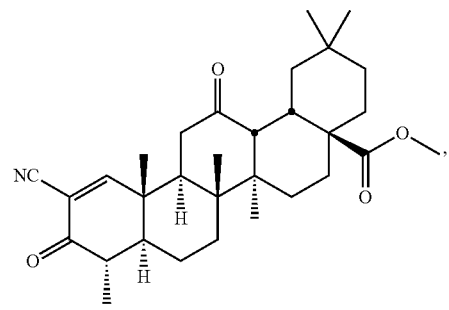
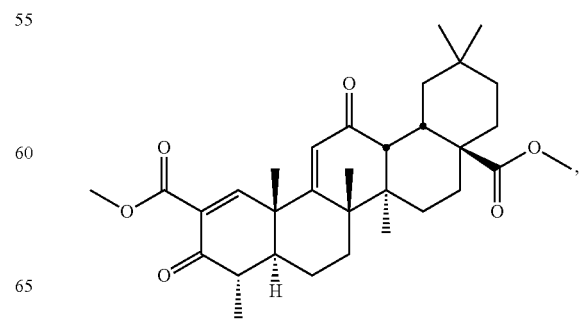

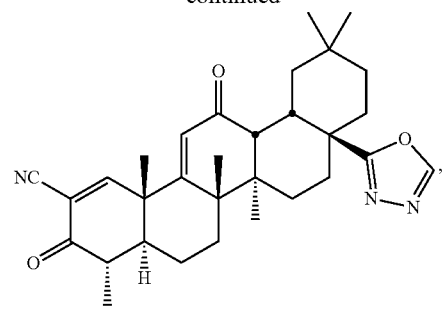
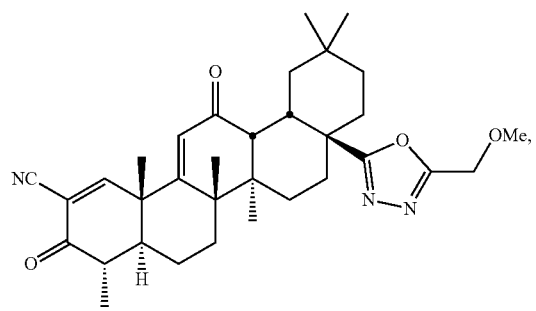
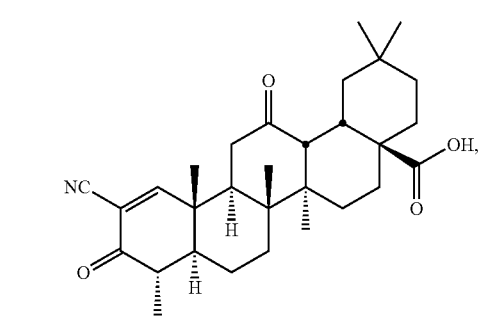
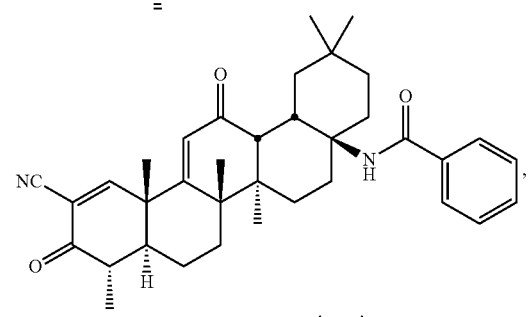
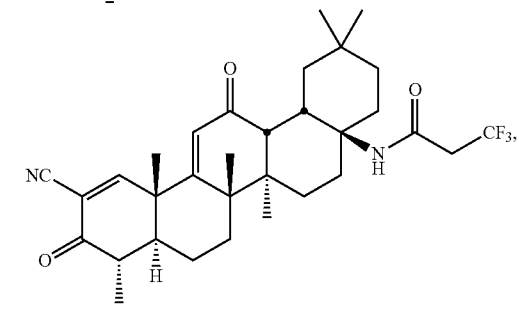
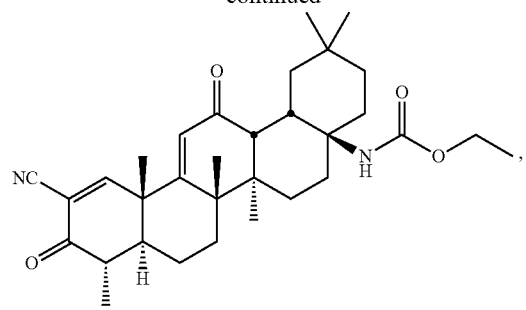
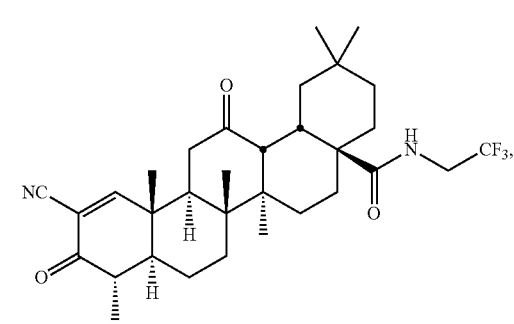
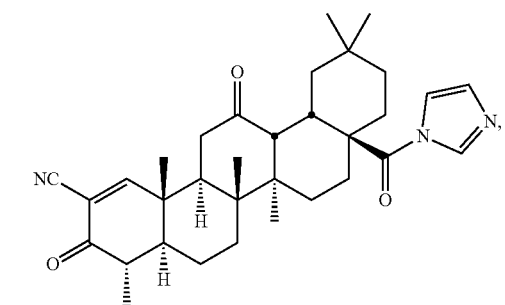
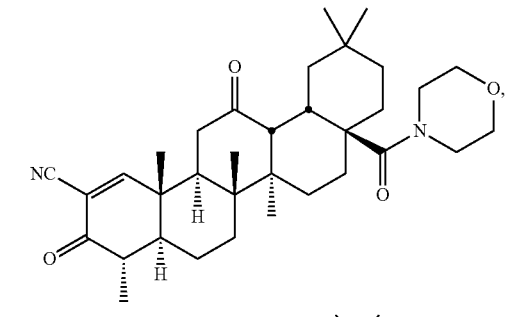
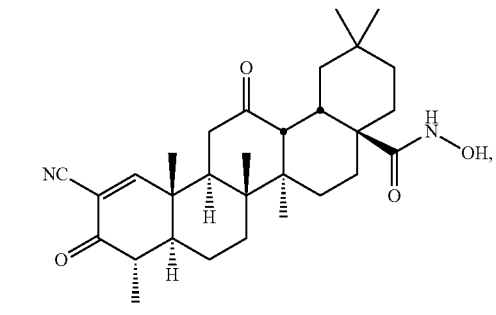

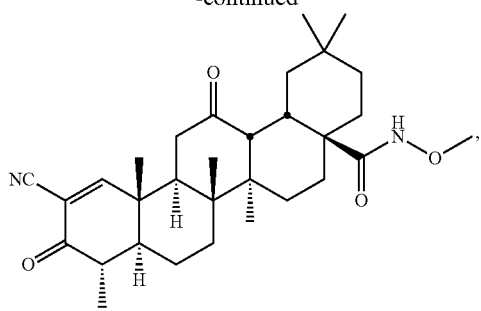
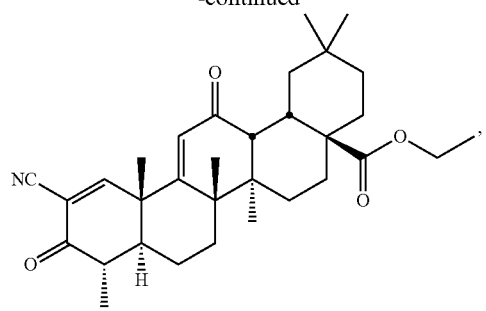
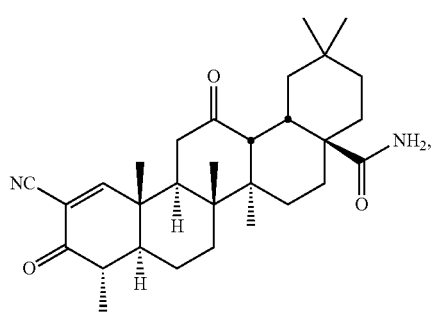
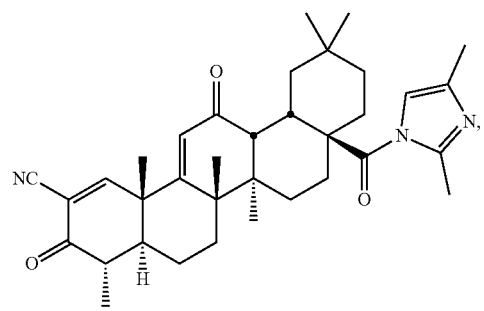
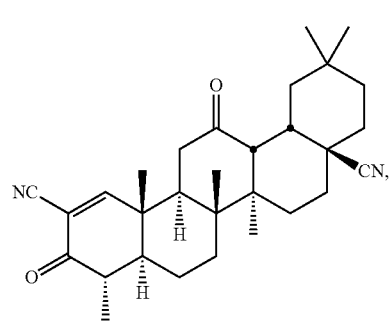
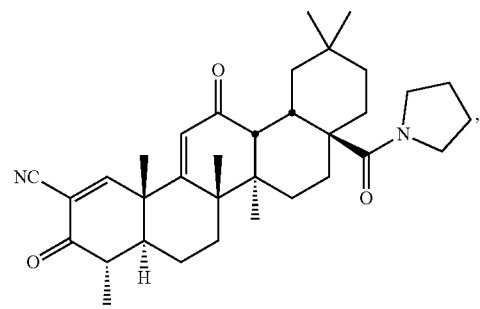
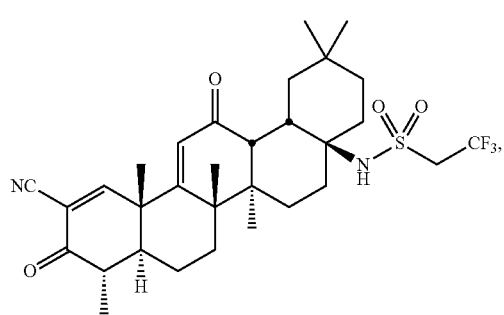
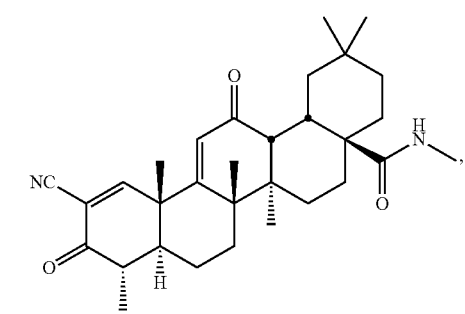
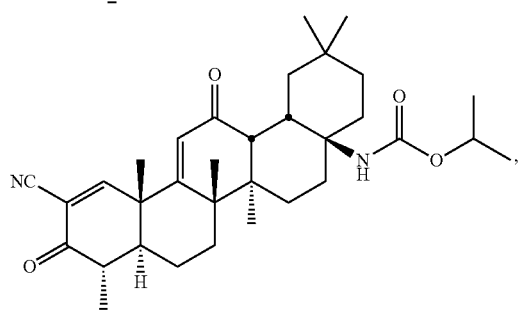

65
-continued
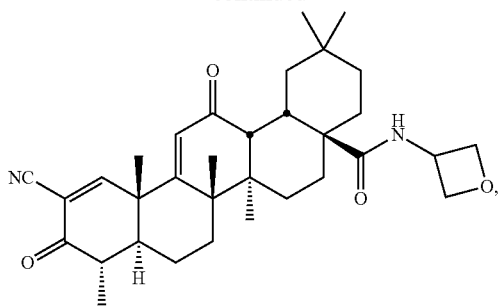
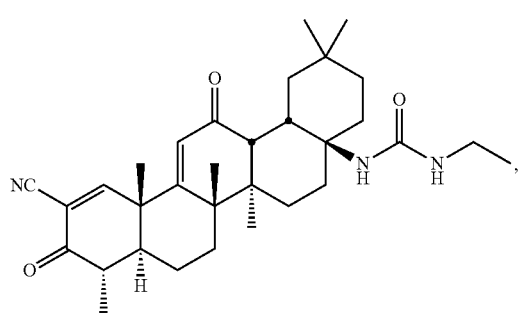
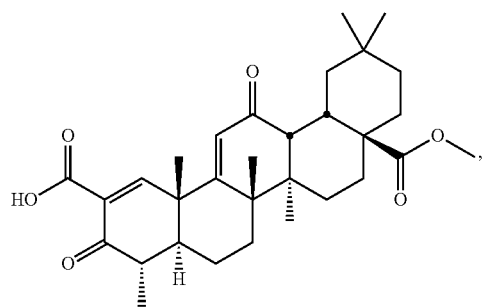
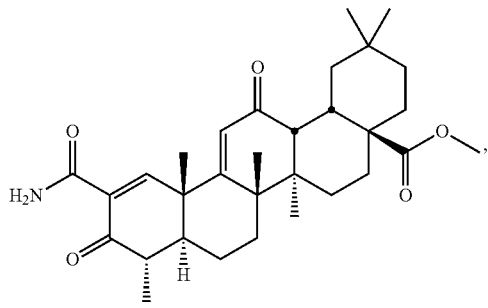
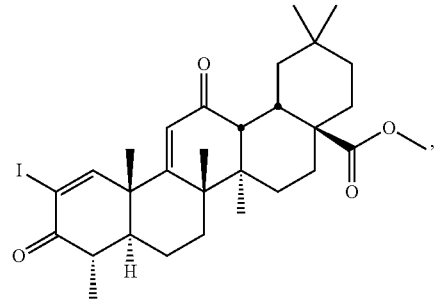
66
-continued
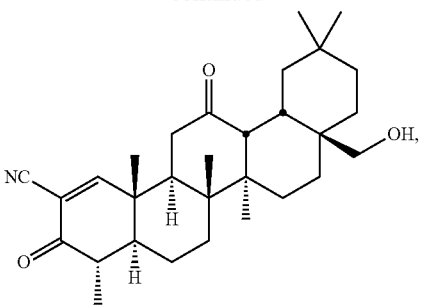
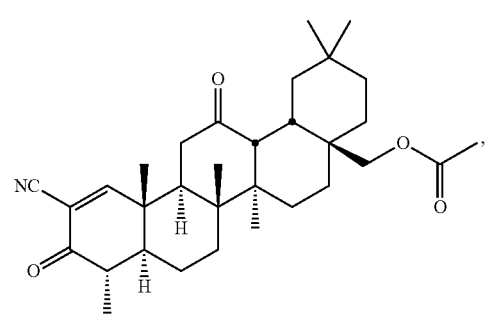
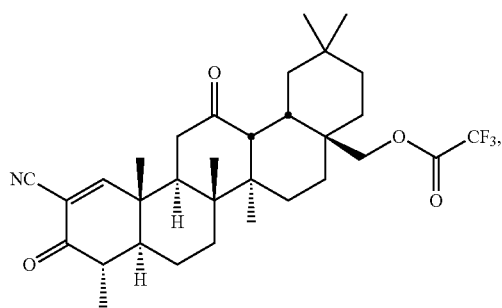
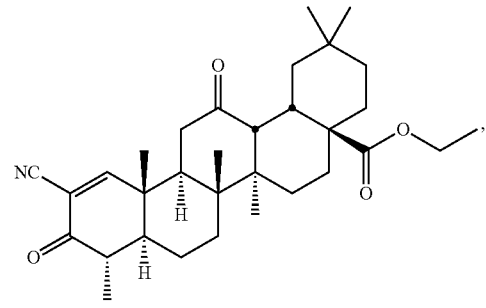
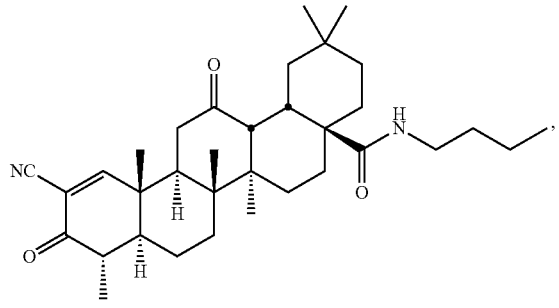

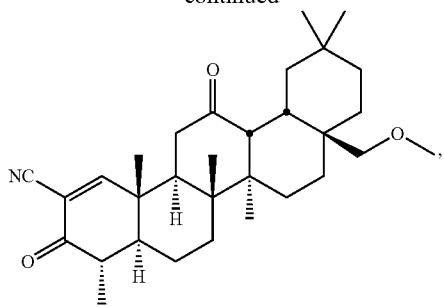
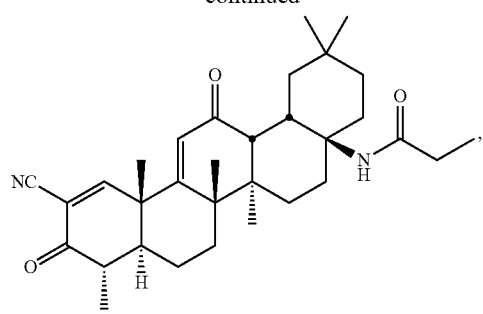
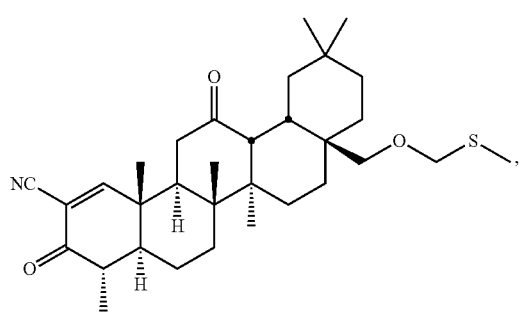
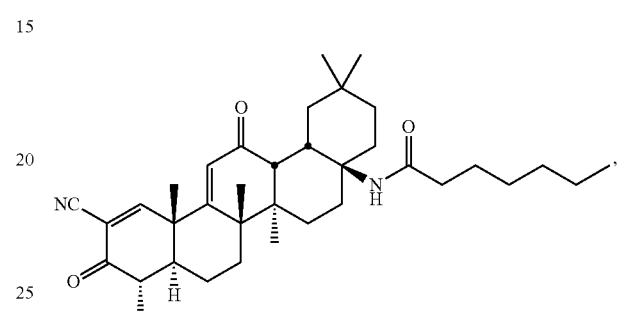
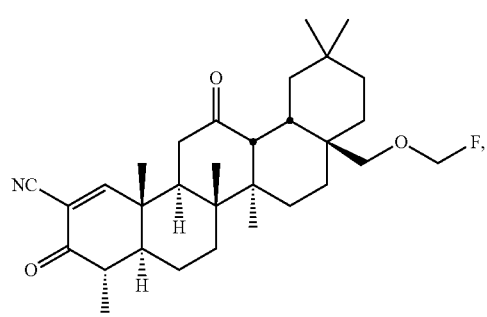
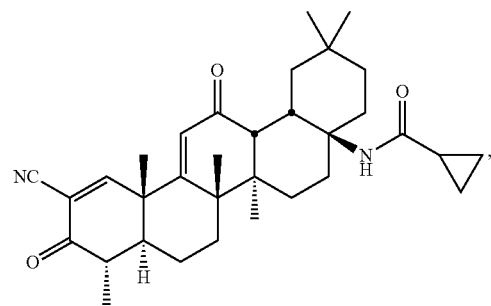
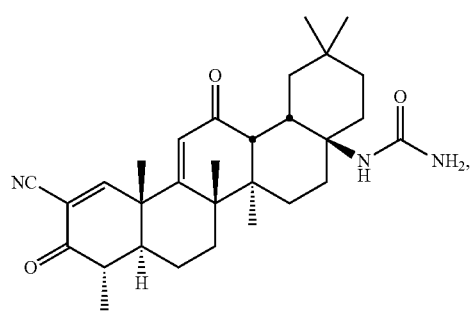
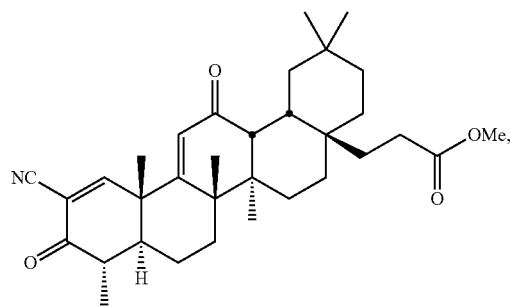
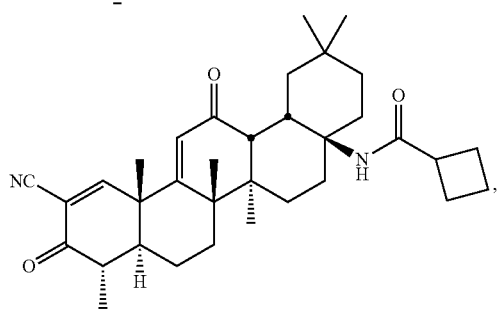
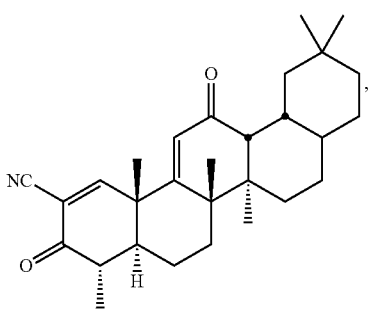

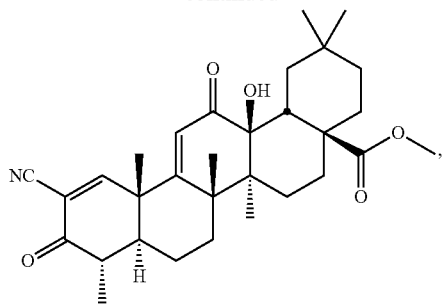
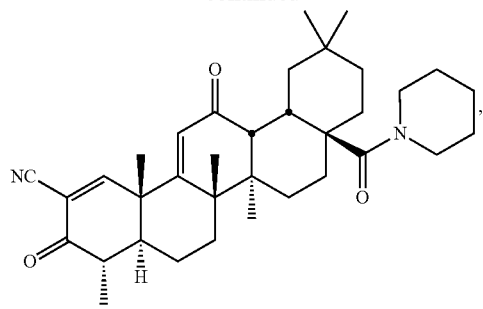
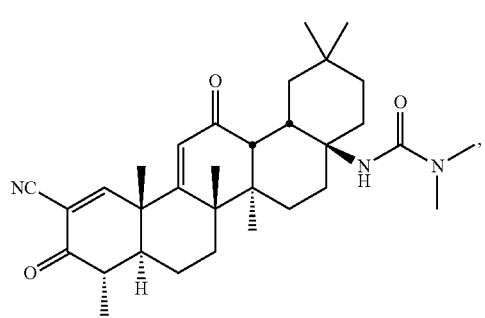
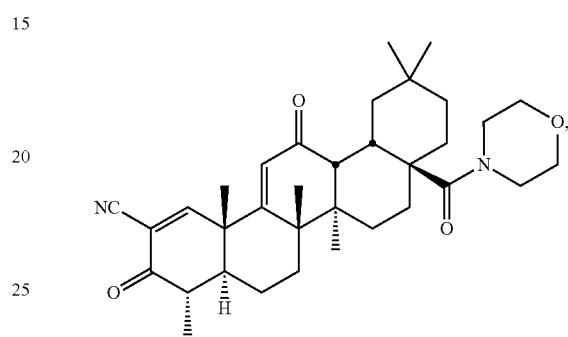
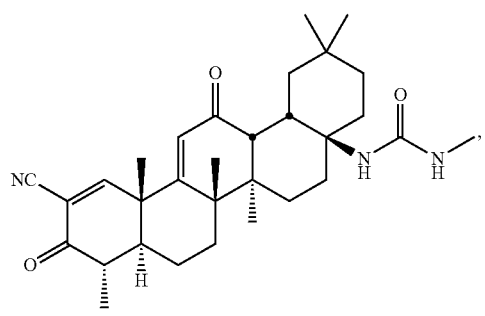
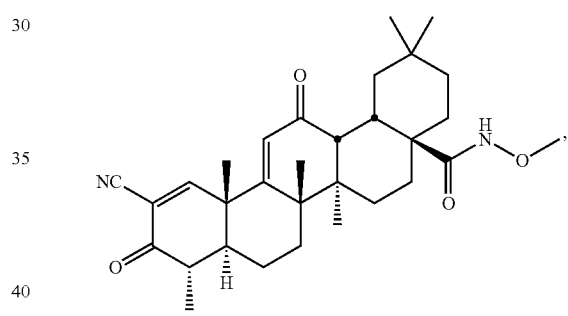
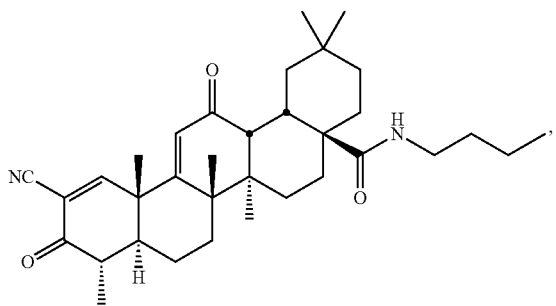
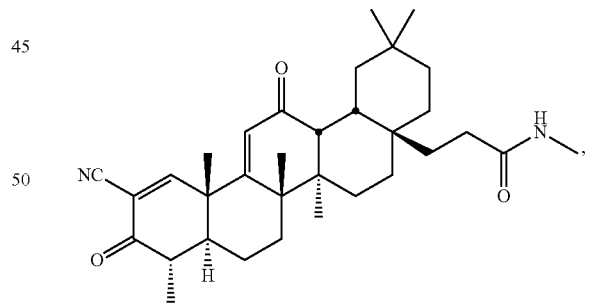
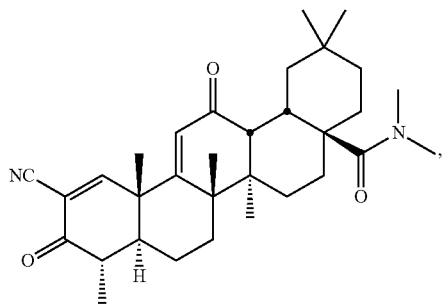
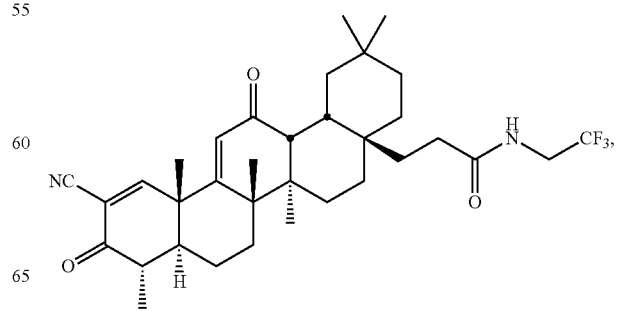

71
-continued
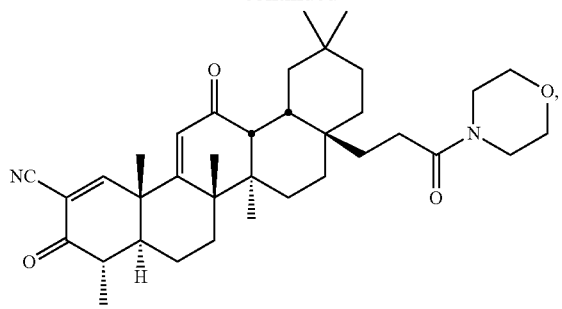
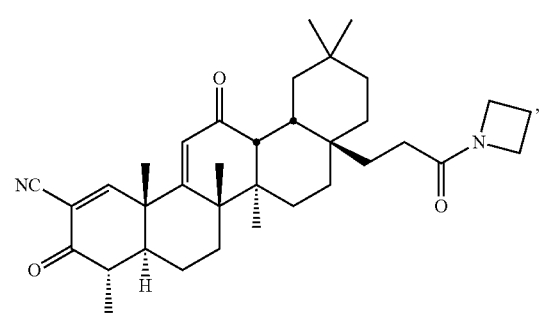
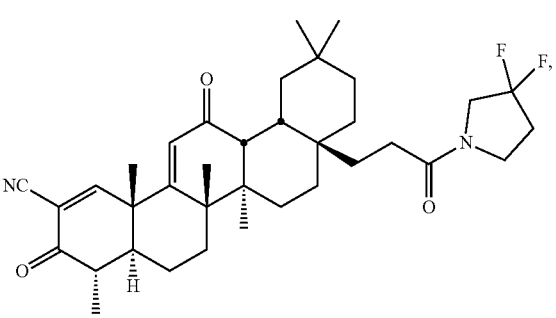
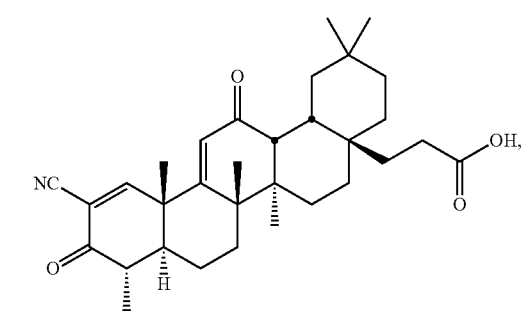
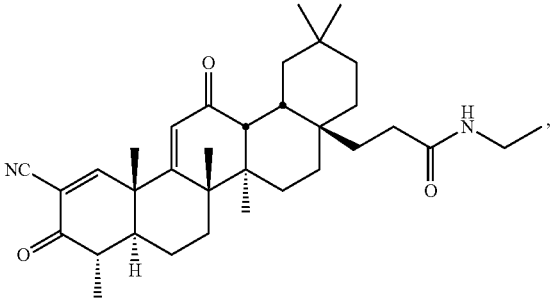
72
-continued
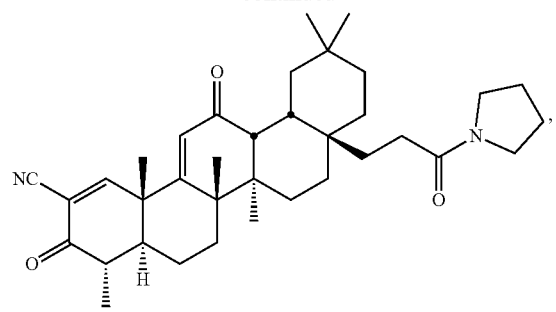
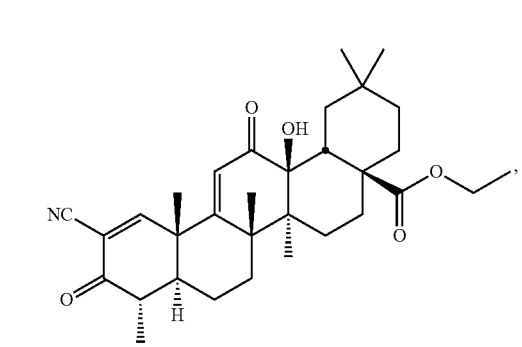
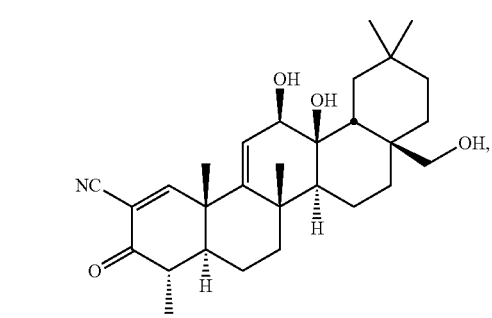
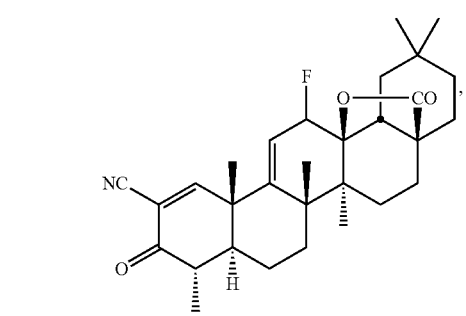
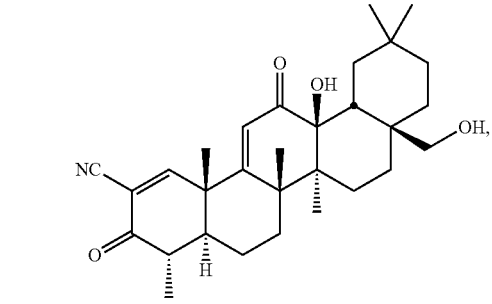

73
-continued
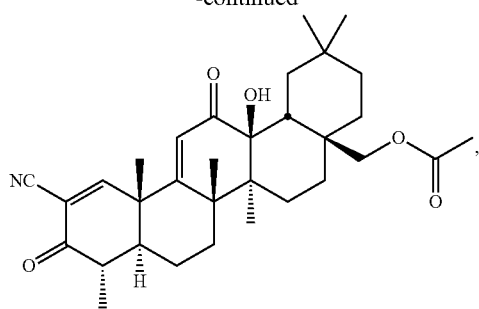
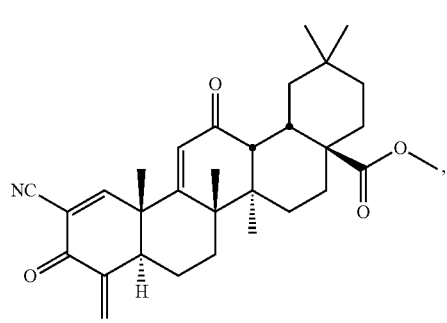
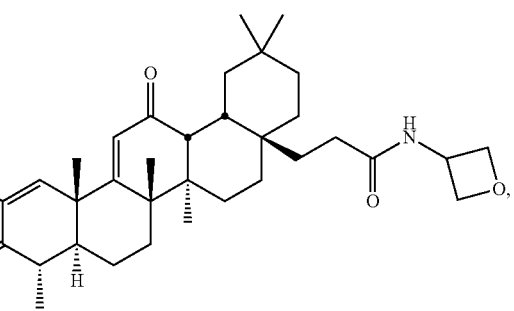
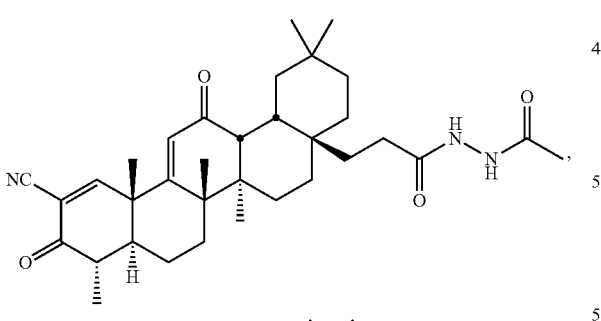
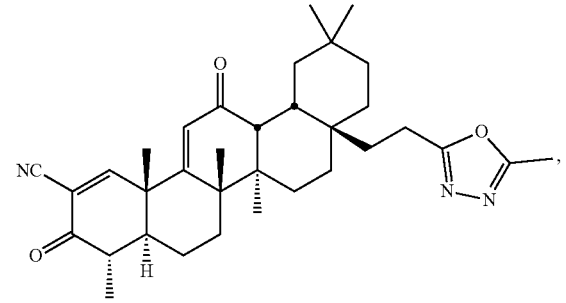
74
-continued
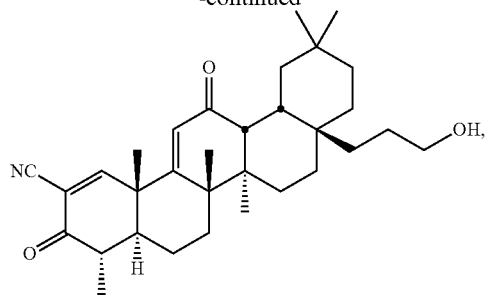
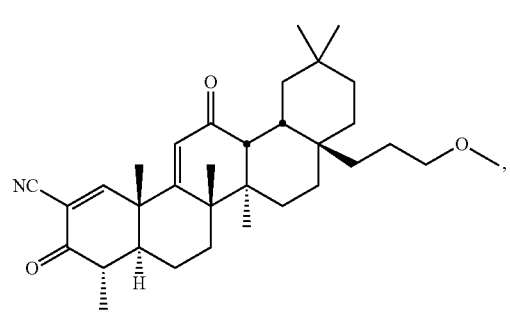
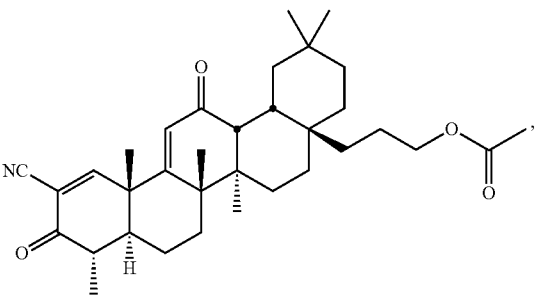
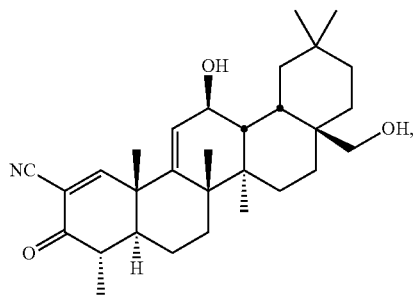
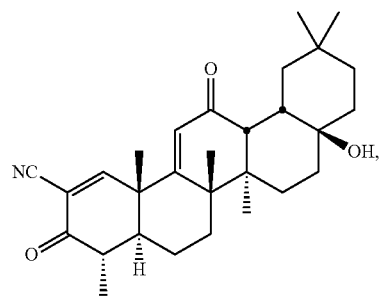

75
-continued
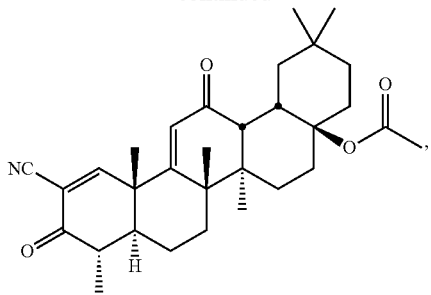
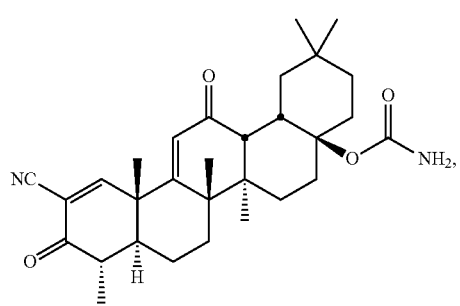
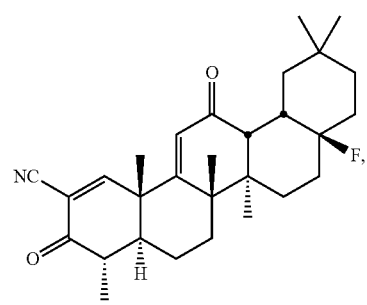
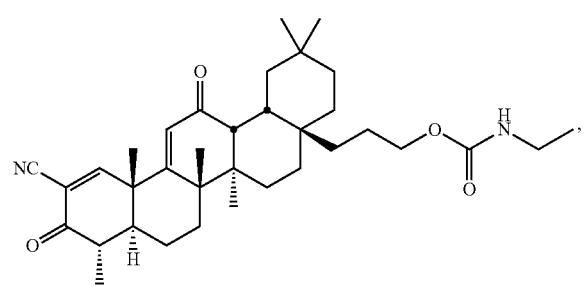
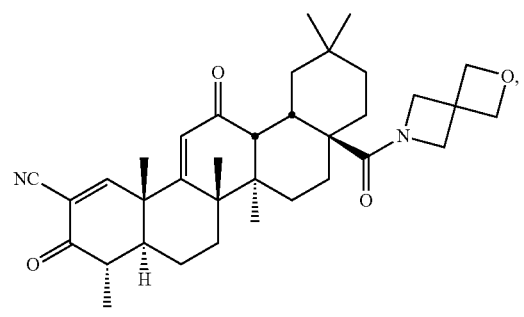
76
-continued
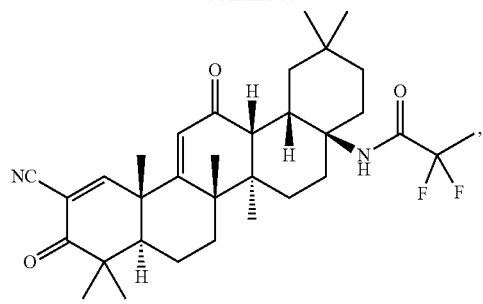
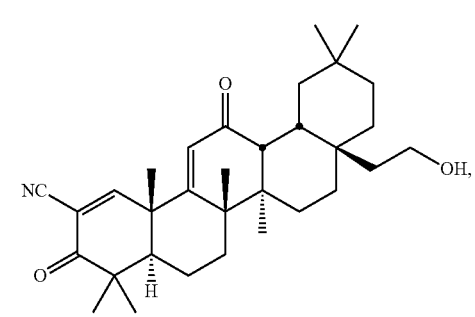
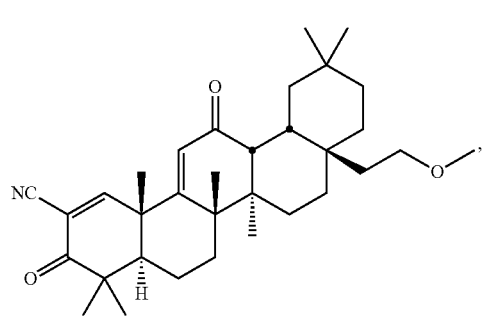
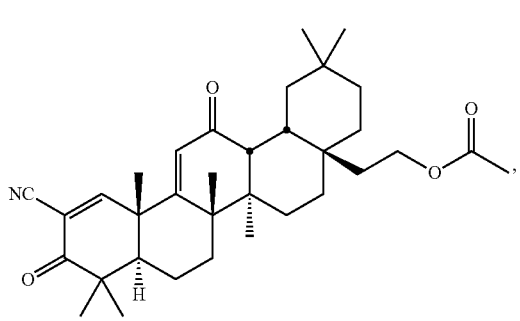
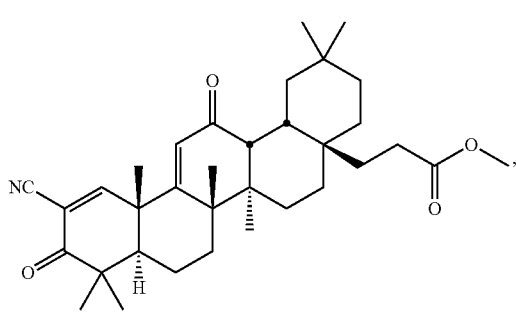

77
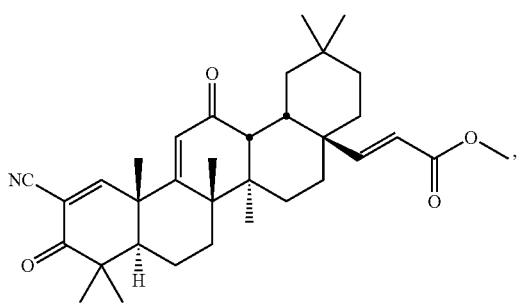
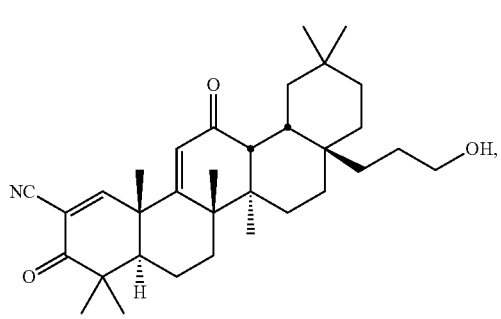
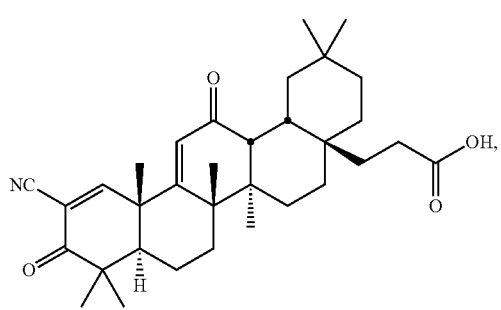
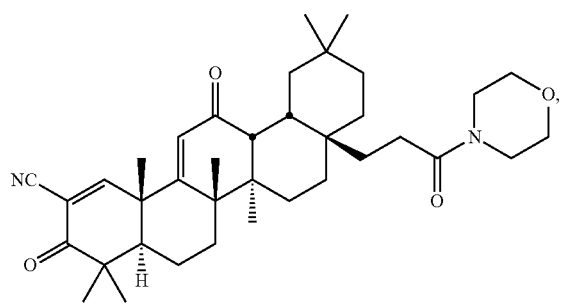
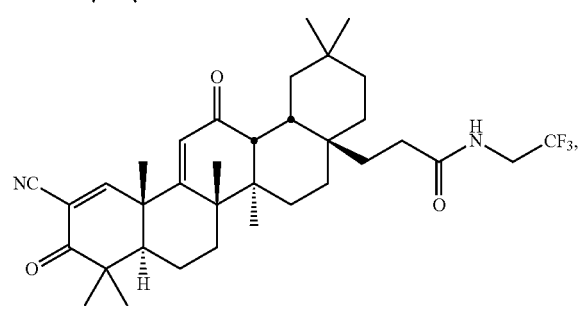
78
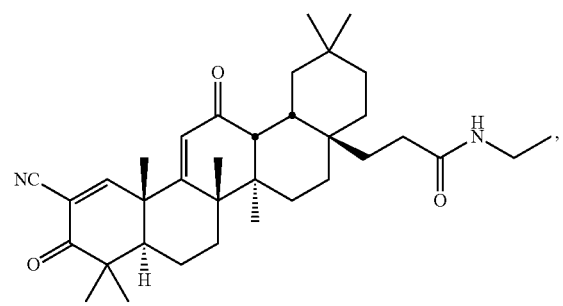
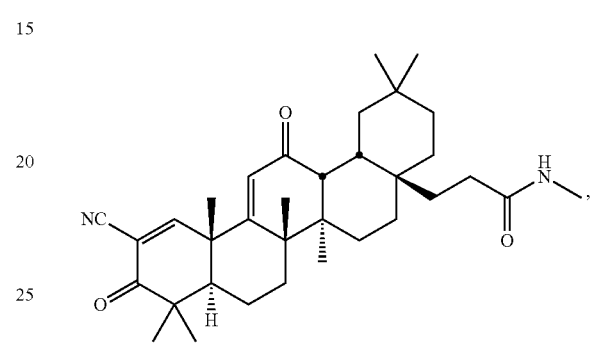
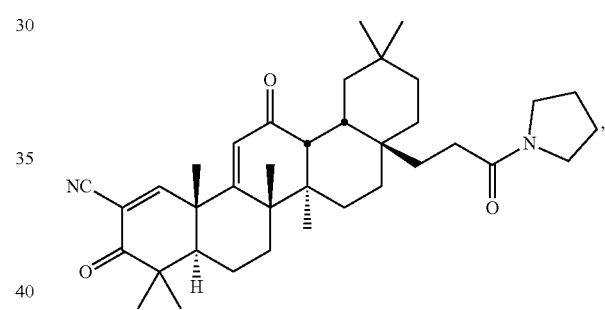
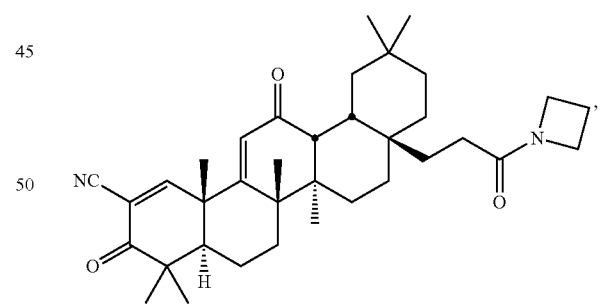
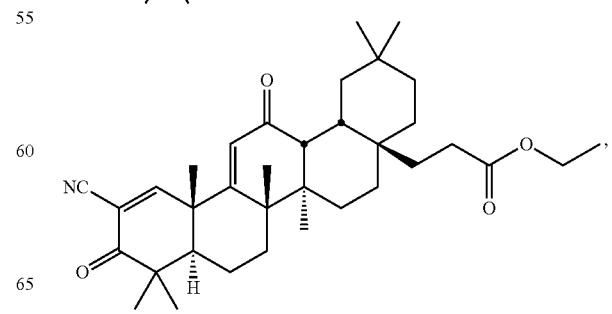

79
-continued
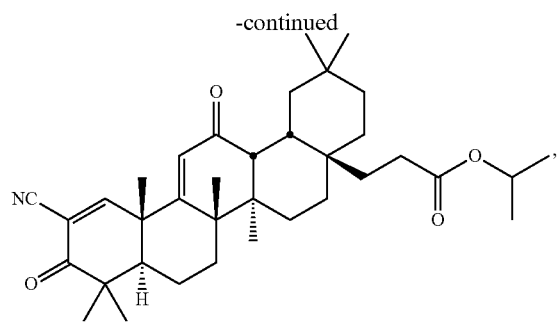
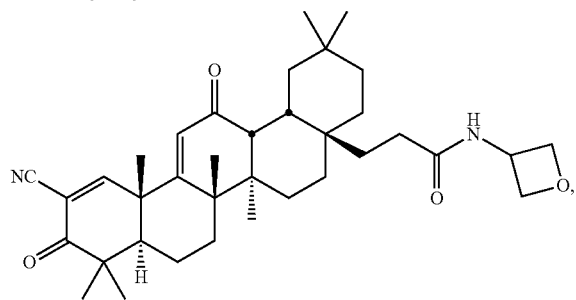
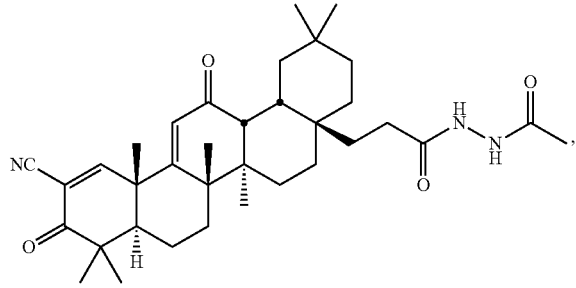
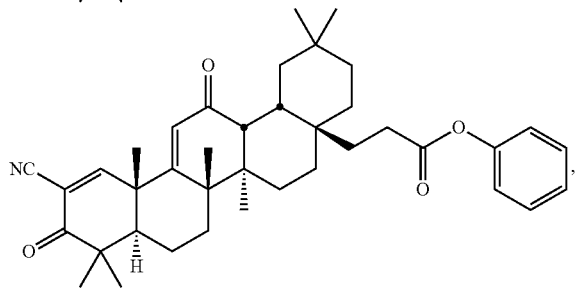
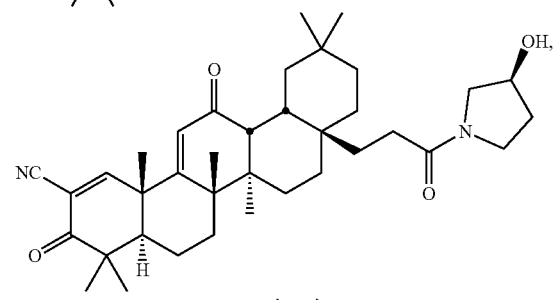
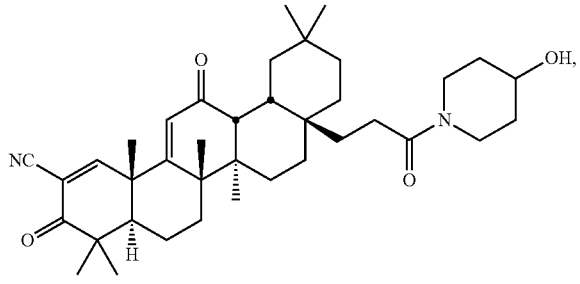
80
-continued
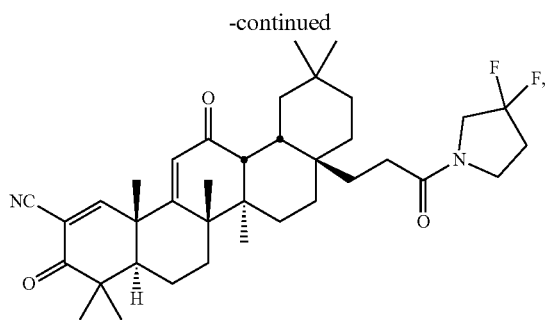
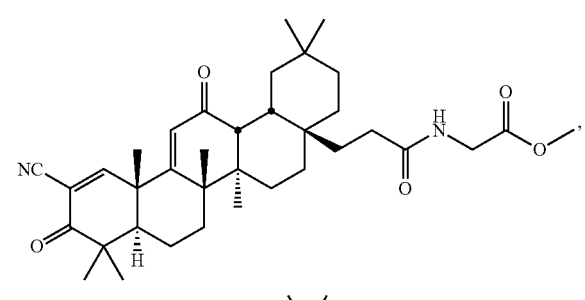
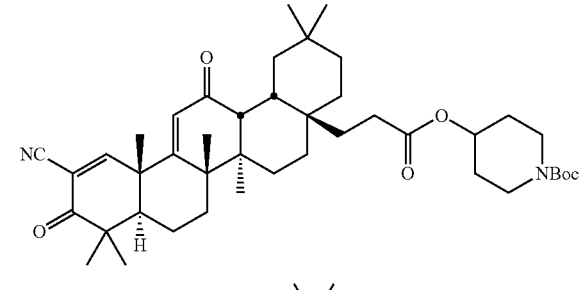
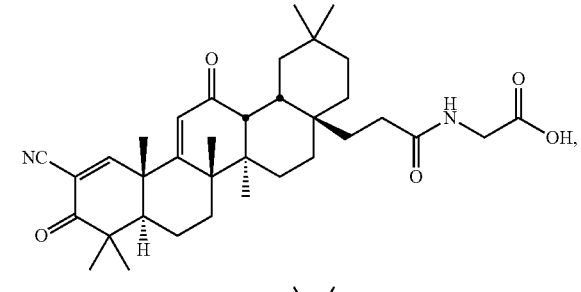
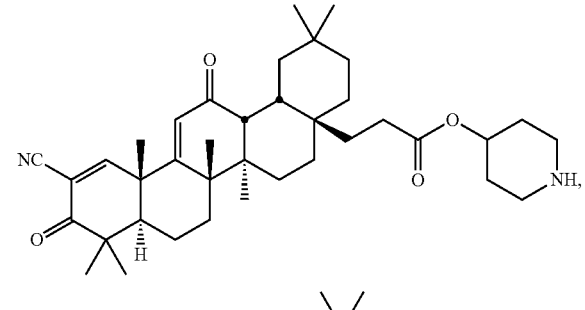
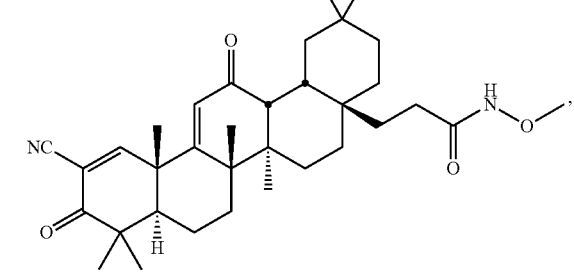

81
-continued
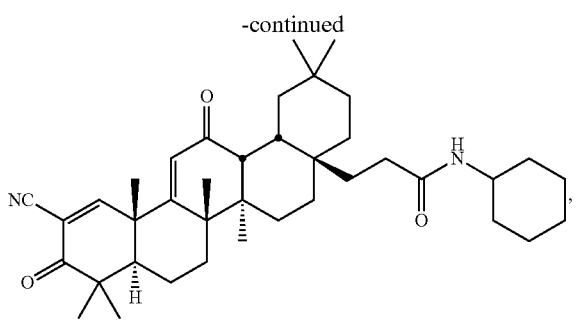
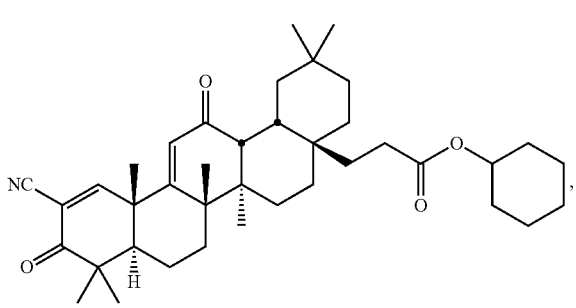
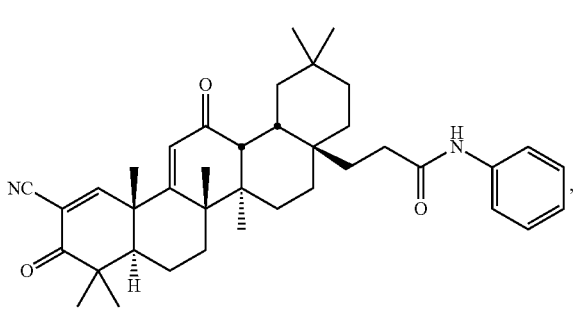
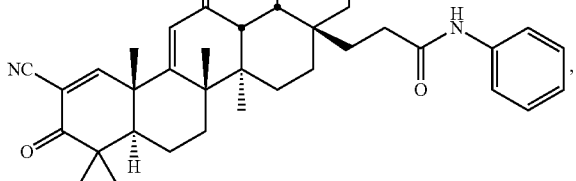
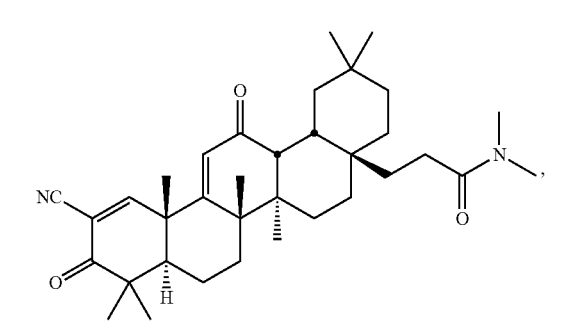
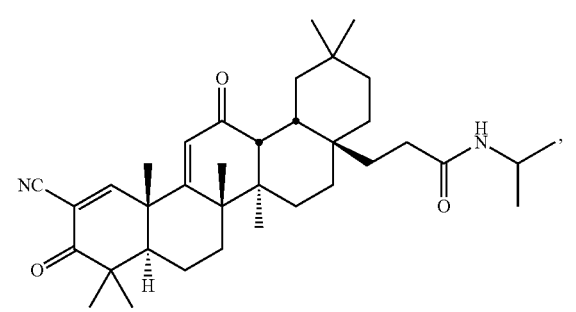
82
-continued
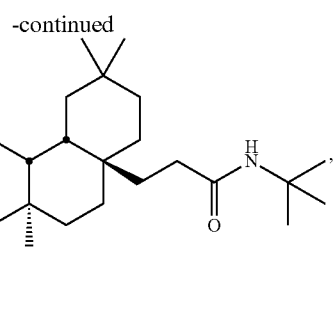
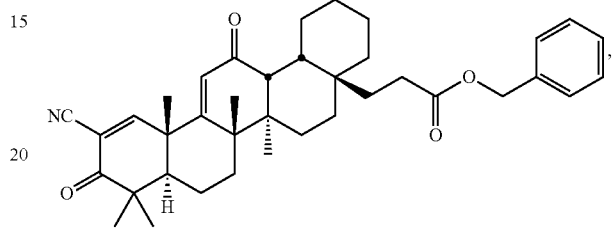
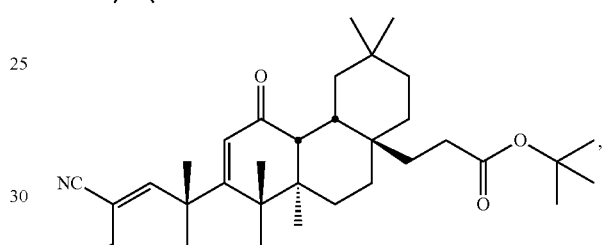
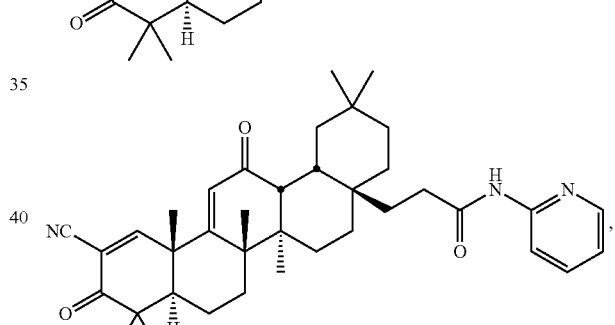
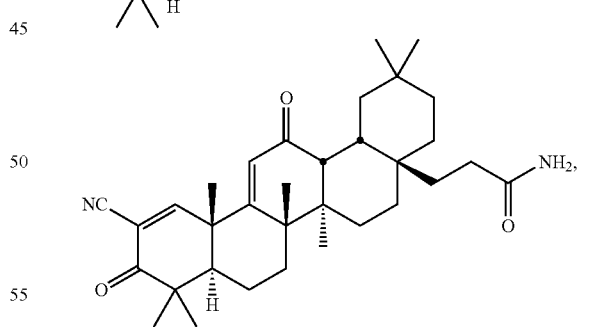
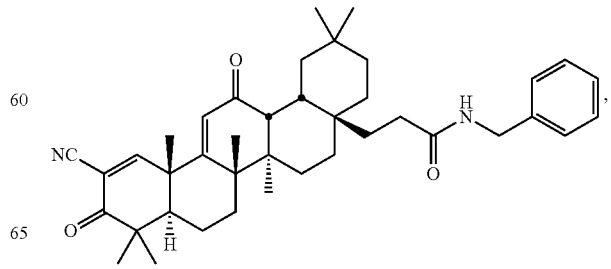

83
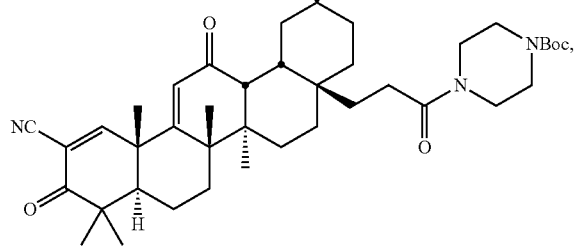
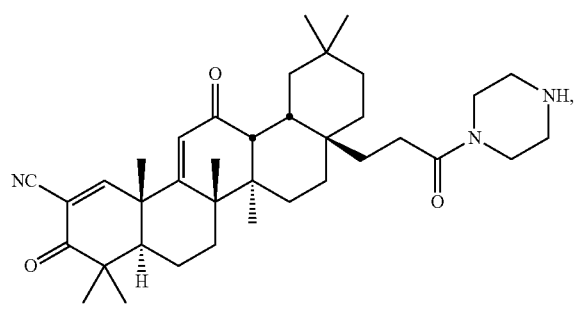
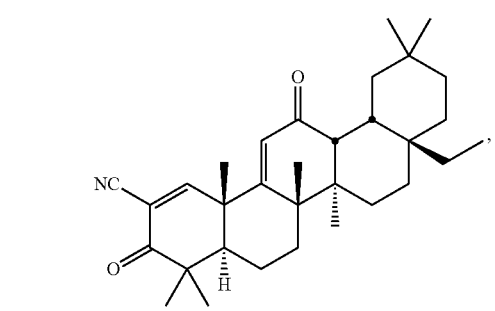
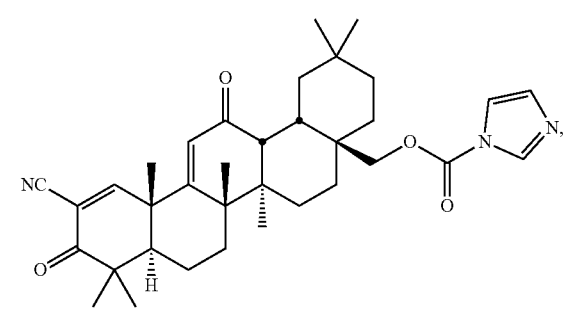
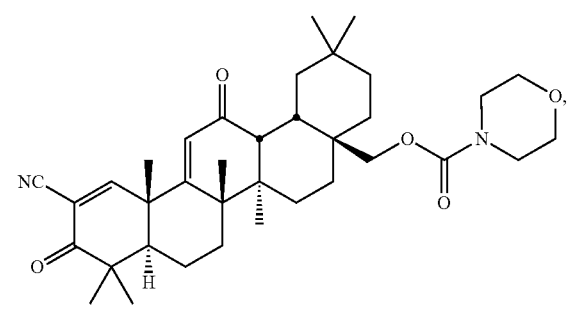
84
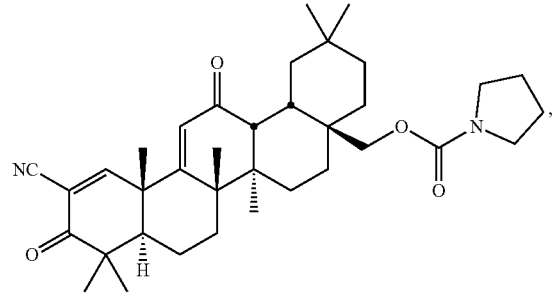
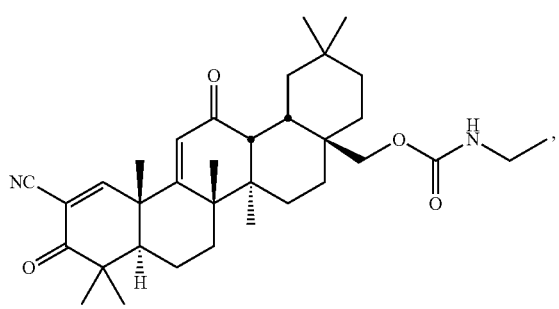
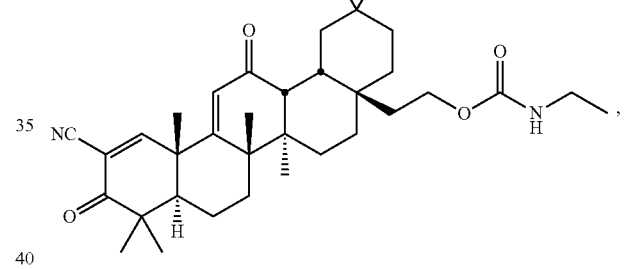
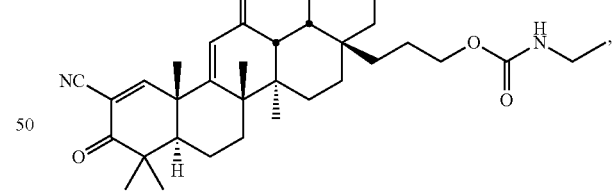
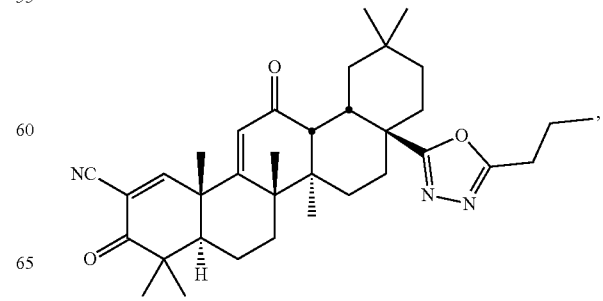

85
-continued
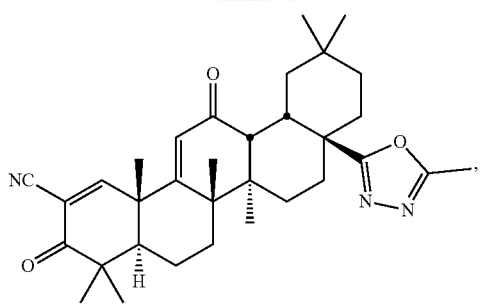
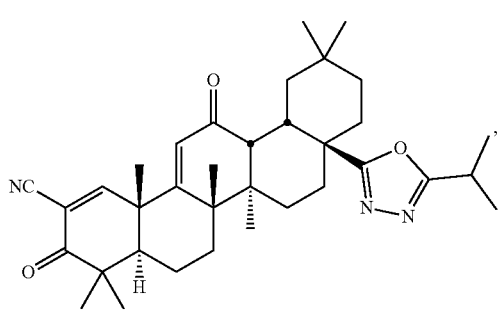
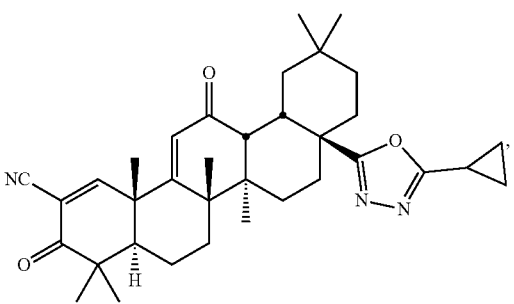
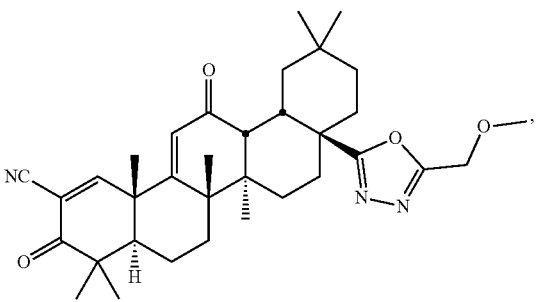
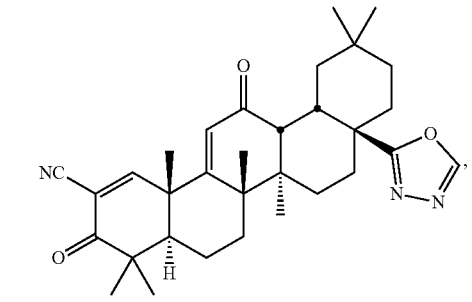
86
-continued
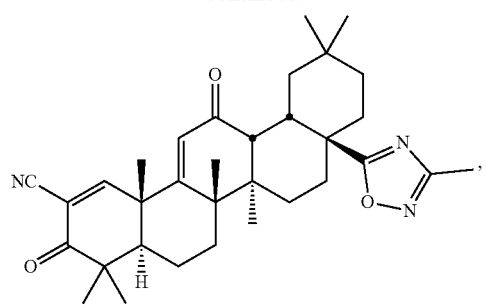
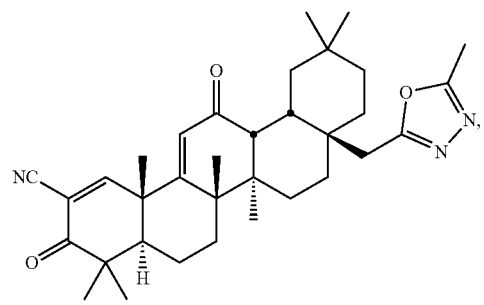
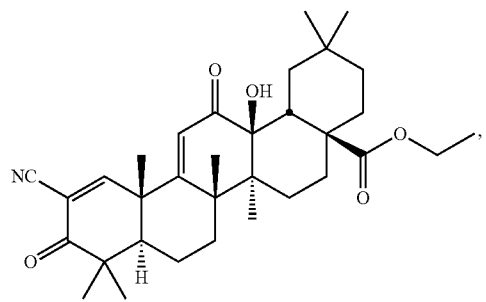
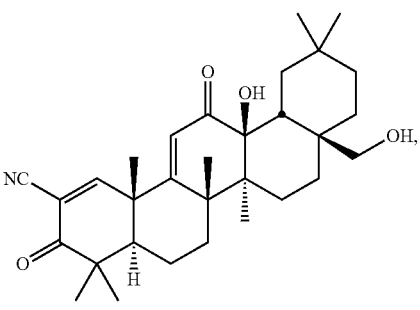

-continued

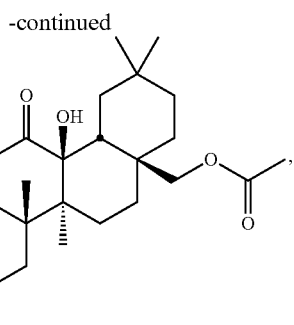

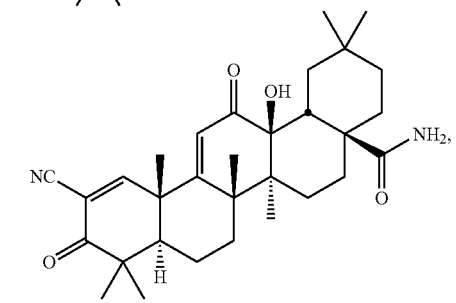

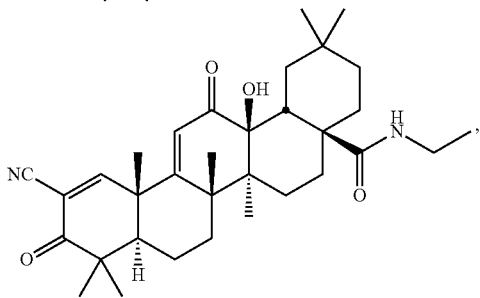

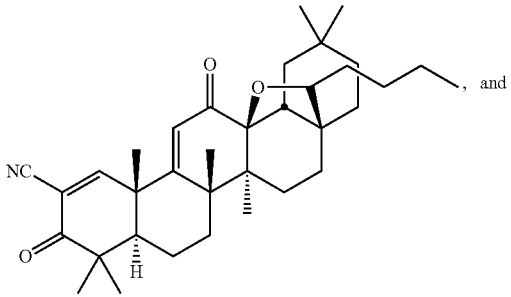, and

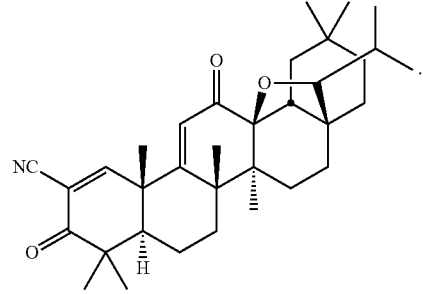.

Table 21 summarizes in vitro results for several of these compounds in which RAW264.7 macrophages were pretreated with DMSO or drugs at various concentrations (nM) for 2 hours, and then treated with 20 ng/mL IFNγ for 24 hours. NO concentration in the media was determined using a Griess reagent system; cell viability was determined using WST-1 reagent. NQO1 CD represents the concentration required to induce a two-fold increase in the expression of NQO1, an Nrf2-regulated antioxidant enzyme, in Hepa1c1c7 murine hepatoma cells (Dinkova-Kostova et al., 2005). All these results are orders of magnitude more active than, for example, the parent oleanolic acid molecule. In part because induction of antioxidant pathways resulting from Nrf2 activation provides important protective effects against oxidative stress and inflammation, analogs of RTA 402 may therefore also be used to for the treatment and/or Alport syndrome or symptoms thereof or prevent the onset of symptoms of Alport syndrome.

TABLE 21

| | Suppression of IFNγ-induced NO production. | | |
|---|---|---|---|
| | RAW264.7 (20 ng/mL IFNγ) | | Hepa1c1c7 cells |
| Working ID | NO IC$_{50}$ | WST-1 IC$_{50}$ | NQO1 CD |
| RTA 401 | ~10 nM | >200 nM | 2.3 nM |
| RTA 402 | 2.2 nM | 80 nM | 1.0 nM |
| RTA 403 | ~0.6 nM | 100 nM | 3.3 nM |
| RTA 404 | 5.8 nM | 100 nM | n/a |
| RTA 405 | 6 nM | ~200 nM | n/a |
| TP-225 | ~0.4 nM | 75 nM | 0.28 nM |

Without being bound by theory, the potency of the compounds of the present invention, e.g., RTA 402, is largely derived from the addition of α,β-unsaturated carbonyl groups. In in vitro assays, most activity of the compounds can be abrogated by the introduction of dithiothreitol (DTT), N-acetyl cysteine (NAC), or glutathione (GSH); thiol containing moieties that interact with α,β-unsaturated carbonyl groups (Wang et al., 2000; Ikeda et al., 2003; 2004; Shishodia et al., 2006). Biochemical assays have established that RTA 402 directly interacts with a critical cysteine residue (C179) on IKKβ (see below) and inhibits its activity (Shishodia et al., 2006; Ahmad et al., 2006). IKKβ controls activation of NF-κB through the "classical" pathway which involves phosphorylation-induced degradation of IκB resulting in release of NF-κB dimers to the nucleus. In macrophages, this pathway is responsible for the production of many pro-inflammatory molecules in response to TNFα and other pro-inflammatory stimuli.

RTA 402 also inhibits the JAK/STAT signaling pathway at multiple levels. JAK proteins are recruited to transmembrane receptors (e.g., IL-6R) upon activation by ligands such as interferons and interleukins. JAKs then phosphorylate the intracellular portion of the receptor causing recruitment of STAT transcription factors. The STATs are then phosphorylated by JAKs, form dimers, and translocate to the nucleus where they activate transcription of several genes involved in inflammation. RTA 402 inhibits constitutive and IL-6-induced STAT3 phosphorylation and dimer formation and directly binds to cysteine residues in STAT3 (C259) and in the kinase domain of JAK1 (C1077). Biochemical assays have also established that the triterpenoids directly interact with critical cysteine residues on Keap1 (Dinkova-Kostova et al., 2005). Keap1 is an actin-tethered protein that keeps the transcription factor Nrf2 sequestered in the cytoplasm under normal conditions (Kobayashi and Yamamoto, 2005). Oxidative stress results in oxidation of the regulatory cysteine residues on Keap1 and causes the release of Nrf2. Nrf2 then translocates to the nucleus and binds to antioxidant response elements (AREs) resulting in transcriptional activation of many antioxidant and anti-inflammatory genes. Another target of the Keap1/Nrf2/ARE pathway is heme oxygenase 1 (HO-1). HO-1 breaks down heme into bilirubin and carbon monoxide and plays many antioxidant and anti-inflammatory roles (Maines and Gibbs, 2005). HO-1 has recently been shown to be potently induced by the triterpenoids (Liby et al., 2005), including RTA 402. RTA 402 and many structural analogs have also been shown to be potent inducers of the expression of other Phase 2 proteins (Yates et al., 2007). RTA 402 is a potent inhibitor of NF-κB activation. Furthermore, RTA 402 activates the Keap1/Nrf2/ARE pathway and induces expression of HO-1.

Compounds employed may be made using the methods described by Honda et al. (2000a); Honda et al. (2000b); Honda et al. (2002); and U.S. Patent Application Publications 2009/0326063, 2010/0056777, 2010/0048892, 2010/0048911, 2010/0041904, 2003/0232786, 2008/0261985 and 2010/0048887, all of which are incorporated by reference herein. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure* (2013), which is incorporated by reference herein. In addition, the synthetic methods may be further modified and optimized for preparative, pilot- or large-scale production, either batch of continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

Compounds of the present invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Polymorphic forms of the compounds of the present invention, e.g., Forms A and B of CDDO-Me, may be used in accordance with the methods of this inventions. Form B displays a bioavailability that is surprisingly better than that of Form A. Specifically the bioavailability of Form B was higher than that of Form A CDDO-Me in monkeys when the monkeys received equivalent dosages of the two forms orally, in gelatin capsules. See U.S. Patent Application Publication 2009/0048204, which is incorporated by reference herein in its entirety.

"Form A" of CDDO-Me (RTA 402) is unsolvated (non-hydrous) and can be characterized by a distinctive crystal structure, with a space group of $P4_3 2_1 2$ (no. 96) unit cell dimensions of a=14.2 Å, b=14.2 Å and c=81.6 Å, and by a packing structure, whereby three molecules are packed in helical fashion down the crystallographic b axis. In some embodiments, Form A can also be characterized by X-ray powder diffraction (XRPD) pattern (CuKα) comprising significant diffraction peaks at about 8.8, 12.9, 13.4, 14.2 and 17.4 °θ. In some variations, the X-ray powder diffraction of Form A is substantially as shown in FIG. 1A or FIG. 1B.

Unlike Form A, "Form B" of CDDO-Me is in a single phase but lacks such a defined crystal structure. Samples of Form B show no long-range molecular correlation, i.e., above roughly 20 Å. Moreover, thermal analysis of Form B samples reveals a glass transition temperature ($T_g$) in a range from about 120° C. to about 130° C. In contrast, a disordered nanocrystalline material does not display a $T_g$ but instead only a melting temperature ($T_m$), above which crystalline structure becomes a liquid. Form B is typified by an XRPD spectrum (FIG. 1C) differing from that of Form A (FIG. 1A or FIG. 1B). Since it does not have a defined crystal structure, Form B likewise lacks distinct XRPD peaks, such as those that typify Form A, and instead is characterized by a general "halo" XRPD pattern. In particular, the non-crystalline Form B falls into the category of "X-ray amorphous" solids because its XRPD pattern exhibits three or fewer primary diffraction halos. Within this category, Form B is a "glassy" material.

Form A and Form B of CDDO-Me are readily prepared from a variety of solutions of the compound. For example, Form B can be prepared by fast evaporation or slow evaporation in MTBE, THF, toluene, or ethyl acetate. Form A can be prepared in several ways, including via fast evaporation, slow evaporation, or slow cooling of a CDDO-Me solution in ethanol or methanol. Preparations of CDDO-Me in acetone can produce either Form A, using fast evaporation, or Form B, using slow evaporation.

Various means of characterization can be used together to distinguish Form A and Form B CDDO-Me from each other and from other forms of CDDO-Me. Illustrative of the techniques suitable for this purpose are solid state Nuclear Magnetic Resonance (NMR), X-ray powder diffraction (compare FIGS. 1A & B with FIG. 1C), X-ray crystallography, differential scanning calorimetry (DSC), dynamic vapor sorption/desorption (DVS), Karl Fischer analysis (KF), hot stage microscopy, modulated differential screening calorimetry, FT-IR, and Raman spectroscopy. In particular, analysis of the XRPD and DSC data can distinguish Form A, Form B, and a hemibenzenate form of CDDO-Me. See U.S. Patent Application Publication 2009/0048204, which is incorporated by reference herein in its entirety.

Additional details regarding polymorphic forms of CDDO-Me are described in U.S. Patent Application Publication 2009/0048204, PCT Publication WO 2009/023232 and PCT Publication WO 2010/093944, which are all incorporated herein by reference in their entireties.

Non-limiting specific formulations of the compounds disclosed herein include CDDO-Me polymer dispersions. See, for example, PCT Publication WO 2010/093944, which is incorporated herein by reference in its entirety. Some of the formulations reported therein exhibit higher bioavailability than either the micronized Form A or nanocrystalline Form A formulations. Additionally, the polymer dispersion based formulations demonstrate further surprising improvements in oral bioavailability relative to the micronized Form B formulations. For example, the methacrylic acid copolymer, Type C and HPMC-P formulations showed the greatest bioavailability in the subject monkeys.

Compounds employed in methods of the invention may also exist in prodrug form. Since prodrugs enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject or patient, cleaves to form a hydroxy, amino, or carboxylic acid, respectively.

It should be recognized that the particular anion or cation forming a part of any salt of this invention is not critical, so long as the salt, as a whole, is pharmacologically acceptable. Examples of pharmaceutically acceptable salts and their methods of preparation and use are presented in *Handbook of Pharmaceutical Salts: Properties, and Use* (2002), which is incorporated herein by reference.

In some embodiments, the compounds employed in the methods described in the present invention have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. PHARMACEUTICAL FORMULATIONS AND ROUTES OF ADMINISTRATION

Administration of the compounds of the present invention to a patient will follow general protocols for the administration of pharmaceuticals, taking into account the toxicity, if any, of the drug. It is expected that the treatment cycles would be repeated as necessary.

The compounds of the present invention may be administered by a variety of methods, e.g., orally or by injection (e.g., subcutaneous, intravenous, intraperitoneal, etc.). Depending on the route of administration, the active compounds may be coated by a material to protect the compound from the action of acids and other natural conditions which may inactivate the compound. They may also be administered by continuous perfusion/infusion of a disease or wound site. Specific examples of formulations, including a polymer-based dispersion of CDDO-Me that showed improved oral bioavailability, are provided in U.S. Patent Application Publication No. 2009/0048204, which is incorporated herein by reference in its entirety. It will be recognized by those skilled in the art that other methods of manufacture may be used to produce dispersions of the present invention with equivalent properties and utility (see, Repka et al., 2002 and references cited therein). Such alternative methods include but are not limited to solvent evaporation, extrusion, such as hot melt extrusion, and other techniques.

To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions may be prepared in, e.g., glycerol, liquid polyethylene glycols, mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's or patient's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects or patients to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The therapeutic compound may be formulated in a biocompatible matrix for use in a drug-eluting stent.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3): 659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present invention or composition comprising a compound of the present invention administered to a subject or a patient may be determined by physical and physiological factors such as age, sex, body weight, severity of condition, the type of disease being treated, previous or concurrent therapeutic interventions, idiopathy of the subject or the patient and on the route of administration. These factors may be determined by a skilled artisan. The practitioner responsible for administration will typically determine the concentration of active ingredient(s) in a composition and appropriate dose(s) for the individual subject or patient. The dosage may be adjusted by the individual physician in the event of any complication.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose of 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is a daily dose of 0.1-1000 mg of compound per kg of body weight. In some variations, the daily dose is 0.15-20 mg of compound per kg of body weight. In some variations, the daily dose is 0.20-10 mg of compound per kg of body weight. In some variations, the daily dose is 0.40-3 mg of compound per kg of body weight. In some variations, the daily dose is 0.50-9 mg of compound per kg of body weight. In some variations, the daily dose is 0.60-8 mg of compound per kg of body weight. In some variations, the daily dose is 0.70-7 mg of compound per kg of body weight. In some variations, the daily dose is 0.80-6 mg of compound per kg of body weight. In some variations, the daily dose is 0.90-5 mg of compound per kg of body weight. In some variations, the daily dose is from about 1 mg to about 5 mg of compound per kg of body weight.

An effective amount typically will vary from about 0.001 mg/kg to about 1,000 mg/kg, from about 0.01 mg/kg to about 750 mg/kg, from about 0.1 mg/kg to about 500 mg/kg, from about 0.2 mg/kg to about 250 mg/kg, from about 0.3 mg/kg to about 150 mg/kg, from about 0.3 mg/kg to about 100 mg/kg, from about 0.4 mg/kg to about 75 mg/kg, from about 0.5 mg/kg to about 50 mg/kg, from about 0.6 mg/kg to about 30 mg/kg, from about 0.7 mg/kg to about 25 mg/kg, from about 0.8 mg/kg to about 15 mg/kg, from about 0.9 mg/kg to about 10 mg/kg, from about 1 mg/kg to about 5 mg/kg, from about 100 mg/kg to about 500 mg/kg, from about 1.0 mg/kg to about 250 mg/kg, or from about 10.0 mg/kg to about 150 mg/kg, in one or more dose administrations daily, for one or several days (depending, of course, of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range, for example, of 750 mg to 9,000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day, less than 10 mg/kg/day, or less than 5 mg/kg/day. It may alternatively be in the range of 1 mg/kg/day to 200 mg/kg/day. For example, regarding treatment of patients with Alport syndrome, the unit dosage may be an amount that reduces urine protein concentration by at least 40% as compared to an untreated subject or patient. In another embodiment, the unit dosage is an amount that reduces urine protein concentration to a level that is within ±10% of the urine protein level of a healthy subject or patient.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1 mg/kg/body weight to about 5 mg/kg/body weight, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present invention may comprise, for example, at least about 0.1% of a compound of the present invention. In other embodiments, the compound of the present invention may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects or patients may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject or patient has eaten or will eat.

Non-limiting specific formulations include CDDO-Me polymer dispersions (see U.S. Patent Application Publication No. 2009/0048204, filed Aug. 13, 2008, which is incorporated herein by reference). Some of the formulations reported therein exhibited higher bioavailability than either the micronized Form A or nanocrystalline Form A formulations. Additionally, the polymer dispersion based formulations demonstrated further surprising improvements in oral bioavailability relative to the micronized Form B formulations. For example, the methacrylic acid copolymer, Type C and HPMC-P formulations showed the greatest bioavailability in the subject monkeys.

IV. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as when a compound of the present invention is "A" and "B" represents a secondary agent, non-limiting examples of which are described below:

| A/B/A | B/A/B | B/B/A | A/A/B | A/B/B |
| B/A/A | A/B/B/B | B/A/B/B | B/B/B/A | B/B/A/B |
| A/A/B/B | A/B/A/B | A/B/B/A | B/B/A/A | B/A/B/A |
| B/A/A/B | A/A/A/B | B/A/A/A | A/B/A/A | A/A/B/A |

It is contemplated that other therapeutic agents may be used in conjunction with the treatments of the current invention. In some embodiments, the present invention contemplates the use of one or more other therapies for the treatment of Alport syndrome in conjunction with the compounds described in the methods therein. These therapies include the use of an angiotensin-converting enzyme (ACE) inhibitor, angiotensin receptor blockade (ARB), or an aldosterone antagonist. Some non-limiting examples of ACE inhibitor include Ramipril, enalapril, Lisinopril, benazepril, fosinopril, quinapril, cilazapril, perinopril, or trandolapril. Similarly, some non-limiting examples of angiotensin receptor blockade agent include losartan, candesartan, irbesartan, telmisartan, valsartan, or epresartan. A non-limiting example of an aldosterone antagonist is spirolactone.

V. DIAGNOSTIC TESTS

A. Measurement of B-type Natriuretic Peptide (BNP) Levels

B-type natriuretic peptide (BNP) is a 32-amino acid neurohormone that is synthesized in the ventricular myocardium and released into circulation in response to ventricular dilation and pressure overload. The functions of BNP include natriuresis, vasodilation, inhibition of the renin-angiotensin-aldosterone axis, and inhibition of sympathetic nerve activity. The plasma concentration of BNP is elevated among patients with congestive heart failure (CHF), and increases in proportion to the degree of left ventricular dysfunction and the severity of CIF symptoms.

Numerous methods and devices are well known to the skilled artisan for measuring BNP levels in patient samples, including serum and plasma. With regard to polypeptides, such as BNP, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,170 and 5,955,377. In a specific example, B-type natriuretic peptide (BNP) levels may be determined by the following method(s): protein immunoassays as described in US Patent Publication 2011/0201130, which is incorporated by reference in its entirety herein. Furthermore, a number of commercially available methods exist (e.g., Rawlins et al., 2005, which is incorporated herein by reference in its entirety).

B. Measurement of Albumin/Creatinine Ratio (ACR)

Conventionally, proteinuria is diagnosed by a simple dipstick test. Traditionally, dipstick protein tests are quantified by measuring the total quantity of protein in a 24-hour urine collection test.

Alternatively the concentration of protein in the urine may be compared to the creatinine level in a spot urine sample. This is termed the protein/creatinine ratio (PCR). The UK Chronic Kidney Disease Guidelines (2005; which are incorporated herein by reference in their entirety) states PCR is a better test than 24-hour urinary protein measurement. Proteinuria is defined as a protein/creatinine ratio greater than 45 mg/mmol (which is equivalent to albumin/creatinine ratio of greater than 30 mg/mmol or approximately 300 mg/g as defined by dipstick proteinuria of 3+) with very high levels of proteinuria being for a PCR greater than 100 mg/mmol.

Protein dipstick measurements should not be confused with the amount of protein detected on a test for microalbuminuria, which denotes values for protein for urine in mg/day versus urine protein dipstick values which denote values for protein in mg/dL. That is, there is a basal level of proteinuria that can occur below 30 mg/day which is considered non-pathological. Values between 30-300 mg/day are termed microalbuminuria which is considered pathologic. Urine protein lab values for microalbumin of >30 mg/day correspond to a detection level within the "trace" to "1+" range of a urine dipstick protein assay. Therefore, positive indication of any protein detected on a urine dipstick assay obviates any need to perform a urine microalbumin test as the upper limit for microalbuminuria has already been exceeded.

C. Measurement of Estimated Glomerular Filtration Rate (eGFR)

A number of formulae have been devised to estimate GFR values on the basis of serum creatinine levels. A commonly used surrogate marker for estimate of creatinine clearance ($eC_{Cr}$) is the Cockcroft-Gault (CG) formula, which in turn estimates GFR in mL/min. It employs serum creatinine measurements and a patient's weight to predict the creatinine clearance. The formula, as originally published, is:

$$eCCr = \frac{(140 - \text{Age}) \times \text{Mass (in kg)}}{72 \times \text{Serum creatinine} \left(\text{in} \frac{\text{mg}}{\text{dL}}\right)}$$

This formula expects weight to be measured in kilograms and creatinine to be measured in mg/dL, as is standard in the USA. The resulting value is multiplied by a constant of 0.85 if the patient is female. This formula is useful because the calculations are simple and can often be performed without the aid of a calculator.

When serum creatinine is measured in µmol/L, then:

$$eCCr = \frac{(140 - \text{Age}) \times \text{Mass (in kg)} \times \text{Constant}}{\text{Serum creatinine}\left(\text{in} \frac{\mu\text{mol}}{\text{L}}\right)}$$

where Constant is 1.23 for men and 1.04 for women.

One interesting feature of the Cockcroft and Gault equation is that it shows how dependent the estimation of $C_{Cr}$ is based on age. The age term is (140–age). This means that a 20-year-old person (140–20=120) will have twice the creatinine clearance as an 80-year-old (140–80=60) for the same level of serum creatinine. The CG equation assumes that a woman will have a 15% lower creatinine clearance than a man at the same level of serum creatinine.

Alternatively, eGFR values may be calculated using the Modification of Diet in Renal Disease (MDRD) formula. The 4-variable formula is as follows:

$$eGFR = 175 \times \text{Standardized serum creatinine}^{-1.154} \times \text{Age}^{-0.203} \times C$$

where C is 1.212 if the patient is a black male, 0.899 if the patient is a black female, and 0.742 if the patient is a non-black female. Serum creatinine values are based on the IDMS-traceable creatinine determination (see below).

Chronic kidney disease is defined as a GFR less than 60 mL/min/1.73 m² that is present for three or more months.

D. Measurement of Serum Creatinine Levels

A serum creatinine test measures the level of creatinine in the blood and provides an estimate glomerular filtration rate. Serum creatinine values in the BEACON and BEAM trials were based on the isotope dilution mass spectrometry (IDMS)-traceable creatinine determinations. Other commonly used creatinine assay methodologies include (1) alkaline picrate methods (e.g., Jaffe method [classic] and compensated [modified] Jaffe methods), (2) enzymatic methods, (3) high-performance liquid chromatography, (4) gas chromatography, and (5) liquid chromatography. The IDMS method is widely considered to be the most accurate assay (Peake and Whiting, 2006, which is incorporated herein by reference in its entirety).

VI. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof, in a divalent context "phosphate" means —OP(O)(OH)O— or a deprotonated form thereof, "mercapto" means —SH; and "thio" means =S; "sulfonyl" means —S(O)₂—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⹀" represents a single bond or a double bond. Thus, the formula

covers for example,

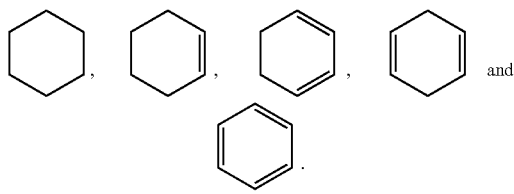

and it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "∿∿", when drawn perpendicularly across a bond

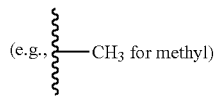

indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫿⫿" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

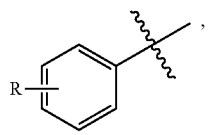

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

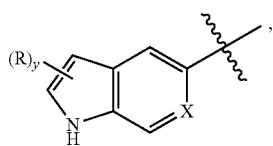

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

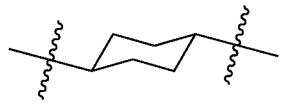 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

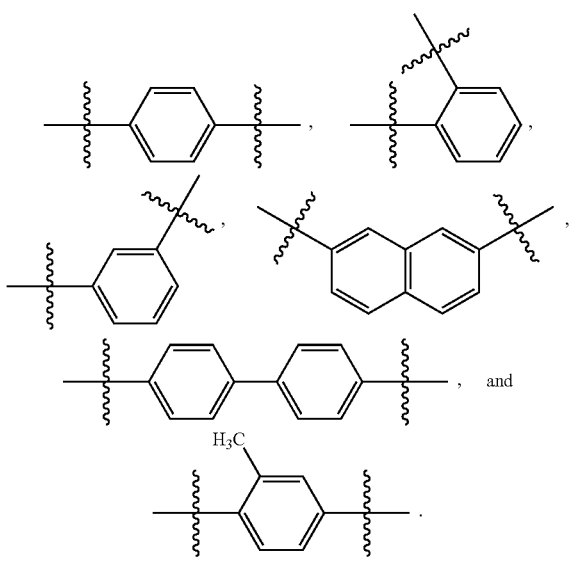

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", "alkylsulfonylamino", or "cycloalkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, alkylsulfonyl, and cycloalkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

As used herein, average molecular weight refers to the weight average molecular weight (Mw) as determined by static light scattering.

The terms "comprise," "have" and "include" are open-ended linking verbs. Any forms or tenses of one or more of these verbs, such as "comprises," "comprising," "has," "having," "includes" and "including," are also open-ended.

For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or a subject with a compound means that amount of the compound which, when administered to the patient or the subject for treating or preventing a disease, is an amount sufficient to effect the treatment or prevention of the disease. For example, within the context of Alport syndrome, one measure of an effective treatment is the reduction of one or more urine biomarkers such as the presence of blood or protein in the urine or the improved glomerular filtration rate. In a particular embodiment, a measure of an effective treatment is a reduction in the concentration of protein in the urine to less than 300 mg/dL. In a preferred embodiment, the therapy is sufficient to reduce the concentration of protein in the urine to less than 100 mg/dL or a more preferred embodiment, less than 30 mg/dL. When the presence of blood is used as a marker of therapeutic effectiveness, an effective therapy results in the absence of macroscopic blood in the urine while microscopic blood may still be present. In a preferred embodiment, an effective therapy results in the absence of any blood including microscopic blood which would only be visible using a microscope or in an urinalysis. Finally, an effective therapy would result in an improvement in the glomerular filtration rate. Glomerular filtration rate can be estimated using a variety of different methods using creatinine including the Cockcroft-Gault formula, the Modification of Diet in Renal Disease (MDRD) formula, the Chronic Kidney Disease Epidemiology Collaboration (CKD-EPI) formula, the Mayo Quadratic formula, or the Schwartz formula. In general, the Schwartz formula may be used for children below the age of 12. These methods are further elaborated on in the sections above and in the Examples below. For example, an effective treatment may result a glomerular filtration rate (or an estimated glomerular filtration rate) of greater than 60 mL/min/1.73 m$^2$. More preferably, the effective treatment may result in an glomerular filtration rate of greater than 90 mL/min/1.73 m$^2$.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Bardoxolone Methyl Increases Renal Function

Bardoxolone methyl has been studied in seven CKD studies enrolling approximately 2,600 patients with Type 2 diabetes and CKD. Improvements in renal function, including inulin clearance, creatinine clearance, and eGFR, have been observed with bardoxolone methyl treatment in a number of clinical studies. A recent study in Japanese CKD patients demonstrated that bardoxolone methyl treatment resulted in a significant improvement in measured GFR, as assessed by inulin clearance, after 16 weeks of treatment compared to placebo. Moreover, measured GFR increases were significantly and positively correlated with improvements in eGFR. Two separate studies (studies 402-C-0804 and 402-C-0903) showed that increases in eGFR in CKD patients treated with bardoxolone methyl were sustained for at least one year. Furthermore, after one year of treatment, a residual eGFR increase from baseline was observed in bardoxolone methyl patients after cessation of drug for four weeks, while an eGFR decline from baseline was observed in placebo patients. In other CKD studies, bardoxolone methyl has been shown to significantly reduce uremic solutes (BUN, uric acid, and phosphate) in inverse correlation to eGFR increases and to numerically reduce renal SAEs and ESRD events.

The data from these studies suggest that bardoxolone methyl has the potential to prevent renal function decline, which could ultimately prevent or delay ESRD. In Alport syndrome patients, who have average eGFR declines of 4.0 mL/min/1.73 m$^2$ per year, the potential impact of a sustained eGFR increase with bardoxolone methyl treatment is clinically meaningful and could provide a multi-year delay in disease progression to ESRD.

Key features of bardoxolone methyl's effects on renal function are summarized below.

A. Bardoxolone Methyl Improves Kidney Function, as Assessed by Measured GFR (Inulin Clearance), Creatinine Clearance, and eGFR In a study in Japanese patients with Stage 3 CKD, bardoxolone methyl treatment resulted in a significant improvement in measured GFR, as assessed by inulin clearance, after 16 weeks of treatment compared to placebo (Table 22).

TABLE 22

Bardoxolone Methyl Increases GFR, as Assessed by Inulin Clearance

| Change from Baseline at Week 16 (mL/min/1.73 m$^2$) | Placebo (N = 23) | Bardoxolone Methyl (N = 17) |
|---|---|---|
| Mean ± SD | −0.42 ± 7.52 | 5.58 ± 7.90 |
| LS Mean | −0.69 | 5.95 |
| 95% CI (LL, UL) | −3.83, 2.45 | 2.29, 9.60 |
| p-value versus Placebo | — | 0.008 |

Moreover, measured GFR increases were significantly and positively correlated with improvements in eGFR (p=0.002). In two studies, bardoxolone methyl significantly increased creatinine clearance. Importantly, these increases were not associated with a change in total 24-hour excretion of creatinine, which demonstrates that bardoxolone methyl does not affect creatinine metabolism. In other CKD studies, bardoxolone methyl has been shown to significantly reduce uremic solutes (BUN, uric acid, and phosphate) in inverse correlation to eGFR increases and to numerically reduce renal SAEs and ESRD events. These data demonstrate that the increases in eGFR observed in seven CKD studies of bardoxolone methyl treatment reflect true increases in GFR and support the use of eGFR as a reliable marker of renal function (Table 23).

TABLE 23

Cross-Study Comparison of Increases in eGFR, Inulin Clearance, Creatinine Clearance with Bardoxolone Methyl Treatment

| Study | Phase/ Country | Patient Population | Mean Placebo-corrected ΔeGFR (mL/min/1.73 m$^2$)[1] |
|---|---|---|---|
| 402-C-0801 (Stratum 1) | 2a/US | Diabetic nephropathy | 6.7 (p < 0.001)[2] |
| 402-C-0801 (Stratum 2) | 2b/US | Diabetic nephropathy | 7.2 (p < 0.001)[2,3] |
| 402-C-0804 (BEAM) | 2/US | CKD/ Diabetes | 8.6 (p < 0.001 vs. PBO) |
| 402-C-0902 | 2/US | CKD/ Diabetes | 6.5 (p < 0.001)[2] |
| 402-C-0903 (BEACON) | 3/Global | CKD/ Diabetes | 6.4 (p < 0.001 vs. PBO)$^c$ |
| 402-C-1102 | 1/US | CKD/ Diabetes | 9.0 (p < 0.05)[2] |
| RTA402-005 (TSUBAKI) | 2/Japan | CKD/ Diabetes | 6.6 (inulin GFR) (p = 0.008 vs. PBO) |
| 402-C-0501 | 1/US | Cancer | 18.2 (p < 0.0001)[2] |
| 402-C-0702 | 1/2/US | Cancer | 32.2 (p = 0.001)[2] |
| 402-C-1302 (LARIAT) | 2/US | Pulmonary hypertension | 14.7 (p < 0.001 vs. PBO) |

[1] Unless noted, data are differences between mean eGFR changes from baseline for bardoxolone methyl versus placebo groups and p-values calculated comparing the difference in means between bardoxolone methyl and placebo groups.
[2] Data are mean eGFR changes from baseline for bardoxolone methyl patients and p-values are calculated from two-sided paired t-tests comparing eGFR change to 0.
[3] Study also demonstrated a significant increase in creatinine clearance.

B. Bardoxolone Methyl Produces a Retained eGFR Increase after Withdrawal of Drug After one year of treatment with bardoxolone methyl, a residual eGFR increase from baseline is observed after cessation of treatment for four weeks, while an eGFR decline from baseline is observed in placebo patients. Subtherapeutic concentrations of drug are achieved within approximately 10 days after drug withdrawal. In studies 402-C-0804 and 402-C-0903, approximately 20% to 25% of the on-treatment eGFR increase (or 1 to 4 mL/min/1.73 m$^2$ improvement relative to baseline) was maintained in bardoxolone methyl-treated patients after withdrawal of drug. The increases above baseline were statistically significant in both studies. Placebo-treated patients in these studies lost approximately 1 mL/min/1.73 m$^2$ over the course of a year, and in study 402-C-0903, this loss from baseline was statistically significant.

The sustained increase in eGFR through one year of treatment and the presence of a sustained eGFR improvement after withdrawal of drug suggest that the maladaptive structural deficits that contribute to declining kidney function (such as mesangium expansion and interstitial fibrosis) may be improved over the course of longer-term treatment with bardoxolone methyl.

Example 2—Alport Syndrome Clinical Trial

CARDINAL is an international, multi-center Phase 2/3 study, initiated in February 2017, enrolling patients from 12 to 60 years old with a confirmed genetic or histological diagnosis of Alport syndrome. Patients must have baseline eGFR values between 30 to 90 mL/min/1.73 m$^2$ and must be receiving stable renin-angiotensin-aldosterone system blockade unless contraindicated. The Phase 2 portion of CARDINAL is open-label and enrolled 27 patients. The primary endpoint of the Phase 2 portion of the study is the eGFR change from baseline at 12 weeks.

The Phase 3 portion of CARDINAL is designed to support regulatory approval of bardoxolone methyl for the treatment of Alport syndrome. It will be double-blind, placebo-controlled and will randomize 150 patients on a 1:1 basis to once-daily, oral bardoxolone or placebo. The eGFR change after 48 weeks will be measured while the patient is on treatment, and after withdrawal of drug for four weeks (retained eGFR). After withdrawal, patients will be restarted on study drug with their original treatment assignments and will continue on study drug for an additional 48 weeks. The change from baseline in eGFR in bardoxolone methyl-treated patients relative to placebo will be measured again at the end of this second 48 week period (week 100 overall). The eGFR change will also be measured following the withdrawal of drug for four weeks (retained eGFR; week 104 overall). If the trial is successful, the year one retained eGFR data could support accelerated approval under subpart H of the Food, Drug, and Cosmetic Act, or the FDA Act, and the year two retained eGFR data could support full approval under the FDA Act.

Inclusion criteria include a positive genetic diagnosis of Alport syndrome and evidence of impaired renal function as measured by eGFR. The study will exclude patients with a history of clinically significant heart disease and elevated baseline BNP, as well as patients with severely compromised renal function (eGFR ≤45 mL/min/1.73 m$^2$ and ACR >2000 mg/g). Patients will be carefully monitored for potential fluid overload.

A. Development of Exclusion Criteria for Clinical Trial

Study 402-C-0903, titled "Bardoxolone Methyl Evaluation in Patients with Chronic Kidney Disease and Type 2 Diabetes: The Occurrence of Renal Events" (BEACON) was a phase 3, randomized, double-blind, placebo-controlled, parallel-group, multinational, multicenter study designed to compare the efficacy and safety of bardoxolone methyl (BARD) to placebo (PBO) in patients with stage 4 chronic kidney disease and type 2 diabetes. A total of 2,185 patients were randomized 1:1 to once-daily administration of bardoxolone methyl (20 mg) or placebo. The primary efficacy endpoint of the study was the time-to-first event in the composite endpoint defined as end-stage renal disease (ESRD; need for chronic dialysis, renal transplantation, or renal death) or cardiovascular (CV) death. The study had three secondary efficacy endpoints: (1) change in estimated glomerular filtration rate (eGFR); (2) time-to-first hospitalization for heart failure or death due to heart failure; and (3) time-to-first event of the composite endpoint consisting of non-fatal myocardial infarction, non-fatal stroke, hospitalization for heart failure, or cardiovascular death.

The BEACON trial was terminated in October 2012, due to excessive mortality and episodes of heart failure in the treatment arm. Subsequent analysis indicated that the elevated risk was associated with fluid overload due to changes in renal processing of sodium, and was largely confined to patients having: (a) a history of left-sided myocardial disease; or (b) an elevated B-type natriuretic peptide (BNP) level. An elevated albumin-creatinine ratio and advanced (stage 4) CKD were also determined to contribute to the risk of fluid overload.

Based on this analysis, a trial of bardoxolone methyl in patients with pulmonary arterial hypertension, known as LARIAT, was proposed and was approved by the United States FDA. Exclusion criteria included the risk factors noted in the BEACON analysis. Based on initial indications of safety and efficacy in PAH patients, the LARIAT trial was expanded to include other forms of pulmonary hypertension. Based on further indications of safety and efficacy in PAH patients, a Phase 3 trial of bardoxolone methyl in patients with PAH associated with connective tissue disease (CTD-PAH), known as CATALYST, was proposed and approved by the FDA.

Alport syndrome patients normally do not have other cardiovascular or metabolic comorbidities (e.g., diabetes), unlike most patients with CKD caused by diabetes. Therefore, Alport syndrome patients are unlikely to suffer from the two principal risk factors identified in the BEACON analysis.

B. Phase 2 Results of the CARDINAL Trial

The Phase 2 portion of the trial enrolled 30 patients, and available data demonstrated that bardoxolone significantly improved kidney function in Alport syndrome patients as measured by estimated glomerular filtration rate ("eGFR"). All patients completed the treatment period without any discontinuations. The mean baseline eGFR (SD) was 54.7±24 mL/min/1.73 m$^2$.

For the first eight patients that reached Week 12, available data showed a mean improvement of 6.9 mL/min/1.73 m$^2$ at Week 4 (n=19; p<0.0005), increasing by 12.7 mL/min/1.73 m$^2$ at Week 12 (n=8; p<0.00005). Over 80% of patients demonstrated a clinically meaningful improvement in eGFR of at least 3.0 mL/min/1.73 m$^2$ by Week 8, and the 95% confidence interval at Week 12 was 7.9 mL/min/1.73 m$^2$ to 17.5 mL/min/1.73 m$^2$. The observed treatment effect surpassed the threshold of 3.0 mL/min/1.73 m$^2$, which was the minimum effect size necessary to proceed to the Phase 3 portion of the trial.

For the full cohort of thirty patients, the mean baseline eGFR (SD) was 54±24 mL/min/1.73 m$^2$. Bardoxolone increased eGFR by 13.4 mL/min/1.73 m$^2$ (n=3-; p<1×10$^{-9}$; 95% CI 10.54 to 16.3) after 12 weeks of treatment. All patients had improvements from baseline, and 87% had an increase of at least 4 mL/min/1.73 m$^2$, which is the approximate annual rate of decline in kidney function in patients with Alport syndrome. The improvements in eGFR translated to an improvement in CKD stage for 22/30 (73%) patients.

No serious adverse events or discontinuations were reported in the trial, and reported adverse events were generally mild to moderate in intensity. An independent data monitoring committee reviewed all available safety data and voted to recommend opening the Phase 3 portion of the trial.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

U.S. Pat. No. 5,480,792
U.S. Pat. No. 5,525,524
U.S. Pat. No. 5,631,170
U.S. Pat. No. 5,679,526
U.S. Pat. No. 5,824,799
U.S. Pat. No. 5,851,776
U.S. Pat. No. 5,885,527
U.S. Pat. No. 5,922,615
U.S. Pat. No. 5,939,272
U.S. Pat. No. 5,947,124
U.S. Pat. No. 5,955,377
U.S. Pat. No. 5,985,579
U.S. Pat. No. 6,019,944
U.S. Pat. No. 6,025,395
U.S. Pat. No. 6,113,855
U.S. Pat. No. 6,143,576
U.S. Pat. Pub. 2003/0232786
U.S. Pat. Pub. 2008/0261985
U.S. Pat. Pub. 2009/0048204
U.S. Pat. Pub. 2009/0326063
U.S. Pat. Pub. 2010/0041904
U.S. Pat. Pub. 2010/0048887
U.S. Pat. Pub. 2010/0048892
U.S. Pat. Pub. 2010/0048911
U.S. Pat. Pub. 2010/0056777
U.S. Pat. Pub. 2011/0201130
PCT Pub. WO 2009/023232
PCT Pub. WO 2009/048204
PCT Pub. WO 2010/093944

Ahmad et al., "Triterpenoid CDDO-Me blocks the NF-κB pathway by direct inhibition of IKKβ on Cys-179," *J. Biol. Chem.*, 281:35764-35769, 2006.

Ahmad et al., "Triterpenoid CDDO-Methyl Ester Inhibits the Janus-Activated Kinase-1 (JAK1)→Signal Transducer and Activator of Transciption-3 (STAT3) Pathway by Direct Inhibition of JAK1 and STAT3," *Cancer Res.*, 68(8):2920-2926, 2008.

Anderson, *Practical Process Research & Development-A Guide for Organic Chemists*, $2^{nd}$ ed., Academic Press, New York, 2012.

Dhaun et al., "Urinary endothelin-1 in chronic kidney disease and as a marker of disease activity in lupus nephritis," *American Journal of Physiology—Renal Physiology*, 296:F1477-F1483, 2009.

Dinkova-Kostova et al., "Extremely Potent Triterpenoid Inducers of the Phase 2 Response: Correlations of Protection Against Oxidant and Inflammatory Stress," *Proc. Natl. Acad. Sci.*, 102(12):4584-4589, 2005.

Honda et al., "New Enone Derivativas of Oleanolic Acid and Ursolic Acid as Inhibitors of Nitric Oxide Production in Mouse Macrophages," 1997.

Honda et al., "Design and Synthesis of 2-cyano-3,12-dioxoolean-1,9-dien-28-oic acid, a Novel and Highly Active Inhibitor of Nitric Oxide Production in Mouse Macrophages," *Bioorg. Med. Chem. Lett.*, 8(19):2711-2714, 1998.

Honda et al., "Novel Synthetic Oleanane Triterpenoids: A Series of Highly Active Inhibitors of Nitric Oxide Production in Mouse Macrophages," *Bioorg. Med. Chem. Lett.*, 9(24):3429-3434, 1999.

Honda et al., "Novel Synthetic Oleanane and Ursane Triterpenoids with Various Enone Functionalities in Ring A as Inhibitors of Nitric Oxide Production in Mouse Macropahges," *J. Med. Chem.*, 43:1866-1877, 2000a.

Honda et al., "Synthetic Oleanane and Ursane Triterpenoids with Modified Rings A and C: A Series of Highly Active Inhibitors of Nitric Oxide Production in Mouse Macrophages," *J. Med. Chem.*, 43:4233-4246, 2000b.

Honda et al., "A novel dicyanotriterpenoid, 2-cyano-3,12-dioxooleana-1,9(11)-dien-28-onitrile, active at picomolar concentrations for Inhibition of Nitric Oxide Production," *Bioorg. Med. Chem. Lett.*, 12:1027-1030, 2002.

*Handbook of Pharmaceutical Salts: Properties, and Use*, Stahl and Wermuth Eds.), Verlag Helvetica Chimica Acta, 2002.

Huang et al., "Inhibition of Skin Tumorigenesis by Rosemary and its Constituents Carnosol and Ursolic Acid," *Cancer Res.*, 54:701-708, 1994.

Ikeda et al., "The Novel Triterpenoid CDDO and its Derivatives Induce Apoptosis by Disruption of Intracellular Redox Balance," *Cancer Res.*, 63:5551-5558, 2003.

Ikeda et al., "Induction of Redox Imbalance and Apoptosis in Multiple Myeloma Cells by the Novel Triterpenoid 2-cyano-3,12-dioxoolean-1,9-dien-28-oic acid," *Mol. Cancer Ther.*, 3:39-45, 2004.

Joint Specialty Committee on Renal Medicine of the Royal College of Physicians and the Renal Association, and the Royal College of General Practitioners. Chronic kidney disease in adults: UK guidelines for identification, management and referral. London: Royal College of Physicians, 2006.

Kobayashi and Yamamoto, "Molecular Mechanism Activating the Nrf2-Keap 1 Pathway of Antioxidant Gene Regulation," *Antioxid. Redox. Signal.*, 7:385-394, 2005.

Liby et al., "The Synthetic Triterpenoids, CDDO and CDDO-imidazolide, are Potent Inducers of Heme Oxygenase-1 and Nrf2/ARE signaling," *Cancer Res.*, 65:4789-4798, 2005.

Maines and Gibbs, "30 Some Years of Heme Oxygenase: From a 'molecular wrecking ball' to a 'mesmerizing' Trigger of Cellular Events," *Biochem. Biophys. Res. Commun.*, 338:568-577, 2005.

*March's Advanced Organic Chemistry: Reactions, Mechanisms, and Structure*, 2007.

Nishino et al., "Inhibition of the Tumor-Promoting Action of 12-O tetradecanoylphorbol-13-acetate by some Oleanane-type Triterpenoid Compounds," *Cancer Res.*, 48:5210-5215, 1988

Peake and Whiting, "Measurement of Serum Creatinine-Current Status and Future Goals," *Clin. Biochem. Rev.*, 27:173-184, 2006.

Pergola et al., "Bardoxolone methyl and kidney function in CKD with type 2 diabetes," *New Engl. J. Med.*, 365, 327-336, 2011.

Place et al., "The Novel Synthetic Triterpenoid, CDDO-Imidazolide, Inhibits Inflammatory Response and Tumor Growth In Vivo," *Clin. Cancer Res.*, 9:2798-2806, 2003.

Rawlins et al., "Performance Characteristics of Four Automated Natriuretic Peptide Assays," *Am. J. Clin. Pathol.*, 123:439-445, 2005.

Reagan-Shaw et al., "Dose Translation From Animal to Human Studies Revisited," *FASEB J.*, 22(3):659-661, 2008

Repka et al., "*Encyclopedia of Pharmaceutical Technology*," New York:Marcel Dekker, 2002.

Schneider et al., "Contrasting actions of endothelin ETA and ETB receptors in cardiovascular disease," *Annual Review of Pharmacology and Toxicology*, 47:731-759, 2007.

Shishodia et al., "A Synthetic Triterpenoid, CDDO-Me, Inhibits IκBa Kinase and Enhances Apoptosis Induced by TNF and Chemotherapeutic Agents Through Down-Regulation of Expression of Nuclear Factor κB-Regulated Gene Products in Human Leukemic Cells," *Clin. Cancer Res.*, 12(6):1828-1838, 2006.

Suh et al., "Novel Triterpenoids Suppress Inducible Nitric Oxide Synthase (iNOS) and Inducible Cyclooxygenase (COX-2) in Mouse Macrophages," *Cancer Res.*, 58:717-723, 1998.

Suh et al., "A Novel Synthetic Oleanane Triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "Synthetic Triterpenoids Enhance Transforming Growth Factor β/Smad Signaling," *Cancer Res.*, 63:1371-1376, 2003.

Vachiéry and Davenport, "The endothelin system in pulmonary and renal vasculopathy: les liaisons dangereuses," *European Respiratory Review*, 18:260-271, 2009.

Vasan et al., "Congestive heart failure in subjects with normal versus reduced left ventricular ejection fraction: Prevalence and mortality in a population-based cohort," *Journal of the American College of Cardiology*, 33:1948-1955, 1999.

Wang et al., "A Synthetic Triterpenoid, 2-cyano-3,12-dioxooleana-1,9-dien-28-oic acid (CDDO), is a Ligand for the Peroxisome Proliferator-Activated Receptor γ," *Mol. Endocrin.*, 14(10):1550-1556, 2000.

Yates et al., "Pharmacodynamic Characterization of Chemopreventive Triterpenoids as Exceptionally Potent Inducers of Nrf2-regulated Genes," *Mol. Cancer. Ther.*, 6:154-162, 2007.

What is claimed is:

1. A method for preventing or delaying progression of Alport syndrome or a symptom thereof in a patient in need thereof, the method comprising administering to the patient a therapeutically effective amount of a compound of the formula:

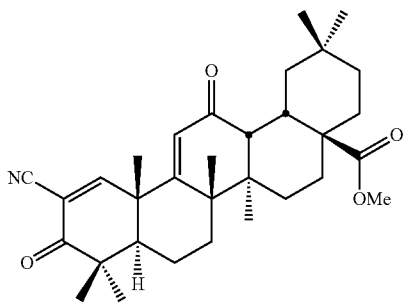

or a pharmaceutically acceptable salt thereof.

2. The method of claim 1, wherein the method prevents or delays renal function decline in the patient.

3. The method of claim 1, wherein the method prevents or delays the progression of kidney disease in the patient.

4. The method of claim 1, wherein the method slows the rate of decline of a glomerular filtration rate (GFR) in the patient.

5. The method of claim 4, wherein the GFR is an estimated GFR (eGFR).

6. The method of claim 5, wherein the method prevents or delays the eGFR from falling below 15 mL/min/1.73 m$^2$.

7. The method of claim 1, wherein the method prevents or delays kidney failure in the patient.

8. The method of claim 1, wherein the method prevents or delays end-stage renal disease in the patient.

9. The method of claim 1, wherein the method prevents or delays chronic kidney disease in the patient.

10. The method of claim 1, wherein the patient does not have a cardiovascular disease.

11. The method of claim 1, wherein the patient does not have Stage 4 or higher chronic kidney disease.

12. The method of claim 1, wherein the patient has an estimated glomerular filtration rate (eGFR) greater than or equal to 45 mL/min/1.73 m$^2$.

13. The method of claim 1, wherein the patient has an estimated glomerular filtration rate (eGFR) greater than or equal to 30 mL/min/1.73 m$^2$.

14. The method of claim 1, wherein the patient has an albumin/creatinine ratio (ACR) less than or equal to 2000 mg/g.

15. The method of claim 1, wherein the patient has a B-type natriuretic peptide (BNP) level that is not elevated.

16. The method of claim 1, wherein the patient has a BNP level that is less than or equal to 200 pg/mL.

17. The method of claim 1, wherein at least a portion of the compound is present as a crystalline form having an X-ray diffraction pattern (CuKα) comprising significant diffraction peaks at about 8.8, 12.9, 13.4, 14.2 and 17.4° 2θ.

18. The method of claim 1, wherein at least a portion of the compound is present as an amorphous form having an X-ray diffraction pattern (CuKα) with a peak at approximately 13.5° 2θ, substantially as shown in FIG. 1C, and a transition glass temperature (T$_g$), wherein the T$_g$ value is in the range of about 120° C. to about 135° C.

19. The method of claim 1, wherein the therapeutically effective amount is a daily dose from about 0.1 mg to about 300 mg of the compound.

20. The method of claim 1, wherein the compound is administered orally, intraarterially or intravenously.

21. The method of claim 1, wherein the compound is formulated as a hard or soft capsule or a tablet.

22. The method of claim 1, wherein the compound is formulated as a solid dispersion comprising (i) the compound and (ii) an excipient.

23. The method of claim 22, wherein the excipient is a methacrylic acid ethyl acrylate copolymer.

24. A method for increasing a glomerular filtration rate (GFR) in a patient having Alport syndrome, the method comprising administering to the patient a therapeutically effective amount of a compound of the formula:

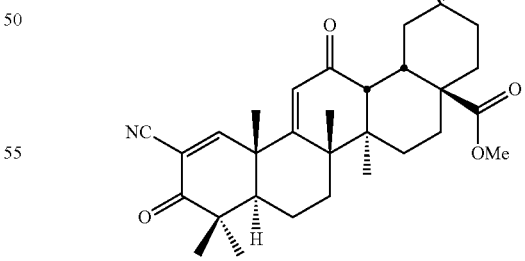

or a pharmaceutically acceptable salt thereof.

25. The method of claim 24, wherein the GFR is an estimated GFR (eGFR).

26. The method of claim 25, wherein the method increases the patient's eGFR at least 3 mL/min/1.73 m$^2$.

27. The method of claim 25, wherein the method increases the patient's eGFR at least 4 mL/min/1.73 m$^2$.

28. A method of treating or preventing Alport syndrome in a patient less than 25 years old, the method comprising administering to the patient a therapeutically effective amount of a compound of the formula:

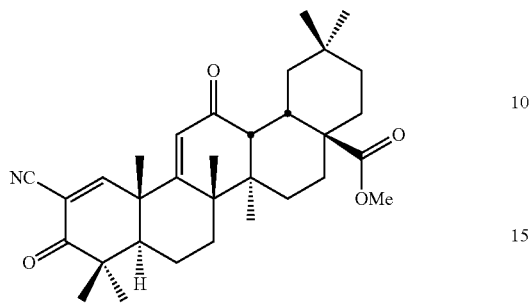

or a pharmaceutically acceptable salt thereof.

29. The method of claim 28, wherein the patient is more than 12 years old.

30. The method of claim 28, wherein the patient is less than 12 years old.

* * * * *